(12) United States Patent
Schunk et al.

(10) Patent No.: US 8,492,559 B2
(45) Date of Patent: Jul. 23, 2013

(54) SUBSTITUTED INDOLE COMPOUNDS

(75) Inventors: Stefan Schunk, Aachen (DE); Melanie Reich, Aachen (DE); Michael Engels, Turnhout (BE); Tieno Germann, Aachen (DE); Ruth Jostock, Stolberg (DE); Sabine Hees, Aachen (DE)

(73) Assignee: Gruenenthal GmbH, Aachen (DE)

( * ) Notice: Subject to any disclaimer, the term of this patent is extended or adjusted under 35 U.S.C. 154(b) by 401 days.

(21) Appl. No.: 12/699,451

(22) Filed: Feb. 3, 2010

(65) Prior Publication Data

US 2010/0222324 A1 Sep. 2, 2010

Related U.S. Application Data

(60) Provisional application No. 61/149,785, filed on Feb. 4, 2009.

(30) Foreign Application Priority Data

Feb. 4, 2009 (EP) ..................................... 09001488

(51) Int. Cl.
C07D 209/26 (2006.01)
(52) U.S. Cl.
USPC ......................................................... 548/468
(58) Field of Classification Search
None
See application file for complete search history.

(56) References Cited

U.S. PATENT DOCUMENTS

| 2002/0022624 A1 | 2/2002 | Dinnell et al. |
| 2006/0128765 A1 | 6/2006 | Wood et al. |

FOREIGN PATENT DOCUMENTS

| EP | 1 600 447 A1 | 11/2005 |
| WO | WO 00/59886 | 10/2000 |
| WO | WO 2007/101007 A | 9/2007 |
| WO | WO 2007/140383 | 12/2007 |
| WO | WO 2008/033739 A | 3/2008 |
| WO | WO 2008/040492 A | 4/2008 |
| WO | WO 2008/046573 A | 4/2008 |

OTHER PUBLICATIONS

Mori, et al. Diabetes, 2008, 1491-1500.*
Bengtson et al., Kinin receptor expression during *Staphylococcus aureus* infection, *Blood*. 2006; 108: 2055-2063.
Calixto et al., Kinin B1 receptors: key G-protein-coupled receptors and their role in inflammatory and painful processes, *British Journal of Pharmacology*. 2004; 143: 803-818.
Gabra et al., The kinin system mediates hyperalgesia through the inducible bradykinin B1 receptor subtype: evidence in various experimental animal models of type 1 and type 2 diabetic neuropathy, *Biol. Chem.* vol. 387, pp. 127-143, Feb. 2006.
Hayashi et al., Bradykinin stimulates IL-6 and IL-8 production by human lung fibroblasts through ERK- and p38 MAPK-dependent mechanisms, *European Respiratory Journal*. 2000; 16: 452-458.
Hess et al., Generation and characterization of a humanized bradykinin B1 receptor mouse, *Biol. Chem.*, vol. 387, pp. 195-201, Feb. 2006.
Leeb-Lundberg et al., International Union of Pharmacology. XLV. Classification of the Kinin Receptor Family: from Molecular Mechanisms to Pathophysiological Consequences, *Pharmacological Reviews*. 57: 27-77, 2005.
Passos et al., Kinin B1 Receptor Up-Regulation after Lipopolysaccharide Administration: Role of Proinflammatory Cytokines and Neutrophil Influx, *The Journal of Immunology*. 2004, 172: 1839-1847.
Pesquero et al., Hypoalgesia and altered inflammatory responses in mice lacking kinin B1 receptors, *Proc. Natl. Acad. Sci.*, vol. 97, No. 14, pp. 8140-8145, Jul. 5, 2000.
Pesquero et al., Genetically altered animal models in the kallikrein-kinin system, *Biol. Chem.*, vol. 387, pp. 119-126, Feb. 2006.
Prat et al., Bradykinin B1 receptor expression and function on T lymphocytes in active multiple sclerosis, *Neurology*, vol. 53 (9), pp. 2087-2092, Dec. 10, 1999.
Stadnicki et al., Immunolocalization and expression of kinin B1R and B2R receptors in human inflammatory bowel disease, *Am. J. Physiol. Gastrointest. Liver Physiol.*, 289: G361-G366, 2005.
International Search Report (Form PCT/ISA/210) dated Apr. 22, 2010 with partial English translation, including Forms PCT/ISA/220 and PCT/ISA/237 (Fourteen (14) pages).

* cited by examiner

*Primary Examiner* — Jason M Nolan
*Assistant Examiner* — Ana Z Muresan
(74) *Attorney, Agent, or Firm* — Crowell & Moring LLP

(57) ABSTRACT

Substituted indole compounds corresponding to the formula I:

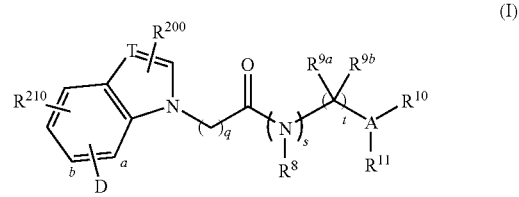

(I)

In which $R^8$, $R^{9a}$, $R^{9b}$, $R^{10}$, $R^{11}$, $R^{200}$, $R^{210}$, A, D, T, q, s and t have defined meanings, processes for the preparation thereof, pharmaceutical compositions containing such compounds and the use of substituted indole compounds for the treatment or inhibition of pain and other conditions which are at least partly mediated by Bradykinin 1 receptors (B1R).

19 Claims, No Drawings

SUBSTITUTED INDOLE COMPOUNDS

CROSS REFERENCE TO RELATED APPLICATIONS

This application claims priority from co-pending provisional application No. 61/149,785, filed Feb. 4, 2009. Priority is also claimed based on European patent application no. EP 09001488.7, likewise filed Feb. 4, 2009.

BACKGROUND OF THE INVENTION

The present invention relates to substituted indole compounds, processes for the preparation thereof, medicinal products containing these compounds and the use of substituted indole compounds for the preparation of medicinal products.

In contrast to the constitutive expression of the bradykinin 2 receptor (B2R), the bradykinin 1 receptor (B1R) is not expressed or is only weakly expressed in most tissues. Nevertheless, expression of the B1R can be induced on various cells. By way of example, in the course of inflammation reactions a rapid and pronounced induction of the B1R takes place on neuronal cells, but also on various peripheral cells, such as fibroblasts, endothelial cells, granulocytes, macrophages and lymphocytes. Thus, in the course of inflammation reactions a switch from a B2R to a B1R dominance occurs on the cells involved. The cytokines interleukin-1 (IL-1) and tumour necrosis factor alpha (TNFα) are substantially involved in this B1R up-regulation (Passos et al. J. Immunol. 2004, 172, 1839-1847). After activation with specific ligands, B1R-expressing cells can subsequently themselves secrete inflammation-promoting cytokines, such as IL-6 and IL-8 (Hayashi et al., Eur. Respir. J. 2000, 16, 452-458). This leads to inwards migration of further inflammation cells, for example neutrophilic granulocytes (Pesquero et al., PNAS 2000, 97, 8140-8145). The bradykinin B1R system can contribute to the chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). In humans too, an increased expression of the B1R is seen, for example on enterocytes and macrophages in the affected tissue of patients with inflammatory bowel diseases (Stadnicki et al., Am. J. Physiol. Gastrointest. Liver Physiol. 2005, 289, G361-366) and on T lymphocytes of patients with multiple sclerosis (Pratet al., Neurology. 1999; 53, 2087-2092), or an activation of the bradykinin B2R-B1R system is seen in the course of infections with *Staphyloccocus aureus* (Bengtson et al., Blood 2006, 108, 2055-2063). Infections with *Staphyloccocus aureus* are responsible for disease profiles such as superficial infections of the skin through to septic shock.

Based on the pathophysiological relationships described, there is great therapeutic potential for the use of B1R antagonists against acute and in particular chronic inflammatory diseases. They include diseases of the respiratory tract (bronchial asthma, allergies, COPD/chronic obstructive pulmonary disease, cystic fibrosis, etc.), inflammatory bowel diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucous membranes (Behcet's disease, chronic pelvic pain, prostatitis, etc.), rheumatic diseases (rheumatoid arthritis, osteoarthritis, etc.), septic shock and reperfusion syndrome (following heart attack or stroke).

The bradykinin (receptor) system is moreover also involved in the regulation of angiogenesis (potential as an angiogenesis inhibitor in cases of cancer and macula degeneration in the eye), and B1R-knockout mice are protected from the induction of obesity by a particularly high-fat diet (Pesquero et al., Biol. Chem. 2006, 387, 119-126). B1R antagonists are therefore also suitable for the treatment of obesity.

B1R antagonists are particularly suitable for the treatment of pain, in particular inflammatory pain and neuropathic pain (Calixto et al., Br. J. Pharmacol 2004, 1-16), and here in particular diabetic neuropathy (Gabra et al., Biol. Chem. 2006, 387, 127-143). They are also suitable for the treatment of migraine.

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already meant that transgenic animals with human B1 receptors have been produced for animal pharmacology studies (Hess et al., Biol. Chem. 2006; 387(2):195-201). Working with transgenic animals is, however, more expensive than working with the unmodified animals.

International patent applications WO 2008/040492 and WO 2008/046573 describe compounds which in in-vitro assays exhibit an antagonistic action both on the human B1 receptor and on the B1 receptor of the rat.

International patent applications WO 2007/140383 and WO 2007/101007 describe compounds which in in-vitro assays exhibit an antagonistic action on the macaque B1 receptor. Experimental data on the activity on the human B1 receptor or the B1 receptor of the rat is not disclosed.

Despite the efforts of the prior art, there remains a need for novel B1R modulators, whereby B1R modulators which bind both to the rat receptor and to the human receptor offer particular advantages.

SUMMARY OF THE INVENTION

An object of the present invention was therefore to provide novel compounds which are suitable in particular as pharmacological active ingredients in medicinal products, preferably in medicinal products for the treatment of disorders or diseases which are at least partly mediated by B1R receptors.

This object is achieved by the substituted indole compounds according to the invention.

The invention therefore provides substituted indole compounds having the formula (I)

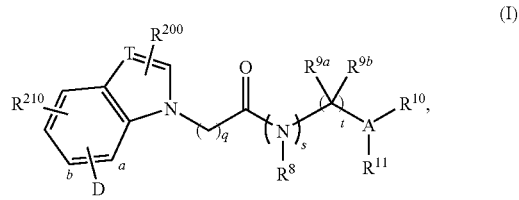

wherein
T denotes CH or N;
q=1, 2 or 3;
s=0 or 1;
t=0, 1, 2 or 3;

D in position a or b is bound to the indole skeleton and denotes one of the following groups D1 or D2

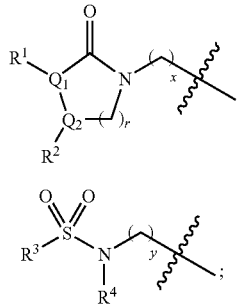

wherein
x and y, each independently, denote 0 or 1;
r denotes 1, 2 or 3;
$Q_1$ and $Q_2$ each independently denote C, CH or N;
$R^1$ and $R^2$ together with the -$Q_1$-$Q_2$-group linking them form a cyclic compound, which can be substituted at one or more of its carbon ring members with one or more substituents independently selected from the group consisting of F, Cl, Br, I, $CF_3$, $C_{1-6}$ alkyl, O—$C_{1-6}$ alkyl, OH, $OCF_3$, SH, $SCF_3$, aryl and heteroaryl and/or can be anellated with at least one aryl or heteroaryl, wherein the cyclic compound is saturated, mono- or polyunsaturated, for example diunsaturated, or aromatic, is 4-, 5-, 6- or 7-membered, can optionally contain one or more, for example 2 or 3, heteroatoms or heteroatom groups each independently selected from the group consisting of N, $NR^{50}$, O, S, S=O and $S(=O)_2$; wherein $R^{50}$ denotes H, $C_{1-6}$ alkyl, —C(=O)—$R^{51}$, $C_{3-8}$ cycloalkyl, aryl, heteroaryl or a $C_{3-8}$ cycloalkyl, aryl or heteroaryl bound via a $C_{1-3}$ alkylene group, and $R^{51}$ denotes $C_{1-6}$ alkyl, $C_{3-8}$ cycloalkyl, aryl, heteroaryl or a $C_{3-8}$ cycloalkyl, aryl or heteroaryl bound via a $C_{1-3}$ alkylene group;
$R^3$ denotes aryl, heteroaryl or an aryl or heteroaryl bound via a $C_{1-3}$ alkylene group, wherein aryl and heteroaryl can each be anellated with a 4-, 5-, 6- or 7-membered cyclic compound, wherein the cyclic compound is in each case saturated or mono- or polyunsaturated, for example diunsaturated, but is not aromatic and can be substituted at one or more of its carbon ring members with one or more substituents independently selected from the group consisting of F, Cl, Br, I, —$CF_3$, —O—$CF_3$, $C_{1-6}$ alkyl and O—$C_{1-6}$ alkyl and can optionally contain one or more, for example 2 or 3, heteroatoms or heteroatom groups each independently selected from the group consisting of N, $NR^{50a}$, O, S, S=O and $S(=O)_2$, wherein $R^{50a}$ denotes H, $C_{1-6}$ alkyl, —C(=O)—$R^{51a}$, $C_{3-8}$ cycloalkyl, aryl, heteroaryl or a $C_{3-8}$ cycloalkyl, aryl or heteroaryl bound via a $C_{1-3}$ alkylene group and $R^{51a}$ denotes $C_{1-6}$ alkyl, $C_{3-8}$ cycloalkyl, aryl, heteroaryl or a $C_{3-8}$ cycloalkyl, aryl or heteroaryl bound via a $C_{1-3}$ alkylene group;
$R^4$ denotes H, $C_{1-6}$ alkyl, $C_{3-8}$ cycloalkyl, aryl or heteroaryl or a $C_{3-8}$ cycloalkyl, aryl or heteroaryl bound via a $C_{1-6}$ alkylene group;
$R^{200}$ denotes 0 to 2 substituents, which are each independently selected from the group consisting of F, Cl, Br, I, $CF_3$, $OCF_3$, OH, O—$C_{1-6}$ alkyl, $C_{1-6}$ alkyl, aryl and heteroaryl and/or two adjacent substituents $R^{200}$ form an anellated aryl or heteroaryl;
$R^{210}$ denotes 0 to 3 substituents which are each independently selected from the group consisting of F, Cl, Br, I, $CF_3$, $OCF_3$, OH, O—$C_{1-6}$ alkyl, $C_{1-6}$ alkyl, aryl and heteroaryl;
$R^8$ denotes H, $C_{1-6}$ alkyl, $C_{3-8}$ cycloalkyl, aryl or heteroaryl or a $C_{3-8}$ cycloalkyl, aryl or heteroaryl bound via a $C_{1-6}$ alkylene group;
$R^{9a}$ and $R^{9b}$ each independently denote H, F, Cl, OH, $C_{1-6}$ alkyl, O—$C_{1-6}$ alkyl, $C_{1-3}$ cycloalkyl, aryl or heteroaryl or a $C_{3-8}$ cycloalkyl, aryl or heteroaryl bound via a $C_{1-6}$ alkylene group;
A denotes N or CH;
with the proviso that if s denotes 1 and t denotes 0 then A denotes CH; and
with the proviso that if s and t each denote 0 then A denotes N;
$R^{10}$ and $R^{11}$ together with A represent a spirocyclic or cyclic group according to one of the formulas (II) or (III),

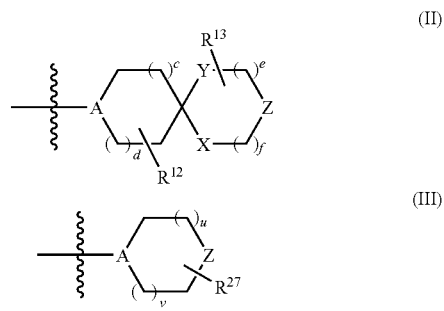

wherein
c, d, e, f, u and v each independently denote 0, 1 or 2;
$R^{12}$, $R^{13}$ and $R^{27}$ each independently denote 0 to 4 substituents which are each independently selected from the group consisting of F, Cl, OH, =O, $C_{1-6}$ alkyl, O—$C_{1-6}$ alkyl, $C_{3-8}$ cycloalkyl, aryl, heteroaryl and $C_{3-8}$ cycloalkyl, aryl or heteroaryl bound via a $C_{1-6}$ alkylene group; and/or
two of the 0 to 4 substituents $R^{27}$ together represent a $C_{1-3}$ alkylene bridge such that the cyclic compound represented in the formula (III) assumes a bicyclically bridged form; and/or
two adjacent substituents out of the 0 to 4 substituents $R^{13}$ form an anellated aryl or heteroaryl group; and/or
two adjacent substituents out of the 0 to 4 substituents $R^{27}$ form an anellated aryl or heteroaryl group;
X denotes $CR^{14a}R^{14b}$, $NR^{15}$ or O;
Y denotes $CR^{16a}R^{16b}$, $NR^{17}$ or O;
with the proviso that X does not denote $NR^{15}$ if Y denotes $NR^{17}$; and
with the proviso that X and Y do not simultaneously denote 0;
wherein
$R^{14a}$, $R^{14b}$, $R^{16a}$ and $R^{16b}$ each independently denote H, F, Cl, OH, $C_{1-6}$ alkyl, O—$C_{1-6}$ alkyl, $C_{3-8}$ cycloalkyl, aryl or heteroaryl or denote a $C_{3-8}$ cycloalkyl, aryl or heteroaryl bound via a $C_{1-6}$ alkylene group, and/or
$R^{14a}$ and $R^{14b}$ can together denote =O, and/or
$R^{16a}$ and $R^{16b}$ can together denote =O;
$R^{15}$ and $R^{17}$ each independently denote H, $C_{1-6}$ alkyl, $C_{3-8}$ cycloalkyl, aryl or heteroaryl or denote a $C_{3-8}$ cycloalkyl, aryl or heteroaryl bound via a $C_{1-6}$ alkylene group;
Z in formula (II) denotes $CR^{18a}R^{18b}$, $NR^{19}$ or O, or
Z in formula (II), if X denotes O and f denotes 0, denotes —(C($R^{124}$)—C($R^{125}$))—, wherein $R^{124}$ and $R^{125}$ together with the carbon atoms linking them form a fused aryl or heteroaryl group; or Z in formula (II), if X denotes O and f denotes 0, denotes =(N(CR$^{126}$))—, wherein the N atom is singly bonded to the O atom, and R$^{126}$ denotes H, C$_{1-6}$ alkyl, C$_{3-8}$ cycloalkyl, aryl or heteroaryl or denotes a C$_{3-8}$ cycloalkyl, aryl or heteroaryl bound via a C$_{1-6}$ alkylene group;

Z in formula (III) denotes CR$^{18a}$R$^{18b}$, NR$^{19}$, O, S, S(=O) or S(=O)$_2$;

wherein

R$^{18a}$ denotes H, C$_{1-6}$ alkyl, C$_{3-8}$ cycloalkyl, aryl or heteroaryl or denotes a C$_{3-8}$ cycloalkyl, aryl or heteroaryl bound via a C$_{1-6}$ alkylene group, or R$^{18a}$ denotes a group according to the formula (IV),

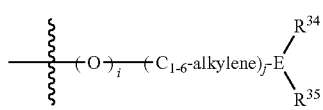

(IV)

wherein i and j each independently denote 0 or 1;

E denotes N or CH, with the proviso that if i denotes 1 and j denotes 0 then E denotes CH;

R$^{34}$ and R$^{35}$ each independently denote H, C$_{1-6}$ alkyl, C$_{3-8}$ cycloalkyl, aryl or heteroaryl or an aryl, heteroaryl or C$_{3-8}$ cycloalkyl bound via a C$_{1-3}$ alkylene group; or R$^{34}$ and R$^{35}$ with inclusion of E form a 5- or 6-membered aryl or heteroaryl; or R$^{34}$ and R$^{35}$ with inclusion of E form a saturated heterocyclic compound according to the formula (V),

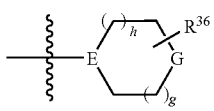

(V)

wherein h and g each independently denote 0, 1 or 2;

G denotes CR$^{37a}$R$^{37b}$, NR$^{38}$, O, S, S=O or S(=O)$_2$, with the proviso that if E denotes CH then G does not denote CR$^{37a}$R$^{37b}$;

R$^{36}$ denotes 0 to 4 substituents each independently selected from the group consisting of F, Cl, Br, I, OH, SH, =O, O—C$_{1-6}$ alkyl, C$_{1-6}$ alkyl, C$_{3-8}$ cycloalkyl, aryl, heteroaryl and C$_{3-8}$ cycloalkyl, aryl or heteroaryl bound via a C$_{1-6}$ alkylene group; and/or two adjacent substituents R$^{36}$ together represent an anellated aryl or heteroaryl;

R$^{37a}$ and R$^{37b}$ each independently denote H, F, Cl, Br, I, OH, SH, =O, O—C$_{1-6}$ alkyl, C$_{1-6}$ alkyl, C$_{3-8}$ cycloalkyl, aryl or heteroaryl or denote a C$_{3-8}$ cycloalkyl, aryl or heteroaryl bound via a C$_{1-6}$ alkylene group;

R$^{38}$ denotes H, C$_{1-6}$ alkyl, C$_{3-8}$ cycloalkyl, aryl or heteroaryl or denotes an aryl, heteroaryl or C$_{3-8}$ cycloalkyl bound via a C$_{1-3}$ alkylene group;

R$^{18b}$ denotes H, OH, C$_{1-6}$ alkyl, C$_{3-8}$ cycloalkyl, O—C$_{1-6}$ alkyl, O—(C$_{3-8}$ cycloalkyl), (C$_{1-6}$ alkylene)-O—C$_{1-6}$ alkyl, (C$_{1-6}$ alkylene)-O—(C$_{3-8}$ cycloalkyl), aryl, heteroaryl, O-aryl or O-heteroaryl or denotes an aryl, O-aryl, heteroaryl or O-heteroaryl bound via a C$_{1-6}$ alkylene group; or R$^{18b}$ denotes a group according to the formula (VI),

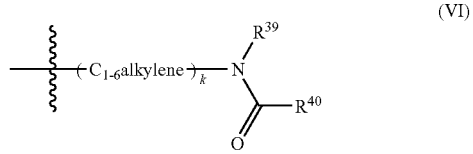

(VI)

wherein k denotes 0 or 1;

R$^{39}$ denotes H, C$_{1-6}$ alkyl, C$_{3-8}$ cycloalkyl, aryl or heteroaryl or denotes a C$_{3-8}$ cycloalkyl, aryl or heteroaryl bound via a C$_{1-3}$ alkylene group;

R$^{40}$ denotes C$_{1-6}$ alkyl, C$_{3-8}$ cycloalkyl, aryl or heteroaryl or denotes a C$_{3-8}$ cycloalkyl, aryl or heteroaryl bound via a C$_{1-6}$ alkylene group; or R$^{39}$ and R$^{40}$ together with the N–C(=O) group linking them form a ring according to the formula (VII),

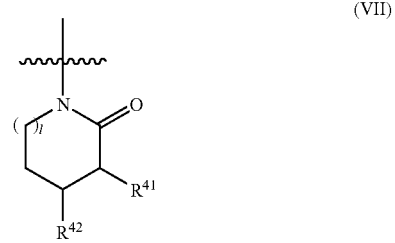

(VII)

wherein l denotes 0, 1 or 2; and

R$^{41}$ and R$^{42}$ together with the carbon atoms linking them form an anellated aryl or heteroaryl;

R$^{19}$ denotes H; or (P)$_z$—R$^{22}$, wherein z denotes 0 or 1;

P denotes (C=O), S(=O)$_2$ or C(=O)—N(R$^{24}$), wherein the N atom in the C(=O)—N(R$^{24}$) group is linked to R$^{22}$, wherein R$^{24}$ denotes H, C$_{1-6}$ alkyl, C$_{3-8}$ cycloalkyl or an aryl, heteroaryl or C$_{3-8}$ cycloalkyl bound via a C$_{1-6}$ alkylene group;

R$^{22}$ denotes C$_{1-6}$ alkyl, C$_{3-8}$ cycloalkyl, aryl or heteroaryl or denotes an aryl or heteroaryl bound via a C$_{1-6}$ alkylene group; or R$^{22}$ denotes a group according to the formula (VIII), wherein

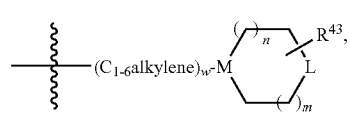

(VIII)

n denotes 0, 1 or 2;

m denotes 0, 1 or 2;

w denotes 0 or 1, and

M denotes CH or N;

with the proviso that if P denotes C(=O)—NR$^{24}$, and w denotes 0, then M denotes CH; and with the proviso that if z and w simultaneously denote 0 then M denotes CH;

L denotes CR$^{44a}$R$^{44b}$, NR$^{45}$, O, S, S=O or S(=O)$_2$;

$R^{43}$ denotes 0 to 4 substituents each independently selected from the group consisting of F, Cl, OH, =O, $C_{1-6}$ alkyl, O—$C_{1-6}$ alkyl, $C_{3-8}$ cycloalkyl, aryl, heteroaryl and $C_{3-8}$ cycloalkyl, aryl or heteroaryl bound via a $C_{1-6}$ alkylene group; and/or two adjacent substituents out of the 0 to 4 substituents $R^{43}$ together represent an anellated aryl or heteroaryl ring structure;

$R^{44a}$ and $R^{44b}$ each independently denote H, F, Cl, Br, I, OH, $C_{1-6}$ alkyl, O—$C_{1-6}$ alkyl, $C_{3-8}$ cycloalkyl, aryl or heteroaryl or denote a $C_{3-8}$ cycloalkyl, aryl or heteroaryl bound via a $C_{1-6}$ alkylene group; or $R^{44a}$ and $R^{44b}$ can together denote =O;

$R^{45}$ denotes H, $C_{1-6}$ alkyl, $C_{3-8}$ cycloalkyl, aryl or heteroaryl or denotes an aryl, heteroaryl or $C_{3-8}$ cycloalkyl bound via a $C_{1-3}$ alkylene group;

wherein the aforementioned $C_{1-6}$ alkyl, $C_{1-3}$ alkylene, $C_{1-6}$ alkylene, $C_{3-8}$ cycloalkyl, aryl and heteroaryl groups may each be unsubstituted or mono- or polysubstituted with identical or different substituents and the aforementioned $C_{1-6}$ alkyl, $C_{1-3}$ alkylene and $C_{1-6}$ alkylene groups may each be branched or unbranched;

optionally in the form of an isolated enantiomer or an isolated diastereomer, the racemate, the enantiomers, the diastereomers, mixtures of enantiomers and/or diastereomers, and each in the form of their bases and/or physiologically compatible salts.

In the formula (IV) used above, the bonds shown between E and $R^{34}$ and $R^{35}$ should not be understood exclusively as single bonds; they can also be part of an aromatic system.

Within the meaning of the present invention the term "halogen" preferably denotes F, Cl, Br and I, in particular F and Cl.

Within the meaning of this invention, the expression "$C_{1-6}$ alkyl" includes acyclic saturated hydrocarbon groups having 1, 2, 3, 4, 5 or 6 carbon atoms, which may be branched or straight-chain (unbranched) and unsubstituted or mono- or polysubstituted, for example di-, tri-, tetra- or pentasubstituted, with identical or different substituents. The alkyl groups are preferably selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl groups are selected from the group consisting of methyl, ethyl, n-propyl, isopropyl, n-butyl, sec-butyl, isobutyl and tert-butyl.

Within the meaning of this invention, the expression "$C_{3-8}$ cycloalkyl" denotes cyclic saturated hydrocarbons having 3, 4, 5, 6, 7 or 8 carbon atoms, which may be unsubstituted or mono- or polysubstituted, for example di-, tri-, tetra- or pentasubstituted, at one or more ring members with identical or different substituents. $C_{3-8}$ cycloalkyl is preferably selected from the group consisting of cyclopropyl, cyclobutyl, cyclopentyl, cyclohexyl, cycloheptyl and cyclooctyl.

Within the meaning of this invention, the expression "aryl" denotes aromatic hydrocarbons, in particular phenyls and naphthyls. The aryl groups may also be fused to other saturated, (partially) unsaturated or aromatic ring systems. Each aryl group may be present in unsubstituted or mono- or polysubstituted form, for example di-, tri-, tetra- or pentasubstituted, wherein the aryl substituents can be identical or different and can be at any desired and possible position of the aryl group. Aryl is advantageously selected from the group consisting of phenyl, 1-naphthyl and 2-naphthyl, each of which may be unsubstituted or mono- or polysubstituted, for example with 2, 3, 4 or 5 substituents.

Within the meaning of the present invention, the expression "heteroaryl" denotes a 5-, 6- or 7-membered cyclic aromatic group containing at least 1, optionally also 2, 3, 4 or 5 heteroatoms, wherein the heteroatoms may be identical or different and the heteroaryl can be unsubstituted or mono- or polysubstituted, for example di-, tri-, tetra- or pentasubstituted, with identical or different substituents. The substituents can be bound to any desired and possible position of the heteroaryl group. The heterocyclic compound can also be part of a bicyclic or polycyclic ring system, in particular a mono-, bi- or tricyclic system, which can then in total be more than 7-membered, for example up to 14-membered. Preferred heteroatoms are selected from the group consisting of N, O and S. The heteroaryl group is preferably selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phthalazinyl, pyrazolyl, imidazolyl, thiazolyl, oxazolyl, oxadiazolyl, triazole, tetrazole, isoxazolyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl; particularly preferably from the group consisting of thienyl (thiophenyl), pyridinyl (pyridyl), pyrimidinyl, thiazolyl, triazolyl, imidazolyl, oxazolyl, oxadiazolyl, quinazolinyl, quinolinyl and isoquinolinyl, wherein the bond to the general structure (I) can be made via any desired and possible ring member of the heteroaryl group. The heteroaryl group is especially preferably selected from the group consisting of thienyl, imidazolyl, thiazolyl, triazolyl, pyridinyl and pyrimidinyl.

Within the meaning of the present invention, the expression "$C_{1-3}$ alkylene group" or "$C_{1-6}$ alkylene group" includes acyclic saturated hydrocarbon groups having respectively 1, 2 or 3 or 1, 2, 3, 4, 5 or 6 carbon atoms, which can be branched or straight-chain (unbranched) and unsubstituted or mono- or polysubstituted, for example di-, tri-, tetra- or pentasubstituted, with identical or different substituents, and which link a respective group to the higher-order general structure. The alkylene groups are preferably selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. The alkylene groups are particularly preferably selected from the group consisting of —$CH_2$—, —$CH_2$—$CH_2$— and —$CH_2$—$CH_2$—$CH_2$—.

Within the meaning of the present invention the expression "—$(O)_{0/1}$—$C_{1-6}$ alkylene group" also includes in addition to the $C_{1-6}$ alkylene groups described above such groups in which these groups are linked by an oxygen atom to the higher-order structure.

Within the meaning of the present invention, the expression "aryl or heteroaryl bound via a $C_{1-3}$ alkylene group or a $C_{1-6}$ alkylene group" means that the $C_{1-3}$ alkylene groups, $C_{1-6}$ alkylene groups and aryl or heteroaryl have the meanings defined above and the aryl or heteroaryl group is bound to the higher-order general structure by a $C_{1-3}$ alkylene group or $C_{1-6}$ alkylene group. Benzyl, phenethyl and phenylpropyl are cited by way of example.

Within the meaning of the present invention, the expression "$C_{3-8}$ cycloalkyl bound via a $C_{1-3}$ alkylene group or $C_{1-6}$ alkylene group" means that the $C_{1-3}$ alkylene group, $C_{1-6}$ alkylene group and $C_{3-8}$ cycloalkyl have the meanings defined above and $C_{3-8}$ cycloalkyl is bound via a $C_{1-3}$ alkylene group or $C_{1-6}$ alkylene group to the higher-order general structure.

In connection with "alkyl", "alkylene" and "cycloalkyl", the term "substituted" within the meaning of this invention is understood to mean the replacement of a hydrogen with F, Cl, Br, I, $CF_3$, $OCF_3$, CN, $NH_2$, NH—$C_{1-6}$ alkyl, NH—$C_{1-6}$ alkylene-OH, $C_{1-6}$ alkyl, N($C_{1-6}$ alkyl)$_2$, N($C_{1-6}$ alkylene-OH)$_2$, $NO_2$, SH, S—$C_{1-6}$ alkyl, $C_{1-6}$ alkyl, S-benzyl, O—$C_{1-6}$ alkyl, OH, O—$C_{1-6}$ alkylene-OH, =O, O-benzyl, C(=O)$C_{1-6}$ alkyl, $CO_2H$, $CO_2$—$C_{1-6}$ alkyl, phenyl, phenoxy, benzyl, naphthyl, furyl, thienyl and pyridinyl, wherein polysubstituted groups are understood to mean groups which are substituted multiple times, for example twice or three times, at different or the same atoms, for example substituted three times at the same C atom, as in the case of $CF_3$ or —$CH_2CF_3$, or at different sites, as in the case of CH(Cl)—CH=CH—OHCl$_2$. The polysubstitution can take place with identical or different substituents, as for example in the case of CH(OH)—CH=CH—CHCl$_2$. It should be understood in particular to be the replacement of one or more hydrogens with F, Cl, $NH_2$, OH, phenyl, O—$CF_3$ or O—$C_{1-6}$ alkyl, in particular methoxy.

In connection with "aryl" and "heteroaryl", the term "substituted" within the meaning of this invention is understood to mean the replacement of one or more hydrogen atoms of the respective ring system, including mono- or polysubstitution, for example the di-, tri-, tetra- or pentasubstitution, with F, Cl, Br, I, CN, $NH_2$, NH—$C_{1-6}$ alkyl, NH—$C_{1-6}$ alkylene-OH, N($C_{1-6}$ alkyl)$_2$, N($C_{1-6}$ alkylene-OH)$_2$, NH aryl$^1$, N(aryl$^1$)$_2$, N($C_{1-6}$ alkyl)aryl$^1$, pyrrolinyl, piperazinyl, morpholinyl, azetidinyl, piperidinyl, thiazolinyl, azepanyl, diazepanyl, ($C_{1-3}$ alkylene)-azetidinyl, ($C_{1-3}$ alkylene)-pyrrolinyl, ($C_{1-3}$ alkylene)-piperidinyl, ($C_{1-3}$ alkylene)-morpholinyl, ($C_{1-3}$ alkylene)-piperazinyl, ($C_{1-3}$ alkylene)-thiazolinyl, ($C_{1-3}$ alkylene)-azepanyl, ($C_{1-3}$ alkylene)-diazepanyl, $NO_2$, SH, S—$C_{1-6}$ alkyl, OH, O—$C_{1-6}$ alkyl, O—$C_{1-6}$ alkyl-OH, C(=O)$C_{1-6}$ alkyl, $NHSO_2C_{1-6}$ alkyl, $NHCOC_{1-6}$ alkyl, $CO_2H$, $CH_2SO_2$ phenyl, $CO_2$—$C_{1-6}$ alkyl, $OCF_3$, $CF_3$, —O—$CH_2$—O—, —O—$CH_2$—$CH_2$—O—, —O—C($CH_3$)$_2$—$CH_2$—, unsubstituted $C_{1-6}$ alkyl, pyrrolidinyl, imidazolyl, benzyloxy, phenoxy, phenyl, naphthyl, pyridinyl, —$C_{1-3}$ alkylene-aryl$^1$, benzyl, thienyl, furyl, wherein aryl$^1$ denotes phenyl, thiazolyl, thienyl or pyridinyl, at one or different atoms, wherein the aforementioned substituents—unless otherwise specified—can themselves be substituted with the cited substituents. The polysubstitution of aryl and heteroaryl can be performed with identical or different substituents. Preferred substituents for aryl and heteroaryl can be selected from the group consisting of —O—$C_{1-3}$ alkyl, unsubstituted $C_{1-6}$ alkyl, F, Cl, Br, I, CN, $CF_3$, $OCF_3$, OH, SH, —$CH_2$ azetidinyl, —$CH_2$ pyrrolidinyl, —$CH_2$ piperidinyl, —$CH_2$ piperazinyl, —$CH_2$ morpholinyl, phenyl, naphthyl, thiazolyl, thienyl and pyridinyl, in particular from the group consisting of F, Cl, CN, $CF_3$, $CH_3$; $OCH_3$, $OCF_3$ and —$CH_2$ azetidinyl.

In the chemical structural formulas which are used here to describe the compounds according to the invention, the symbol

is also used to describe one or more substitution models, wherein unlike the representation of a bond to a specific atom, this group is not bound to a specific atom within the chemical structural formula (by way of example $R^a$ here represents a substituent R having a number represented by the variable "a"). This can be explained by way of example by reference to the group

from the foregoing formula (III). The definition for $R^{27}$ indicates that $R^{27}$ can denote 0 to 4 substituents. Thus $R^{27}$ can be absent, or 1, 2, 3 or 4 of the hydrogen atoms attached to carbon atoms of the substructure represented by the formula (III) can be replaced by one of the substituents provided in the definition of $R^{27}$, wherein each of the substituents can be selected independently, in other words they can have different meanings, and hydrogen atoms attached to carbon atoms can be replaced at one or more carbon atoms. As explained in the definition of $R^{27}$, two of the substituents $R^{27}$ can also together represent a $C_{1-3}$ alkylene bridge or an anellated aryl or heteroaryl (also referred to as a fused aryl or heteroaryl or anellated/fused aryl or heteroaryl group), such that $R^{27}$ in formula (III) also has the meanings shown below by way of example, in which $R^{27}$ denotes two substituents at different carbon atoms and in the second example the variable u denotes 1:

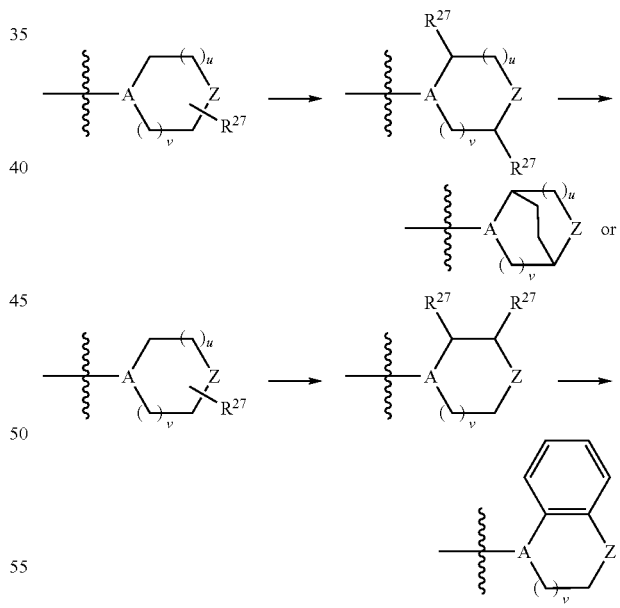

In the context of the present invention, the symbol

used in formulas represents a linking of a respective group to the higher-order general structure.

Persons skilled in the art understand that identical substituents used for the definition of different substituents are mutually independent.

Within the meaning of this invention the term "physiologically compatible salt" is understood to mean salts of the compounds according to the invention with inorganic or organic acids which are physiologically compatible, particularly when used in humans and/or mammals. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1λ$^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, hippuric acid, phosphoric acid and/or aspartic acid. The salts of hydrochloric acid (hydrochlorides) and of citric acid (citrates) are particularly preferred.

Within the scope of this invention the term "isolated" used with reference to a stereoisomer (i.e., an enantiomer or diasteromer) means that the stereoisomer is substantially completely separated from the opposite stereoisomer, but not necessarily from other substances.

In preferred embodiments of the compounds according to the invention according to the formula (I) T, $R^{200}$ and $R^{210}$ are selected such that the formula I assumes one of the formulas (Ia), (Ib) or (Ic)

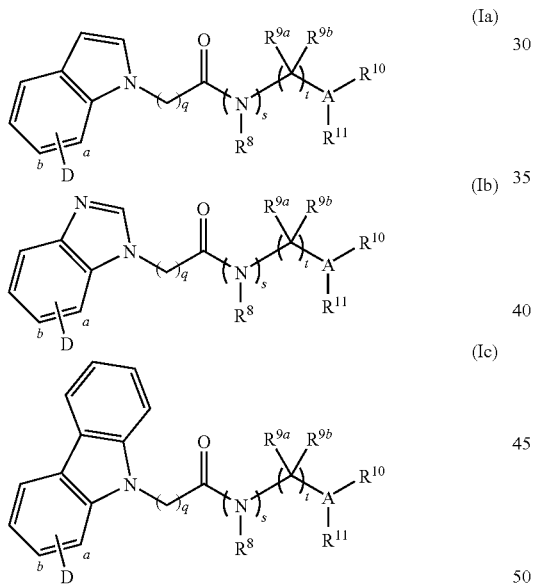

wherein the various groups, variables and indices have the meanings described herein in connection with the compounds according to the invention and the preferred embodiments thereof. The formula (I) can in particular assume the formula (Ia).

In likewise preferred embodiments of the compounds according to the invention x denotes 0, such that the radical D1 assumes the following form D1':

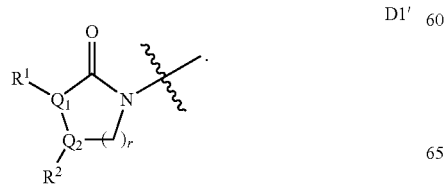

In further preferred embodiments of the compounds according to the invention D denotes a group selected from the group consisting of

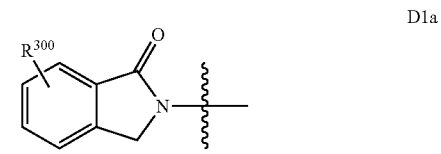

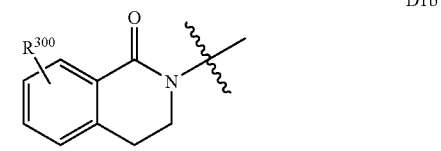

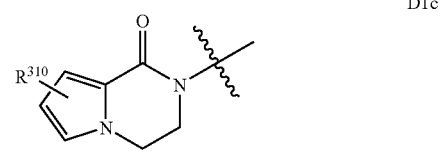

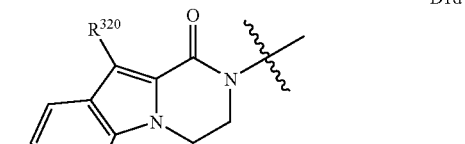

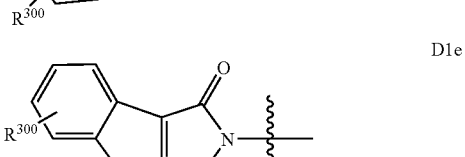

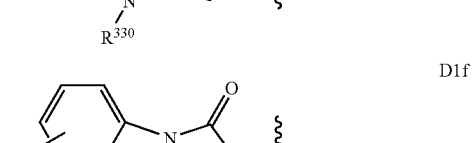

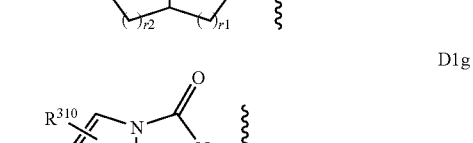

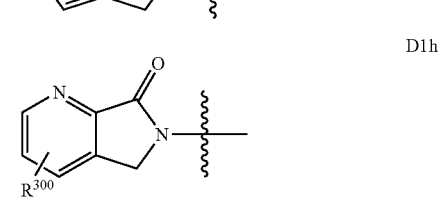

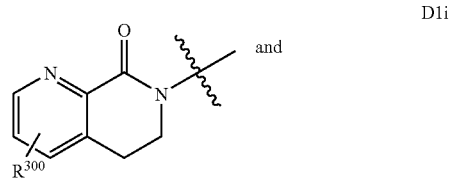

-continued

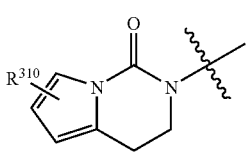
D1j wherein
R$^{300}$ denotes 0, 1, 2, 3 or 4 substituents each independently selected from the group consisting of F, Cl, Br, I, —CF$_3$, —O—CF$_3$, C$_{1-4}$ alkyl and O—C$_{1-4}$ alkyl;
R$^{310}$ denotes 0, 1, 2 or 3 substituents each independently selected from the group consisting of F, Cl, Br, I, —CF$_3$, —O—CF$_3$, C$_{1-4}$ alkyl and O—C$_{1-4}$ alkyl;
R$^{320}$ denotes a substituent selected from the group consisting of H, F, Cl, Br, I, —CF$_3$, —O—CF$_3$ and C$_{1-4}$ alkyl;
R$^{330}$ denotes a substituent selected from the group consisting of H, C$_{1-4}$ alkyl, aryl, —CH$_2$ aryl and heteroaryl;
r1 denotes 1 or 2, and
r2 denotes 1 or 2.

In likewise preferred embodiments of the compounds according to the invention D denotes a group selected from the group consisting of

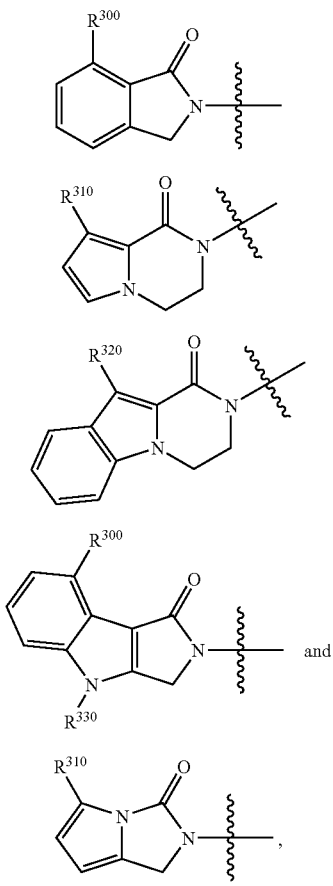

wherein
R$^{300}$ denotes a substituent selected from the group consisting of F, Cl, Br, I, —CF$_3$, —O—CF$_3$, C$_{1-4}$ alkyl and O—C$_{1-4}$ alkyl;
R$^{310}$ denotes a substituent selected from the group consisting of F, Cl, Br, I, —CF$_3$, —O—CF$_3$, C$_{1-4}$ alkyl and O—C$_{1-4}$ alkyl;

R$^{320}$ denotes a substituent selected from the group consisting of H, F, Cl, Br, I, —CF$_3$, —O—CF$_3$ and C$_{1-4}$ alkyl, and
R$^{330}$ denotes a substituent selected from the group consisting of H, C$_{1-4}$ alkyl, aryl, —CH$_2$ aryl and heteroaryl.

In further preferred embodiments of the compounds according to the invention D denotes a group selected from the group consisting of

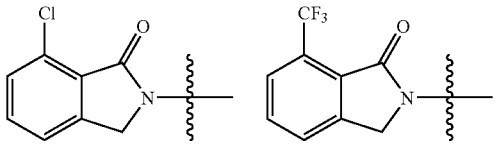

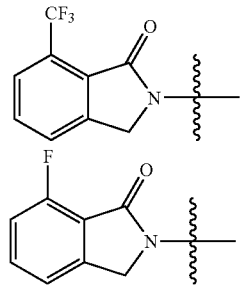

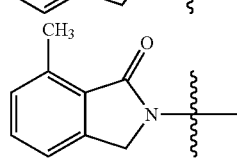

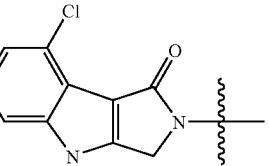

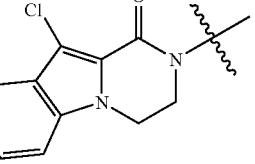

and 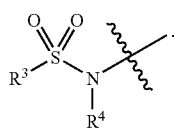

In likewise preferred embodiments of the compounds according to the invention y denotes 0, such that the group D2 assumes the following form D2':

D2'

In the compounds according to the invention R$^3$ preferably denotes phenyl, naphthyl, chromanyl, indolyl, benzofuranyl, benzothiophenyl (benzothienyl); benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl) or a phenyl or naphthyl bound via a C$_{1-3}$ alkylene group, particularly preferably for phenyl, naphthyl, chromanyl, benzothiophenyl (benzothienyl), benzooxadiazolyl, thienyl, pyridinyl, imidazothiazolyl, dibenzofuranyl or a phenyl bound via a C$_{1-3}$ alkylene group, most particularly preferably phenyl, naphthyl, chromanyl, benzothiophenyl (benzothienyl) or a phenyl bound via a C$_{1\ or\ 2}$ alkylene group, wherein the aforementioned aryl or heteroaryl groups may each be unsubstituted or mono- or polysubstituted, identically or differently, wherein the substituents are each independently selected in particular from the group consisting of —O—C$_{1-3}$ alkyl, C$_{1-6}$ alkyl, F, Cl, Br, I, CF$_3$, OCF$_3$, OH, SH, phenyl, phenoxy, naphthyl, furyl, thienyl and pyridinyl and wherein the aforementioned alkylene groups are each unsubstituted or mono- or polysubstituted, identically or differently, wherein the substituents are each independently selected in particular from the group consisting of —O—$C_{1-3}$ alkyl, F, Cl, Br, I, $CF_3$, $OCF_3$, OH, SH, phenyl, phenoxy, naphthyl, furyl, thienyl and pyridinyl.

$R^3$ can in particular denote phenyl or naphthyl, wherein the phenyl or naphthyl may be unsubstituted or mono- or polysubstituted, for example di-, tri-, tetra- or pentasubstituted, with identical or different substituents selected from the group consisting of methyl, methoxy, $CF_3$, $OCF_3$, F and Cl.

In likewise preferred embodiments of the compounds according to the invention $R^3$ is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 1,3-dichloro-5-trifluoromethylphenyl, 2-chloro-6-(trifluoromethyl)phenyl, 2,6-dichloro-4-methoxyphenyl, 2,6-dichloro-4-trifluoromethyl, 2-methylnaphthyl, 2-chloronaphthyl, 2-fluoronaphthyl, 2-chloro-4-(trifluoromethoxy)phenyl, 4-chloro-2,5-dimethylphenyl, 2-chloro-6-methylphenyl, 2,3-dichlorophenyl, 3,4-dichlorophenyl, 2,4-dichlorophenyl, 2,4,5-trichlorophenyl, 2,4,6-trichlorophenyl, 2-(trifluoromethyl)phenyl, 3-(trifluoromethyl)phenyl, 4-(trifluoromethyl)phenyl, 1-naphthyl and 2-naphthyl.

In particular $R^3$ can denote 4-methoxy-2,6-dimethylphenyl, 4-chloro-2,5-dimethylphenyl, 1-naphthyl or 2-(trifluoromethyl)phenyl.

In the compounds according to the invention $R^4$ can in particular denote a substituent selected from the group consisting of H, methyl, ethyl, n-propyl, isopropyl, n-butyl, isobutyl, sec-butyl, tert-butyl and cyclopropyl. $R^4$ particularly preferably denotes H.

In likewise preferred embodiments of the compounds according to the invention q denotes 1 or 2.

Likewise preferred embodiments of the compounds according to the invention are those in which $R^8$ denotes H; $C_{1-6}$ alkyl, in particular methyl, ethyl, n-propyl, isopropyl, n-butyl, isobutyl, sec-butyl or tert-butyl; cyclopropyl, cyclobutyl, cyclopentyl, cyclohexyl, —$CH_2CF_3$, phenyl, benzyl, phenylethyl, phenylpropyl, or cyclopropyl, cyclobutyl, cyclopentyl, cyclohexyl bound via a $C_{1-3}$ alkylene group, each unsubstituted or mono- or polysubstituted with identical or different substituents. In particular $R^8$ can denote H, methyl, ethyl, isopropyl or cyclopropyl.

Likewise preferred embodiments of the compounds according to the invention are those in which $R^{9a}$ and $R^{9b}$ each each independently denote H; F; methyl; ethyl, isopropyl, $CF_3$, methoxy; cyclopropyl; phenyl; benzyl, phenylethyl, $C_{1-3}$ alkylene-cyclopropyl, $C_{1-3}$ alkylene-cyclobutyl, $C_{1-3}$ alkylene-cyclopentyl, $C_{1-3}$ alkylene-cyclohexyl or $C_{1-3}$ alkylene-$CF_3$, each unsubstituted or mono- or polysubstituted with identical or different substituents. In particular $R^{9a}$ and $R^{9b}$ each denote H.

Likewise preferred embodiments of the compounds according to the invention are those in which the foregoing formula (II) assumes the following substructure (IIa):

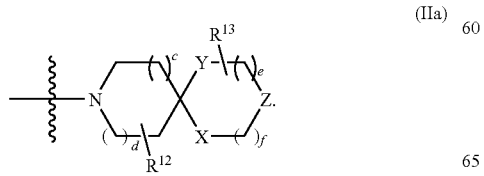

(IIa)

Likewise preferred embodiments of the compounds according to the invention are those in which the foregoing formula (III) assumes one of the following substructures (IIIa) or (IIIb):

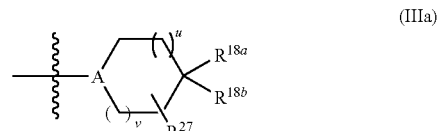

(IIIa)

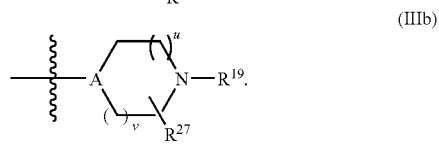

(IIIb)

Likewise preferred embodiments of the compounds according to the invention are those in which the substructure according to the formula (IIa) shown above assumes the following substructure (IIb):

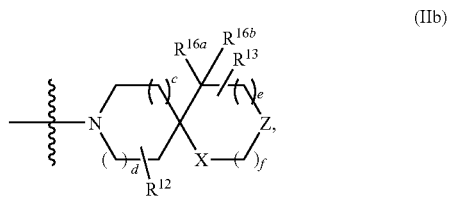

(IIb)

wherein in certain embodiments of these compounds according to the invention $R^8$ can denote H or $C_{1-6}$ alkyl, in each case unsubstituted or mono- or polysubstituted with identical or different substituents, and $R^{9a}$ and $R^{9b}$ each denote H.

Likewise preferred embodiments of the compounds according to the invention are those in which the substructures according to formulas (IIIa) and (IIIb) shown above assume one of the following substructures (IIIc), (IIId), (IIIe) or (IIIf):

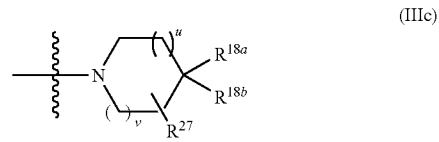

(IIIc)

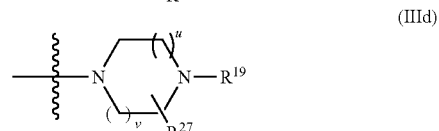

(IIId)

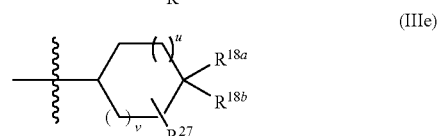

(IIIe)

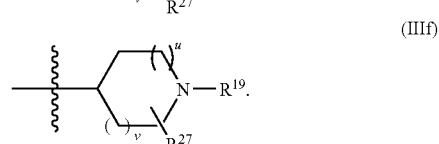

(IIIf)

In certain embodiments of these compounds according to the invention s and t each denote 0.

Likewise preferred embodiments of the compounds according to the invention are those in which
(a1) the substructure having formula (IIa) assumes the substructure (IIIb) and s and t each denote 0; or
(a2) the substructures having formulas (IIIa) and (IIIb) assume one of the substructures (IIIc) or (IIId) and s and t each denote 0; or
(a3) the substructures having formulas (IIIa) and (IIIb) assume one of the substructures (IIIc) or (IIId) and two of the substituents $R^{27}$ together form a $C_{1-3}$ alkylene bridge such that the cyclic compound represented in substructure (IIIc) or (IIId) assumes a bicyclically bridged form, and s and t each denote 0; or
(a4) the substructures having formulas (IIIa) and (IIIb) assume one of the substructures (IIIc), (IIId), (IIIe) or (IIIf), s denotes 1 and t denotes 0, 1, 2 or 3 and $R^8$ denotes H, $C_{1-6}$ alkyl or $C_{3-6}$ cycloalkyl, in each case unsubstituted or mono- or polysubstituted with identical or different substituents, and $R^{9a}$ and $R^{9b}$ each independently denote H, $C_{1-6}$ alkyl or $C_{3-6}$ cycloalkyl.

Likewise preferred embodiments of the compounds according to the invention are those in which s and t each denote 0 and the formula (II) assumes the following substructure (IIc)

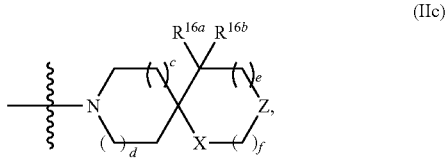

(IIc)

wherein
c, d, e and f each independently denote 0, 1 or 2;
X denotes $CR^{14a}R^{14b}$, $NR^{15}$ or O,
Z denotes $CR^{18a}R^{18b}$ or $NR^{19}$, or
if X denotes O and f denotes 0, then Z denotes =(N(CR$^{126}$))—, wherein the N atom is singly bonded to the O atom,
$R^{126}$ denotes H, $C_{1-4}$ alkyl or an unsubstituted or mono- or polysubstituted phenyl, pyridyl, imidazolyl, triazolyl, pyrimidyl, thiazolyl or thienyl optionally bound via a $C_{1-3}$ alkylene group, wherein the substituents are preferably each independently selected from the group consisting of F, Cl, $CF_3$, $C_{1-4}$ alkyl, $OCF_3$, OH and O—$C_{1-4}$ alkyl,
$R^{14a}$, $R^{14b}$, $R^{16a}$ and $R^{16b}$ each independently denote H or an unsubstituted or mono- or polysubstituted phenyl, pyridyl, imidazolyl, triazolyl, pyrimidyl, thiazolyl or thienyl optionally bound via a $C_{1-3}$ alkylene group, wherein the substituents are preferably each independently selected from the group consisting of F, Cl, $CF_3$, $C_{1-4}$ alkyl, $OCF_3$, OH and O—$C_{1-4}$ alkyl, and/or $R^{16a}$ and $R^{16b}$ together denote =O;
$R^{15}$ denotes H, $C_{1-4}$ alkyl or an unsubstituted or mono- or polysubstituted phenyl, pyridyl, imidazolyl, triazolyl, pyrimidyl, thiazolyl or thienyl optionally bound via a $C_{1-3}$ alkylene group, wherein the substituents are preferably selected from the group consisting of F, Cl, $CF_3$, $C_{1-4}$ alkyl, $OCF_3$, OH and O—$C_{1-4}$ alkyl,
$R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or an unsubstituted or mono- or polysubstituted phenyl, pyridyl, imidazolyl, triazolyl, pyrimidyl, thiazolyl or thienyl bound by an —(O)$_{0-1}$—$C_{1-6}$ alkylene group; wherein the substituents are preferably each independently selected from the group consisting of F, Cl, $CF_3$, $C_{1-4}$ alkyl, $OCF_3$, OH and O—$C_{1-4}$ alkyl, or $R^{18a}$ denotes the radical according to the formula (IVa)

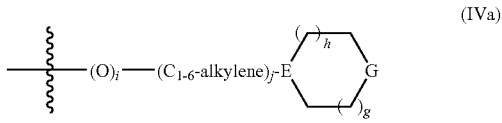

(IVa)

wherein
i denotes 0 or 1;
j denotes 0 or 1;
h and g, each independently, denote 0 or 1,
E denotes N or CH; with the proviso that if i denotes 1 and j denotes 0 then E denotes CH,
G denotes $CR^{37a}R^{37b}$ or $NR^{38}$;
wherein
$R^{37a}$ and $R^{37b}$ each independently denote H; F or $C_{1-4}$ alkyl, each unsubstituted or mono- or polysubstituted with identical or different substituents,
$R^{38}$ denotes H; $C_{1-6}$ alkyl, $C_{3-6}$ cycloalkyl or pyridyl;
$R^{18b}$ denotes H, OH, $C_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a $C_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by $C_{1-6}$ alkylene-NH(C=O), each unsubstituted or mono- or polysubstituted with identical or different substituents, wherein the substituents are preferably each independently selected from the group consisting of F, Cl, $CF_3$, $C_{1-4}$ alkyl, $OCF_3$, OH and O—$C_{1-4}$ alkyl,
$R^{19}$ denotes H, $C_{1-6}$ alkyl, $C_{3-8}$ cycloalkyl, —(C=O)—$C_{1-6}$ alkyl; $C_{1-6}$ alkylene-NH($C_{1-6}$ alkyl), $C_{1-6}$ alkylene-N($C_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a $C_{1-6}$ alkylene group; each unsubstituted or mono- or polysubstituted with identical or different substituents, wherein the substituents are preferably each independently selected from the group consisting of F, Cl, $CF_3$, $C_{1-4}$ alkyl, $OCF_3$, OH and O—$C_{1-4}$ alkyl, or a group according to the formula (VIIIa)

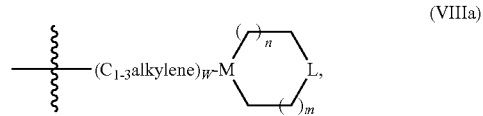

(VIIIa)

wherein
w denotes 0 or 1;
n denotes 0 or 1;
m denotes 0 or 1;
M denotes CH or N, with the proviso that if w denotes 0 then M denotes CH;
L denotes $CR^{44a}R^{44b}$ or $NR^{45}$;

wherein

R$^{44a}$ and R$^{44b}$ each independently denote H; F or C$_{1-6}$ alkyl, each unsubstituted or mono- or polysubstituted with identical or different substituents; and R$^{45}$ denotes H, C$_{1-6}$ alkyl, C$_{3-6}$ cycloalkyl or pyridyl.

Other preferred embodiments of the compounds according to the invention are those in which s and t each denote 0 and the formula (III) assumes one of the substructures (IIIc') or (IIId')

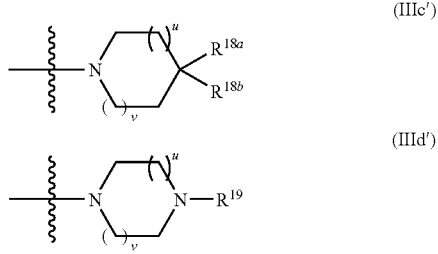

wherein u and v each independently denote 0, 1 or 2,

R$^{18a}$ denotes H, C$_{1-4}$ alkyl, C$_{3-6}$ cycloalkyl, —NH(C$_{1-6}$ alkyl), —N(C$_{1-6}$ alkyl)$_2$, unsubstituted or mono- or polysubstituted phenyl, pyridyl, imidazolyl, triazolyl, pyrimidyl, thiazolyl or thienyl, or an unsubstituted or mono- or polysubstituted phenyl, pyridyl, imidazolyl, triazolyl, pyrimidyl, thiazolyl or thienyl bound by an —(O)$_{0-1}$—C$_{1-6}$ alkylene group; wherein the substituents are preferably each independently selected from the group consisting of F, Cl, CF$_3$, C$_{1-4}$ alkyl, OCF$_3$, OH and O—C$_{1-4}$ alkyl, or R$^{18a}$ denotes the radical according to the formula (IVa)

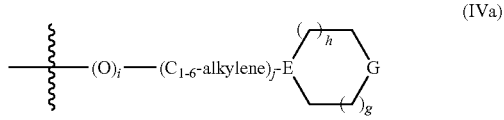

wherein
i denotes 0 or 1;
j denotes 0 or 1;
h and g, each independently, denote 0 or 1,
E denotes N or CH; with the proviso that if i denotes 1 and j denotes 0 then E denotes CH,
G denotes CR$^{37a}$R$^{37b}$ or NR$^{38}$;
wherein
R$^{37a}$ and R$^{37b}$ each independently denote H; F or C$_{1-4}$ alkyl, each unsubstituted or mono- or polysubstituted with identical or different substituents,
R$^{38}$ denotes H; C$_{1-6}$ alkyl, C$_{3-6}$ cycloalkyl or pyridyl; or R$^{18a}$ denotes the following radical:

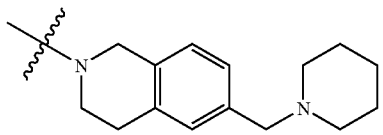 [SMILES: *N1CCc2cc(CN3CCCCC3)ccc2C1]

R$^{18b}$ denotes H, OH, C$_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a C$_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by C$_{1-6}$ alkylene-NH(C=O), each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl, R$^{19}$ denotes H, C$_{1-6}$ alkyl, C$_{3-8}$ cycloalkyl, —(C=O)—C$_{1-6}$ alkyl; C$_{1-6}$ alkylene-NH(C$_{1-6}$ alkyl), C$_{1-6}$ alkylene-N(C$_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a C$_{1-6}$ alkylene group; each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl, or a group according to the formula (VIIIa)

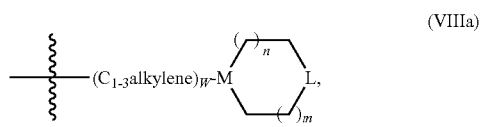

wherein
w denotes 0 or 1;
n denotes 0 or 1;
m denotes 0 or 1;
M denotes CH or N, with the proviso that if w denotes 0, then M denotes CH;
L denotes CR$^{44a}$R$^{44b}$ or NR$^{45}$; wherein
R$^{44a}$ and R$^{44b}$ each independently denote H; F or C$_{1-6}$ alkyl, each unsubstituted or mono- or polysubstituted with identical or different substituents; and
R$^{45}$ denotes H, C$_{1-6}$ alkyl, C$_{3-8}$ cycloalkyl or pyridyl.

Preferred embodiments of the compounds according to the invention are also those in which s and t each denote 0, and the formula (III) assumes one of the following substructures (A) to (H)

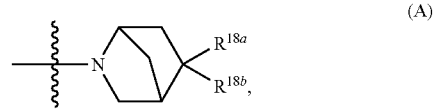

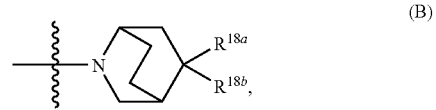

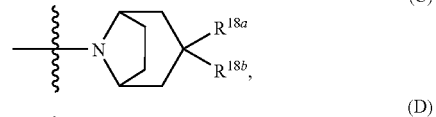

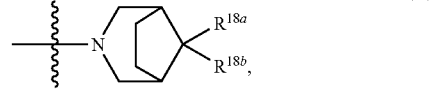

-continued

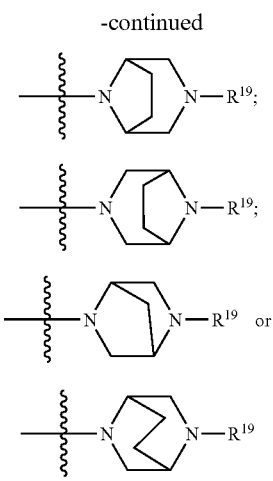

and wherein
$R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or an unsubstituted or mono- or polysubstituted phenyl, pyridyl, imidazolyl, triazolyl, pyrimidyl, thiazolyl or thienyl bound by an —(O)$_{0-1}$—$C_{1-6}$ alkylene group; wherein the substituents are preferably each each independently selected from the group consisting of F, Cl, CF$_3$, $C_{1-4}$ alkyl, OCF$_3$, OH and O—$C_{1-4}$ alkyl, or
$R^{18a}$ denotes a group according to the formula (IVa)

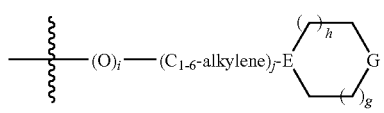 (IVa)

wherein
I denotes 0 or 1;
J denotes 0 or 1;
h and g, each independently, denote 0 or 1,
E denotes N or CH; with the proviso that if i denotes 1 and j denotes 0, then E denotes CH;
G denotes CR$^{37a}$R$^{37b}$ or NR$^{38}$; wherein
  $R^{37a}$ and $R^{37b}$ each independently denote H; F or $C_{1-4}$ alkyl, each unsubstituted or mono- or polysubstituted with identical or different substituents,
  $R^{38}$ denotes H; $C_{1-6}$ alkyl, $C_{3-6}$ cycloalkyl or pyridyl;
$R^{18b}$ denotes H, OH, $C_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a $C_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by $C_{1-6}$ alkylene-NH(C=O), each unsubstituted or mono- or polysubstituted with identical or different substituents, wherein the substituents are preferably each independently selected from the group consisting of F, Cl, CF$_3$, $C_{1-4}$ alkyl, OCF$_3$, OH and O—$C_{1-4}$ alkyl;
$R^{19}$ denotes H, $C_{1-6}$ alkyl, $C_{3-8}$ cycloalkyl, —(C=O)—$C_{1-6}$ alkyl; $C_{1-6}$ alkylene-NH($C_{1-6}$ alkyl), $C_{1-6}$ alkylene-N($C_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a $C_{1-6}$ alkylene group; each unsubstituted or mono- or polysubstituted with identical or different substituents, wherein the substituents are preferably each independently selected from the group consisting of F, Cl, CF$_3$, $C_{1-4}$ alkyl, OCF$_3$, OH and O—$C_{1-4}$ alkyl, or a group according to the formula (VIIIa)

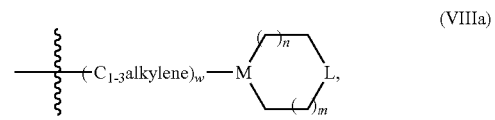 (VIIIa)

wherein
w denotes 0 or 1;
n denotes 0 or 1;
m denotes 0 or 1;
M denotes CH or N, with the proviso that if w denotes 0 then M denotes CH;
L denotes CR$^{44a}$R$^{44b}$ or NR$^{45}$; wherein
  $R^{44a}$ and $R^{44b}$ each independently denote H; F or $C_{1-6}$ alkyl, each unsubstituted or mono- or polysubstituted with identical or different substituents; and
  $R^{45}$ denotes H, $C_{1-6}$ alkyl, $C_{3-6}$ cycloalkyl or pyridyl.
Preferred embodiments of the compounds according to the invention are also those in which
s denotes 1,
t denotes 0, 1, 2 or 3,
$R^8$ denotes H, $C_{1-4}$ alkyl or $C_{3-6}$ cycloalkyl
$R^{9a}$ and $R^{9b}$ each independently denote H, $C_{1-4}$ alkyl or $C_{3-6}$ cycloalkyl, and preferably both denote H;
the formula (III) assumes one of the following substructures (IIIc'), (IIId'), (IIIe') or (IIIf')

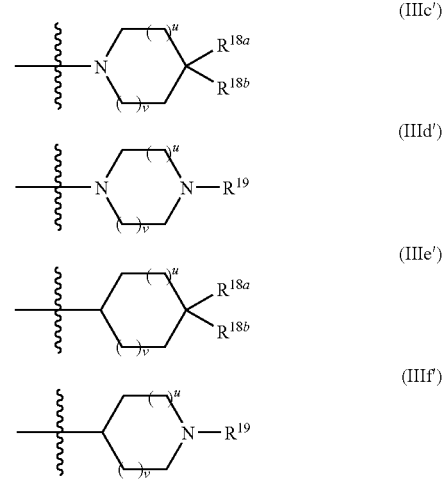

wherein
u and v each independently denote 0, 1 or 2,
$R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or unsubstituted or mono- or polysubstituted phenyl, pyridyl, imidazolyl, triazolyl, pyrimidyl, thiazolyl or thienyl bound by an —(O)$_{0-1}$—C$_{1-6}$ alkylene group; wherein the substituents are preferably each independently selected from the group consisting of F, Cl, CF$_3$, C$_{1-4}$ alkyl, OCF$_3$, OH and O—C$_{1-4}$ alkyl, or R$^{18a}$ denotes a group according to the formula (IVa)

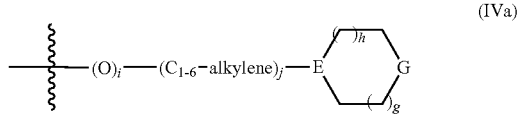

(IVa)

wherein
I denotes 0 or 1;
J denotes 0 or 1;
h and g each independently denote 0 or 1,
E denotes N or CH; with the proviso that if i denotes 1 and j denotes 0, then E denotes CH,
G denotes CR$^{37a}$R$^{37b}$ or NR$^{38}$; wherein
   R$^{37a}$ and R$^{37b}$ each independently denote H; F or C$_{1-4}$ alkyl, each unsubstituted or mono- or polysubstituted with identical or different substituents,
   R$^{38}$ denotes H; C$_{1-6}$ alkyl, C$_{3-6}$ cycloalkyl or pyridyl;
R$^{18b}$ denotes H, OH, C$_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a C$_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by C$_{1-6}$ alkylene-NH(C=O), each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl,
R$^{19}$ denotes H, C$_{1-6}$ alkyl, C$_{3-8}$ cycloalkyl, —(C=O)—C$_{1-6}$ alkyl; C$_{1-6}$ alkylene-NH(C$_{1-6}$ alkyl), C$_{1-6}$ alkylene-N(C$_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a C$_{1-6}$ alkylene group; each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl, or a group according to the formula (VIIIa)

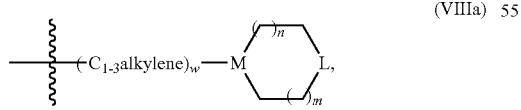

(VIIIa)

wherein
w denotes 0 or 1;
n denotes 0 or 1;
m denotes 0 or 1;
M denotes CH or N; with the proviso that if w denotes 0, then M denotes CH;
L denotes CR$^{44a}$R$^{44b}$ or NR$^{45}$; wherein R$^{44a}$ and R$^{44b}$ each independently denote H; F or C$_{1-6}$ alkyl, each unsubstituted or mono- or polysubstituted with identical or different substituents;

R$^{45}$ denotes H, C$_{1-6}$ alkyl, C$_{3-6}$ cycloalkyl or pyridyl.

Other preferred embodiments of the compounds according to the invention are compounds in which the substructure according to formula II shown above assumes one of the following substructures SP:

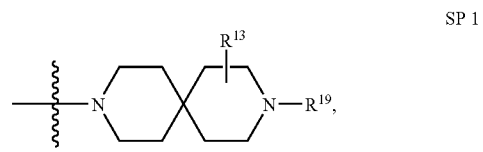

SP 1

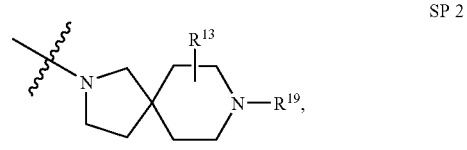

SP 2

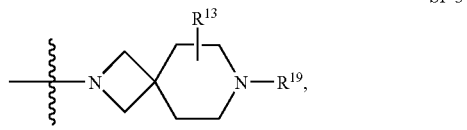

SP 3

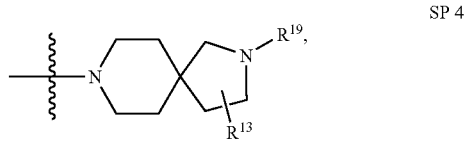

SP 4

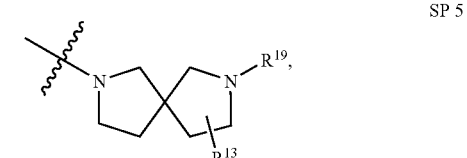

SP 5

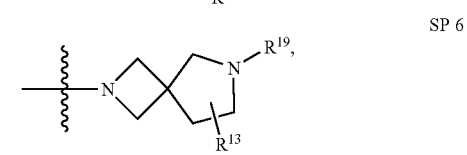

SP 6

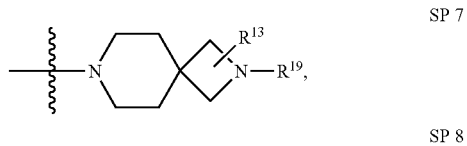

SP 7

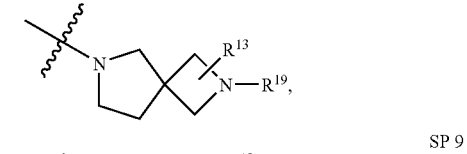

SP 8

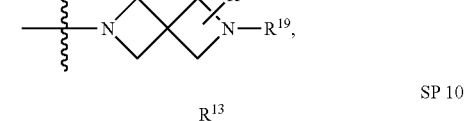

SP 9

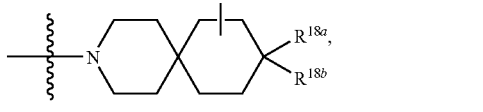

SP 10

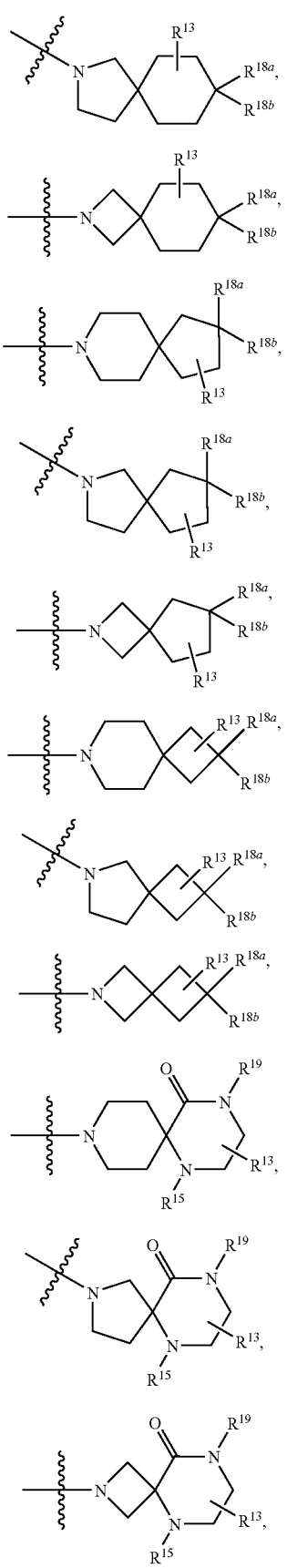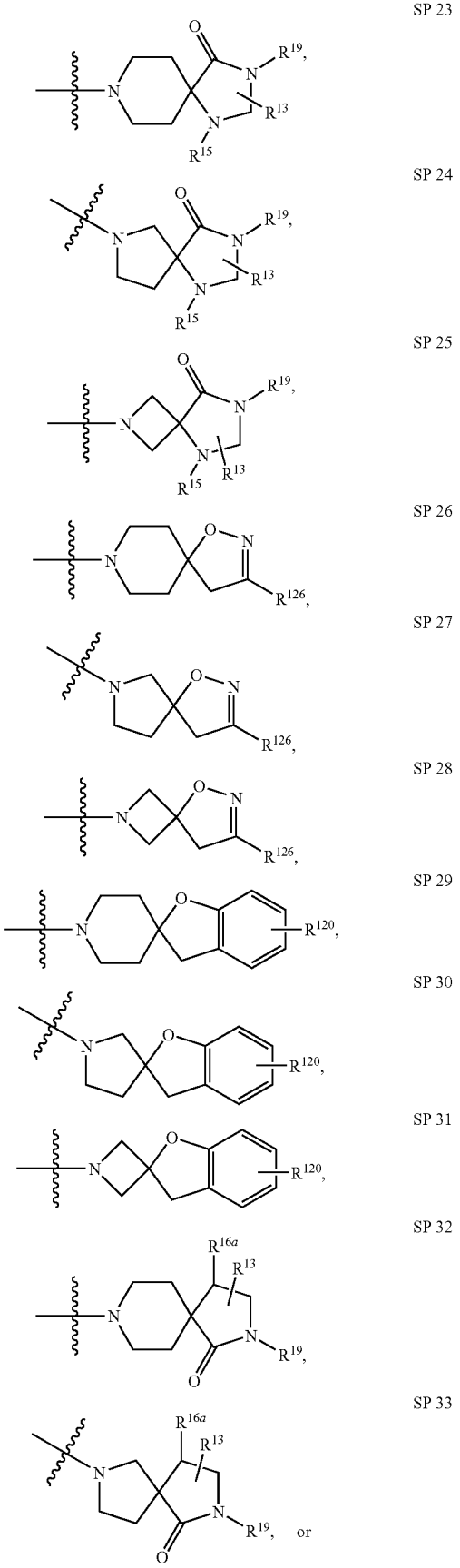

SP 34

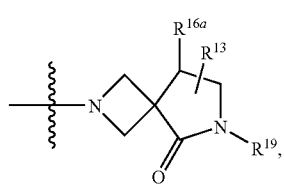

wherein
R$^{13}$ denotes 1 or 2 groups selected from H and phenyl, unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl; and/or
two substituents R$^{13}$ together form =O; and/or
two adjacent substituents R$^{13}$ together form an anellated aryl or heteroaryl, in particular a benzo group, each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl;
R$^{15}$ denotes H; C$_{1-6}$ alkyl; C$_{3-8}$ cycloalkyl or unsubstituted or identically or differently mono- or polysubstituted phenyl or pyridyl or a phenyl or pyridyl bound via a C$_{1-6}$ alkylene group, each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl;
R$^{16a}$ denotes H, C$_{1-6}$ alkyl, or phenyl or pyridyl, each unsubstituted or mono- or polysubstituted with identical or different substituents, wherein the substituents are preferably each independently selected from the group consisting of F, Cl, CF$_3$, C$_{1-4}$ alkyl, OCF$_3$, OH and O—C$_{1-4}$ alkyl;
R$^{18a}$ denotes H; C$_{1-6}$ alkyl; C$_{3-8}$ cycloalkyl, N(C$_{1-6}$ alkyl)$_2$; NH(C$_{1-6}$ alkyl), azetidinyl; pyrrolidinyl, piperidinyl, 4-(C$_{1-6}$ alkyl)-piperazinyl; phenyl or pyridyl, each unsubstituted or mono- or polysubstituted with identical or different substituents; or N(C$_{1-6}$ alkyl)$_2$; NH(C$_{1-6}$ alkyl), azetidinyl; pyrrolidinyl, piperidinyl, 4-(C$_{1-6}$ alkyl)-piperazinyl; phenyl, imidazolyl, triazolyl or pyridyl bound by an —(O)$_{0/1}$—C$_{1-6}$ alkylene group, each unsubstituted or mono- or polysubstituted with identical or different substituents, wherein the substituents of C$_{1-6}$ alkyl; C$_{3-8}$ cycloalkyl, azetidinyl; pyrrolidinyl, piperidinyl and 4-(C$_{1-6}$ alkyl)-piperazinyl are preferably each independently selected from the group consisting of F, Cl, CF$_3$, =O, C$_{1-4}$ alkyl, OCF$_3$, OH and O—C$_{1-4}$ alkyl, and wherein the substituents of phenyl, imidazolyl, triazolyl or pyridyl are preferably each independently selected from the group consisting of F, Cl, CF$_3$, C$_{1-4}$ alkyl, OCF$_3$, OH and O—C$_{1-4}$ alkyl;
R$^{18b}$ denotes H; OH; C$_{1-6}$ alkyl; phenyl or pyridyl, each unsubstituted or mono- or polysubstituted with identical or different substituents, or phenyl or pyridyl bound via a C$_{1-6}$ alkylene group, each unsubstituted or mono- or polysubstituted with identical or different substituents; wherein the substituents of phenyl and pyridyl are preferably each independently selected from the group consisting of F, Cl, CF$_3$, C$_{1-4}$ alkyl, OCF$_3$, OH and O—C$_{1-4}$ alkyl;
R$^{19}$ denotes H; C$_{1-6}$ alkyl; C$_{3-8}$ cycloalkyl, phenyl, pyridyl, thienyl, imidazolyl, thiazolyl or triazolyl, each unsubstituted or mono- or polysubstituted with identical or different substituents, or phenyl or pyridyl bound via a C$_{1-6}$ alkylene group or (C=O) group, each unsubstituted or mono- or polysubstituted with identical or different substituents, wherein the substituents of phenyl, pyridyl, thienyl, imidazolyl, thiazolyl and triazolyl are preferably each independently selected from the group consisting of F, Cl, CF$_3$, C$_{1-4}$ alkyl, OCF$_3$, OH and O—C$_{1-4}$ alkyl;
R$^{120}$ denotes H; F; Cl; OH; OCH$_3$, O—CF$_3$, C$_{1-6}$ alkyl; CF$_3$, phenyl, unsubstituted or mono- or polysubstituted, wherein the substituents of phenyl are preferably each independently selected from the group consisting of F, Cl, CF$_3$, C$_{1-4}$ alkyl, OCF$_3$, OH and O—C$_{1-4}$ alkyl;
R$^{126}$ denotes H; C$_{1-6}$ alkyl; C$_{3-6}$ cycloalkyl; phenyl or pyridyl; or C$_{3-6}$ cycloalkyl, phenyl or pyridyl bound via a C$_{1-3}$ alkylene group, each unsubstituted or mono- or polysubstituted with identical or different substituents, wherein the substituents of phenyl and pyridyl are preferably each independently selected from the group consisting of F, Cl, CF$_3$, C$_{1-4}$ alkyl, OCF$_3$, OH and O—C$_{1-4}$ alkyl.

Of the substructures SP, substructures SP1, SP2, SP5, SP10, SP23, SP32 and SP26 are preferably present in the compounds according to the invention.

Other preferred embodiments of the compounds according to the invention are compounds in which the following substructure (B) in the formula I shown above

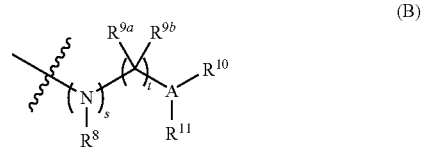

is selected from one of the following substructures B.1. to B.57.

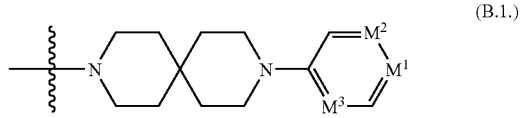
(B.1.)

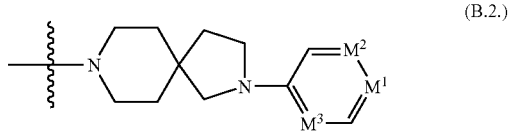
(B.2.)

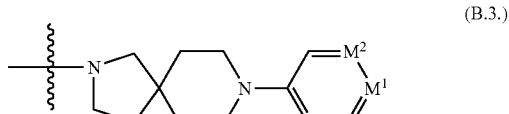
(B.3.)

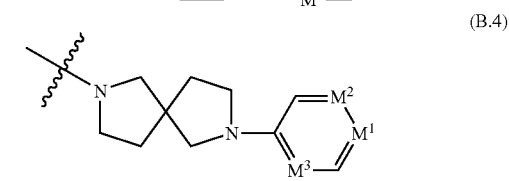
(B.4)

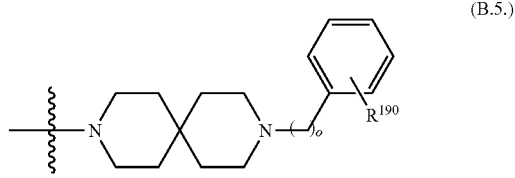
(B.5.)

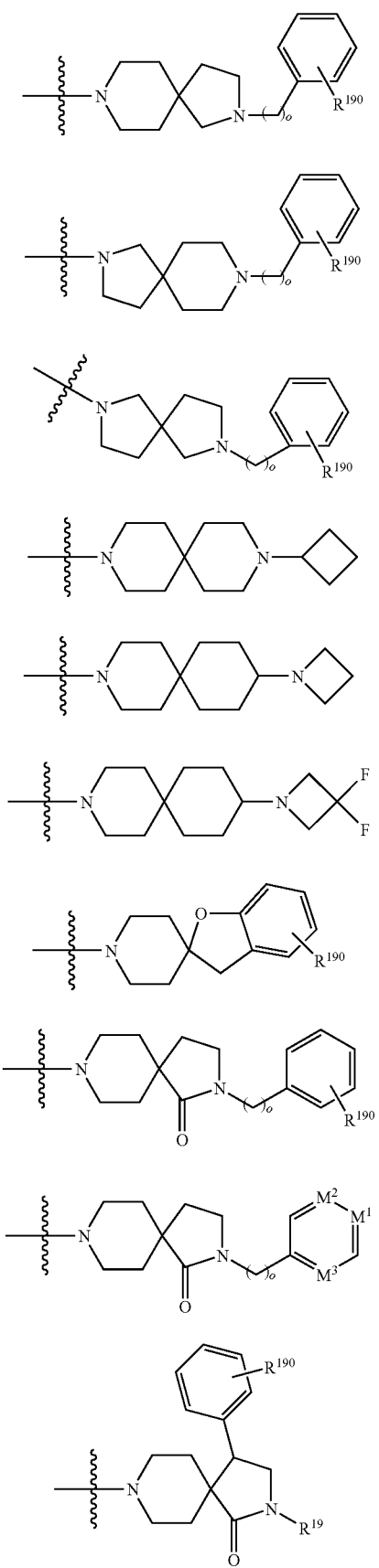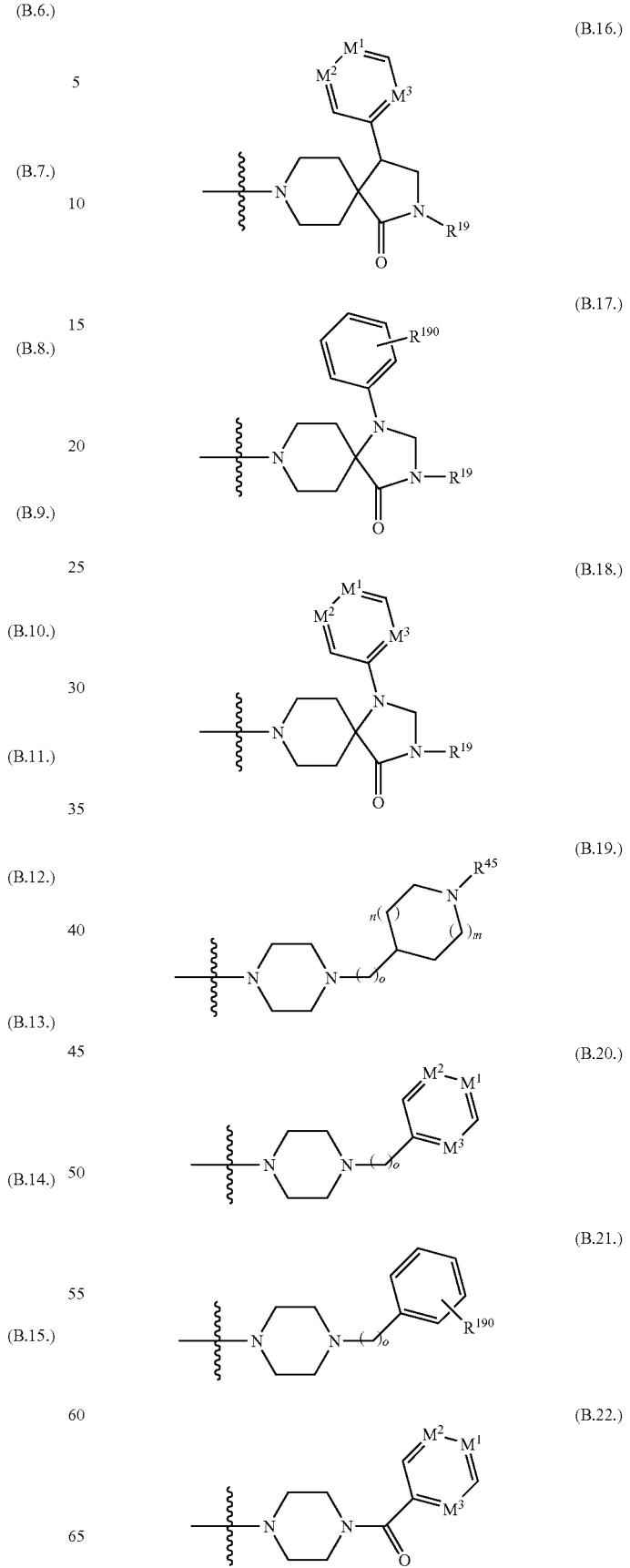

-continued
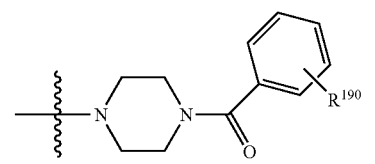 (B.23.)
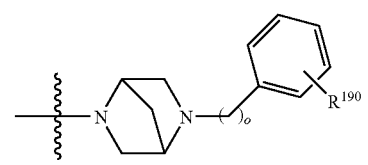 (B.24.)
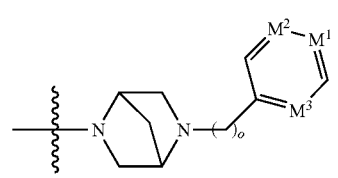 (B.25.)
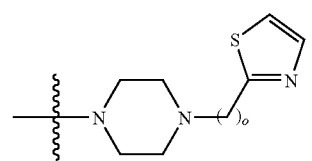 (B.26.)
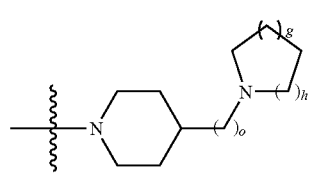 (B.27.)
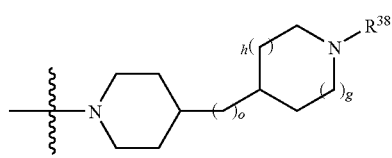 (B.28.)
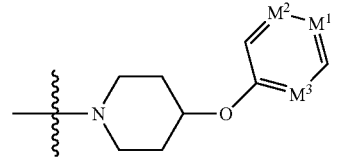 (B.29.)
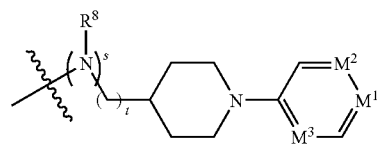 (B.30.)
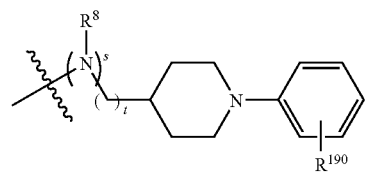 (B.31.)
-continued
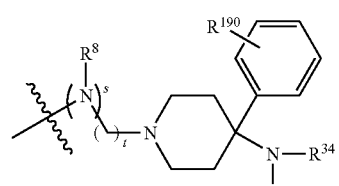 (B.32.)
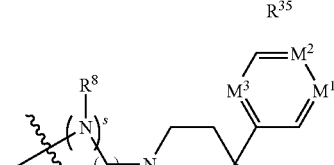 (B.33.)
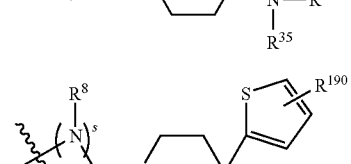 (B.34.)
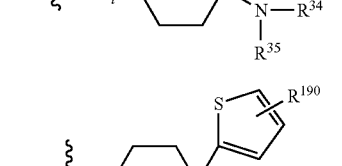 (B.35.)
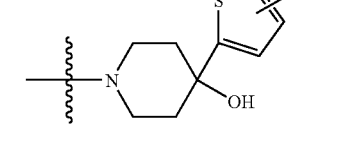 (B.36.)
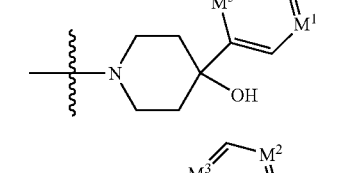 (B.37.)
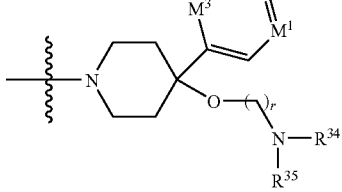 (B.38.)
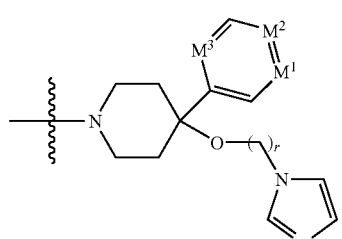 (B.39.)
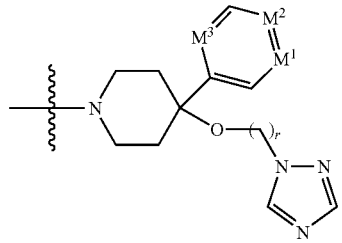

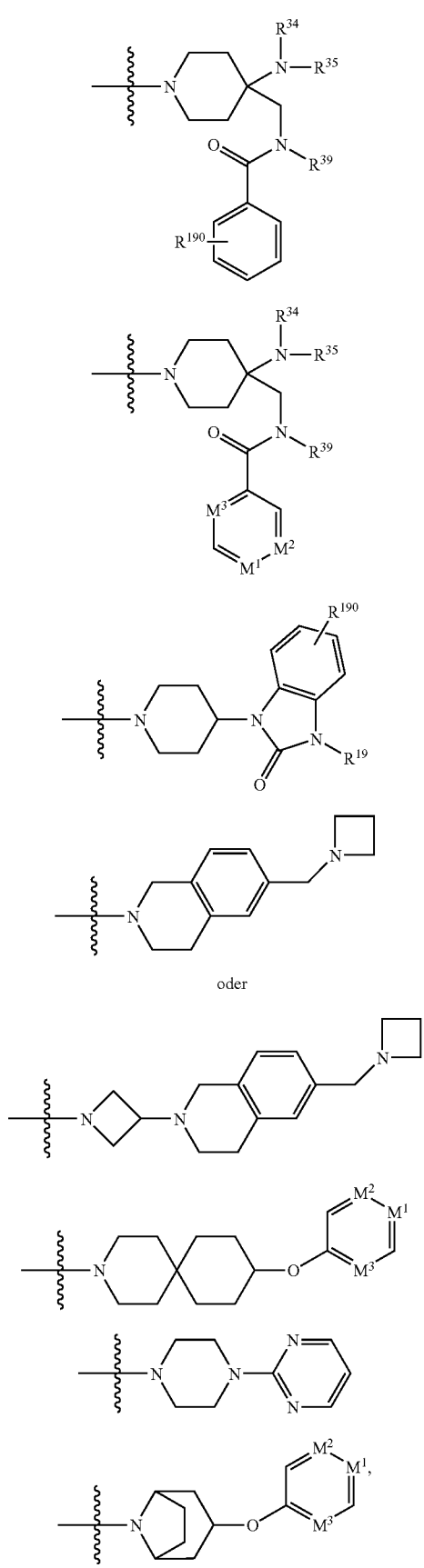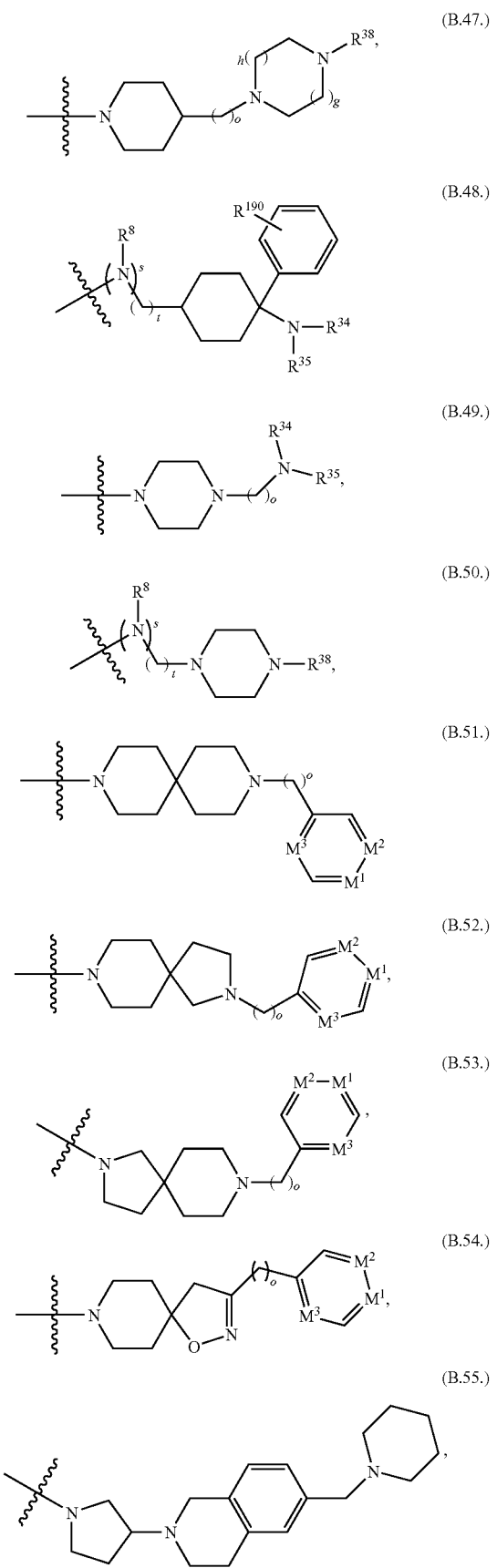

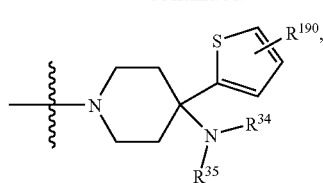
(B.56)

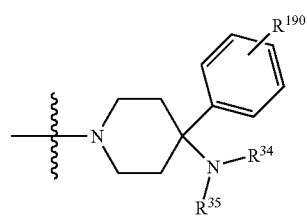
(B.57)

wherein
h=0 or 1;
g=0 or 1;
m=0 or 1;
n=0 or 1;
o=0, 1, 2 or 3;
r=1, 2 or 3, in particular 1 or 2;
s=0 or 1;
t=0, 1, 2 or 3, in particular 0, 1 or 2, with the proviso that if s denotes 0, then t likewise denotes 0;
$M^1$, $M^2$ and $M^3$ each denote N or CH, wherein one variable out of $M^1$, $M^2$ and $M^3$ denotes N, and the other two each denote CH;
$R^8$ denotes H; $C_{1-6}$ alkyl, in particular methyl, ethyl, n-propyl, isopropyl, n-butyl, sec-butyl, isobutyl or tert-butyl; $C_{3-6}$ cycloalkyl, in particular cyclopropyl, each unsubstituted or mono- or polysubstituted with identical or different substituents;
$R^{19}$ denotes H; $C_{1-6}$ alkyl, in particular methyl, ethyl, n-propyl, isopropyl, n-butyl, sec-butyl, isobutyl or tert-butyl; $C_{3-6}$ cycloalkyl, in particular cyclopropyl; each unsubstituted or mono- or polysubstituted with identical or different substituents;
$R^{34}$ and $R^{35}$ are preferably each independently methyl or ethyl or together with the N-atom linking them form an azetidinyl; pyrrolidinyl, piperidinyl or 4-($C_{1-6}$ alkyl)-piperazinyl group, each unsubstituted or mono- or polysubstituted with identical or different substituents;
$R^{38}$ denotes H, $C_{1-6}$ alkyl, $C_{3-8}$ cycloalkyl or pyridyl;
$R^{39}$ denotes H; $C_{1-6}$ alkyl, in particular methyl, ethyl, n-propyl, isopropyl, n-butyl, sec-butyl, isobutyl or tert-butyl; $C_{3-6}$ cycloalkyl, in particular cyclopropyl, each unsubstituted or mono- or polysubstituted with identical or different substituents;
$R^{45}$ denotes H, $C_{1-6}$ alkyl, $C_{3-8}$ cycloalkyl or pyridyl; and
$R^{190}$ represents 0 to 4 substituents, which are each independently selected from F, Cl, O—$CF_3$, $CF_3$ or CN.

Of the substructures B, substructures B.1., B.3., B.4., B.10., B.11., B.44., B.8., B.17., B.15., B.54., B.13., B.19., B.20., B.45., B.21., B.49., B.24., B.25., B.27., B.29., B.47., B.55., B.37., B.36., B.57., B.30., B.32., B.34., B.48. and B.50. are preferably present in the compounds according to the invention.

In substructures B.1., B.3., B.4., B.29., B.44. and B.54., preferably $M^1$ denotes N and $M^2$ and $M^3$ each denote CH. In substructure B.8. preferably o denotes 1 and $R^{190}$ denotes H. In substructure B.17. preferably $R^{19}$ denotes H. In substructure B.15. preferably $R^{19}$ denotes $CH_3$ and $R^{190}$ denotes F in the 4-position. In substructure B.13. preferably o denotes 0 or 1, and $R^{190}$ denotes H or F in the 4-position. In substructure B.30. preferably $R^8$ denotes H, s denotes 1, t denotes 1 or 2, $M^1$ denotes N and $M^2$ and $M^3$ each denote CH. In substructure B.32. preferably $R^8$ denotes $CH_3$, S denotes 1, t denotes 3, $R^{34}$ and $R^{35}$ each denote $CH_3$ and $R^{190}$ denotes H. In substructure B.34. preferably $R^8$ denotes $CH_3$, s denotes 1, t denotes 2 or 3, $R^{34}$ and $R^{35}$ each denote $CH_3$ and $R^{190}$ denotes H. In substructure B.48. preferably $R^8$ denotes H, s denotes 1, t denotes 0, $R^{34}$ and $R^{35}$ together with the nitrogen atom linking them form an azetidinyl group, and $R^{190}$ denotes H. In substructure B.50. preferably $R^8$ denotes H, s denotes 1, t denotes 3 and $R^{38}$ denotes ethyl. In substructure B.27. preferably o denotes 2, and g and h each denote 1. In substructure B.47. preferably o denotes 0, h and g each denote 1, and $R^{38}$ denotes $CH_3$. In substructure B.37. preferably $M^1$ denotes N, $M^2$ and $M^3$ each denote CH, r denotes 2, and $R^{34}$ and $R^{35}$ together with the nitrogen atom linking them form a pyrrolidinyl group. In substructures B.56. and B.57. preferably $R^{190}$ denotes H, and $R^{34}$ and $R^{35}$ each denote $CH_3$. In substructure B.19. preferably o denotes 0 or 1, n and m each denote 1, and $R^{45}$ denotes $CH_3$. In substructure B.21. preferably o denotes 0, and $R^{199}$ denotes F in the 4-position. In substructure B.49. preferably o denotes 3, and $R^{34}$ and $R^{35}$ each denote $CH_3$. In substructure B.20. preferably o denotes 0, $M^1$ denotes N, and $M^2$ and $M^3$ each denote CH. In substructure B.24. preferably o denotes 1, and $R^{190}$ denotes F in the 4-position. In substructure B.25. preferably o denotes 1, $M^1$ denotes N, and $M^2$ and $M^3$ each denote CH.

Further embodiments of the compounds according to the invention are those which are represented by the following formulas C1 to C14:

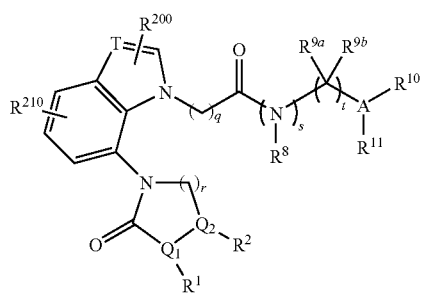
C1

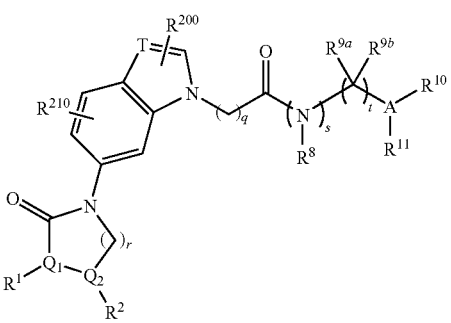
C2

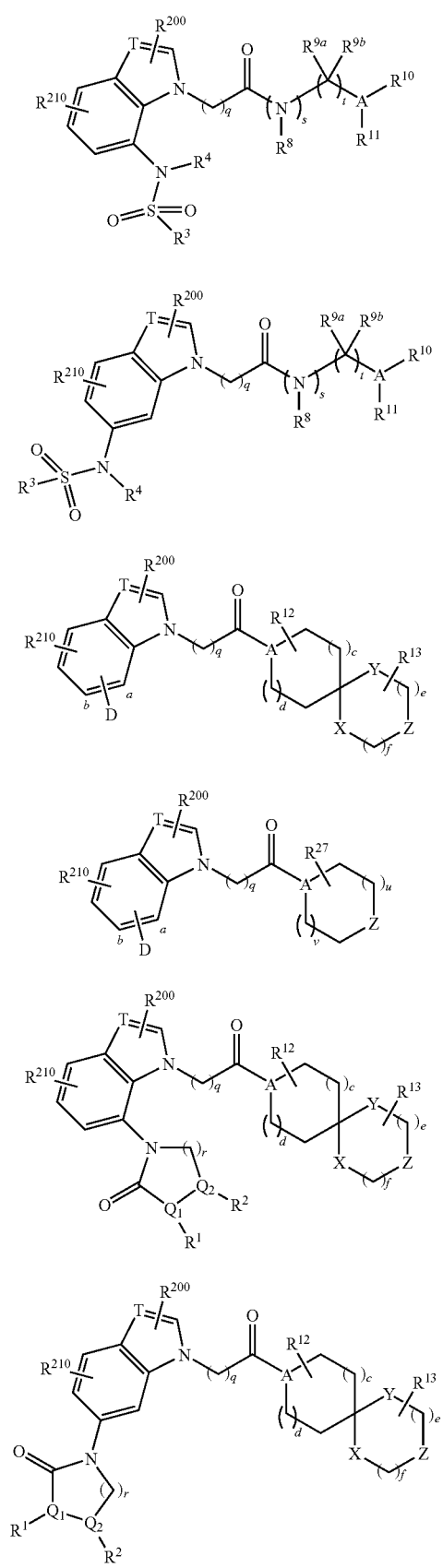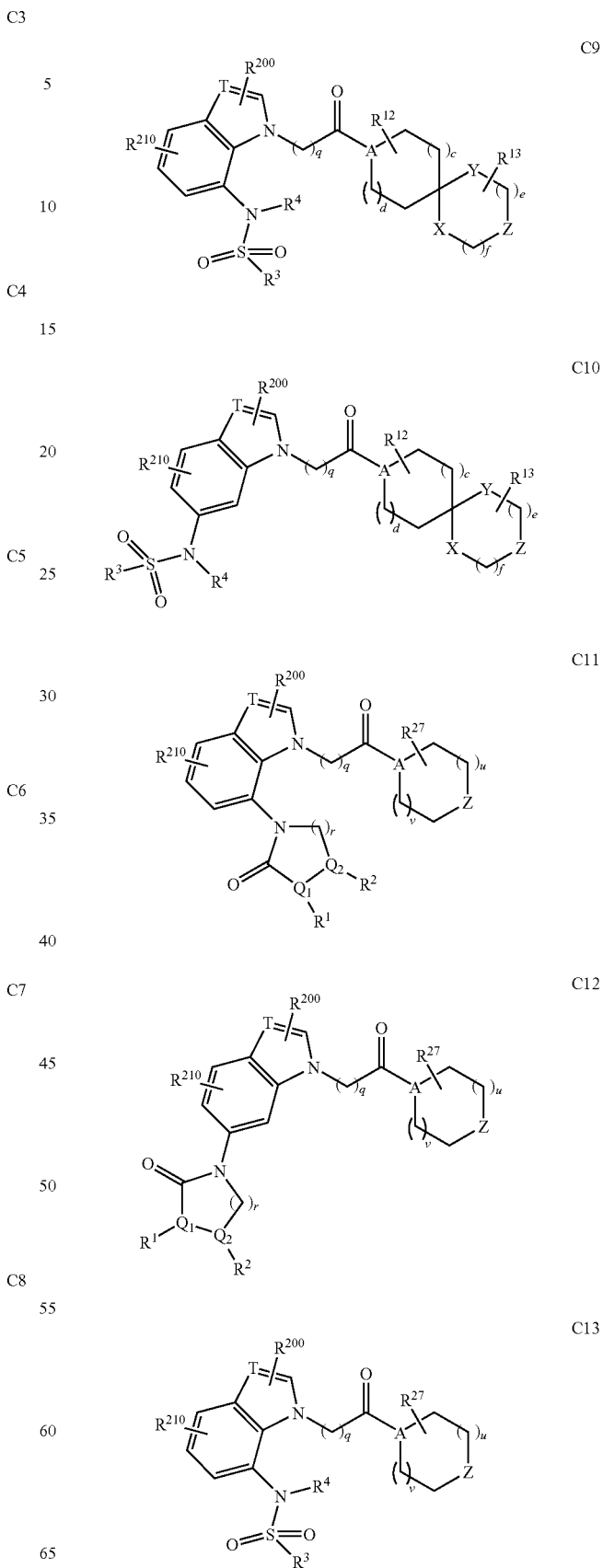

-continued

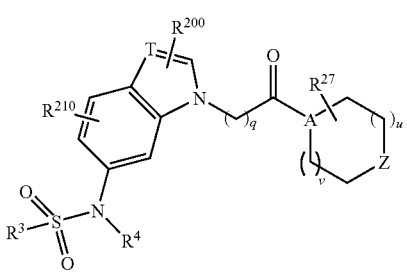

C14 wherein the various groups, variables and indices have the meanings described above in connection with the compounds according to the invention and the preferred embodiments thereof.

In a further preferred embodiment of the present invention the substituted compounds according to the invention can be selected from the group consisting of

| No. | Compound |
|---|---|
| G-01 | 4-Methoxy-2,6-dimethyl-N-[1-[2-oxo-2-[4-(2-pyrrolidin-1-yl-ethyl)-piperidin-1-yl]-ethyl]-1H-indol-6-yl]-benzenesulfonic acid amide |
| G-02 | 4-Methoxy-2,6-dimethyl-N-[1-[2-oxo-2-[4-(2-pyrrolidin-1-yl-ethyl)-piperidin-1-yl]-ethyl]-1H-indol-7-yl]-benzenesulfonic acid amide |
| G-03 | 4-Methoxy-2,6-dimethyl-N-[1-[2-oxo-2-(4-pyridin-4-yloxy-piperidin-1-yl)-ethyl]-1H-indol-7-yl]-benzenesulfonic acid amide |
| G-04 | 4-Methoxy-2,6-dimethyl-N-[1-[2-oxo-2-(1-oxo-4-phenyl-2,4,8-triazaspiro[4.5]decan-8-yl)-ethyl]-1H-indol-7-yl]-benzenesulfonic acid amide |
| G-05 | 4-Methoxy-2,6-dimethyl-N-[1-[2-oxo-2-(9-pyridin-4-yl-3,9-diazaspiro[5.5]undecan-3-yl)-ethyl]-1H-indol-7-yl]-benzenesulfonic acid amide |
| G-06 | 4-Methoxy-2,6-dimethyl-N-[1-[2-oxo-2-[4-pyridin-3-yl-4-(2-pyrrolidin-1-yl-ethoxy)-piperidin-1-yl]-ethyl]-1H-indol-7-yl]-benzenesulfonic acid amide |
| G-07 | 7-Chloro-2-[1-[3-oxo-3-(9-pyridin-4-yl-3,9-diazaspiro[5.5]undecan-3-yl)-propyl]-1H-indol-6-yl]-2,3-dihydro-isoindol-1-one |
| G-08 | 7-Chloro-2-[1-[2-oxo-2-(9-pyridin-4-yl-3,9-diazaspiro[5.5]undecan-3-yl)-ethyl]-1H-indol-6-yl]-2,3-dihydro-isoindol-1-one |
| G-10 | 7-Chloro-2-(1-(3-oxo-3-(9-(pyridin-4-yl)-3,9-diazaspiro[5.5]undecan-3-yl)propyl)-1H-indol-7-yl)isoindolin-1-one |
| G-11 | 7-Chloro-2-(1-(2-oxo-2-(9-(pyridin-4-yl)-3,9-diazaspiro[5.5]undecan-3-yl)ethyl)-1H-indol-7-yl)isoindolin-1-one |
| G-12 | 7-Chloro-2-(1-(2-oxo-2-(8-(pyridin-4-yl)-2,8-diazaspiro[4.5]decan-2-yl)ethyl)-1H-indol-6-yl)isoindolin-1-one |
| G-13 | 4-Methoxy-2,6-dimethyl-N-(1-(2-oxo-2-(3-(pyridin-4-yl)-1-oxa-2,8-diazaspiro[4.5]dec-2-en-8-yl)ethyl)-1H-indol-7-yl)benzenesulfonic acid amide |
| G-14 | 4-Methoxy-2,6-dimethyl-N-(1-(2-oxo-2-(8-(pyridin-4-yl)-2,8-diazaspiro[4.5]decan-2-yl)ethyl)-1H-indol-7-yl)benzenesulfonic acid amide |
| G-15 | 7-Chloro-2-(1-(2-oxo-2-(3-(pyridin-4-yl)-1-oxa-2,8-diazaspiro[4.5]dec-2-en-8-yl)ethyl)-1H-indol-6-yl)isoindolin-1-one |
| G-16 | 4-Methoxy-2,6-dimethyl-N-(1-(2-oxo-2-(3-(6-(piperidin-1-ylmethyl)-3,4-dihydroisoquinolin-2(1H)-yl)pyrrolidin-1-yl)ethyl)-1H-indol-7-yl)benzenesulfonic acid amide |
| G-17 | 4-Methoxy-2,6-dimethyl-N-(1-(2-oxo-2-(7-(pyridin-4-yl)-2,7-diazaspiro[4.4]nonan-2-yl)ethyl)-1H-indol-7-yl)benzenesulfonic acid amide |
| G-18 | N-(1-(2-(9-(azetidin-1-yl)-3-azaspiro[5.5]undecan-3-yl)-2-oxoethyl)-1H-indol-7-yl)-4-methoxy-2,6-dimethylbenzenesulfonic acid amide |
| G-19 | 7-Chloro-2-(1-(2-oxo-2-(9-(pyridin-4-yloxy)-3-azaspiro[5.5]undecan-3-yl)ethyl)-1H-indol-6-yl)isoindolin-1-one |
| G-20 | 7-Chloro-2-(1-(2-(9-(3,3-difluoroazetidin-1-yl)-3-azaspiro[5.5]undecan-3-yl)-2-oxoethyl)-1H-indol-6-yl)isoindolin-1-one |
| G-21 | 2-(1-(2-(9-(Azetidin-1-yl)-3-azaspiro[5.5]undecan-3-yl)-2-oxoethyl)-1H-indol-6-yl)-7-chloroisoindolin-1-one |
| G-22 | 4-Methoxy-2,6-dimethyl-N-(1-(2-oxo-2-(9-(pyridin-4-yloxy)-3-azaspiro[5.5]undecan-3-yl)ethyl)-1H-indol-7-yl)benzenesulfonic acid amide |
| G-23 | 8-Chloro-4-methyl-2-[1-[2-oxo-2-(9-pyridin-4-yl-3,9-diazaspiro[5.5]undecan-3-yl)-ethyl]-1H-indol-6-yl]-3,4-dihydro-2H-pyrrolo[3,4-b]indol-1-one |
| G-24 | 4-Methoxy-2,6-dimethyl-N-[[1-[2-oxo-2-(9-pyridin-4-yl-3,9-diazaspiro[5.5]undecan-3-yl)-ethyl]-1H-indol-7-yl]-methyl]-benzenesulfonic acid amide |
| G-26 | 7-Methyl-2-[1-[2-oxo-2-(9-pyridin-4-yl-3,9-diazaspiro[5.5]undecan-3-yl)-ethyl]-1H-indol-6-yl]-2,3-dihydro-isoindol-1-one |
| G-27 | 5-Methyl-2-[1-[2-oxo-2-(9-pyridin-4-yl-3,9-diazaspiro[5.5]undecan-3-yl)-ethyl]-1H-indol-6-yl]-1,2-dihydro-pyrrolo[2,1-e]imidazol-3-one |
| G-31 | 10-Chloro-2-[1-[2-oxo-2-(9-pyridin-4-yl-3,9-diazaspiro[5.5]undecan-3-yl)-ethyl]-1H-indol-6-yl]-3,4-dihydro-2H-pyrazino[1,2-a]indol-1-one |
| G-33 | 8-Chloro-2-[1-[2-oxo-2-(9-pyridin-4-yl-3,9-diazaspiro[5.5]undecan-3-yl)-ethyl]-1H-indol-6-yl]-3,4-dihydro-2H-pyrrolo[1,2-a]pyrazin-1-one |

-continued

| No. | Compound |
|---|---|
| G_CC-1 | 4-Methoxy-2,6-dimethyl-N-[1-[2-[4-(1-methyl-piperidin-4-yl)-piperazin-1-yl]-2-oxo-ethyl]-1H-indol-6-yl]-benzenesulfonic acid amide |
| G_CC-2 | 4-Methoxy-2,6-dimethyl-N-[1-[2-[4-(4-methyl-piperazin-1-yl)-piperidin-1-yl]-2-oxo-ethyl]-1H-indol-6-yl]-benzenesulfonic acid amide |
| G_CC-3 | 4-Methoxy-2,6-dimethyl-N-[1-[2-oxo-2-(4-pyrimidin-2-yl-piperazin-1-yl)-ethyl]-1H-indol-6-yl]-benzenesulfonic acid amide |
| G_CC-4 | 4-Methoxy-2,6-dimethyl-N-[1-[2-[4-[(1-methyl-piperdin-4-yl)-methyl]-piperazin-1-yl]-2-oxo-ethyl]-1H-indol-6-yl]-benzenesulfonic acid amide |
| G_CC-5 | N-[1-[2-[4-(4-fluorophenyl)-piperazin-1-yl]-2-oxo-ethyl]-1H-indol-7-yl]-4-methoxy-2,6-dimethyl-benzenesulfonic acid amide |
| G_CC-6 | 4-Methoxy-2,6-dimethyl-N-[1-[2-oxo-2-(4-pyrimidin-2-yl-piperazin-1-yl)-ethyl]-1H-indol-7-yl]-benzenesulfonic acid amide |
| G_CC-7 | 4-Methoxy-2,6-dimethyl-N-[1-[2-[4-[(1-methyl-piperdin-4-yl)-methyl]-piperazin-1-yl]-2-oxo-ethyl]-1H-indol-7-yl]-benzenesulfonic acid amide |
| G_CC-8 | 4-Chloro-2,5-dimethyl-N-[1-[2-[4-[(1-methyl-piperidin-4-yl)-methyl]-piperazin-1-yl]-2-oxo-ethyl]-1H-indol-6-yl]-benzenesulfonic acid amide |
| G_CC-9 | 2-[6-[[(4-Methoxy-2,6-dimethyl-phenyl)sulfonyl]amino]-1H-indol-1-yl]-N-[(1-pyridin-4-yl-piperidin-4-yl)-methyl]-acetamide |
| G_CC-10 | N-[1-[2-(3-Benzyl-3,7-diazaspiro[4.4]nonan-7-yl)-2-oxo-ethyl]-1H-indol-6-yl]-4-methoxy-2,6-dimethyl-benzenesulfonic acid amide |
| G_CC-11 | N-[3-(4-Dimethylamino-4-phenyl-piperidin-1-yl)-propyl]-2-[6-[[(4-methoxy-2,6-dimethyl-phenyl)sulfonyl]amino]-1H-indol-1-yl]-N-methyl-acetamide |
| G_CC-12 | N-[1-[2-[3-(4-Fluorophenyl)-4-oxo-3,8-diazaspiro[4.5]decan-8-yl]-2-oxo-ethyl]-1H-indol-7-yl]-4-methoxy-2,6-dimethyl-benzenesulfonic acid amide |
| G_CC-13 | N-[1-[2-(3-Benzyl-3,7-diazaspiro[4.4]nonan-7-yl)-2-oxo-ethyl]-1H-indol-7-yl]-4-methoxy-2,6-dimethyl-benzenesulfonic acid amide |
| G_CC-14 | N-[3-(4-Dimethylamino-4-phenyl-piperidin-1-yl)-propyl]-2-[7-[[(4-methoxy-2,6-dimethyl-phenyl)sulfonyl]amino]-1H-indol-1-yl]-N-methyl-acetamide |
| G_CC-15 | 2-[6-[[(4-Chloro-2,5-dimethyl-phenyl)sulfonyl]amino]-1H-indol-1-yl]-N-[3-(4-dimethylamino-4-phenyl-piperidin-1-yl)-propyl]-N-methyl-acetamide |
| G_CC-16 | N-[3-(4-Dimethylamino-4-phenyl-piperidin-1-yl)-propyl]-N-methyl-2-[7-[(naphthalen-1-ylsulfonyl)amino]-1H-indol-1-yl]-acetamide |
| G_CC-17 | N-[4-(Azetidin-1-yl)-4-phenyl-cyclohexyl]-2-[7-[[(4-methoxy-2,6-dimethyl-phenyl)sulfonyl]amino]-1H-indol-1-yl]-acetamide |
| G_CC-18 | N-[3-(4-Dimethylamino-4-thiophen-2-yl-piperidin-1-yl)-propyl]-2-[7-[[(4-methoxy-2,6-dimethyl-phenyl)sulfonyl]amino]-1H-indol-1-yl]-N-methyl-acetamide |
| G_CC-19 | N-[2-(4-Dimethylamino-4-thiophen-2-yl-piperidin-1-yl)-ethyl]-2-[7-[[(4-methoxy-2,6-dimethyl-phenyl)sulfonyl]amino]-1H-indol-1-yl]-acetamide |
| G_CC-20 | N-[1-[2-(4-Dimethylamino-4-thiophen-2-yl-piperidin-1-yl)-2-oxo-ethyl]-1H-indol-7-yl]-4-methoxy-2,6-dimethyl-benzenesulfonic acid amide |
| G_CC-21 | 2-[7-[[(4-Methoxy-2,6-dimethyl-phenyl)sulfonyl]amino]-1H-indol-1-yl]-N-[2-(1-pyridin-4-yl-piperidin-4-yl)-ethyl]-acetamide |
| G_CC-22 | N-[2-(4-Dimethylamino-4-thiophen-2-yl-piperidin-1-yl)-ethyl]-3-[6-[[(4-methoxy-2,6-dimethyl-phenyl)sulfonyl]amino]-1H-indol-1-yl]-propionamide |
| G_CC-23 | 3-[6-[[(4-Methoxy-2,6-dimethyl-phenyl)sulfonyl]amino]-1H-indol-1-yl]-N-[2-(1-pyridin-4-yl-piperidin-4-yl)-ethyl]-propionamide |
| G_CC-24 | 2-[6-[[(4-Chloro-2,5-dimethyl-phenyl)sulfonyl]amino]-1H-indol-1-yl]-N-[2-(1-pyridin-4-yl-piperidin-4-yl)-ethyl]-acetamide |
| G_CC-25 | N-[3-(4-Dimethylamino-4-thiophen-2-yl-piperidin-1-yl)-propyl]-N-methyl-2-[7-[(naphthalen-1-ylsulfonyl)amino]-1H-indol-1-yl]-acetamide |
| G_CC-26 | 2-[7-[[(4-Chloro-2,5-dimethyl-phenyl)sulfonyl]amino]-1H-indol-1-yl]-N-[3-(4-dimethylamino-4-thiophen-2-yl-piperidin-1-yl)-propyl]-N-methyl-acetamide |
| G_CC-27 | 2-[7-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-acetamide |
| G_CC-28 | 2-[7-[[(4-Chloro-2,5-dimethyl-phenyl)sulfonyl]amino]-1H-indol-1-yl]-N-[2-(1-pyridin-4-yl-piperidin-4-yl)-ethyl]-acetamide |
| G_CC-29 | N-[3-(4-Dimethylamino-4-thiophen-2-yl-piperidin-1-yl)-propyl]-2-[6-[[(4-methoxy-2,6-dimethyl-phenyl)sulfonyl]amino]-1H-indol-1-yl]-N-methyl-acetamide |
| G_CC-30 | N-[2-(4-Dimethylamino-4-thiophen-2-yl-piperidin-1-yl)-ethyl]-2-[6-[[(4-methoxy-2,6-dimethyl-phenyl)sulfonyl]amino]-1H-indol-1-yl]-acetamide |
| G_CC-31 | N-[1-[2-[1-(4-Fluorophenyl)-3-methyl-4-oxo-3,8-diazaspiro[4.5]decan-8-yl]-2-oxo-ethyl]-1H-indol-7-yl]-4-methoxy-2,6-dimethyl-benzenesulfonic acid amide |
| G_CC-32 | N-[1-[2-(3-Benzyl-4-oxo-3,8-diazaspiro[4.5]decan-8-yl)-2-oxo-ethyl]-1H-indol-7-yl]-4-methoxy-2,6-dimethyl-benzenesulfonic acid amide |
| G_CC-33 | N-[1-[2-[2-[(4-Fluorophenyl)-methyl]-2,5-diazabicyclo[2.2.1]heptan-5-yl]-2-oxo-ethyl]-1H-indol-6-yl]-4-methoxy-2,6-dimethyl-benzenesulfonic acid amide |
| G_CC-34 | 4-Methoxy-2,6-dimethyl-N-[1-[2-oxo-2-[2-(pyridin-4-yl-methyl)-2,5-diazabicyclo[2.2.1]heptan-5-yl]-ethyl]-1H-indol-7-yl]-benzenesulfonic acid amide |
| G_CC-35 | 4-Methoxy-2,6-dimethyl-N-[1-[3-oxo-3-(3-pyridin-4-yl-3,9-diazaspiro[5.5]undecan-9-yl)-propyl]-1H-indol-6-yl]-benzenesulfonic acid amide |

-continued

| No. | Compound |
|---|---|
| G_CC-36 | 4-Chloro-2,5-dimethyl-N-[1-[2-oxo-2-(3-pyridin-4-yl-3,9-diazaspiro[5.5]undecan-9-yl)-ethyl]-1H-indol-6-yl]-benzenesulfonic acid amide |
| G_CC-37 | N-[1-[2-Oxo-2-(3-pyridin-4-yl-3,9-diazaspiro[5.5]undecan-9-yl)-ethyl]-1H-indol-6-yl]-2-(trifluoromethyl)-benzenesulfonic acid amide |
| G_CC-38 | N-[1-[2-Oxo-2-(3-pyridin-4-yl-3,9-diazaspiro[5.5]undecan-9-yl)-ethyl]-1H-indol-7-yl]-naphthalene-1-sulfonic acid amide |
| G_CC-39 | 4-Chloro-2,5-dimethyl-N-[1-[2-oxo-2-(3-pyridin-4-yl-3,9-diazaspiro[5.5]undecan-9-yl)-ethyl]-1H-indol-7-yl]-benzenesulfonic acid amide |
| G_CC-40 | 4-Methoxy-2,6-dimethyl-N-[1-[3-[4-(1-methyl-piperidin-4-yl)-piperazin-1-yl]-3-oxo-propyl]-1H-indol-7-yl]-benzenesulfonic acid amide |
| G_CC-41 | 4-Methoxy-2,6-dimethyl-N-[1-[3-oxo-3-[4-(2-pyrrolidin-1-yl-ethyl)-piperidin-1-yl]-propyl]-1H-indol-7-yl]-benzenesulfonic acid amide |
| G_CC-42 | 4-Methoxy-2,6-dimethyl-N-[1-[3-[4-(4-methyl-piperazin-1-yl)-piperidin-1-yl]-3-oxo-propyl]-1H-indol-7-yl]-benzenesulfonic acid amide |
| G_CC-43 | 4-Methoxy-2,6-dimethyl-N-[1-[3-[4-[(1-methyl-piperidin-4-yl)-methyl]-piperazin-1-yl]-3-oxo-propyl]-1H-indol-7-yl]-benzenesulfonic acid amide |
| G_CC-44 | N-[1-[3-[4-(3-Dimethylamino-propyl)-piperazin-1-yl]-3-oxo-propyl]-1H-indol-7-yl]-4-methoxy-2,6-dimethyl-benzenesulfonic acid amide |
| G_CC-45 | N-[1-[3-(4-Hydroxy-4-pyridin-2-yl-piperidin-1-yl)-3-oxo-propyl]-1H-indol-7-yl]-4-methoxy-2,6-dimethyl-benzenesulfonic acid amide |
| G_CC-46 | N-[3-(4-Dimethylamino-4-thiophen-2-yl-piperidin-1-yl)-propyl]-3-[7-[[(4-methoxy-2,6-dimethyl-phenyl)sulfonyl]amino]-1H-indol-1-yl]-N-methyl-propionamide |
| G_CC-47 | 3-[7-[[(4-Methoxy-2,6-dimethyl-phenyl)sulfonyl]amino]-1H-indol-1-yl]-N-[2-(1-pyridin-4-yl-piperidin-4-yl)-ethyl]-propionamide |
| G_CC-48 | N-[1-[3-(4-Dimethylamino-4-phenyl-piperidin-1-yl)-3-oxo-propyl]-1H-indol-7-yl]-4-methoxy-2,6-dimethyl-benzenesulfonic acid amide |
| G_CC-49 | N-[3-(4-Dimethylamino-4-phenyl-piperidin-1-yl)-propyl]-3-[7-[[(4-methoxy-2,6-dimethyl-phenyl)sulfonyl]amino]-1H-indol-1-yl]-N-methyl-propionamide |
| G_CC-50 | N-[4-(Azetidin-1-yl)-4-phenyl-cyclohexyl]-3-[7-[[(4-methoxy-2,6-dimethyl-phenyl)sulfonyl]amino]-1H-indol-1-yl]-propionamide |
| G_CC-51 | N-[2-(4-Dimethylamino-4-thiophen-2-yl-piperidin-1-yl)-ethyl]-3-[7-[[(4-methoxy-2,6-dimethyl-phenyl)sulfonyl]amino]-1H-indol-1-yl]-propionamide |
| G_CC-52 | N-[1-[3-Oxo-3-(3-pyridin-4-yl-3,9-diazaspiro[5.5]undecan-9-yl)-propyl]-1H-indol-7-yl]-2-(trifluoromethyl)-benzenesulfonic acid amide |
| G_CC-53 | N-[1-[2-Oxo-2-(3-pyridin-4-yl-3,9-diazaspiro[5.5]undecan-9-yl)-ethyl]-1H-indol-7-yl]-2-(trifluoromethyl)-benzenesulfonic acid amide |
| G_CC-54 | 4-Methoxy-2,6-dimethyl-N-[1-[3-oxo-3-(3-pyridin-4-yl-3,9-diazaspiro[5.5]undecan-9-yl)-propyl]-1H-indol-7-yl]-benzenesulfonic acid amide |
| G_CC-56 | N-[3-(4-Ethyl-piperazin-1-yl)-propyl]-3-[7-[[(4-methoxy-2,6-dimethyl-phenyl)sulfonyl]amino]-1H-indol-1-yl]-propionamide |
| G_CC-57 | 4-Methoxy-2,6-dimethyl-N-[1-[2-oxo-2-[4-pyridin-3-yl-4-(2-pyrrolidin-1-yl-ethoxy)-piperidin-1-yl]-ethyl]-1H-indol-6-yl]-benzenesulfonic acid amide |
| G_CC-59 | 4-Chloro-2,5-dimethyl-N-[1-[3-[4-(1-methyl-piperidin-4-yl)-piperazin-1-yl]-3-oxo-propyl]-1H-indol-7-yl]-benzenesulfonic acid amide |
| G_CC-60 | 4-Chloro-2,5-dimethyl-N-[1-[3-oxo-3-[4-(2-pyrrolidin-1-yl-ethyl)-piperidin-1-yl]-propyl]-1H-indol-7-yl]-benzenesulfonic acid amide |
| G_CC-61 | 4-Chloro-2,5-dimethyl-N-[1-[3-[4-(4-methyl-piperazin-1-yl)-piperidin-1-yl]-3-oxo-propyl]-1H-indol-7-yl]-benzenesulfonic acid amide |
| G_CC-62 | 4-Chloro-2,5-dimethyl-N-[1-[3-[4-[(1-methyl-piperidin-4-yl)-methyl]-piperazin-1-yl]-3-oxo-propyl]-1H-indol-7-yl]-benzenesulfonic acid amide |
| G_CC-63 | 7-Chloro-2-[1-[3-oxo-3-(4-pyridin-4-yl-piperazin-1-yl)-propyl]-1H-indol-6-yl]-2,3-dihydro-isoindol-1-one |
| G_CC-64 | 7-Chloro-2-[1-[3-[4-[(1-methyl-piperidin-4-yl)-methyl]-piperazin-1-yl]-3-oxo-propyl]-1H-indol-6-yl]-2,3-dihydro-isoindol-1-one |
| G_CC-65 | 4-Chloro-2,5-dimethyl-N-[1-[3-oxo-3-(3-pyridin-4-yl-3,9-diazaspiro[5.5]undecan-9-yl)-propyl]-1H-indol-6-yl]-benzenesulfonic acid amide |
| G_CC-66 | 8-[3-[6-(4-Chloro-3-oxo-1,2-dihydro-isoindol-2-yl)-1H-indol-1-yl]-propanoyl]-3-[(4-fluorophenyl)-methyl]-3,8-diazaspiro[4.5]decan-4-one |
| G_CC-67 | 7-Chloro-2-[1-[3-oxo-3-(3-pyridin-4-yl-3,9-diazaspiro[5.5]undecan-9-yl)-propyl]-1H-indol-6-yl]-2,3-dihydro-isoindol-1-one |
| G_CC-68 | 7-Chloro-2-[1-[3-oxo-3-(4-pyridin-4-yloxy-piperidin-1-yl)-propyl]-1H-indol-6-yl]-2,3-dihydro-isoindol-1-one |
| G_CC-69 | 7-Chloro-2-[1-[3-(4-hydroxy-4-pyridin-3-yl-piperidin-1-yl)-3-oxo-propyl]-1H-indol-6-yl]-2,3-dihydro-isoindol-1-one |
| G_CC-70 | 3-[7-[[(4-Chloro-2,5-dimethyl-phenyl)sulfonyl]amino]-1H-indol-1-yl]-N-[2-(1-pyridin-4-yl-piperidin-4-yl)-ethyl]-propionamide |
| G_CC-71 | 3-[6-[[(4-Chloro-2,5-dimethyl-phenyl)sulfonyl]amino]-1H-indol-1-yl]-N-[2-(1-pyridin-4-yl-piperidin-4-yl)-ethyl]-propionamide |
| G_CC-72 | 3-[6-(4-Chloro-3-oxo-1,2-dihydro-isoindol-2-yl)-1H-indol-1-yl]-N-[2-(1-pyridin-4-yl-piperidin-4-yl)-ethyl]-propionamide |
| G_CC-73 | 3-[7-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-propionamide |

| No. | Compound |
|---|---|
| G_CC-74 | 3-[6-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-propionamide |
| G_CC-76 | 2-[6-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-acetamide |
| G_CC-77 | N-[2-(4-Dimethylamino-4-phenyl-cyclohexyl)-ethyl]-2-[7-[[(4-methoxy-2,6-dimethyl-phenyl)sulfonyl]amino]-1H-indol-1-yl]-N-methyl-acetamide |
| G_CC-81 | N-[2-[4-(3-Fluorophenyl)-4-(4-methyl-piperazin-1-yl)-piperidin-1-yl]-ethyl]-3-[6-[[(methoxy-2,6-dimethyl-phenyl)sulfonyl]amino]-1H-indol-1-yl]-N-methyl-propionamide |
| G_CC-84 | N-[1-[2-[4-(3-Fluorophenyl)-4-(4-methyl-piperazin-1-yl)-piperidin-1-yl]-2-oxo-ethyl]-1H-indol-7-yl]-4-methoxy-2,6-dimethyl-benzenesulfonic acid amide |
| G_CC-88 | 2-[7-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-acetamide |
| G_CC-91 | 4-Methoxy-2,6-dimethyl-N-[1-[2-oxo-2-(3-pyridin-4-yl-3,9-diazaspiro-[5.5]undecan-9-yl)-ethyl]-1H-indol-7-yl]-benzenesulfonic acid amide |
| G_CC-92 | 4-Methoxy-2,6-dimethyl-N-[1-[2-oxo-2-(4-pyridin-4-yloxy-piperidin-1-yl)-ethyl]-1H-indol-7-yl]-benzenesulfonic acid amide |
| G_CC-95 | N-[2-(4-Dimethylamino-4-phenyl-cyclohexyl)-ethyl]-2-[6-[[(4-methoxy-2,6-dimethyl-phenyl)sulfonyl]amino]-1H-indol-1-yl]-N-methyl-acetamide |
| G_CC-99 | N-[2-[4-(3-Fluorophenyl)-4-(4-methyl-piperazin-1-yl)-piperidin-1-yl]-ethyl]-2-[6-[[(4-methoxy-2,6-dimethyl-phenyl)sulfonyl]amino]-1H-indol-1-yl]-N-methyl-acetamide |
| G_CC-102 | N-[2-[4-(3-Fluorophenyl)-4-(4-methyl-piperazin-1-yl)-piperidin-1-yl]-ethyl]-2-[7-[[(4-methoxy-2,6-dimethyl-phenyl)sulfonyl]amino]-1H-indol-1-yl]-N-methyl-acetamide |
| G_CC-103 | 2-[6-(4-Chloro-3-oxo-1,2-dihydro-isoindol-2-yl)-1H-indol-1-yl]-N-[2-(1-pyridin-4-yl-piperidin-4-yl)-ethyl]-acetamide |
| G_CC-106 | 7-Chloro-2-[1-[3-oxo-3-(3-pyridin-4-yl-3,9-diazaspiro[5.5]undecan-9-yl)-propyl]-1H-indol-7-yl]-2,3-dihydro-isoindol-1-one |
| G_CC-108 | N-[[1-[2-[6-[[(4-Methoxy-2,6-dimethyl-phenyl)sulfonyl]amino]-1H-indol-1-yl]-acetyl]-4-(4-methyl-piperazin-1-yl)-piperidin-4-yl]-methyl]-pyridine-4-carboxylic acid amide |
| G_CC-111 | 2-[6-(4-Chloro-3-oxo-1,2-dihydro-isoindol-2-yl)-1H-indol-1-yl]-N-[(1-pyridin-4-yl-piperidin-4-yl)-methyl]-acetamide |
| G_CC-113 | 2-[6-(4-Chloro-3-oxo-1,2-dihydro-isoindol-2-yl)-1H-indol-1-yl]-N-[2-[4-(3-fluorophenyl)-4-(4-methyl-piperazin-1-yl)-piperidin-1-yl]-ethyl]-N-methyl-acetamide |
| G_CC-116 | 3-[6-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-propionamide |
| G_CC-117 | N-[2-(4-Dimethylamino-4-phenyl-cyclohexyl)-ethyl]-3-[6-[[(4-methoxy-2,6-dimethyl-phenyl)sulfonyl]amino]-1H-indol-1-yl]-N-methyl-propionamide |
| G_CC-119 | 3-[6-(4-Chloro-3-oxo-1,2-dihydro-isoindol-2-yl)-1H-indol-1-yl]-N-methyl-N-[3-(4-pyridin-4-yl-piperazin-1-yl)-propyl]-propionamide |
| G_CC-120 | 4-Methoxy-2,6-dimethyl-N-[1-[2-oxo-2-[4-(2-pyrrolidin-1-yl-ethyl)-piperidin-1-yl]-ethyl]-1H-indol-6-yl]-benzenesulfonic acid amide |
| G_CC-123 | 3-[7-(4-Chloro-3-oxo-1,2-dihydro-isoindol-2-yl)-1H-indol-1-yl]-N-[(1-pyridin-4-yl-piperidin-4-yl)-methyl]-propionamide |
| G_CC-127 | 3-[6-(4-Chloro-3-oxo-1,2-dihydro-isoindol-2-yl)-1H-indol-1-yl]-N-[2-(4-dimethylamino-4-phenyl-cyclohexyl)-ethyl]-N-methyl-propionamide |
| G_CC-128 | 7-Chloro-2-[1-[2-[4-(3-fluorophenyl)-4-(4-methyl-piperazin-1-yl)-piperidin-1-yl]-2-oxo-ethyl]-1H-indol-6-yl]-2,3-dihydro-isoindol-1-one |
| G_CC-138 | 2-[6-(4-Chloro-3-oxo-1,2-dihydro-isoindol-2-yl)-1H-indol-1-yl]-N-methyl-N-[3-(4-pyridin-4-yl-piperazin-1-yl)-propyl]-acetamide |
| G_CC-139 | 4-Methoxy-2,6-dimethyl-N-[1-[2-oxo-2-[4-(pyridin-3-carbonyl)-piperazin-1-yl]-ethyl]-1H-indol-7-yl]-benzenesulfonic acid amide | optionally in the form of an isolated enantiomer or an isolated diastereomer, the racemate, the enantiomers, the diastereomers, mixtures of enantiomers or diastereomers, each in the form of their bases and/or physiologically compatible salts, in particular hydrochloride salts.

The numbering of the individual embodiments of the compounds according to the invention used above is retained in the following explanations of the present invention, particularly in the description of the examples.

According to one aspect of the present invention the compounds according to the invention preferably have an antagonistic action on the human B1R receptor or the B1R receptor of the rat. In a preferred embodiment of the invention the compounds according to the invention have an antagonistic action on both the human B1R receptor (hB1R) and on the B1R receptor of the rat (rB1R).

In a preferred embodiment of the present invention the compounds according to the invention exhibit at least 15%, 25%, 50%, 70%, 80% or 90% inhibition on the human B1R receptor and/or on the B1R receptor of the rat in the FLIPR assay at a concentration of 10 µM. Most particularly preferred are compounds which exhibit at least 70%, in particular at least 80% and particularly preferably at least 90% inhibition on the human B1R receptor and on the B1R receptor of the rat at a concentration of 10 µM.

The agonistic or antagonistic action of substances can be quantified on the bradykinin 1 receptor (B1R) of the human and rat species with ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-Arg$^9$ bradykinin (0.5 nM) or Des-Arg$^9$ bradykinin (100 nM). Antagonists lead to a suppression of the Ca$^{2+}$ influx following administration of the agonist. The % inhibition in comparison with the maximum achievable inhibition is indicated.

The substances according to the invention preferably act for example on the B1R of relevance in connection with various diseases, such that they are suitable as a pharmaceutical active ingredient in medicinal products.

The invention therefore also provides medicinal products containing at least one compound according to the invention, optionally along with suitable additives and/or auxiliary substances and/or optionally further active ingredients.

The medicinal products according to the invention optionally contain, in addition to at least one compound according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amounts thereof to use depend on whether the medicinal product is to be administered by oral, peroral, parenteral, intravenous, intraperitoneal, intradermal, intramuscular, nasal, buccal, rectal or topical means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Substituted indole compounds according to the invention in a depot formulation, in dissolved form or in a plaster, optionally with addition of agents promoting skin penetration, are suitable preparations for percutaneous administration. Preparation forms suitable for oral or percutaneous administration can deliver the substituted indole compounds according to the invention on a delayed release basis. The substituted indole compounds according to the invention can also be used in parenteral long-term depot forms, such as implants or implanted pumps, for example. Other additional active ingredients known to the person skilled in the art can be added in principle to the medicinal products according to the invention.

The amount of active ingredient to be administered to the patient varies according to the weight of the patient, the manner of administration, the indication and the severity of the illness. Generally 0.00005 to 50 mg/kg, in particular 0.01 to 5 mg/kg, of at least one compound according to the invention are conventionally administered.

One form of the medicinal product contains a substituted indole compound according to the invention optionally as an isolated diastereomer and/or enantiomer, as a racemate or as a non-equimolar or equimolar mixture of diastereomers and/or enantiomers.

B1R is involved in particular in the pain mechanism. The substituted indole compounds according to the invention can accordingly be used in particular for the preparation of a medicinal product for the treatment of pain, in particular acute, visceral, neuropathic or chronic pain or inflammatory pain.

The invention therefore also provides the use of at least one substituted indole compound according to the invention to prepare a medicinal product for the treatment of pain, in particular acute, visceral, neuropathic or chronic pain. A particular embodiment of the present invention is the use of at least one of the substituted indole compounds according to the invention to prepare a medicinal product for the treatment of inflammatory pain.

The invention also provides the use of at least one substituted indole compound according to the invention for the treatment of pain, in particular acute, visceral, neuropathic or chronic pain or inflammatory pain.

The invention also provides the use of at least one substituted indole compound according to the invention to prepare a medicinal product for the treatment of diabetes, diseases of the respiratory tract, for example bronchial asthma, allergies, COPD/chronic obstructive pulmonary disease or cystic fibrosis; inflammatory bowel diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following heart attack or stroke; obesity; and as an angiogenesis inhibitor.

The invention also provides the use of at least one substituted indole compound according to the invention for treating any of the foregoing indications.

In the above uses it may be preferable for a substituted indole compound that is used to be in the form of an isolated diastereomer and/or enantiomer, a racemate or a non-equimolar or equimolar mixture of diastereomers and/or enantiomers.

The invention also provides a process for treating, in particular one of the aforementioned indications, in a non-human mammal or human requiring treatment of the corresponding indication, by administration of a therapeutically active dose of a substituted indole compound according to the invention or of a medicinal product according to the invention.

The invention also provides a process for treating pain, in particular one of the aforementioned forms of pain, in a non-human mammal or human requiring in particular treatment of pain, in particular of acute, visceral, neuropathic or chronic pain or inflammatory pain, by administration of a therapeutically active dose of a substituted indole compound according to the invention or of a medicinal product according to the invention.

The present invention also provides methods for preparing the substituted indole compounds according to the invention as listed in the description and in the examples.

General Method for Preparing the Indolamide Derivative G

Scheme 1: Synthesis of the indolamide derivative G

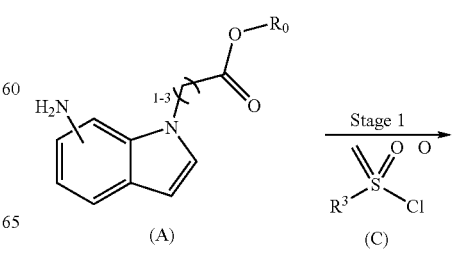

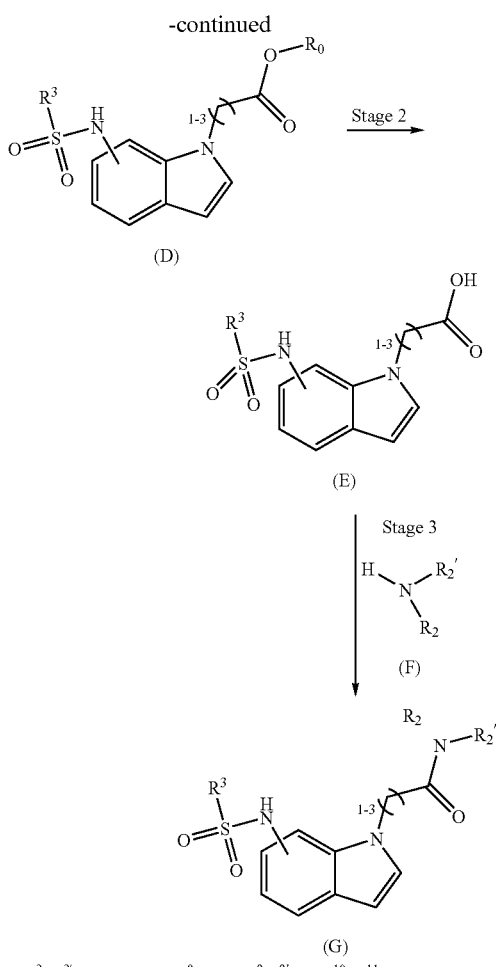

wherein N(H)(R²)(R²') denotes N(H)(R⁸)—[CR⁹ᵃR⁹ᵇ]₁-A(R¹⁰)(R¹¹)

In stage 1 sulfonyl chlorides having the formula (C), wherein R³ has the meaning given above, in at least one solvent, preferably selected from the group consisting of dichloromethane, acetonitrile, dimethyl formamide, diethyl ether, dioxane, tetrahydrofuran, methanol, ethanol and isopropanol, are reacted with amino acid esters (A), in the presence of at least one inorganic base, preferably selected from the group consisting of potassium carbonate and caesium carbonate, or an organic base, preferably selected from the group consisting of triethylamine, diisopropylethylamine and pyridine, and optionally with addition of 4-(dimethylamino)pyridine or 1-hydroxybenzotriazole, at temperatures of preferably −15° C. to 50° C., to form compounds having the formula (D).

In stage 2 compounds of formula (D) in at least one solvent, preferably selected from the group consisting of water, methanol, ethanol, isopropanol, diethyl ether, tetrahydrofuran, toluene, acetonitrile, dimethyl formamide, dioxane and dimethyl sulfoxide, are reacted with an inorganic base, preferably selected from the group consisting of lithium hydroxide, sodium hydroxide, potassium hydroxide, potassium tert-butanolate, lithium propanethiolate and sodium phenyl selenolate, optionally with addition of HMPA or lithium chloride, or with a Lewis acid, preferably selected from the group consisting of trimethylsilyl chloride, boron tribromide and aluminium trichloride, optionally with addition of thiolene, sodium iodide or lithium chloride, at temperatures of preferably 0° C. to 100° C., to form compounds of formula (E).

In stage 3 compounds of formula (E) in at least one solvent, preferably selected from the group consisting of dichloromethane, acetonitrile, dimethyl formamide, diethyl ether, dioxane and tetrahydrofuran, are reacted with amines (F), with addition of at least one coupling reagent, preferably selected from the group consisting of carbonyl diimidazole (CDI), 2-chloro-1-methylpyridinium iodide (Mukaiyama reagent), N-(3-dimethylaminopropyl)-N'-ethylcarbodiimide (EDCI), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with addition of 4-(dimethylamino)-pyridine or 1-hydroxybenzotriazole, to form compounds of formula (G).

Pharmacological Methods

1. Functional Investigation on the Bradykinin 1 Receptor (B1R)

The agonistic or antagonistic action of substances can be determined on the bradykinin 1 receptor (B1R) of the human and rat species with the following assay. According to this assay, the $Ca^{2+}$ inflow through the channel is quantified with the aid of a $Ca^{2+}$-sensitive dye (Fluo-4 type, Molecular Probes Europe BV, Leiden, Netherlands) in a fluorescent imaging plate reader (FLIPR, Molecular Devices, Sunnyvale, USA).

2. Method:

Chinese hamster ovary cells (CHO K1 cells) which are stably transfected with the human B1R gene (hB1R cells) or the B1R gene of the rat (rB1R cells) are used. For functional investigations these cells are plated-out onto black 96-well plates with a clear base (BD Biosciences, Heidelberg, Germany or Greiner, Frickenhausen, Germany) in a density of 20,000-35,000 cells/well. Overnight the cells are incubated at 37° C. and 5% $CO_2$ in culture medium (hB1R cells: Ham's Nutrient Mixture F12, Gibco Invitrogen GmbH, Karlsruhe, Germany or DMEM, Sigma-Aldrich, Taufkirchen, Germany; rB1R cells: D-MEM/F12, Gibco Invitrogen, Karlsruhe, Germany) with 10 vol. % FBS (foetal bovine serum, Gibco Invitrogen GmbH, Karlsruhe, Germany or PAN Biotech GmbH, Aidenbach, Germany).

On the following day the cells are loaded with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany) for 60 min at 37° C. The plates are subsequently washed twice with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for $Ca^{2+}$ measurement.

Alternatively they are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid) and loaded with buffer A with added 2.5 µM Fluo-4 and 0.025% Pluronic F127 (Sigma-Aldrich, Taufkirchen, Germany). The cells are then washed twice with buffer A and incubated for 30 minutes with buffer A, which additionally contains 0.05% BSA and 0.05% gelatine, at room temperature and then used for $Ca^{2+}$ measurement in the FLIPR. The $Ca^{2+}$-dependent fluorescence is measured here before and after addition of substances ($\lambda_{ex}$=488 nm, $\lambda_{em}$=540 nm). The quantification is performed by measuring the highest fluorescence intensity (FC, fluorescence counts) over time.

3. FLIPR Assay:

The FLIPR protocol comprises two additions of substance. Test substances (10 µM) are first pipetted onto the cells and the Ca$^{2+}$ inflow is compared with the control (hB1R: Lys-Des-Arg$^9$ bradykinin>=50 nM; rB1R: Des-Arg$^9$ bradykinin 10 μM). The value in % activation based on the Ca$^{2+}$ signal after addition of Lys-Des-Arg$^9$ bradykinin (>=50 nM) or Des-Arg$^9$ bradykinin (10 μM) is obtained therefrom. After incubation for 10-20 minutes, Lys-Des-Arg$^9$ bradykinin (hB1R) or Des-Arg$^9$ bradykinin (rB1R) is applied in the EC$_{80}$ concentration and the inflow of Ca$^{2+}$ is likewise determined.

Antagonists lead to a suppression of the Ca$^{2+}$ inflow. The % inhibition in comparison with the maximum achievable inhibition is calculated.

The substances are added in varying concentrations in order to determine the IC$_{50}$ value. Double or triple determinations (n=2 or n=3) are performed and these are repeated in at least one further independent experiment (N>=2).

The compounds preferably exhibit a B1R antagonistic action on the human receptor and/or on the rat receptor.

The invention is described below with reference to examples, without limiting the general concept or scope of the invention.

EXAMPLES

List of Abbreviations

DIPEA diisopropylethylamine
EDCI N-ethyl-N'-(3-dimethylaminopropyl)-carbodiimide hydrochloride
h hour(s)
HOBt 1-hydroxy-1H-benzotriazole
conc. concentrated
min minute(s)
N normal
RT room temperature
THF tetrahydrofuran
TFA trifluoroacetic acid
abs. absolute
eq. equivalent(s)
equiv. equivalent(s)
Boc tert-butyl carbamate
DCM dichloromethane
M molar
EtOAc ethyl acetate
Et$_3$N triethylamine
Cbz benzyl carbamate
DMF dimethyl formamide
DBU 1,8-diazabicyclo[5.4.0]undec-7-ene 1) Synthesis of Amino Indole Esters A Structural unit A-01: tert-Butyl 2-(7-amino-1H-indol-1-yl) acetate Stage 1: tert-Butyl 2-(7-nitro-1H-indol-1-yl) acetate 7-Nitroindole (77 mmol, 1 equiv.) dissolved in dimethyl formamide (25 ml) was added slowly to a suspension of sodium hydride (85 mmol, 1.1 equiv.) in dimethyl formamide (75 ml) at 0° C., the reaction mixture obtained was stirred for 30 min, then tert-butyl bromoacetate (85 mmol, 1.1 equiv.) was added and the mixture was stirred for 12 h at room temperature.

The reaction mixture was processed by adding methanol, diluting with diethyl ether and washing 3 times with water. The organic phase was dried over magnesium sulfate and concentrated under reduced pressure. The solid that accumulated was filtered out and washed with a little diethyl ether. The desired product was obtained in this way in a yield of 89% (75 mmol).

Stage 2: tert-Butyl 2-(7-amino-1H-indol-1-yl) acetate (A-01)

10% palladium on activated carbon (500 mg) was added to a solution of tert-butyl 2-(7-nitro-1H-indol-1-yl)acetate (68 mmol, 1 equiv.) in ethyl acetate/methanol (1:1) and the mixture obtained was hydrogenated under 2.5 bar hydrogen pressure for 12 h. The reaction mixture was processed by filtering over celite, rewashing with ethyl acetate, concentrating under reduced pressure and recrystallizing from isopropanol. The desired product was obtained in a yield of 80% (54.4 mmol).

Structural unit A-02: tert-Butyl 2-(6-amino-1H-indol-1-yl) acetate

Stage 1: tert-Butyl 2-(6-nitro-1H-indol-1-yl) acetate

6-Nitroindole (77 mmol, 1 equiv.) dissolved in dimethyl formamide (25 ml) was added slowly to a suspension of sodium hydride (85 mmol, 1.1 equiv.) in dimethyl formamide (70 ml) at 0° C., the reaction mixture obtained was stirred for 30 min, then tert-butyl bromoacetate (85 mmol, 1.1 equiv.) was added and the mixture was stirred for 12 h at room temperature.

The reaction mixture was processed by adding methanol, diluting with diethyl ether and washing 3 times with water. The organic phase was dried over magnesium sulfate and concentrated under reduced pressure and recrystallized from diethyl ether. The desired product was obtained in this way in a yield of 69% (53 mmol).

Stage 2: tert-Butyl 2-(6-amino-1H-indol-1-yl) acetate (A-02)

10% palladium on activated carbon (500 mg) was added to a solution of tert-butyl 2-(6-nitro-1H-indol-1-yl)acetate (54 mmol, 1 equiv.) in ethyl acetate/methanol (3:1) and the mixture obtained was hydrogenated under 2.5 bar hydrogen pressure for 12 h. The reaction mixture was processed by filtering over celite, rewashing with ethyl acetate and concentrating under reduced pressure. The desired product was obtained in a quantitative yield.

Structural unit A-03: Methyl 3-(6-amino-1H-indol-1-yl) propanoate

Stage 1: Methyl 3-(6-nitro-1H-indol-1-yl) propanoate 1,8-Diazabicyclo[5.4.0]undec-7-ene (23 mmol, 0.5 equiv.) was added to a solution of 6-nitroindole (46 mmol, 1 equiv.) and methyl acrylate (69 mmol, 1.5 equiv.) in acetonitrile (25 ml) at 0° C. and stirred for 12 h at room temperature. The reaction solution was concentrated under reduced pressure and the residue was purified by column chromatography (silica, ethyl acetate/hexane). The desired product was obtained in a yield of 80% (36.8 mmol).

Stage 2: Methyl 3-(6-amino-1H-indol-1-yl) propanoate (A-03)

10% palladium on activated carbon (500 mg) was added to a solution of methyl 3-(6-nitro-1H-indol-1-yl) propanoate (60 mmol, 1 equiv.) in ethyl acetate/methanol (3:1) and the mixture obtained was hydrogenated under 2.5 bar hydrogen pressure for 12 h. The reaction mixture was processed by filtering over celite, rewashing with ethyl acetate and concentrating under reduced pressure. The desired product was obtained in a quantitative yield.

Structural unit A-04: Methyl 3-(7-amino-1H-indol-1-yl) propanoate

Stage 1: Methyl 3-(7-nitro-1H-indol-1-yl) propanoate 1,8-Diazabicyclo[5.4.0]undec-7-ene (31 mmol, 0.5 equiv.) was added to a solution of 7-nitroindole (62 mmol, 1 equiv.)

and methyl acrylate (93 mmol, 1.5 equiv.) in acetonitrile (30 ml) at 0° C. and stirred for 12 h at room temperature. The reaction solution was concentrated under reduced pressure and the residue was purified by column chromatography (silica, ethyl acetate/hexane). The desired product was obtained in a yield of 38% (23 mmol).

Stage 2: Methyl 3-(7-amino-1H-indol-1-yl) propanoate (A-04)

10% palladium on activated carbon (500 mg) was added to a solution of methyl 3-(7-nitro-1H-indol-1-yl) propanoate (43 mmol, 1 equiv.) in ethyl acetate/methanol (3:1) and the mixture obtained was hydrogenated under 2.5 bar hydrogen pressure for 12 h. The reaction mixture was processed by filtering over celite, washing with ethyl acetate and concentrating under reduced pressure. The desired product was obtained in a quantitative yield.

2) Synthesis of Sulfonyl Chlorides C

Sulfonyl chloride C-01:
2-(Trifluoromethyl)phenyl-1-sulfonyl chloride (CAS No: 776-04-5) is commercially available from e.g. ABCR.

Sulfonyl chloride C-02:
4-Chloro-2,5-dimethylphenyl-1-sulfonyl chloride (CAS No: 88-49-3) is commercially available from e.g. ABCR.

Sulfonyl chloride C-03:
4-Methoxy-2,6-dimethylphenyl-1-sulfonyl chloride

Chlorosulfuric acid (1.83 ml, 2.3 equiv.) in dichloromethane (10 ml) was added dropwise to a solution of 3,5-dimethyl anisole (1.632 g, 11.982 mmol) in dichloromethane (15 ml) over 20 min at 0° C. The reaction mixture was then stirred for 10 min at room temperature. The reaction mixture was poured over iced water (3 ml, 5 equiv. relative to chlorosulfuric acid) and the aqueous phase was extracted with dichloromethane (3×100 ml). The organic phase was dried ($Na_2SO_4$) and concentrated to small volume under vacuum. Yield: 2.6 g (92%)

Sulfonyl chloride C-04: Naphthalene-1-sulfonyl chloride (CAS No: 85-46-1) is commercially available from e.g. ABCR.

3) Synthesis of Sulfonylated Indole Esters D

General Method for the Synthesis of Sulfonylated Indole Esters D

Scheme 2: Synthesis of sulfonylated indole esters D

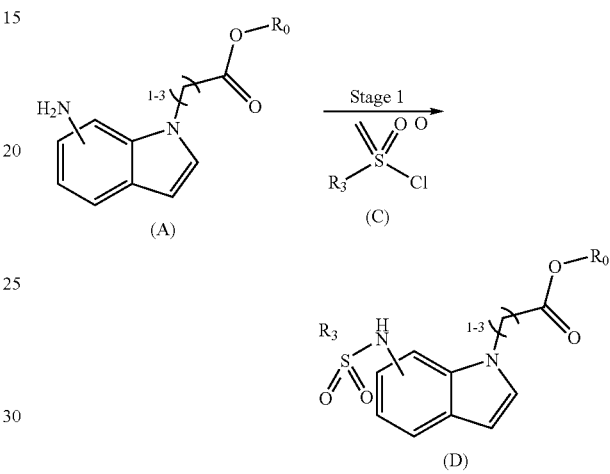

General procedure GP I—sulfonylation: A solution of sulfonyl chloride C (1.1 equiv.) in dichloromethane was added to a solution of the corresponding aminoindole ester A (1 equiv.) and diisopropyl ethylamine (1.25 equiv.) in dichloromethane at 0° C. The reaction mixture was stirred for 12 h at room temperature, then washed 3 times with a saturated sodium hydrogen carbonate solution, dried over magnesium sulfate and concentrated under reduced pressure. The desired product was obtained after purification by column chromatography (silica; ethyl acetate/hexane).

TABLE 1

| Synthesis of sulfonylated indole esters D | | | |
|---|---|---|---|
| Ester no. | Structure | Name | Amino acid ester (A) |
| D-02 | (structure) | tert-Butyl 2-(7-(4-methoxy-2,6-dimethylphenylsulfonamido)-1H-indol-1-yl) acetic acid (D-02) | tert-Butyl 2-(7-amino-1H-indol-1-yl) acetic acid (A-01) |

TABLE 1-continued

| | Structure | Name | Starting material |
|---|---|---|---|
| D-03 | 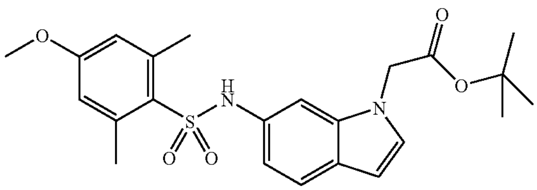 [SMILES: COc1cc(C)c(S(=O)(=O)Nc2ccc3ccn(CC(=O)OC(C)(C)C)c3c2)c(C)c1] | tert-Butyl 2-(6-(4-methoxy-2,6-dimethylphenylsulfonamido)-1H-indol-1-yl) acetic acid (D-03) | tert-Butyl 2-(6-amino-1H-indol-1-yl) acetic acid (A-02) |
| D-04 | 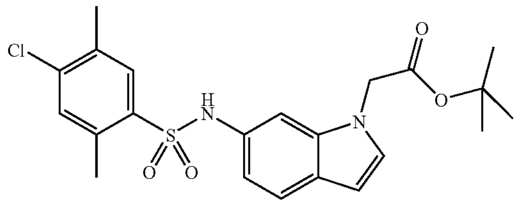 [SMILES: Cc1cc(S(=O)(=O)Nc2ccc3ccn(CC(=O)OC(C)(C)C)c3c2)c(C)cc1Cl] | tert-Butyl 2-(6-(4-chloro-2,5-dimethylphenylsulfonamido)-1H-indol-1-yl) acetic acid (D-04) | tert-Butyl 2-(6-amino-1H-indol-1-yl) acetic acid (A-02) |
| D-05 | 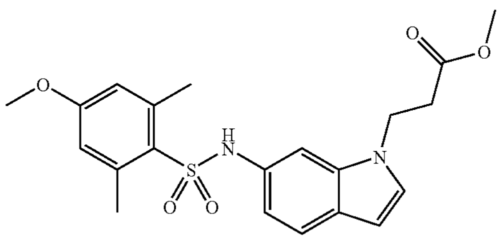 | Methyl 3-(6-(4-methoxy-2,6-dimethylphenylsulfonamido)-1H-indol-1-yl) propionic acid (D-05) | Methyl 3-(6-amino-1H-indol-1-yl) propionic acid (A-03) |
| D-06 | 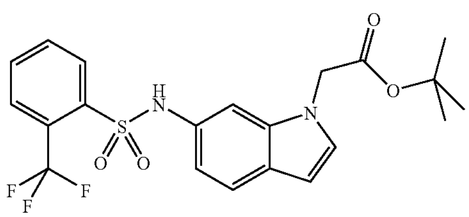 [SMILES: CC(C)(C)OC(=O)Cn1ccc2ccc(NS(=O)(=O)c3ccccc3C(F)(F)F)cc21] | tert-Butyl 2-(6-(2-(trifluoromethyl)phenylsulfonamido)-1H-indol-1-yl) acetic acid (D-06) | tert-Butyl 2-(6-amino-2-1H-indol-1-yl) acetic acid (A-02) |
| D-07 | 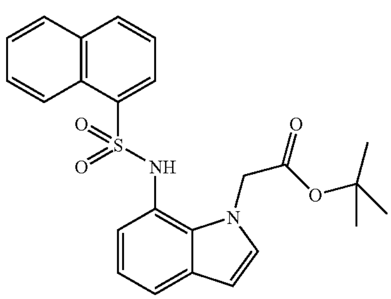 [SMILES: CC(C)(C)OC(=O)Cn1ccc2cccc(NS(=O)(=O)c3cccc4ccccc34)c21] | tert-Butyl 2-(7-(naphthalene-1-sulfonamido)-1H-indol-1-yl) acetic acid (D-07) | tert-Butyl 2-(7-amino-1H-indol-1-yl) acetic acid (A-01) |
| D-08 | 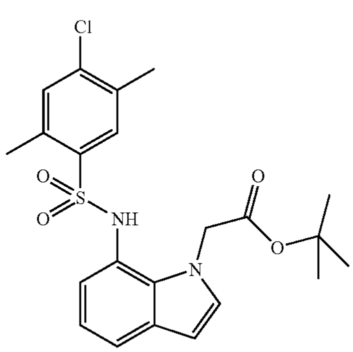 [SMILES: Cc1cc(S(=O)(=O)Nc2cccc3ccn(CC(=O)OC(C)(C)C)c23)c(C)cc1Cl] | tert-Butyl 2-(7-(4-chloro-2,5-dimethylphenylsulfonamido)-1H-indol-1-yl) acetic acid (D-08) | tert-Butyl 2-(7-amino-1H-indol-1-yl) acetic acid (A-01) |

TABLE 1-continued

| | | | |
|---|---|---|---|
| D-09 | | Methyl 3-(7-(2-(trifluoromethyl)phenyl-sulfonamido)-1H-indol-1-yl) propionic acid (D-09) | Methyl 3-(7-amino-1H-indol-1-yl) propionic acid (A-04) |
| D-10 | | Methyl 3-(7-(4-chloro-2,5-dimethylphenylsulfon-amido)-1H-indol-1-yl) propionic acid (D-10) | Methyl 3-(7-amino-1H-indol-1-yl) propionic acid (A-04) |
| D-11 | | Methyl 3-(6-(2-(trifluoromethyl)phenyl-sulfonamido)-1H-indol-1-yl) propionic acid (D-11) | Methyl 3-(6-amino-1H-indol-1-yl) propionic acid (A-03) |
| D-12 | | Methyl 3-(6-(4-chloro-2,5-dimethylphenylsulfon-amido)-1H-indol-1-yl) propionic acid (D-12) | Methyl 3-(6-amino-1H-indol-1-yl) propionic acid (A-03) |
| D-13 | | tert-Butyl 2-(7-(2-(trifluoromethyl)phenyl-sulfonamido)-1H-indol-1-yl) acetic acid (D-13) | tert-Butyl 2-(7-amino-1H-indol-1-yl) acetic acid (A-01) |
| D-14 | | Methyl 3-(7-(4-methoxy-2,6-dimethylphenylsulfon-amido)-1H-indol-1-yl) propionic acid (D-14) | Methyl 3-(7-amino-1H-indol-1-yl) propionic acid (A-04) |

TABLE 1-continued

| | | | | | |
|---|---|---|---|---|---|
| D-15 |  | Methyl 3-(6-(7-chloro-1-oxoisoindolin-2-yl)-1H-indol-1-yl) propionic acid (D-15) | | | |
| D-16 | | tert-Butyl 2-(6-(7-chloro-1-oxoisoindolin-2-yl)-1H-indol-1-yl) acetic acid (D-16) | | | |
| D-17 | 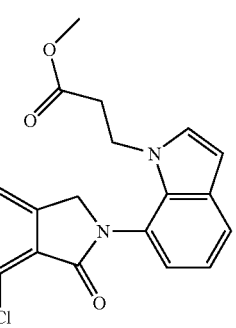 | Methyl 3-(7-(7-chloro-1-oxoisoindolin-2-yl)-1H-indol-1-yl) propionic acid (D-17) | | | |
| D-18 | 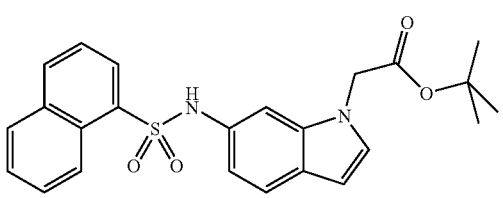 [SMILES: CC(C)(C)OC(=O)Cn1ccc2ccc(NS(=O)(=O)c3cccc4ccccc34)cc21] | tert-Butyl 2-(6-(naphthalene-1-sulfonamido)-1H-indol-1-yl) acetic acid (D-18) | tert-Butyl 2-(6-amino-1H-indol-1-yl) acetic acid (A-02) | | |
| D-19 | 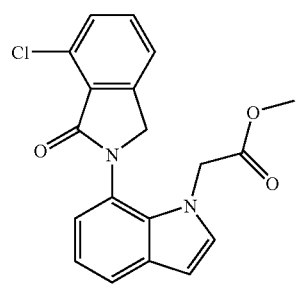 [SMILES: COC(=O)Cn1ccc2cccc(N3Cc4cccc(Cl)c4C3=O)c21] | Methyl 2-(7-(7-chloro-1-oxoisoindolin-2-yl)-1H-indol-1-yl) acetic acid (D-19) | | | |

| Ester no. | Carboxylic acid chloride (B) or sulfonyl chloride (C) | Synthesis by | Yield | Note |
|---|---|---|---|---|
| D-02 | 4-Methoxy-2,6-dimethylphenyl-1-sulfonyl chloride (C-03) | GP I | 62% (12.0 mmol) | |
| D-03 | 4-Methoxy-2,6-dimethylphenyl-1-sulfonyl chloride (C-03) | GP I | 53% (10.3 mmol) | |
| D-04 | 4-Chloro-2,5-dimethylphenyl-1-sulfonyl chloride (C-02) | GP I | 62% (17.7 mmol) | |
| D-05 | 4-Methoxy-2,6-dimethylphenyl-1-sulfonyl chloride (C-03) | GP I | 69% (17.4 mmol) | |

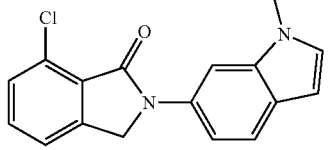

TABLE 1-continued

| | | | | | |
|---|---|---|---|---|---|
| | D-06 | 2-(Trifluoromethyl)phenyl-1-sulfonyl chloride (C-01) | GP I | 92% (16.9 mmol) | |
| | D-07 | Naphthalene-1-sulfonyl chloride (C-04) | GP I | 43% (7.8 mmol) | (a1) |
| | D-08 | 4-Chloro-2,5-dimethylphenyl-1-sulfonyl chloride (C-02) | GP I | 52% (14.7 mmol) | |
| | D-09 | 2-(Trifluoromethyl)phenyl-1-sulfonyl chloride (C-01) | GP I | 48% (10.1 mmol) | |
| | D-10 | 4-Chloro-2,5-dimethylphenyl-1-sulfonyl chloride (C-02) | GP I | 49% (9.5 mmol) | |
| | D-11 | 2-(Trifluoromethyl)phenyl-1-sulfonyl chloride (C-01) | GP I | 60% (13.7 mmol) | |
| | D-12 | 4-Chloro-2,5-dimethylphenyl-1-sulfonyl chloride (C-02) | GP I | 84% (21.3 mmol) | |
| | D-13 | 2-(Trifluoromethyl)phenyl-1-sulfonyl chloride (C-01) | GP I | 42% (8.5 mmol) | |
| | D-14 | 4-Methoxy-2,6-dimethylphenyl-1-sulfonyl chloride (C-03) | GP I | 17% (4.3 mmol) | |
| | D-15 | | | | See E-15 |
| | D-16 | | | | See E-16 |
| | D-17 | | | | See E-17 |
| | D-18 | Naphthalene-1-sulfonyl chloride (C-04) | GP I | 71% (13.0 mmol) | |
| | D-19 | | | | See E-19 |

(a1) The crude product was taken up in 70 ml dichloromethane. A solid was precipitated which was siphoned off and washed with a little dichloromethane. The parent liquor was concentrated and purified by column chromatography.

4) Synthesis of Sulfonylated Indole Acids E

General Method for the Synthesis of Sulfonylated Indole Acids E

Scheme 1: Synthesis of sulfonylated indole acids E

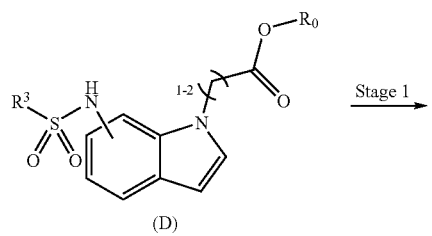

(D)

(E)

General procedure GP III: Potassium hydroxide (5 to 9 equiv.) and water were added to a solution of ester D (1 equiv.) in methanol/tetrahydrofuran with ice cooling. The mixture was stirred at room temperature for 5 hours, diluted with water, washed 3 times with diethyl ether and adjusted to ~pH 4 with 6N hydrochloric acid. The solid that was precipitated was filtered out, washed with a little water and dried.

TABLE 2

Synthesis of sulfonylated indole acids E

| Amino acid no. | Structure | Name |
|---|---|---|
| E-02 | 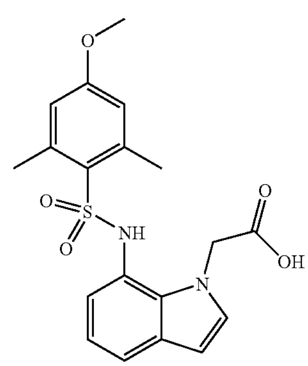 [SMILES: COc1cc(C)c(S(=O)(=O)Nc2cccc3ccn(CC(=O)O)c23)c(C)c1] | 2-[7-[[(4-Methoxy-2,6-dimethyl-phenyl)sulfonyl]amino]-1H-indol-1-yl]acetic acid (E-02) |

TABLE 2-continued

| | | |
|---|---|---|
| E-03 | 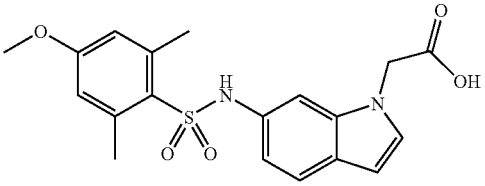 [SMILES: COc1cc(C)c(S(=O)(=O)Nc2ccc3ccn(CC(=O)O)c3c2)c(C)c1] | 2-[6-[[(4-Methoxy-2,6-dimethyl-phenyl)sulfonyl]amino]-1H-indol-1-yl]acetic acid (E-03) |
| E-04 | 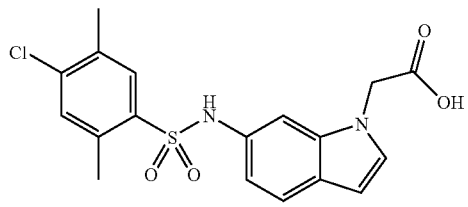 [SMILES: Cc1cc(S(=O)(=O)Nc2ccc3ccn(CC(=O)O)c3c2)c(C)cc1Cl] | 2-[6-[[(4-Chloro-2,5-dimethyl-phenyl)sulfonyl]amino]-1H-indol-1-yl]acetic acid (E-04) |
| E-05 | 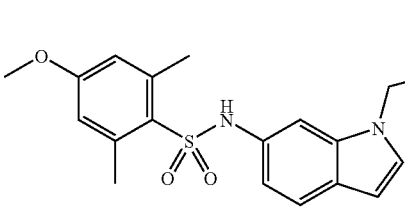 | 3-[6-[[(4-Methoxy-2,6-dimethyl-phenyl)sulfonyl]amino]-1H-indol-1-yl]propionic acid (E-05) |
| E-06 | 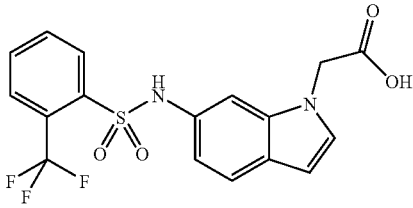 [SMILES: O=C(O)Cn1ccc2ccc(NS(=O)(=O)c3ccccc3C(F)(F)F)cc21] | 2-[6-[[[2-(Trifluoromethyl)-phenyl]sulfonyl]amino]-1H-indol-1-yl]acetic acid (E-06) |
| E-07 | 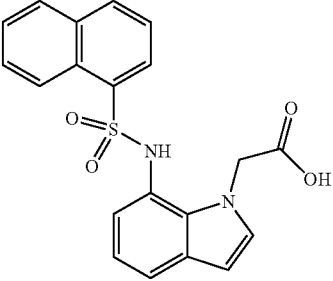 [SMILES: O=C(O)Cn1ccc2cccc(NS(=O)(=O)c3cccc4ccccc34)c21] | 2-[7-[(Naphthalen-1-ylsulfonyl)amino]-1H-indol-1-yl]acetic acid (E-07) |
| E-08 | 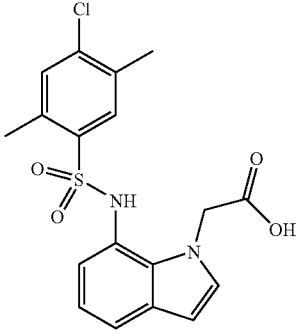 [SMILES: Cc1cc(S(=O)(=O)Nc2cccc3ccn(CC(=O)O)c23)c(C)cc1Cl] | 2-[7-[[(4-Chloro-2,5-dimethyl-phenyl)sulfonyl]amino]-1H-indol-1-yl]acetic acid (E-08) |

TABLE 2-continued

| | | |
|---|---|---|
| E-09 | | 3-[7-[[[2-(Trifluoromethyl)-phenyl]sulfonyl]amino]-1H-indol-1-yl] propionic acid (E-09) |
| E-10 | | 3-[7-[[(4-Chloro-2,5-dimethyl-phenyl)sulfonyl]amino]-1H-indol-1-yl] propionic acid (E-10) |
| E-11 | | 3-[6-[[[2-(Trifluoromethyl)-phenyl]sulfonyl]amino]-1H-indol-1-yl] propionic acid (E-11) |
| E-12 | | 3-[6-[[(4-Chloro-2,5-dimethyl-phenyl)sulfonyl]amino]-1H-indol-1-yl] propionic acid (E-12) |
| E-13 | | 2-[7-[[[2-(Trifluoromethyl)-phenyl]sulfonyl]amino]-1H-indol-1-yl] acetic acid (E-13) |
| E-14 | | 3-[7-[[(4-Methoxy-2,6-dimethyl-phenyl)sulfonyl]amino]-1H-indol-1-yl] propionic acid (E-14) |

TABLE 2-continued

| | | |
|---|---|---|
| E-15 | | 3-[6-(4-Chloro-3-oxo-1,2-dihydro-isoindol-2-yl)-1H-indol-1-yl] propionic acid (E-15) |
| E-16 | | 2-[6-(4-Chloro-3-oxo-1,2-dihydro-isoindol-2-yl)-1H-indol-1-yl] acetic acid (E-16) |
| E-17 | | 3-[7-(4-Chloro-3-oxo-1,2-dihydro-isoindol-2-yl)-1H-indol-1-yl] propionic acid (E-17) |
| E-18 | | 2-[6-[(Naphthalen-1-ylsulfonyl)amino]-1H-indol-1-yl] acetic acid (E-18) |
| E-19 | | 2-[7-(4-Chloro-3-oxo-1,2-dihydro-isoindol-2-yl)-1H-indol-1-yl] acetic acid (E-19) |
| E-20 | | 2-(6-(8-Chloro-4-methyl-1-oxopyrrolo[3,4-b]indol-2(1H,3H,4H)-yl)-1H-indol-1-yl)acetic acid (E-20) |

TABLE 2-continued

| | | |
|---|---|---|
| E-21 | 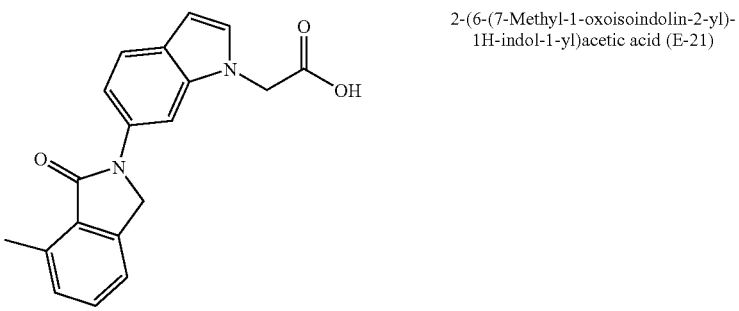 | 2-(6-(7-Methyl-1-oxoisoindolin-2-yl)-1H-indol-1-yl)acetic acid (E-21) |
| E-22 | 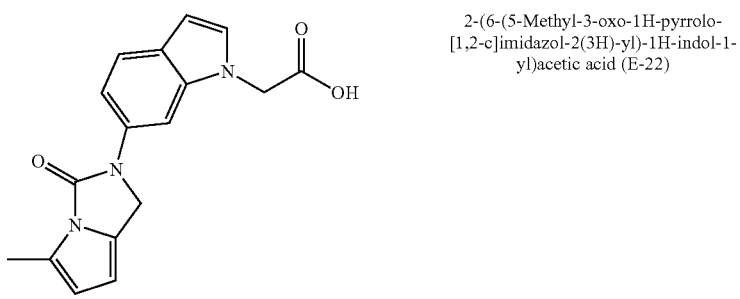 | 2-(6-(5-Methyl-3-oxo-1H-pyrrolo-[1,2-c]imidazol-2(3H)-yl)-1H-indol-1-yl)acetic acid (E-22) |
| E-23 | 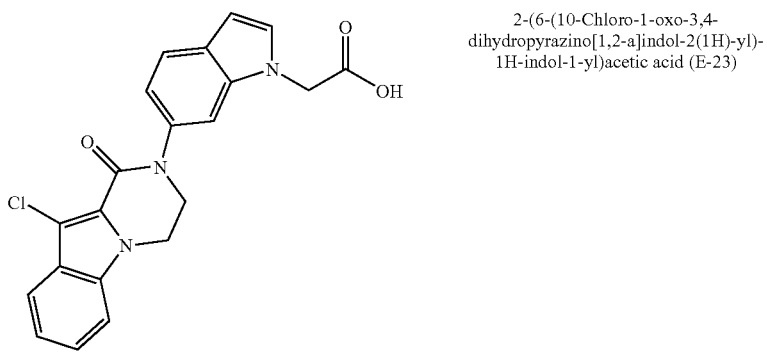 | 2-(6-(10-Chloro-1-oxo-3,4-dihydropyrazino[1,2-a]indol-2(1H)-yl)-1H-indol-1-yl)acetic acid (E-23) |
| E-24 | 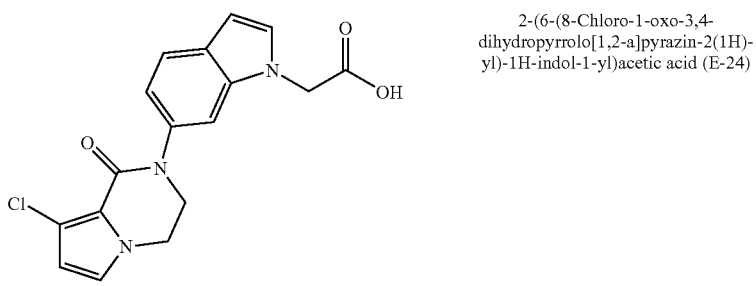 | 2-(6-(8-Chloro-1-oxo-3,4-dihydropyrrolo[1,2-a]pyrazin-2(1H)-yl)-1H-indol-1-yl)acetic acid (E-24) |

| Amino acid no. | Amino acid ester (D) | Synthesis by | Yield | Note |
|---|---|---|---|---|
| E-02 | tert-Butyl 2-(7-(4-methoxy-2,6-dimethylphenylsulfonamido)-1H-acetic acid (D-02) | GP III | 95% (11.3 mmol) | |
| E-03 | tert-Butyl 2-(6-(4-methoxy-2,6-dimethylphenylsulfonamido)-1H-indol-1-yl) acetic acid (D-03) | GP III | 96% (9.9 mmol) | |
| E-04 | tert-Butyl 2-(6-(4-chloro-2,5-dimethylphenylsulfonamido)-1H-indol-1-yl) acetic acid (D-04) | GP III | 98% (17.4 mmol) | |
| E-05 | Methyl 3-(6-(4-methoxy-2,6-dimethylphenylsulfonamido)-1H-indol-1-yl) propionic acid (D-05) | GP III | 96% (16.3 mmol) | |

TABLE 2-continued

| | | | | |
|---|---|---|---|---|
| E-06 | tert-Butyl 2-(6-(2-(trifluoromethyl)phenylsulfonamido)-1H-indol-1-yl) acetic acid (D-06) | GP III | 107% (18.0 mmol) | (a2) |
| E-07 | tert-Butyl 2-(7-(naphthalene-1-sulfonamido)-1H-indol-1-yl) acetic acid (D-07) | GP III | 110% (8.3 mmol) | (a2) |
| E-08 | tert-Butyl 2-(7-(4-chloro-2,5-dimethylphenylsulfonamido)-1H-indol-1-yl) acetic acid (D-08) | GP III | 104% (15.3 mmol) | |
| E-09 | Methyl 3-(7-(2-(trifluoromethyl)phenylsulfonamido)-1H-indol-1-yl) propionic acid (D-09) | GP III | 97% (9.3 mmol) | |
| E-10 | Methyl 3-(7-(4-chloro-2,5-dimethylphenylsulfonamido)-1H-indol-1-yl) propionic acid (D-10) | GP III | 101% (9.0 mmol) | |
| E-11 | Methyl 3-(6-(2-(trifluoromethyl)phenylsulfonamido)-1H-indol-1-yl) propionic acid (D-11) | GP III | 105% (14.3 mmol) | (a2) |
| E-12 | Methyl 3-(6-(4-chloro-2,5-dimethylphenylsulfonamido)-1H-indol-1-yl) propionic acid (D-12) | GP III | 96% (20.4 mmol) | (a2) |
| E-13 | tert-Butyl 2-(7-(2-(trifluoromethyl)phenylsulfonamido)-1H-indol-1-yl) acetic acid (D-13) | GP III | 96% (8.1 mmol) | (a2) |
| E-14 | Methyl 3-(7-(4-methoxy-2,6-dimethylphenylsulfonamido)-1H-indol-1-yl) propionic acid (D-14) | GP III | 88% (5.0 mmol) | |
| E-15 | | | | See E-15 |
| E-16 | | | | See E-16 |
| E-17 | | | | See E-17 |
| E-18 | tert-Butyl 2-(6-(naphthalene-1-sulfonamido)-1H-indol-1-yl) acetic acid (D-18) | GP III | 92% (11.8 mmol) | |
| E-19 | | | | See E-19 |
| E-20 | | | | See E-20 |
| E-21 | | | | See E-21 |
| E-22 | | | | See E-22 |
| E-23 | | | | See E-23 |
| E-24 | | | | See E-24 |

(a2) After adjusting to pH 4 a brown oil was precipitated which was extracted 3 times with ethyl acetate. The organic phases were combined, dried over magnesium sulfate and concentrated under reduced pressure.

Structural unit E-15: 3-(6-(7-Chloro-1-oxoisoindolin-2-yl)-1H-indol-1-yl) propionic acid

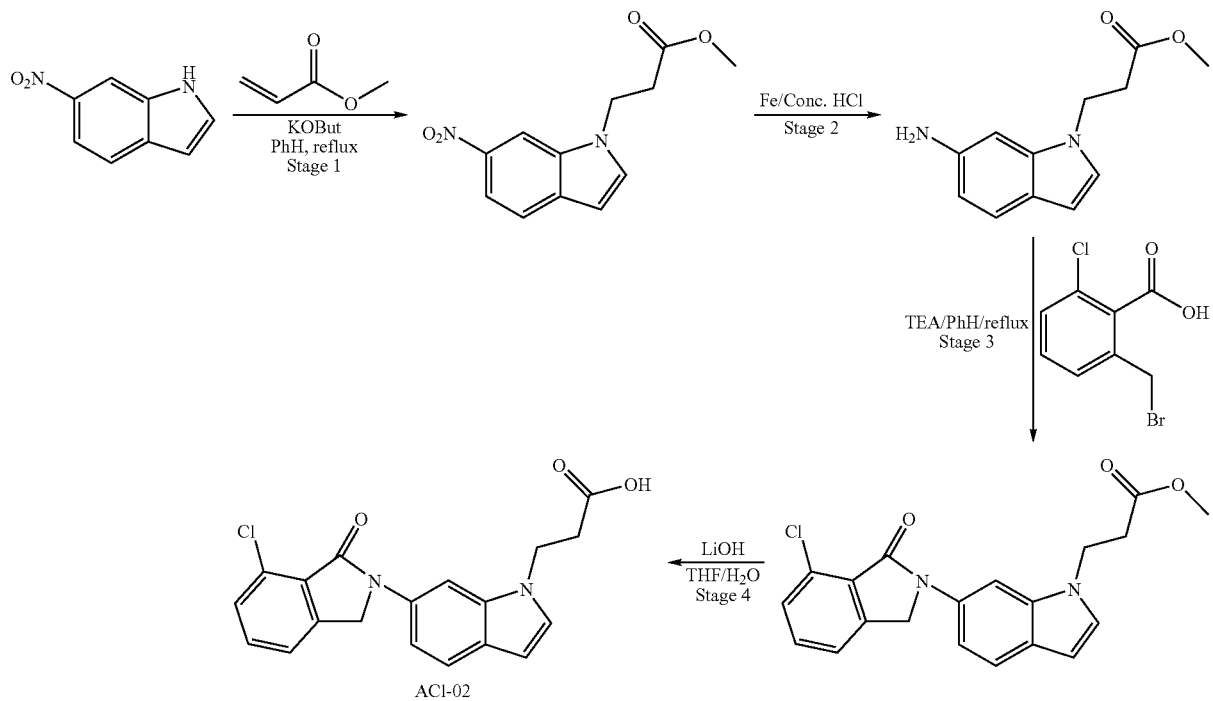

ACl-02

Stage 1: A solution of 6-nitroindole (3 mmol) in dry benzene (15 ml) was added slowly to a solution of potassium tert-butanolate (1 eq.) in dry benzene (5 ml) in an ice bath under a nitrogen atmosphere. Then methyl acrylate (2 eq.) was added and the batch was refluxed for 16 h. After cooling to room temperature the reaction mixture was diluted with water and adjusted to pH 4 with concentrated HCl. The reaction mixture was extracted with dichloromethane. The organic phase was washed successively with water and saturated NaCl solution, dried over anhydrous sodium sulfate and concentrated to small volume under reduced pressure. The crude product was purified by column chromatography with silica gel (DCM/MeOH) and the desired first-stage product was obtained. Yield: 53%

Stage 2: A mixture of the first-stage product (0.9 mmol), iron powder (3.3 eq.) and concentrated HCl (0.1 ml) was refluxed in ethanol (5 ml) for 4 h. After cooling to RT it was filtered through celite. The filtrate was concentrated to small volume, the concentrated mass was taken up with water and adjusted to pH 4 with concentrated HCl. The mixture was extracted with dichloromethane. The organic phase was washed successively with water and saturated NaCl solution, dried over anhydrous sodium sulfate and concentrated to small volume under reduced pressure. The crude product obtained was used directly in the next stage. Yield: 90%

Stage 3: A mixture of the second-stage product (0.45 mmol), 2-bromomethyl-6-chlorobenzoate (1 eq.) and TEA (1.2 eq.) was refluxed in benzene (10 ml) under a nitrogen atmosphere for 16 h. The reaction mixture was concentrated to small volume and the concentrated mass was taken up with DCM. The organic phase was washed successively with water and saturated NaCl solution, dried over anhydrous sodium sulfate and concentrated to small volume under reduced pressure. The crude product was purified by column chromatography with silica gel (DCM/MeOH) and the desired third-stage product was obtained. Yield: 48.5%

Stage 4: LiOH.H$_2$O (5 eq.) was added to a suspension of the third-stage product (0.5 mmol) in methanol (40 ml), tetrahydrofuran (40 ml) and water (30 ml) and the reaction mixture was stirred overnight at 25° C. Methanol and THF were drawn off completely. The aqueous phase was acidified with 1(N)HCl and then filtered. The white solid was stirred for 1 h in a mixture of 350 ml acetone and 50 ml methanol. After filtration the white solid was dried under reduced pressure and the desired pure product E-15 was obtained. Yield: 61%

Structural unit E-16: 2-(6-(7-Chloro-1-oxoisoindolin-2-yl)-1H-indol-1-yl)acetic acid

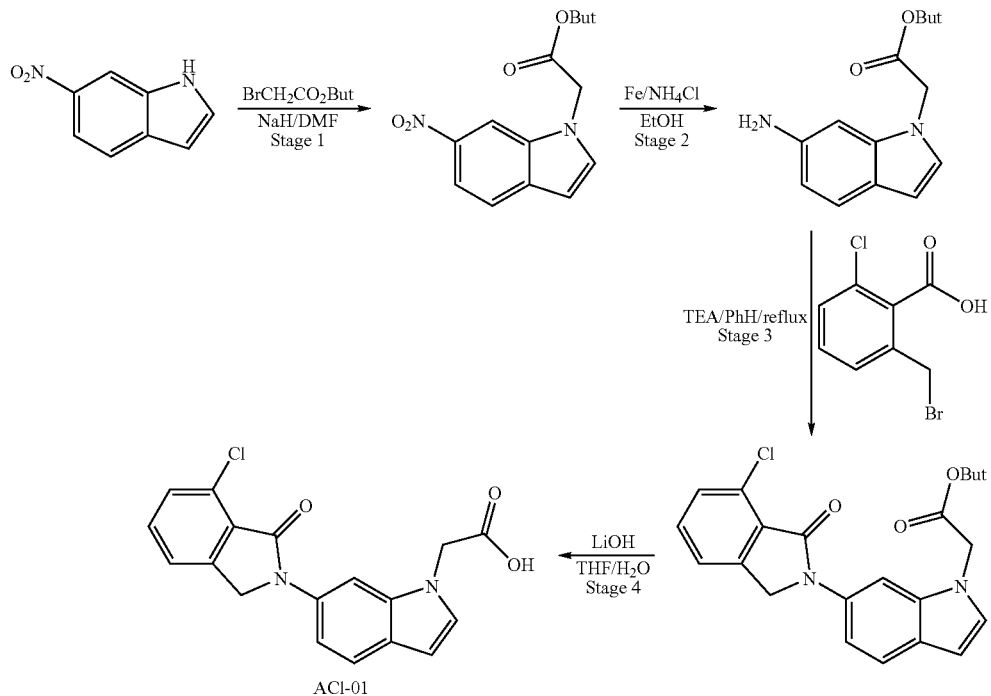

ACI-01

Stage 1: 6-Nitroindole (3 mmol) dissolved in DMF (5 ml) was added to a suspension of sodium hydride (1.5 eq.) in DMF (5 ml) at 0° C. and stirred for 30 min. Then tert-butylbromoacetate (1.2 eq.) was added and the mixture was stirred at RT for 15 h. The batch was quenched with saturated NH$_4$Cl solution and extracted with ethyl acetate. The organic phase was washed successively with water and saturated NaCl solution, dried over anhydrous sodium sulfate and concentrated to small volume under reduced pressure. The crude product was purified by column chromatography with silica gel (ethyl acetate/hexane) and the desired first-stage product was obtained. Yield: 47%

Stage 2: A mixture of the first-stage product (1.44 mmol), iron powder (4 eq.) and ammonium chloride (0.4 eq.) was refluxed in ethanol (10 ml) for 4 h. After cooling to RT it was filtered through celite. The filtrate was concentrated to small volume and the concentrated mass was taken up with water. It was extracted with dichloromethane. The organic phase was washed successively with water and saturated NaCl solution, dried over anhydrous sodium sulfate and concentrated to small volume under reduced pressure. The crude product was purified by recrystallization with ethyl acetate/hexane. Yield: 61%

Stage 3: A mixture of the second-stage product (25 mmol), 2-bromomethyl-6-chlorobenzoate (1.2 eq.) and TEA (1.2 eq.) was refluxed in benzene (150 ml) under a nitrogen atmosphere for 16 h. The reaction mixture was concentrated to small volume and the concentrated mass was taken up with DCM. The organic phase was washed successively with water and saturated NaCl solution, dried over anhydrous sodium sulfate and concentrated to small volume under reduced pressure. The crude product was purified by column chromatography with silica gel (DCM/MeOH) and the desired third-stage product was obtained. Yield: 42%

Stage 4: LiOH.H$_2$O (5 eq.) was added to a suspension of the third-stage product (15 mmol) in methanol (25 ml), tetrahydrofuran (25 ml) and water (50 ml) and the reaction mixture was stirred overnight at 25° C. Methanol and THF were drawn off completely. The aqueous phase was acidified with 1(N)HCl and then filtered. The white solid was dried under reduced pressure and the desired product E-16 was obtained. Yield: 98%

Structural unit E-17: 3-(7-(7-Chloro-1-oxoisoindolin-2-yl)-1H-indol-1-yl) propionic acid Stage 2: Pd/C 10% was added to a solution of the first-stage product (1.2 mmol) in methanol (10 ml) under a nitrogen atmosphere and the mixture was hydrogenated for 16 h under a pressure of 2 bar. The batch was filtered and the filtrate concentrated to small volume. The second-stage product was obtained and was used directly in the next stage with no further purification. Yield: 63.5%

Stage 3: A mixture of the second-stage product (0.45 mmol), 2-bromomethyl-6-chlorobenzoate (1 eq.) and TEA (1.2 eq.) was refluxed in benzene (10 ml) under a nitrogen atmosphere for 16 h. The reaction mixture was concentrated to small volume and the concentrated mass was taken up with DCM. The organic phase was washed successively with water and saturated NaCl solution, dried over anhydrous sodium sulfate and concentrated to small volume under reduced pressure. The crude product was purified by column chromatography with silica gel (DCM/MeOH) and the desired third-stage product was obtained. Yield: 40%

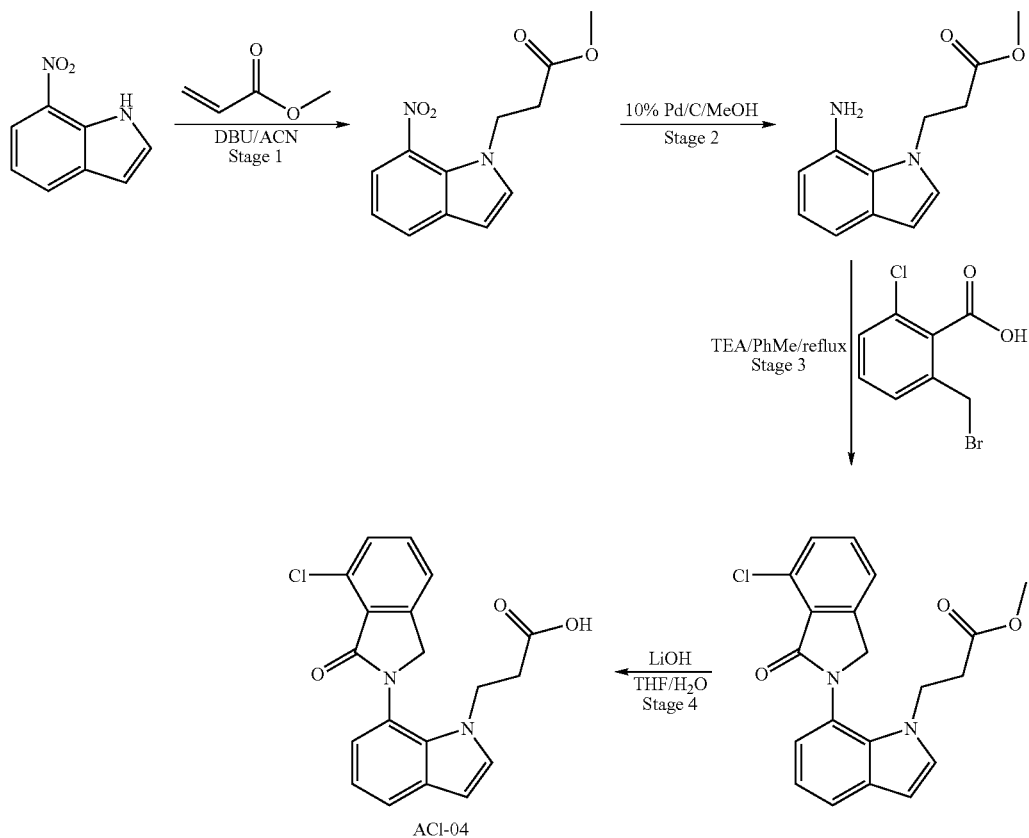

Stage 1: The DBU was added slowly to a solution of 7-nitroindole (6 mmol) in acetonitrile (10 ml) at 0° C. The solution was stirred for 20 h at RT. Then the reaction mixture was concentrated and the crude mass was diluted with ethyl acetate. The ethyl acetate phase was washed with saturated NH$_4$Cl solution, water and saturated NaCl solution, dried over anhydrous sodium sulfate and concentrated to small volume under reduced pressure. The crude product was purified by column chromatography with silica gel (ethyl acetate/hexane) and the desired first-stage product was obtained. Yield: 35%

Stage 4: LiOH.H$_2$O (5 eq.) was added to a suspension of the third-stage product (0.5 mmol) in methanol (40 ml), tetrahydrofuran (40 ml) and water (30 ml) and the reaction mixture was stirred overnight at 25° C. Methanol and THF were drawn off completely. The aqueous phase was acidified with 1(N)HCl and then filtered. The white solid was stirred for 1 h in a mixture of 350 ml acetone and 50 ml methanol. After filtration the white solid was dried under reduced pressure and the desired pure product E-17 was obtained. Yield: 55%

Structural unit E-19: 2-(7-(7-Chloro-1-oxoisoindo-lin-2-yl)-1H-indol-1-yl)acetic acid

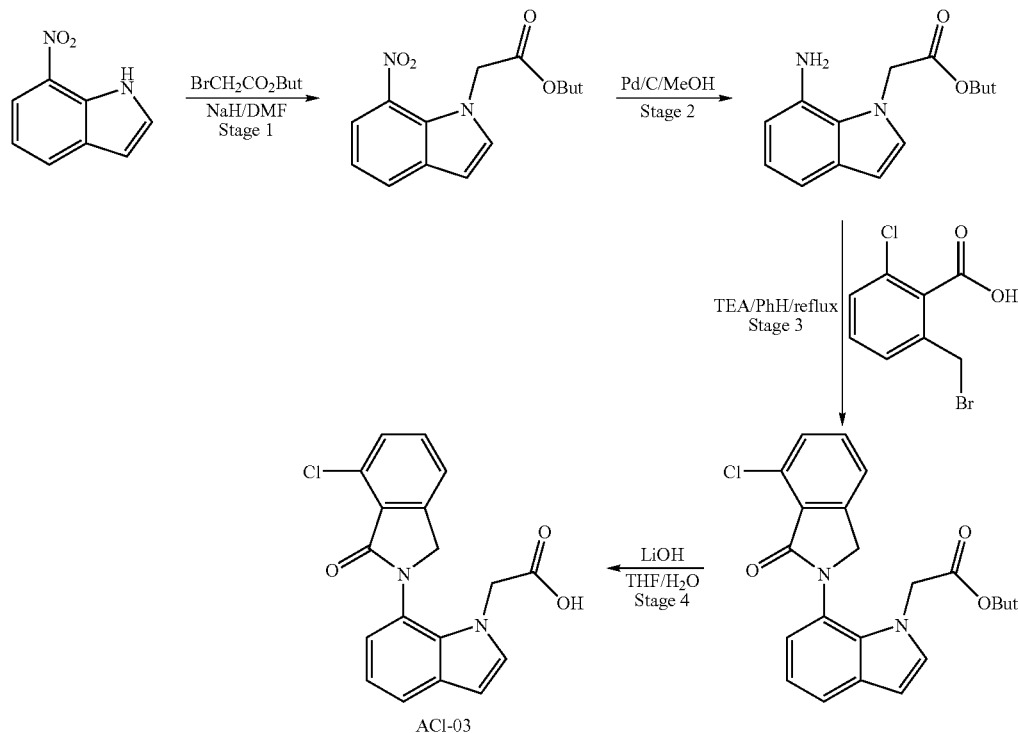

Stage 1: 6-Nitroindole (30 mmol) dissolved in DMF (100 ml) was added to a suspension of sodium hydride (1.5 eq.) in DMF (5 ml) at 0° C. and stirred for 30 min. Then tert-butyl-bromoacetate (1.2 eq.) was added and the mixture was stirred at RT for 15 h. The batch was quenched with saturated $NH_4Cl$ solution and extracted with ethyl acetate. The organic phase was washed successively with water and saturated NaCl solution, dried over anhydrous sodium sulfate and concentrated to small volume under reduced pressure. The crude product was purified by column chromatography with silica gel (ethyl acetate/hexane) and the desired first-stage product was obtained. Yield: 82%

Stage 2: Pd/C 10% was added to a solution of the first-stage product (1.44 mmol) in methanol (10 ml) under a nitrogen atmosphere and the mixture was hydrogenated for 16 h under a pressure of 2 bar. The batch was filtered and the filtrate concentrated to small volume. The second-stage product was obtained and was used directly in the next stage with no further purification. Yield: 89%

Stage 3: A mixture of the second-stage product (25 mmol), 2-bromomethyl-6-chlorobenzoate (1.2 eq.) and TEA (1.2 eq.) was refluxed in benzene (150 ml) under a nitrogen atmosphere for 16 h. The reaction mixture was concentrated to small volume and the concentrated mass was taken up with DCM. The organic phase was washed successively with water and saturated NaCl solution, dried over anhydrous sodium sulfate and concentrated to small volume under reduced pressure. The crude product was purified by column chromatography with silica gel (DCM/MeOH) and the desired third-stage product was obtained. Yield: 48.5%

Stage 4: $LiOH.H_2O$ (5 eq.) was added to a suspension of the third-stage product (15 mmol) in methanol (25 ml), tetrahydrofuran (25 ml) and water (50 ml) and the reaction mixture was stirred overnight at 25° C. Methanol and THF were drawn off completely. The aqueous phase was acidified with 1(N)HCl and then filtered. The white solid was stirred for 1 h in a mixture of 350 ml acetone and 50 ml methanol. After filtration the white solid was dried under reduced pressure and the desired pure product E-18 was obtained. Yield: 80%

Structural unit E-20: 2-(6-(8-Chloro-4-methyl-1-oxopyrrolo[3,4-b]indol-2(1H,3H,4H)-yl)-1H-indol-1-yl)acetic acid

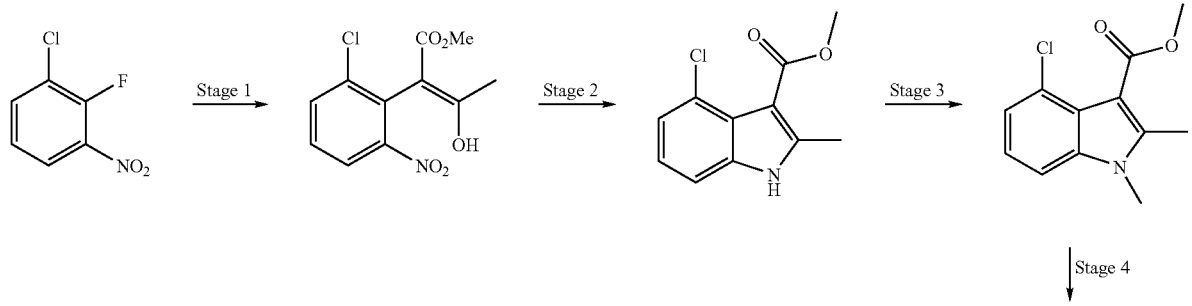

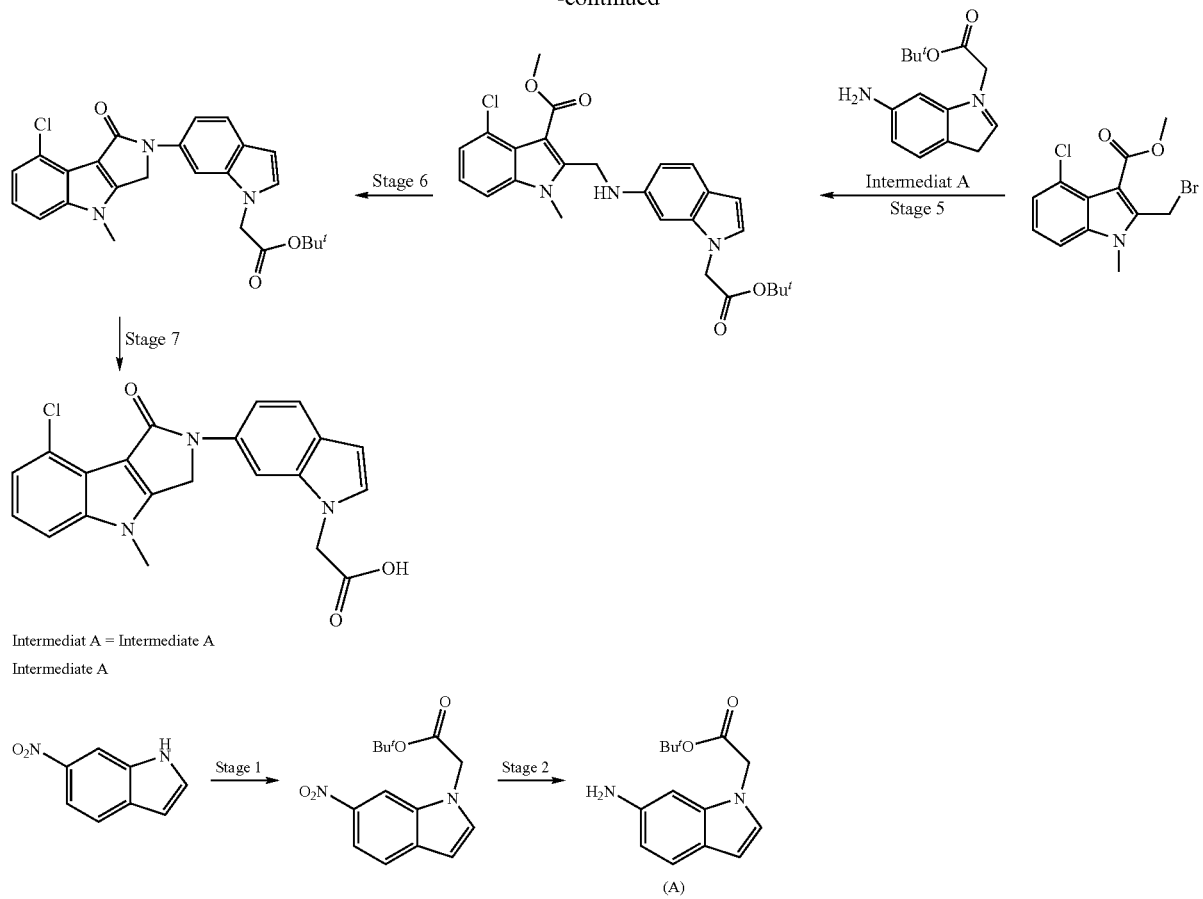

Intermediat A = Intermediate A
Intermediate A

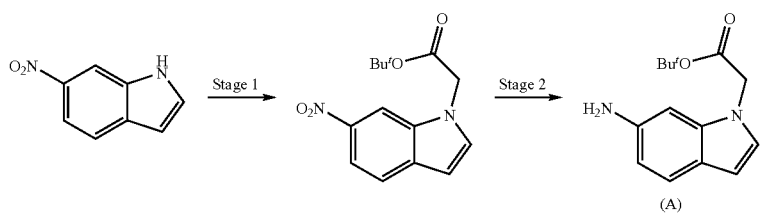

(A)

Stage 1: (E)-Methyl 2-(2-chloro-6-nitrophenyl)-3-hydroxybut-2-enoate

Methyl acetoacetate (59.82 mmol, 2.1 equiv.) was added dropwise at 0° C. to a suspension of NaH (65.52 mmol, 2.3 equiv.) in DMF (40 ml). Then the mixture was stirred for 10 min and subsequently heated to 25° C. 2-Fluoro-3-chloronitrobenzene (28.49 mmol, 1.0 equiv.) was cooled with an ice bath in a reaction flask, and the NaH suspension was added. Then stirring was carried out for 16 h at 25° C. 2 M HCl (5 ml) and water (10 ml) were then added, and extraction with diethyl ether (3×20 ml) was carried out. The combined organic phases were washed with water (10 ml) and sat. NaCl solution (20 ml), dried over $Na_2SO_4$ and reduced under reduced pressure. The residue was purified by column chromatography (5% ethyl acetate in hexane). Yield: 51%

Stage 2: Methyl 4-chloro-2-methyl-1H-indole-3-carboxylate (E)-Methyl 2-(2-chloro-6-nitrophenyl)-3-hydroxybut-2-enoate (14.76 mmol, 1.0 equiv.) was dissolved in acetic acid (96 ml), and a solution of $TiCl_3$ (20%-w/w in 2 N HCl, 71.6 ml) was added, with stirring. The mixture was then heated for 5-10 min at 90° C. The reaction mixture was cooled with an ice bath and diluted with water and DCM/methanol (9:1, 100 ml). The phases were separated and the organic phase was washed with water and sat. NaCl solution. Drying over $Na_2SO_4$ was then carried out, followed by concentration under reduced pressure. The product was crystallized from hexane. Yield: 91%

Stage 3: Methyl 4-chloro-1,2-dimethyl-1H-indole-3-carboxylate

Methyl 4-chloro-2-methyl-1H-indole-3-carboxylate (13.45 mmol, 1.0 equiv.) was dissolved in DMF (7 ml) and added at 0° C. to a suspension of NaH (26.90 mmol, 2.0 equiv.) in DMF (13 ml). The mixture was then stirred for 30 min. Methyl iodide (20.17 mmol, 1.5 equiv.) was added dropwise at 0° C. and stirring was carried out for 2 h at 25° C. The reaction mixture was diluted with $NH_4Cl$ solution (20 ml) and extracted with ethyl acetate (3×50 ml). The combined organic phases were washed with water and sat. NaCl solution (in each case 50 ml), dried over $Na_2SO_4$ and concentrated to dryness under reduced pressure. Yield: 72%

Stage 4: Methyl 2-(bromo-methyl)-4-chloro-1-methyl-1H-indole-3-carboxylate

Methyl 4-chloro-1,2-dimethyl-1H-indole-3-carboxylate (9.70 mmol, 1.0 equiv.) was dissolved in $CCl_4$ (97 ml), and NBS (9.70 mmol, 1.0 equiv.) and benzoyl peroxide (0.19 mmol, 0.02 equiv.) were added. The mixture was heated for 1 h at 85° C. The resulting succinimide was filtered out, the filtrate was concentrated, and the residue was purified by column chromatography (20% ethyl acetate in hexane). Yield: 48%

Stage 5: Methyl 2-((1-(2-tert-butoxy-2-oxoethyl)-1H-indol-6-ylamino)methyl)-4-chloro-1-methyl-1H-indole-3-carboxylate Methyl 2-(bromo-methyl)-4-chloro-1-methyl-1H-indole-3-carboxylate (1.10 mmol, 1.0 equiv.) and tert-butyl 2-(6-amino-1H-indol-1-yl)acetate (intermediate A) (1.10 mmol, 1.0 equiv.) were dissolved in benzene (5 ml) and triethylamine (1.3 mmol, 1.2 equiv.) and refluxed for 16 h. The reaction mixture was cooled to 25° C., diluted with ethyl acetate and washed with water and sat. NaCl solution. Drying over Na₂SO₄ was then carried out, followed by concentration under reduced pressure. The crude product was purified by column chromatography (40% ethyl acetate in hexane). Yield: 55%

Stage 6: tert-Butyl 2-(6-(8-chloro-4-methyl-1-oxopyrrolo[3,4-b]indol-2(1H,3H,4H)-yl)-1H-indol-1-yl)acetate Methyl 2-((1-(2-tert-butoxy-2-oxoethyl)-1H-indol-6-ylamino)methyl)-4-chloro-1-methyl-1H-indole-3-carboxylate (2.416 mmol, 1 equiv.) was dissolved in dichloromethane (36 ml), and (CH₃)₃Al (2 M solution in toluene, 4.83 mmol) was added at 0° C., under nitrogen. After 10 min, the reaction mixture was heated to 25° C. and then stirred for 2 h. The reaction mixture was diluted with dichloromethane and hydrolysed with 2 M HCl. The phases were separated, and the organic phase was washed with water and sat. NaCl solution (in each case 10 ml). Drying over Na₂SO₄ was then carried out, followed by concentration under reduced pressure. The product was crystallized from ethyl acetate. Yield: 89%

Stage 7: 2-(6-(8-Chloro-4-methyl-1-oxopyrrolo[3,4-b]indol-2(1H,3H,4H)-yl)-1H-indol-1-yl)acetic acid tert-Butyl 2-(6-(8-chloro-4-methyl-1-oxopyrrolo[3,4-b]indol-2(1H,3H,4H)-yl)-1H-indol-1-yl)acetate (1.6 mmol, 1 equiv.) was dissolved in DCM (40 ml); TFA (16 ml) was added and the mixture was stirred for 2 h at 25° C. The solvent was reduced under reduced pressure, dichloromethane was added 2× to the residue, and in each case concentration to dryness again was carried out. The residue was used in the next step without being purified further.

Intermediate A

Stage 1: tert-Butyl 2-(6-nitro-1H-indol-1-yl)acetate

NaH (4.5 mmol, 1.5 equiv.) was suspended in DMF (5 ml), and 6-nitro-indole (3 mmol, 1 equiv.), dissolved in DMF (5 ml), was added at 0° C. The mixture was stirred for 30 min. Then tert-butyl bromoacetate (3.6 mmol, 1.2 equiv.) was added and the mixture was stirred for 15 h at 25° C. The reaction mixture was hydrolysed with ammonium chloride and extracted with ethyl acetate (3×20 ml). The combined organic phases were washed with water and sat. NaCl solution (in each case 20 ml), dried over Na₂SO₄ and concentrated under reduced pressure. The crude product was purified by column chromatography. Yield: 47%

Stage 2: tert-Butyl 2-(6-amino-1H-indol-1-yl)acetate

A mixture of tert-butyl 2-(6-nitro-1H-indol-1-yl)acetate (1.44 mmol, 1 equiv.), iron powder (5.76 mmol, 4 equiv.), ammonium chloride (4 equiv.) and ethanol (10 ml) was stirred for 4 h at boiling temperature. The reaction mixture was cooled to 25° C. and filtered over celite. The filtrate was concentrated, diluted with water (50 ml) and extracted with dichloromethane (3×20 ml). The combined organic phases were washed with water and sat. NaCl solution (in each case 10 ml), dried over Na₂SO₄ and concentrated under reduced pressure. For purification, the product was recrystallized from ethyl acetate/hexane. Yield: 61%

Structural unit E-21: 2-(6-(7-Methyl-1-oxoisoindolin-2-yl)-1H-indol-1-yl)acetic acid

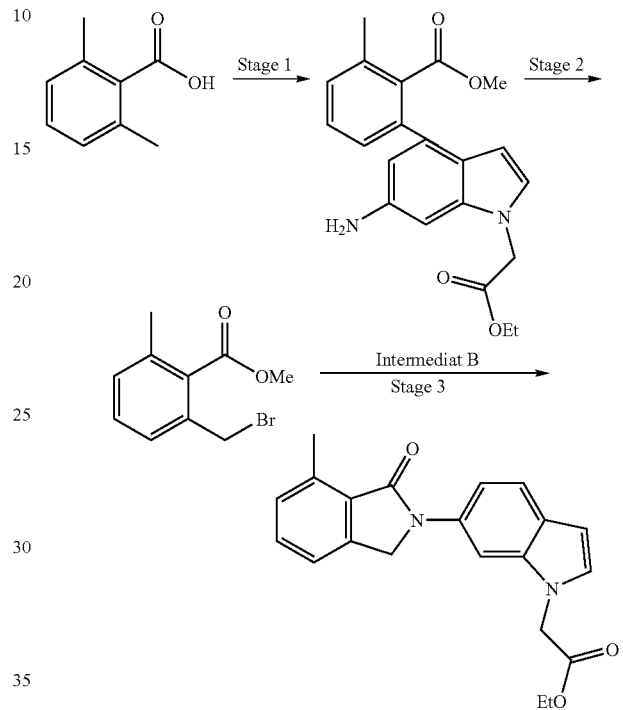

Intermediat B = Intermediate B
Intermediate B

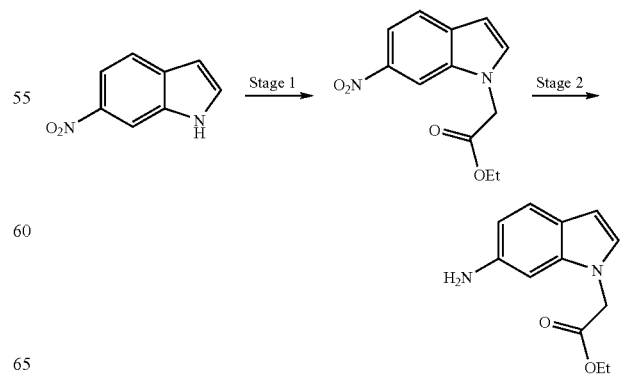

Stage 1: Methyl 2,6-dimethylbenzoate

K$_2$CO$_3$ (10.1 mmol, 1.5 equiv.) and dimethyl sulfate (7.4 mmol, 1.1 equiv.) were added at 25° C. to a solution of 2,6-dimethylbenzoic acid (6.7 mmol, 1 equiv.), and the mixture was stirred for 1 h. The solvent was reduced under reduced pressure, the residue was taken up in ethyl acetate (100 ml), and water (20 ml) was added. The phases were separated and the aqueous phase was extracted with ethyl acetate (2×50 ml). The combined organic phases were washed with sat. NaCl solution, dried over Na$_2$SO$_4$ and concentrated under reduced pressure. The crude product was used in the next stage without being purified further. Yield: quantitative

Stage 2: Methyl 2-(bromo-methyl)-6-methylbenzoate

NBS (40.85 mmol, 1 equiv.) and benzoyl peroxide (10.21 mmol, 0.25 equiv.) were added to a solution of methyl 2,6-dimethylbenzoate (40 mmol, 1 equiv.) in CCL$_4$ (75 ml), and the mixture was heated for 20 min at boiling temperature. The reaction mixture was filtered out over celite and the filtrate was concentrated under reduced pressure. The residue was purified by column chromatography (1.5% ethyl acetate/hexane). Yield: 32%

Stage 3: Ethyl 2-(6-(7-methyl-1-oxoisoindolin-2-yl)-1H-indol-1-yl)acetate

Ethyl 2-(6-amino-1H-indol-1-yl)acetate (intermediate B) (7.66 mmol, 1 equiv.) was dissolved in benzene (30 ml), and methyl 2-(bromo-methyl)-6-methylbenzoate (8.42 mol, 1.1 equiv.) and TEA (9.19 mmol, 1.2 equiv.) were added at 25° C. and the mixture was refluxed for 12 h. The reaction mixture was reduced under reduced pressure and the residue was taken up in dichloromethane (30 ml), washed with water and sat. NaCl solution (5 ml), dried over sodium sulfate and concentrated under reduced pressure. The crude product was purified by column chromatography (10% ethyl acetate in hexane). Yield: 64%

Stage 4: 2-(6-(7-Methyl-1-oxoisoindolin-2-yl)-1H-indol-1-yl)acetic acid

NaOH (1.86 mmol, 1.3 equiv.), dissolved in water (6 ml), was added to a solution of ethyl 2-(6-(7-methyl-1-oxoisoindolin-2-yl)-1H-indol-1-yl)acetate (1.44 mmol, 1 equiv.) in THF/MeOH (1:1, 5 ml), and the mixture was stirred for 2 h at 25° C. The reaction solution was concentrated under reduced pressure, and the aqueous residue was adjusted to pH 3 with 1 M HCl and extracted with ethyl acetate (3×50 ml). The combined organic phases were dried over Na$_2$SO$_4$ and concentrated under reduced pressure. Yield: quantitative

Intermediate B

Stage 1: Ethyl 2-(6-nitro-1H-indol-1-yl)acetate

NaH (37 mmol, 2 equiv.) was taken up in DMF (25 ml) and cooled to 0° C. 6-Nitro-1H-indole (18.5 mmol, 1 equiv.) was added in portions, and the mixture was stirred for 1 h at 25° C. The reaction mixture was cooled to 0° C. again, ethyl bromoacetate (22.22 mmol, 1.2 equiv.) was added dropwise, and the mixture was stirred for 2 h at 25° C. The reaction mixture was then poured into ice-water and extracted with ethyl acetate (2×100 ml). The combined organic phases were washed with sat. NaCl solution (30 ml), dried over Na$_2$SO$_4$ and concentrated under reduced pressure. The product was crystallized from hexane and was used in the next step without being purified further. Yield: 57%

Stage 2: Ethyl 2-(6-amino-1H-indol-1-yl)acetate

A mixture of ethyl 2-(6-nitro-1H-indol-1-yl)acetate (20.96 mmol, 1 equiv.), iron powder (83.8 mmol, 4 equiv.), ammonium chloride (83.87 mmol, 1 equiv.) and ethanol/water (2.5:1, 56 ml) was stirred for 2 h at boiling temperature. The reaction mixture was cooled to 25° C. and filtered over celite. The filtrate was diluted with ethyl acetate and water, the phases were separated, and the organic phase was washed with sodium hydrogen carbonate solution and sat. NaCl solution, dried over Na$_2$SO$_4$ and concentrated under reduced pressure. The crude product was purified by column chromatography (15% ethyl acetate in hexane). Yield: 55%

Structural unit E-22: 2-(6-(5-Methyl-3-oxo-1H-pyrrolo[1,2-c]imidazol-2(3H)-yl)-1H-indol-1-yl)acetic acid

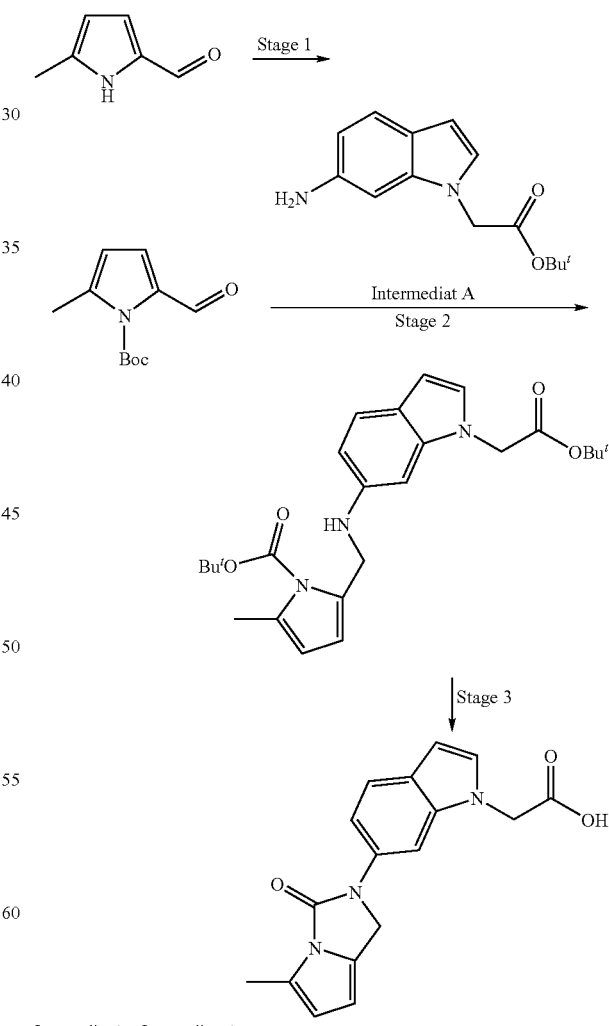

Intermediat A = Intermediate A

Stage 1: tert-Butyl 2-formyl-5-methyl-1H-pyrrole-1-carboxylate (Boc)$_2$O (5.498 mmol, 1.2 equiv.) was added at 0° C. to a solution of 5-methyl-1H-pyrrole-2-carbaldehyde (4.58 mmol, 1.0 equiv.) and DMAP (0.3665 mmol, 0.08 equiv.) in acetonitrile (10 ml), and the mixture was stirred for 2 h at 25° C. The solvent was reduced under reduced pressure and the residue was purified by column chromatography (4% ethyl acetate in hexane). Yield: 94%

Stage 2: tert-Butyl 2-((1-(2-tert-butoxy-2-oxoethyl)-1H-indol-6-ylamino)methyl)-5-methyl-1H-pyrrole-1-carboxylate A solution of tert-butyl 2-(6-amino-1H-indol-1-yl)acetate (intermediate A—for synthesis see above) (1.7368 mmol, 1.1 equiv.) in DCM (3 ml) was added at 0° C. to tert-butyl 2-formyl-5-methyl-1H-pyrrole-1-carboxylate (1.5789 mmol, 1.0 equiv.), dissolved in DCM (12 ml), and the mixture was stirred for 30 min at 25° C. At 0° C., Na(OAc)$_3$BH (4.7368 mmol, 3.0 equiv.) was added in portions, and then the mixture was stirred for 12 h at 25° C. The reaction mixture was diluted with DCM (100 ml), washed with water and sat. NaCl solution (in each case 2×50 ml), dried over Na$_2$SO$_4$ and concentrated under reduced pressure. The crude product was purified by column chromatography (5% ethyl acetate in hexane). Yield: 58%

Stage 3: 2-(6-(5-Methyl-3-oxo-1H-pyrrolo[1,2-c]imidazol-2(3H)-yl)-1H-indol-1-yl)acetic acid NaH (2.0 equiv., 60% in mineral oil) was suspended at 0° C. in THF (6 ml). A solution of tert-butyl 2-((1-(2-tert-butoxy-2-oxoethyl)-1H-indol-6-ylamino)methyl)-5-methyl-1H-pyrrole-1-carboxylate (0.797 mmol, 1.0 equiv.) in THF (2 ml) was added, and the mixture was stirred for 14 h at 25° C. The reaction mixture was hydrolysed with water (50 ml) and diluted with ethyl acetate (100 ml). The aqueous phase was adjusted to an acidic pH value with acetic acid and extracted with ethyl acetate (2×50 ml). The combined organic phases were dried over Na$_2$SO$_4$ and concentrated under reduced pressure. The product was crystallized from the residue with hexane. Yield: 81%

Structural unit E-23: 2-(6-(10-Chloro-1-oxo-3,4-dihydropyrazino[1,2-a]indol-2(1H)-yl)-1H-indol-1-yl)acetic acid

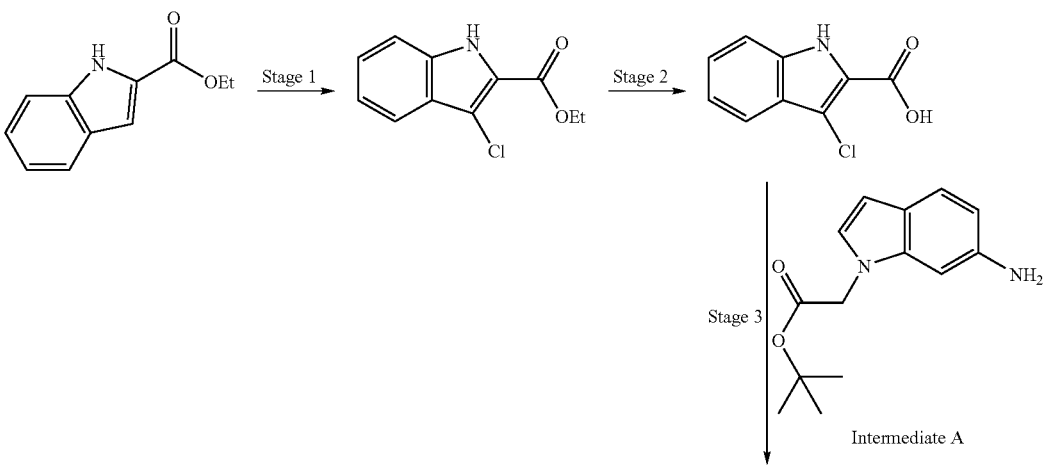

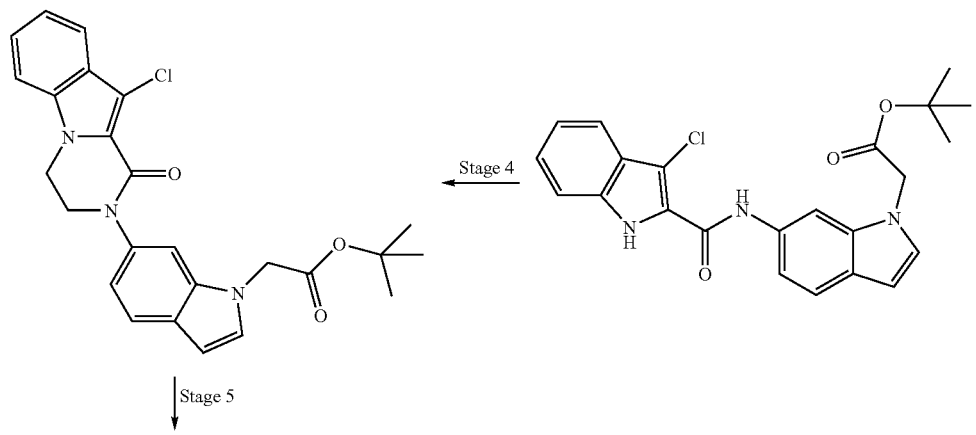

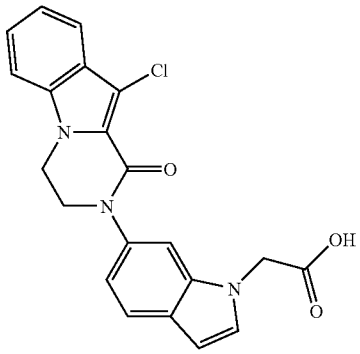

Stage 1: Ethyl 3-chloro-1H-indole-2-carboxylate

Ethyl 1H-indole-2-carboxylate (26.45 mmol, 1.0 equiv.) was dissolved in CCl₄ (26 ml); NCS (29.10 mmol, 1.1 equiv.) was added and the mixture was heated for 16 h at boiling temperature. The resulting solid was filtered out, and the filtrate was washed with water (2×50 ml) and sat. NaCl solution (50 ml), dried over Na₂SO₄ and concentrated under reduced pressure. The crude product was purified by column chromatography (10% ethyl acetate in hexane). Yield: 73%

Stage 2: 3-Chloro-1H-indole-2-carboxylic acid

Ethyl 3-chloro-1H-indole-2-carboxylate (19.28 mmol, 1.0 equiv.) was dissolved in THF-MeOH—H₂O (2:1:1; 85 ml); LiOH.H₂O (57.84 mmol, 3.0 equiv.) was added at 0° C. and the mixture was stirred for 12 h at 25° C. The solvent was reduced under reduced pressure, and the residue was taken up in water (50 ml), adjusted to pH 3 with 1 M HCl and extracted with ethyl acetate (2×100 ml). The combined organic phases were dried over Na₂SO₄ and concentrated under reduced pressure, and then the product was crystallized with hexane. Yield: 82%

Stage 3: tert-Butyl 2-(6-(3-chloro-1H-indole-2-carboxamido)-1H-indol-1-yl)acetate DIPEA (2.5 equiv.), EDCI (2.73 mmol, 1.2 equiv.) and HOBt (2.73 mmol, 1.2 equiv.) were added at 0° C. to a solution of 3-chloro-1H-indole-2-carboxylic acid (2.27 mmol, 1.0 equiv.) in DMF (6 ml), and the mixture was stirred for 15 min. tert-Butyl 2-(6-amino-1H-indol-1-yl)acetate (intermediate A—for synthesis see above) (2.27 mmol, 1.0 equiv.) was dissolved in DMF (1 ml) and added, with stirring, and the reaction mixture was then stirred for 12 h at 25° C. The mixture was diluted with dichloromethane (50 ml), washed with sat. ammonium chloride solution (20 ml), water (20 ml) and sat. NaCl solution (20 ml), dried over Na₂SO₄ and concentrated under reduced pressure. The crude product was purified by column chromatography (10-15% ethyl acetate in hexane). Yield: 55%

Stage 4: tert-Butyl 2-(6-(10-chloro-1-oxo-3,4-dihydropyrazino[1,2-a]indol-2(1H)-yl)-1H-indol-1-yl)acetate tert-Butyl 2-(6-(3-chloro-1H-indole-2-carboxamido)-1H-indol-1-yl)acetate (1.41 mmol, 1.0 equiv.) and TBAB (1.41 mmol, 1.0 equiv.) were dissolved in 1 N NaOH (12 ml); 1,2-dibromoethane (14.18 mmol, 10.0 equiv.) was added, and the mixture was stirred for 12 h at 25° C. The reaction mixture was diluted with water (50 ml) and extracted with ethyl acetate (100 ml). The organic phase was washed with sat. NaCl solution (50 ml), dried over Na₂SO₄ and concentrated under reduced pressure, and the desired product was obtained by purification by column chromatography. Yield: 78%

Stage 5: 2-(6-(10-Chloro-1-oxo-3,4-dihydropyrazino[1,2-a]indol-2(1H)-yl)-1H-indol-1-yl)acetic acid tert-Butyl 2-(6-(10-chloro-1-oxo-3,4-dihydropyrazino[1,2-a]indol-2(1H)-yl)-1H-indol-1-yl)acetate (2.22 mmol, 1.0 equiv.) was dissolved in DCM (15 ml); TFA (3 ml) was added, and the mixture was stirred for 2 h at 25° C. The solvent was concentrated under reduced pressure, and the residue was taken up in DCM (60 ml), washed with water (25 ml) and sat. NaCl solution (25 ml), dried over Na₂SO₄ and concentrated to dryness under reduced pressure. Yield: 91%

Structural unit E-24: 2-(6-(8-Chloro-1-oxo-3,4-dihydropyrrolo[1,2-a]pyrazin-2(1H)-yl)-1H-indol-1-yl)acetic acid

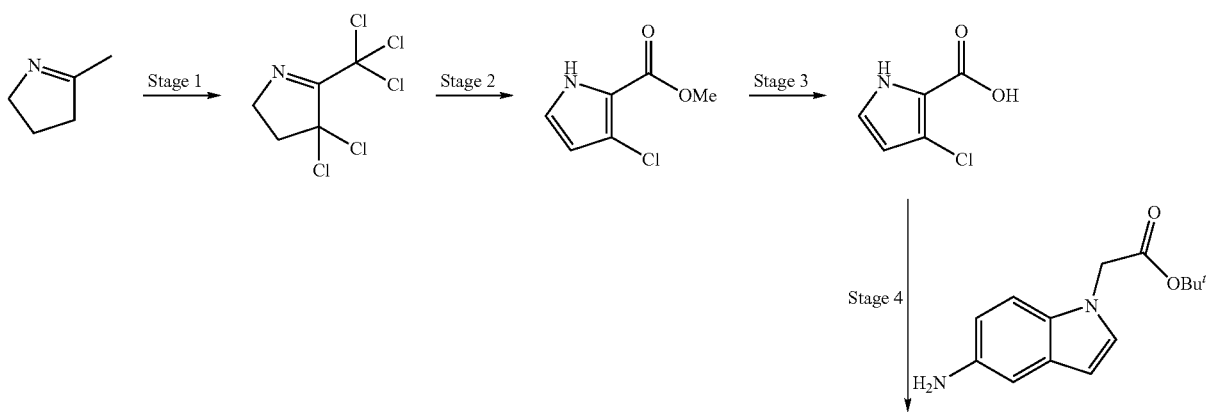

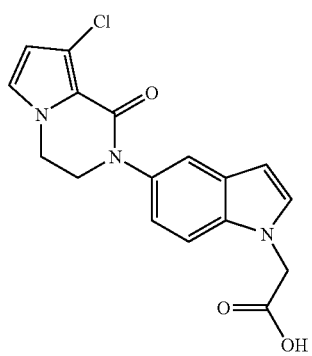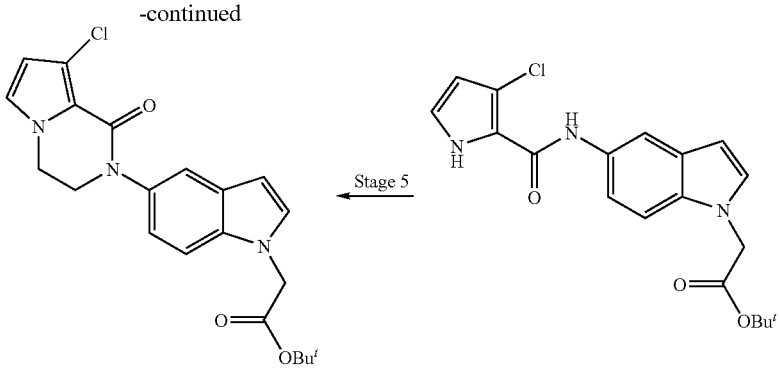

Stage 1: 4,4-Dichloro-5-(trichloromethyl)-3,4-dihydro-2H-pyrrole

5-Methyl-3,4-dihydro-2H-pyrrole (60.2 mmol, 1.0 equiv.) was dissolved in $CCl_4$ (100 ml); at 0° C., N-chlorosuccinimide (8.0 equiv.) was added in portions, and the mixture was heated for 72 h at boiling temperature. The reaction mixture was cooled to 0° C., and the resulting solid was filtered out and washed with cooled (0° C.) $CCL_4$ (2×50 ml). The filtrate was concentrated to dryness under reduced pressure. Yield: 90%

Stage 2: Methyl 3-chloro-1H-pyrrole-2-carboxylate 4,4-Dichloro-5-(trichloromethyl)-3,4-dihydro-2H-pyrrole (47.4 mmol, 1.0 equiv.) was added to a solution of sodium methanolate (284.5 mmol, 6.0 equiv.) in methanol (126 ml), and the mixture was heated for 1.5 h at boiling temperature. The reaction mixture was cooled to 25° C., the solvent was concentrated under reduced pressure, the residue was taken up in diethyl ether (470 ml), and the mixture was stirred for 30 min. The resulting solid (sodium chloride) was filtered out, and the filtrate was dried over $K_2CO_3$ and concentrated under reduced pressure. The residue was taken up in DCM (600 ml), extracted with 2 N HCl (2×150 ml), dried over $Na_2SO_4$ and concentrated under reduced pressure. The crude product was used in the next step without being purified further. Yield: 83%

Stage 3: 3-Chloro-1H-pyrrole-2-carboxylic acid

Methyl 3-chloro-1H-pyrrole-2-carboxylate (18.86 mmol, 1.0 equiv.) was dissolved in MeOH—$H_2O$ (2:1, 120 ml); at 0° C., $LiOH.H_2O$ (75.4 mmol, 4 equiv.) was added and the mixture was stirred for 16 h at 25° C. The methanol was concentrated under reduced pressure, and the aqueous residue was diluted with water (60 ml) and extracted with ethyl acetate (2×50 ml). The aqueous phase was adjusted to pH 3-4 with 1 M HCl, and the resulting solid was filtered out. Yield: 90%

Stage 4: tert-Butyl 2-(5-(3-chloro-1H-pyrrole-2-carboxamido)-1H-indol-1-yl)acetate DIPEA (4.0 equiv.), EDCI (1.5 equiv.) and HOBt (1.0 equiv.) were added at 0° C. to a solution of 3-chloro-1H-pyrrole-2-carboxylic acid (5.24 mmol, 1.0 equiv.) in DCM (25 ml). The mixture was stirred for 15 min at 25° C. and then cooled to 0° C. again. A solution of tert-butyl 2-(6-amino-1H-indol-1-yl)acetate (intermediate A—for synthesis see above) (5.24 mmol, 1.0 equiv.) in DCM (10 ml) was added, and the reaction mixture was stirred for 16 h at 25° C. It was then diluted with DCM (200 ml), washed with sat. ammonium chloride solution (2×50 ml), sat. sodium hydrogen carbonate solution (2×50 ml) and sat. NaCl solution (2×50 ml), dried over $Na_2SO_4$ and concentrated under reduced pressure. The crude product was purified by column chromatography (6% methanol in DCM). Yield: 56%

Stage 5: tert-Butyl 2-(5-(8-chloro-1-oxo-3,4-dihydropyrrolo[1,2-a]pyrazin-2(1H)-yl)-1H-indol-1-yl)acetate 1,2-Dibromoethane (22.7 mmol, 10.0 equiv.) was added to a solution of tert-butyl 2-(5-(8-chloro-1-oxo-3,4-dihydropyrrolo[1,2-a]pyrazin-2(1H)-yl)-1H-indol-1-yl)acetate (2.27 mmol, 1.0 equiv.) and tetrabutylammonium bromide (2.27 mmol, 1.0 equiv.) in 1 N NaOH (14 ml), and the mixture was stirred for 12 h at 25° C. The reaction mixture was diluted with water (50 ml) and extracted with ethyl acetate (150 ml). The organic phase was washed with water (2×50 ml) and sat. NaCl solution (2×50 ml), dried over $Na_2SO_4$ and concentrated under reduced pressure. The crude product was purified by column chromatography (10-12% ethyl acetate in hexane). Yield: 93%

Stage 6: 2-(5-(8-Chloro-1-oxo-3,4-dihydropyrrolo[1,2-a]pyrazin-2(1H)-yl)-1H-indol-1-yl)acetic acid A solution of $LiOH.H_2O$ (4.0 equiv.) in water (5 ml) was added at 0° C. to a solution of tert-butyl 2-(5-(8-chloro-1-oxo-3,4-dihydropyrrolo[1,2-a]pyrazin-2(1H)-yl)-1H-indol-1-yl)acetate (1.5 mmol, 1.0 equiv.) in MeOH (20 ml), and the mixture was heated for 16 h at 50° C. The methanol was concentrated under reduced pressure, and the aqueous residue was diluted with water (20 ml) and extracted with ethyl acetate (2×15 ml). The aqueous phase was adjusted to pH 4 with 1 M HCl, the desired product precipitating in the form of a white solid. The solid was filtered out and dried. Yield: 78%

5) Synthesis of Amine Structural Units F

Amine F-01: Dimethyl-(3-piperazin-1-yl propyl)amine

[877-96-3] commercially available from e.g. Acros.

Amine F-02: 1-(1-Methylpiperidin-4-yl)piperazine

[12345-34-56] commercially available from e.g. Aldrich.

Amine F-03: 3-(4-Ethylpiperazin-1-yl) propylamine

[4524-96-3] commercially available from e.g. Fluorochem.

Amine F-05: 4-(2-Pyrrolidin-1-yl ethyl)piperidine

[14759-08-1] commercially available from e.g. ABCR.

Amine F-07: Dimethyl-(4-phenyl piperidin-4-yl)amine dihydrochloride

Stage 1: 1-Benzyl-4-(dimethylamino)piperidine-4-carbonitrile 208 g (3 eq.) N,N-dimethylamine hydrochloride, 154 g (3 eq.) potassium cyanide in 154 ml water and 1050 ml (7 eq.) of a 40% dimethylamine solution were added to a solution of 150 g (1 eq.) 1-benzylpiperidin-4-one in 300 ml methanol and the mixture was cooled to 0° C. 75 ml (0.5 eq.) concentrated hydrochloric acid were then added at 0° C. and the reaction mixture was stirred for 24 h at room temperature. The reaction course was monitored by thin-layer chromatography (20% EtOAc/hexane). Once the conversion was complete, the solid that had formed was filtered out and washed with iced water (4 l). The solid obtained was then dissolved in ethyl acetate and dried with $Na_2SO_4$. Following removal of the solvent under reduced pressure, 165 g (85%) of crude product were obtained in the form of a solid.

Stage 2: 1-Benzyl-N,N-dimethyl-4-phenylpiperidin-4-amine

A little iodine was added to a mixture of 34.5 g (3.5 eq.) magnesium and 100 ml dry diethyl ether, followed over a period of 10 min by 10 g (0.15 eq.) bromobenzene, and the mixture was stirred for a further 10 min. Once the reaction had started, 183 g (2.85 eq.) bromobenzene dissolved in 500 ml diethyl ether were added dropwise over a period of 2 h and the mixture was stirred for a further 15 min. 100 g (1 eq.) 1-benzyl-4-(dimethylamino)piperidine-4-carbonitrile dissolved in 900 ml diethyl ether were added over a period of 2 h to the Grignard reagent prepared in the preceding step and the mixture was then heated for 12 h at 80° C. The reaction course was monitored by thin-layer chromatography (10% MeOH/$CHCl_3$). Once the conversion was complete, the reaction solution was cooled to 0° C., mixed with saturated $NH_4Cl$ solution, extracted with ethyl acetate (3×300 ml) and the combined organic phases were dried with $Na_2SO_4$. Following removal of the solvent under reduced pressure, the residue was purified by column chromatography (silica gel; 1% MeOH/$CHCl_3$). 30 g (35%) of product were obtained in the form of a yellow solid.

Stage 3: Benzyloxycarbonyl-4-(dimethylamino)-4-phenylpiperidine 500 ml (10 eq.) Cbz chloride were added dropwise to 50 g (1 eq.) 1-benzyl-N,N-dimethyl-4-phenylpiperidin-4-amine over a period of 1 h and the reaction mixture obtained was stirred for 2 h at room temperature. The reaction course was monitored by thin-layer chromatography (10% MeOH/$CHCl_3$). Once the conversion was complete, the reaction mixture was cooled to 0° C., made alkaline with saturated sodium hydrogen carbonate solution and extracted 3 times with 300 ml EtOAc. The combined organic phases were dried with $Na_2SO_4$. Following removal of the solvent under reduced pressure, the residue was purified by column chromatography (silica gel; 50% EtOAc/heptane). 12 g (21%) of product were obtained in the form of an oil.

Stage 4: tert-Butyloxycarbonyl-4-(dimethylamino)-4-phenylpiperidine 12.2 g KOH were added to a solution of 12 g (1 eq.) benzyloxycarbonyl-4-(dimethylamino)-4-phenylpiperidine in 120 ml ethanol and the reaction mixture was refluxed for 48 h. The reaction course was monitored by thin-layer chromatography (20% MeOH/$CHCl_3$). Once the conversion was complete, the solvent was distilled off completely, the residue suspended in ethyl acetate, filtered, and the organic phase dried over sodium sulfate. Following removal of the solvent under reduced pressure, the crude product was dissolved in dioxane, mixed with saturated sodium hydrogen carbonate solution and 11.9 g (1.5 eq.) of Boc anhydride and stirred for 30 min at room temperature. Once the conversion was complete, the reaction mixture was extracted with 3×200 ml ethyl acetate and the combined organic phases were dried over $Na_2SO_4$. Following removal of the solvent under reduced pressure, 8.5 g (77%) of crude product were obtained in the form of a colorless solid.

Stage 5: N,N-Dimethyl-4-phenylpiperidin-4-amine dihydrochloride 10 equivalents of acetyl chloride were added to a solution of tert-butyloxycarbonyl-4-(dimethylamino)-4-phenylpiperidine in methanol at 0° C. The reaction course was monitored by thin-layer chromatography (10% MeOH/$CHCl_3$). Once the conversion was complete, the solvent was removed under reduced pressure and the product obtained in the form of a solid.

Amine F-08: [1-(2-Aminoethyl)-4-thiophen-2-yl-piperidin-4-yl] dimethylamine trihydrochloride

Stage 1: tert-Butyloxycarbonyl-4-cyano-4-(dimethylamino)piperidine 500 ml (10 eq.) dimethylamine solution and 109.9 g (5 eq.) dimethylamine hydrochloride were added to a solution of 50 g (1 eq.) tert-butyloxycarbonyl-4-oxopiperidine in 100 ml methanol and the mixture was cooled to 5° C. 5 ml (0.1 eq.) hydrochloric acid were then added dropwise to the reaction mixture over a period of 10 min and the mixture was stirred for 60 min at room temperature. 48.9 g (3 eq.) potassium cyanide were added in portions to this reaction mixture and the mixture was stirred for 24 h at room temperature. The reaction course was monitored by thin-layer chromatography (50% EtOAc/hexane). Once the conversion was complete, 150 ml water were added to the reaction mixture and it was extracted 3 times with 100 ml ethyl acetate. The combined organic phases were dried with $Na_2SO_4$. Following removal of the solvent under reduced pressure, crude product was obtained which was recrystallized out of hexane. 57 g (90%) of product were obtained in the form of a colorless solid.

Stage 2: tert-Butyloxycarbonyl-4-(dimethylamino)-4-(thiophen-2-yl)piperidine A little iodine was added to a mixture of 5.6 g (3 eq.) magnesium and 20 ml dry diethyl ether, followed over a period of 10 min by 5 g 2-bromothiophene, and the mixture was stirred for a further 10 min. Once the reaction had started, 33.5 g (2.6 eq.) 2-bromothiophene dissolved in 80 ml diethyl ether were added dropwise and the mixture was stirred for a period of 2 h at room temperature. The Grignard reagent prepared in the preceding step was added dropwise to a solution of 20 g (1 eq.) tert-butyloxycarbonyl-4-cyano-4-(dimethylamino)piperidine dissolved in 200 ml THF and stirred overnight at room temperature. The reaction course was monitored by thin-layer chromatography (50% EtOAc/hexane). Once the conversion was complete, the reaction solution was cooled to 0° C., mixed with saturated NH$_4$Cl solution, extracted with ethyl acetate (3×100 ml) and the combined organic phases were dried with Na$_2$SO$_4$. Following removal of the solvent under reduced pressure, the residue was purified by column chromatography (alox neutral; 30% EtOAc/hexane). 6.1 g (25%) of product were obtained in the form of a white solid.

Stage 3:
N,N-Dimethyl-4-(thiophen-2-yl)piperidin-4-amine

HCl gas was passed through a solution of 10 g (1 eq.) tert-butyloxycarbonyl-4-(dimethylamino)-4-(thiophen-2-yl) piperidine in chloroform at 0° C. for ±1 h. Once the conversion was complete, 200 ml water were added to the reaction mixture, it was adjusted to a pH of ~8 with Na$_2$CO$_3$ and then extracted with 15% IPA/CHCl$_3$. The combined organic phases were dried over Na$_2$SO$_4$. Following removal of the solvent under reduced pressure, 6 g (89%) of product were obtained in the form of a white solid.

Stage 4: tert-Butyl 2-(4-(dimethylamino)-4-(thiophen-2-yl)piperidin-1-yl)ethylcarbamate 11.1 g (1.5 eq.) tert-butyl-2-bromoethylcarbamate dissolved in 65 ml THF and 9.19 g (2 eq.) potassium carbonate were added to a solution of 7 g (1 eq.) N,N-dimethyl-4-(thiophen-2-yl)piperidin-4-amine in 40 ml THF. The reaction mixture was heated for 6 h at 70° C. The reaction course was monitored by thin-layer chromatography (20% MeOH/CHCl$_3$). Once the conversion was complete, the solvent was distilled off completely, the residue mixed with 200 ml water and the aqueous phase extracted with 20% IPA/CHCl$_3$. The combined organic phases were dried over Na$_2$SO$_4$. Following removal of the solvent under reduced pressure, the residue was purified by column chromatography (silica gel; 10% MeOH/CHCl$_3$). 9 g (76%) of product were obtained in the form of an oil.

Stage 5: 1-(2-Aminoethyl)-N,N-dimethyl-4-(thiophen-2-yl)piperidin-4-amine tris hydrochloride HCl gas was passed through a solution of 9 g (1 eq.) tert-butyl 2-(4-(dimethylamino)-4-(thiophen-2-yl)piperidin-1-yl)ethylcarbamate in chloroform at 0° C. for ~30 min. The reaction mixture was then stirred at room temperature for one hour. The reaction course was monitored by thin-layer chromatography (10% MeOH/CHCl$_3$). Once the conversion was complete, the solvent was removed under reduced pressure and 9 g (97%) of product were obtained in the form of a white solid.

Amine F-09: Dimethyl-[1-(3-methylaminopropyl)-4-thiophen-2-yl-piperidin-4-yl]amine

Stage 1:
tert-Butyl-3-hydroxypropyl(methyl)carbamate 84.2 g (1.2 eq.) sodium carbonate followed by 100 ml water were added in portions to a solution of 50 g (1 eq.) 3-aminopropan-1-ol in 500 ml THF at 0° C. 156.5 ml (1.02 eq.) di-tert-butyl dicarbonate were added dropwise over a period of 30 min to the solution at 0° C. On completion of the addition, the mixture was stirred for 30 min at room temperature. The reaction course was monitored by thin-layer chromatography (10% MeOH/CHCl$_3$). Once the conversion was complete, the reaction mixture was filtered over celite and the filtrate concentrated under reduced pressure. The residue was mixed with 300 ml water and extracted with 2×250 ml ethyl acetate. The combined organic phases were dried over Na$_2$SO$_4$. Following removal of the solvent under reduced pressure, 116 g (100%) of product were obtained in the form of an oil.

Stage 2: tert-Butyl-3-(tert-butyldimethylsilyloxy) propylcarbamate 11.6 g (1.3 eq.) imidazole were added to a solution of 23 g (1 eq.) tert-butyl 3-hydroxypropylcarbamate in 230 ml dichloromethane. The reaction solution was stirred for 10 min at room temperature and then cooled to 0° C. 21.79 g (1.1 eq.) TBDMSCl were added to this solution at 0° C. and on completion of the addition the mixture was stirred for 1 h at room temperature. The reaction course was monitored by thin-layer chromatography (30% EtOAc/hexane). Once the conversion was complete, the reaction mixture was filtered over celite and the filtrate mixed with 200 ml water and extracted with dichloromethane. The combined organic phases were dried over Na$_2$SO$_4$. Following removal of the solvent under reduced pressure, 32 g (84%) of product were obtained in the form of an oil.

Stage 3: tert-Butyl 3-(tert-butyldimethylsilyloxy) propyl(methyl)carbamate 50 g (1 eq.) tert-butyl 3-(tert-butyldimethylsilyloxy)propylcarbamate dissolved in 200 ml THF were added dropwise to a mixture of 20.7 g (5 eq.) sodium hydride and 300 ml THF at 0° C. After heating the reaction mixture to 10° C., 32.3 ml (3 eq.) methyl iodide were added dropwise. On completion of the addition, the mixture was stirred for 3 h at room temperature. The reaction course was monitored by thin-layer chromatography (30% EtOAc/hexane). Once the conversion was complete, the reaction mixture was quenched with saturated NH$_4$Cl solution and then extracted with ethyl acetate. The combined organic phases were dried over Na$_2$SO$_4$. Following removal of the solvent under reduced pressure, 48 g (92%) of product were obtained in the form of an oil.

Stage 4:
tert-Butyl-3-hydroxypropyl(methyl)carbamate 482.5 ml (5 eq.) acetic acid dissolved in 386 ml water were added dropwise over a period of 45 min to a solution of 95.6 g (1 eq.) tert-butyl 3-(tert-butyldimethylsilyloxy)propyl(methyl)carbamate dissolved in 386 ml THF at 0° C. and the reaction mixture was then stirred for 20 h at room temperature. As the starting product had not yet been completely converted, the mixture was cooled to 0° C., 50 ml dilute acetic acid were added over a period of 20 min and the mixture was stirred for a further 1 h at 0° C. The reaction course was monitored by thin-layer chromatography (10% EtOAc/hexane). Once the conversion was almost complete, the reaction mixture was concentrated under reduced pressure, adjusted to a pH of ~9 with saturated Na$_2$CO$_3$ solution and extracted with 10% IPA/CH$_3$Cl. The combined organic phases were dried over Na$_2$SO$_4$. Following removal of the solvent under reduced pressure, the residue was purified by column chromatography (silica gel; 10% EtOAc/hexane). 40 g (66%) of product were obtained in the form of a colorless oil.

Stage 5: tert-Butyl methyl(3-oxopropyl)carbamate

A catalytic amount of TEMPO was added to a mixture of 20 g (1 eq.) tert-butyl 3-hydroxypropyl(methyl)carbamate in 200 ml dichloromethane and 17.7 g (2 eq.) sodium hydrogen carbonate in 100 ml water at 0° C. 140 ml (7 eq.) NaOCl were then added dropwise over a period of 30 min to the solution at a temperature of 0° C. and the reaction mixture obtained was stirred for a further 15 min at 0° C. The reaction course was monitored by thin-layer chromatography (40% EtOAc/hexane). Once the conversion was complete, the reaction mixture was mixed with 150 ml water and the phases were separated. The organic phase was dried over $Na_2SO_4$. Following removal of the solvent under reduced pressure, 16 g (85%) of product were obtained in the form of a yellowish oil.

Stage 6:
N,N-Dimethyl-4-(thiophen-2-yl)piperidin-4-amine bis hydrochloride

HCl gas was passed through a solution of 6 g (1 eq.) tert-butyloxycarbonyl-4-(dimethylamino)-4-(thiophen-2-yl) piperidine in 120 ml chloroform at 0° C. for 1 h. The reaction course was monitored by thin-layer chromatography (75% EtOAc/hexane). Once the conversion was complete, the solvent was removed under reduced pressure and 5.3 g (98%) of product were obtained in the form of a white solid.

Stage 7: tert-Butyl 3-(4-(dimethylamino)-4-(thiophen-2-yl)piperidin-1-yl)propyl(methyl)carbamate 6.4 g (1.3 eq.) tert-butyl methyl(3-oxopropyl)carbamate were added to a solution of 7.5 g (1 eq.) N,N-dimethyl-4-(thiophen-2-yl)piperidin-4-amine bis hydrochloride in 75 ml methanol at 0° C. and the reaction mixture was stirred for 15 min at 0° C. 4.9 g (3 eq.) sodium cyanoboron hydride were then added in portions and the mixture was stirred for 90 min at room temperature. The reaction course was monitored by thin-layer chromatography (20% MeOH/$CHCl_3$). As the conversion was not yet complete, the pH of the reaction mixture was adjusted to 5-6 with acetic acid and the mixture was stirred for 12 h at room temperature. Once the conversion was complete, the methanol was distilled off, water was added, the mixture obtained was extracted with IPA/chloroform (2×100 ml) and the combined organic phases were dried over $Na_2SO_4$. Following removal of the solvent under reduced pressure, the residue was purified by column chromatography (silica gel; 5% MeOH/$CHCl_3$). 8.5 g (84%) of product were obtained.

Stage 8: N,N-Dimethyl-1-(3-(methylamino)propyl)-4-(thiophen-2-yl)piperidin-4-amine tris hydrochloride HCl gas was passed through a solution of 1.5 g (1 eq.) tert-butyl 3-(4-(dimethylamino)-4-(thiophen-2-yl)piperidin-1-yl)propyl(methyl)carbamate in 30 ml chloroform at 0° C. for ~30 min. The reaction course was monitored by thin-layer chromatography (20% MeOH/$CHCl_3$). Once the conversion was complete, the solvent was removed under reduced pressure. After trituration with diethyl ether, 1.5 g (98%) of product were obtained in the form of a white solid. The corresponding free base was released using potassium hydroxide.

Amine F-10: Dimethyl-(4-thiophen-2-yl piperidin-4-yl)amine dihydrochloride

Stage 1: tert-Butyloxycarbonyl-4-cyano-4-(dimethylamino)piperidine 500 ml (10 eq.) dimethylamine solution and 109.9 g (5 eq.) dimethylamine hydrochloride were added to a solution of 50 g (1 eq.) tert-butyloxycarbonyl-4-oxopiperidine in 100 ml methanol and the mixture was cooled to 5° C. 5 ml (0.1 eq.) hydrochloric acid were then added dropwise to the reaction mixture over a period of 10 min and the mixture was stirred for 60 min at room temperature. 48.9 g (3 eq.) potassium cyanide were added in portions to this reaction mixture and the mixture was stirred for 24 h at room temperature. Once the conversion was complete, 150 ml water were added to the reaction mixture and it was extracted 3 times with 100 ml ethyl acetate. The combined organic phases were dried with $Na_2SO_4$. Following removal of the solvent under reduced pressure, crude product was obtained which was recrystallized out of hexane. 57 g (90%) of product were obtained in the form of a colorless solid.

Stage 2: tert-Butyloxycarbonyl-4-(dimethylamino)-4-(thiophen-2-yl)piperidine

A little iodine was added to a mixture of 5.6 g (3 eq.) magnesium and 20 ml dry diethyl ether, followed over a period of 10 min by 5 g 2-bromothiophene, and the mixture was stirred for a further 10 min. Once the reaction had started, 33.5 g (2.6 eq.) 2-bromothiophene dissolved in 80 ml diethyl ether were added dropwise and the mixture was stirred for a period of 2 h at room temperature. The Grignard reagent prepared in the preceding step was added dropwise to a solution of 20 g (1 eq.) tert-butyloxycarbonyl-4-cyano-4-(dimethylamino)piperidine dissolved in 200 ml THF and stirred overnight at room temperature. Once the conversion was complete, the reaction solution was cooled to 0° C., mixed with saturated $NH_4Cl$ solution, extracted with ethyl acetate (3×100 ml) and the combined organic phases were dried with $Na_2SO_4$. Following removal of the solvent under reduced pressure, the residue was purified by column chromatography (alox neutral; 30% EtOAc/hexane). 6.1 g (25%) of product were obtained in the form of a white solid.

Stage 3:
N,N-Dimethyl-4-(thiophen-2-yl)piperidin-4-amine bishydrochloride

HCl gas was passed through a solution of 10 g (1 eq.) tert-butyloxycarbonyl-4-(dimethylamino)-4-(thiophen-2-yl) piperidine in chloroform at 0° C. for ±1 h. Once the conversion was complete, 200 ml water were added to the reaction mixture, it was adjusted to a pH of ~8 with $Na_2CO_3$ and then extracted with 15% IPA/$CHCl_3$. The combined organic phases were dried over $Na_2SO_4$. Following removal of the solvent under reduced pressure, 6 g (89%) of product were obtained in the form of a white solid.

Amine F-11:
Dimethyl-[1-(3-methylaminopropyl)-4-phenyl piperidin-4-yl]amine trihydrochloride Stage 1: tert-Butyl 3-(4-(dimethylamino)-4-phenylpiperidin-1-yl)propyl(methyl)carbamate 11.1 g (1.3 eq.) tert-butyl methyl(3-oxopropyl)carbamate were added to a solution of 11 g (1 eq.) N,N-dimethyl-4- phenylpiperidin-4-amine dihydrochloride in 110 ml methanol at 0° C. and the reaction mixture was stirred for 15 min at 0° C. 6.2 g (3 eq.) sodium cyanoboron hydride were then added in portions and the mixture was stirred for 30 min at room temperature. The reaction mixture obtained was adjusted to a pH of 5-6 with acetic acid and stirred for 12 h at room temperature. The reaction course was monitored by thin-layer chromatography (20% MeOH/CHCl$_3$). As the conversion was still not complete, 2.4 g sodium cyanoboron hydride were added and the reaction mixture obtained was adjusted to pH 5-6 with acetic acid and stirred for 60 min at room temperature. Once the conversion was complete, the methanol was distilled off, the mixture was made alkaline with saturated NaHCO$_3$ solution, the mixture obtained was extracted with chloroform (3×100 ml) and the combined organic phases were dried over Na$_2$SO$_4$. Following removal of the solvent under reduced pressure, the residue was purified by column chromatography (silica gel; 5% MeOH/CHCl$_3$). 9 g (60%) of product were obtained.

Stage 2: N,N-Dimethyl-1-(3-(methylamino)propyl)-4-phenylpiperidin-4-amine hydrochloride HCl gas was passed through a solution of 9 g (1 eq.) tert-butyl 3-(4-(dimethylamino)-4-phenylpiperidin-1-yl)propyl(methyl)carbamate in 100 ml chloroform at 0° C. for 1 h. The reaction course was monitored by thin-layer chromatography (20% MeOH/CHCl$_3$). Once the conversion was complete, the solvent was removed under reduced pressure and after trituration with diethyl ether 10 g (100%) of product were obtained in the form of a white solid.

Amine F-12:
[4-(Azetidin-1-yl)-4-phenyl-cyclohexyl]amine hydrochloride

Stage 1: 4-(Azetidin-1-yl)-4-phenylcyclohexanone oxime

A solution of 4-(azetidin-1-yl)-4-phenylcyclohexanone (8.4 g) in methanol (84 ml), water (84 ml) and sodium hydrogen carbonate (10.08 g) was stirred for 5 min at room temperature, then hydroxylamine hydrochloride (6.95 g) was added in portions and the mixture was stirred for 8 hours at RT. A further 0.4 equiv. of sodium hydrogen carbonate and hydroxylamine hydrochloride were then added, and stirring was carried out for 16 h at room temperature. Then the reaction mixture was concentrated under reduced pressure, the organic phase was separated off and the aqueous phase was extracted with dichloromethane. The combined organic phases were dried over sodium sulfate and concentrated under reduced pressure to yield the desired crude product. Yield: 6 g (67% crude)

Stage 2:
[4-(Azetidin-1-yl)-4-phenyl-cyclohexyl]-amine

To a solution of the oxime (6 g) obtained above in methanol (60 ml) there was added Raney nickel (2 g) followed by ammonia (30 ml), and the reaction mixture was stirred for 24 hours at room temperature under a hydrogen atmosphere. The reaction mixture was filtered over celite and then washed with methanol. Methanol was distilled off, and the solid residue was washed with ethyl acetate/hexane, dried and purified to yield the desired product. Yield: 5 g (88%)

Amine F-13:
2-(1-Pyridin-4-yl-piperidin-4-yl)ethylamine dihydrochloride (i): tert-Butyl 2-(piperidin-4-yl)ethylcarbamate (0.2 g, 0.876 mmol), 4-chloropyridinium chloride (0.197 g, 1.314 mmol) and N-ethyl diisopropylamine (0.37 ml, 2.19 mmol) were refluxed in 2-propanol (10 ml) for 15 h. Saturated sodium hydrogen carbonate solution (20 ml) and ethyl acetate (50 ml) were added, the phases were separated and the aqueous phase was extracted with ethyl acetate (2×50 ml). The combined organic phases were dried over magnesium sulfate and concentrated to small volume under vacuum. The crude product was purified by column chromatography (silica gel) with ethyl acetate/dichloromethane/methanol/ammonia (25% eq.) 400/100/50/1. Yield: 80 mg, 30%

(ii): Hydrogen chloride (1.25 M solution in methanol, 1.25 ml) was added to a solution of tert-butyl 2-(1-(pyridin-4-yl)piperidin-4-yl)ethylcarbamate (0.12 g, 0.393 mmol) in methanol (3 ml) at room temperature and the reaction mixture was refluxed for 1 h. The solvent was removed under vacuum and the residue was dried.
Yield: quantitative Amine F-14:
3-Pyridin-4-yl-3,9-diazaspiro[5.5]undecane dihydrochloride (i): tert-Butyl 3,9-diazaspiro[5.5]undecane-3-carboxylate (1 g, 3.931 mmol), 4-chloropyridinium chloride (1.765 g, 11.794 mmol) and triethylamine (2.2 ml, 15.725 mmol) were refluxed for 15 h in 1-butanol (50 ml). Saturated sodium hydrogen carbonate solution (30 ml) and ethyl acetate (80 ml) were added, the phases were separated and the aqueous phase was extracted with ethyl acetate (2×80 ml). The combined organic phases were dried over magnesium sulfate and concentrated to small volume under vacuum. The crude product was purified by column chromatography (silica gel) with ethyl acetate/hexane/methanol/ammonia (25% eq.) 400/40/40/1. Yield: 0.52 g, 39%

(ii): Hydrogen chloride in methanol (1.25 mol/l, 6.3 ml) was added to tert-butyl 9-(pyridin-4-yl)-3,9-diazaspiro[5.5]undecane-3-carboxylate (0.52 g, 1.569 mmol) and refluxed for 1 h. The solvent was removed under vacuum, the residue taken up in ethanol (3 ml) and cooled. Acetone (80 ml) was added and the mixture was stirred for 30 min in an ice bath. The precipitate was separated, washed with diethyl ether and dried under vacuum. Yield: 0.4 g, 83%. Alternatively, the Boc cleavage can also be carried out in the presence of TFA in DCM.

Amine F-15:
(1-Pyridin-4-yl-piperidin-4-yl)methylamine dihydrochloride (i) Potassium carbonate (3 eq.), L-proline (0.4 eq.), CuI (0.2 eq.) and 4-bromopyridine (1 eq.) were added to a solution of tert-butyl piperidin-4-ylmethylcarbamate (3 g, 15 mmol) in DMSO under a protective gas atmosphere. The reaction mixture was heated to 100° C. for 20 hours, diluted with ethyl acetate and saturated sodium chloride solution after cooling to room temperature, filtered over celite and the residue was rewashed with ethyl acetate. The phases were separated, dried and concentrated under reduced pressure. The crude product was processed by column chromatography. Yield 30%

(ii) tert-Butyl (1-(pyridin-4-yl)piperidin-4-yl)methylcarbamate (7 g, 24.4 mmol) was dissolved in methanol, cooled in an ice bath, mixed with acetyl chloride (8.6 ml, 121.8 mmol) and stirred at room temperature for 3 h. The solvent was removed under reduced pressure and the residue was taken up in water/dichloromethane. The phases were separated, the aqueous phase was washed with dichloromethane (twice) and freeze dried. Yield: quantitative Amine F-16: 1-(4-Fluorophenyl)-piperazine

[16141-90-5] commercially available from e.g. Aldrich.

Amine F-17: 2-piperazin-1-yl-pyrimidine

[20980-22-7] commercially available from e.g. Aldrich.

Amine F-18: 1-Pyridin-4-yl piperazine

[1008-91-9] commercially available from e.g. ABCR.

Amine F-19: 4-Pyridin-3-yl piperidin-4-ol (i) (Apparatus: 1-l three-necked flask with nitrogen balloon flask) Magnesium (5.7 g) was introduced into anhydrous ether (125 ml), 1,1-dibromoethane (0.5 g) and isopropylchloride (17.3 ml) were added dropwise and the mixture was stirred for 15 min to initiate the magnesium. A solution of 3-bromopyridine (25 g) in anhydrous tetrahydrofuran (400 ml) was added dropwise over 20 min at 40° C., then the mixture was refluxed for 2 h. Then a solution of 1-benzylpiperidin-4-one (30 g) in anhydrous tetrahydrofuran (100 ml) was added dropwise over 20 min at 40° C. and the mixture was stirred overnight at room temperature. Analysis by thin-layer chromatography: 10% methanol in chloroform. The reaction mixture was hydrolysed at 0° C. with water (50 ml) and filtered over celite. It was extracted with dichloromethane (2×100 ml), the combined organic phases were washed with water (50 ml), dried over sodium sulfate and concentrated to small volume under vacuum. The crude product was purified by column chromatography (alox neutral) with 5% methanol in chloroform. Yield: 8.2 g (19.3%)

(ii) (Apparatus: 1-l three-necked flask with cooler) Palladium on carbon (10%, catalytic amount) followed by ammonium formate solution (22.7 g in 50 ml water) was added to a solution of 1-benzyl-4-(pyridin-3-yl)piperidin-4-ol (32 g) in methanol (220 ml). The reaction mixture was refluxed overnight at 68° C. Analysis by thin-layer chromatography: 20% methanol in chloroform. The mixture was filtered over celite and the filtrate concentrated to small volume under vacuum. The residue was washed with acetone (100 ml) in order to obtain the desired compound in a clean state. Yield: 17.3 g (81.3%)

Amine F-20: 4-Pyridin-2-yl piperidin-4-ol

[50461-56-8] commercially available from e.g. Tyger Scientific.

Amine F-21: 1-Methyl-4-piperidin-4-yl piperazine

[436099-90-0] commercially available from e.g. ABCR.

Amine F-22: 1-[(1-Methyl-piperidin-4-yl)-methyl]piperazine

[735262-46-1] commercially available from e.g. Otava.

Amine F-23: 3-(4-Fluorophenyl)-3,8-diazaspiro[4.5]decan-4-one hydrochloride (MDL No.: MFCD05861564) commercially available from e.g. ASW MedChem.

Amine F-24: 4-Piperidin-4-yloxypyridine hydrochloride (i) tert-Butyl-4-hydroxypiperidine-1-carboxylate (6.348 g, 31.546 mmol) and triphenylphosphine (10.256 g, 39.432 mmol) were added to a solution of 4-hydroxypyridine (3 g, 31.546 mmol) in tetrahydrofuran (50 ml) at room temperature. Then diisopropyl azodicarboxylate (7.66 ml, 39.432 mmol) was added dropwise and the mixture was then stirred for 15 h at 55° C. Saturated sodium hydrogen carbonate solution (50 ml) was added to the reaction mixture and it was extracted with ethyl acetate (4×80 ml). The combined organic phases were washed with saturated sodium chloride solution (20 ml), dried ($Na_2SO_4$) and concentrated to small volume under vacuum. Then the crude product was purified by column chromatography (silica gel) with ethyl acetate/hexane (4:1). Yield: 4.11 g (46%)

(ii) Hydrogen chloride (47 ml, 59 mmol, 1.25 M solution in methanol) was added to a solution of tert-butyl 4-(pyridin-3-yloxy)piperidine-1-carboxylate (4.1 g, 14.727 mmol) in methanol (10 ml) at room temperature and the reaction mixture was refluxed for 30 min. The solvent was removed under vacuum and the residue taken up in a little ethanol and mixed with diethyl ether. Then the mixture was cooled for 30 min in an ice bath and the solid that was formed was filtered out and dried. Yield: 3.46 g (93%)

Amine F-25: 1-(4-Fluorophenyl)-3-methyl-3,8-diazaspiro[4.5]decan-4-one hydrochloride (MDL No: MFCD08460813) commercially available from e.g. ASW MedChem.

Amine F-26: 3-[(4-Fluorophenyl)-methyl]-3,8-diazaspiro[4.5]decan-4-one hydrochloride (MDL No: MFCD08461093) commercially available from e.g. ASW MedChem.

Amine F-27: 3-Benzyl-3,8-diazaspiro[4.5]decan-4-one hydrochloride (MDL No: MFCD02179153) commercially available from e.g. ASW MedChem.

Amine F-28: 3-Benzyl-3,7-diazaspiro[4.4]nonane (MDL No: MFCD04115133) commercially available from e.g. Tyger.

Amine F-29: 3-[4-(2-Pyrrolidin-1-yl-ethoxy)piperidin-4-yl]pyridine dihydrochloride (i) n-Butyl lithium (2 eq.) was added to a solution of 3-bromopyridine (7.94 g, 1 eq.) in dry THF (1600 ml) at −70° C. and the mixture was stirred at this temperature for 1 h. Then a solution of N-Boc piperidone (10 g, 1 eq.) in THF (400 ml) was added at −70° C. and the mixture was stirred at this temperature for 2 h (DC control). On completion of the reaction the mixture was hydrolysed with saturated ammonium chloride solution and then slowly heated to RT. It was diluted with ethyl acetate. The organic phase was washed with sodium chloride solution and dried over sodium sulfate. The solvent was removed in a rotary evaporator and the crude product obtained was purified by column chromatography (silica gel, DCM/methanol, 9:1).

(ii) The alcohol (2 g) was dissolved in benzene (20 ml), mixed with sodium amide (10 eq.) at 25° C. and stirred at this temperature for 15 min. Then 1-(2-chloroethyl)pyrrolidine (1.2 eq.) was added and the mixture was refluxed for 16 h. On completion of the reaction (DC control) the mixture was cooled to 0° C. and hydrolysed with ice. The aqueous phase was extracted with ethyl acetate. The organic phase was washed with water and saturated NaCl solution and dried over $Na_2SO_4$. The solvent was removed in a rotary evaporator and the crude product obtained was purified by column chromatography (silica gel, DCM/methanol, 95:5).

(iii) tert-Butyl 4-(pyridin-3-yl)-4-(2-(pyrrolidin-1-yl) ethoxy)piperidine-1-carboxylate (12.7 g, 33.82 mmol) was dissolved in methanol (80 ml), cooled in an ice bath and mixed with acetyl chloride (12 ml, 169.1 mmol). After 3 h DC control (dichloromethane/methanol 9/1) indicated that the reaction was complete; the solvent was removed under vacuum and the residue taken up in water/dichloromethane. The phases were separated, the aqueous phase was washed with dichloromethane (twice) and freeze dried. Yield: quantitative Amine F-30: 2-(Pyridin-4-yl-methyl)-2,5-diazabicyclo[2.2.1]heptane dihydrochloride (i): tert-Butyl 2,5-diazabicyclo[2.2.1]heptane-2-carboxylate (5 g, 25.214 mmol) and pyridine-4-carbaldehyde (2.97 g, 27.74 mmol) were introduced into dichloromethane (650 ml), mixed with sodium triacetoxyboron hydride (10.6 g, 50.43 mmol) and glacial acetic acid (0.14 ml, 2.521 mmol) and the reaction mixture was stirred at room temperature for 15 h. The mixture was then hydrolysed with saturated sodium hydrogen carbonate solution, the phases were separated and the aqueous phase was extracted twice with diethyl ether. The combined organic phases were washed with saturated sodium chloride solution, dried over magnesium sulfate and concentrated under vacuum. The crude product was purified by column chromatography (silica gel; dichloromethane/methanol). Yield: 5.8 g, 79%

(ii): tert-Butyl 5-(pyridin-4-ylmethyl)-2,5-diazabicyclo [2.2.1]heptane-2-carboxylate (5.8 g, 20.0 mmol) was dissolved in methanol (50 ml), cooled in an ice bath and mixed with acetyl chloride (7.1 ml). The reaction mixture was stirred for 15 h at room temperature and then concentrated under reduced pressure. The residue was taken up in water, the aqueous phase was washed twice with dichloromethane, frozen and the water removed by freeze drying. Yield: 5.2 g, 99%

Amine F-31 was prepared from tert-butyl 2,5-diazabicyclo [2.2.1]heptane-2-carboxylate by reacting it with the corresponding aldehyde and then eliminating the protective group in a manner analogous to amine F-31.

| Amine | Aldehyde | Yield (after 2 stages) |
|---|---|---|
| 2-[(4-Fluorophenyl)methyl]-2,5-diazabicyclo[2.2.1]heptane dihydrochloride (F-31) | 4-Fluoro-benzaldehyde | 77% |

Amine F-32: (1-Pyridin-4-yl-piperidin-4-yl)amine dihydrochloride (MDL No: MFCD06797043) commercially available from e.g. ABCR.

Amine F-33: 4-Phenyl-2,4,8-triazaspiro[4.5]decan-1-one (MDL No: MFCD00005977) commercially available from e.g. ABCR.

Amine F-34: N-[[4-(4-Methylpiperazin-1-yl)-piperidin-4-yl]methyl]pyridine-4-carboxylic acid amide dihydrochloride Stage 1: Water (1.2 ml), N-methylpiperazine (1 eq.), acetic acid (1 eq.) and KCN (1.1 eq.) were added to a methanolic solution (20 ml) of N-benzyl piperidone (52.9 mmol). The reaction mixture was stirred for 1 h at 25° C. and a solid was precipitated. 35% ammonium hydroxide (300 ml) and ice (100 g) were then added to the batch. The solid was filtered out, washed repeatedly with water and then dried. Yield: 45%

Stage 2: A solution of concentrated $H_2SO_4$ (1.5 eq.) in THF (1 ml/mmol) was added dropwise to a cold (0° C.) suspension of LiAlH (3 eq.) in THF (2 ml/mmol) under an argon atmosphere (very exothermic). The suspension was stirred for 90 min at 25° C. and then cooled to 0° C. The cyano component (1 eq.) in THF (2 ml/mmol) was added dropwise to this cold reaction mixture and on completion of the addition the mixture was heated for 12 h at 50° C. (DC control). The batch was carefully quenched with a saturated sodium sulfate solution and filtered through celite. The residue was washed with ethyl acetate, the organic phase was dried over sodium sulfate and concentrated to small volume under reduced pressure. The crude amine was obtained and was used directly in the next stage with no further purification. Yield: 79%

Stage 3: TEA (5 eq.) and trifluoroacetic acid anhydride (2 eq.) were added to a solution of the amine from the second stage (74.5 mmol) in dichloromethane (5 ml/mmol) at 0° C. The reaction mixture was stirred for 2 h at 25° C. (DC control). It was diluted with dichloromethane, washed successively with water and saturated NaCl solution and dried over sodium sulfate. Concentration to small volume under reduced pressure resulted in the crude product, which was purified by column chromatography (10% methanol in dichloromethane). Yield: 64%

Stage 4: A solution of the benzylated product from the third stage (19 g) in methanol (285 ml) was degassed under argon. This was done by adding $Pd(OH)_2$ 10% (9.5 g) and AcOH (7.6 ml) and hydrogenating the mixture for 16 h under normal pressure (DC and LCMS control). The mixture was filtered through celite, the residue washed with methanol and the combined organic phases evaporated to dryness under reduced pressure. The crude product that was obtained was used directly in the next stage with no further purification. Yield: 14.8 g (quantitative)

Stage 5: DIPEA (1.5 eq.) and Boc anhydride (1.2 eq.) were added to a solution of the amine from the fourth stage (14.8 g, 48 mmol) in dichloromethane (240 ml) at 0° C. The reaction mixture was stirred for 3 h at room temperature. It was diluted with dichloromethane, washed successively with water and saturated NaCl solution and dried over sodium sulfate. Concentration to small volume under reduced pressure resulted in the crude product, which was purified by column chromatography (10% methanol in dichloromethane). Yield: 12.5 g (63%)

Stage 6: 1N NaOH (120 ml) was added to a solution of the Boc-protected product from the fifth stage in methanol (80 ml) at 0° C. and the reaction mixture was stirred for 2 h at 25°

C. (DC control). The mixture was diluted with ethyl acetate, the aqueous phase was extracted repeatedly with ethyl acetate and the combined organic phases were washed with saturated NaCl solution. After drying over sodium sulfate the organic phase was concentrated to small volume under reduced pressure and the crude product obtained was used directly in the next stage with no further purification. Yield: 7.7 g (83%)

Stage 7: Triethylamine (2.5 eq.) and isonicotinoyl chloride hydrochloride (1 eq.) were added to a cold (0° C.) solution of the amino component from the sixth stage (1 eq.) in dichloromethane. The reaction mixture was stirred for 2 h at 25° C. (DC control). The mixture was quenched with crushed ice, diluted with dichloromethane and the organic phase was washed successively with water and saturated NaCl solution. After drying over sodium sulfate the organic phase was concentrated to small volume under reduced pressure and the crude product obtained was purified by column chromatography (aluminium oxide neutral, methanol in dichloromethane 1:9). Yield: 70%

Stage 8: HCl in dioxane (2M, 6 ml/mmol) was added to a solution of the Boc-protected product from the seventh stage in dioxane (2 ml/mmol) at 0° C. and the reaction mixture was stirred for 3 h at 25° C. (DC control). The precipitated solid was filtered out, washed with ether under inert gas (very hygroscopic) and then dried under vacuum. Yield: 80%

Amine F-35: 1-(Pyridin-2-yl-methyl)-[1,4]diazepan

[247118-06-5] available commercially from ChemCollect, for example.

Amine F-36: 4-Pyrrolidin-3-yl-pyridine

[150281-47-3] available commercially from Interchim, for example.

Amine F-37: piperazin-1-yl-pyridin-3-yl-methanone

[39640-08-9] available commercially from Fluorochem, for example.

Amine F-38:
8-(Pyridin-4-yl)-2,8-diazaspiro[4.5]decane dihydrochloride

The synthesis was carried out analogously to the synthesis of amine F-14. To that end, tert-butyl 2,8-diazaspiro[4.5]decane-2-carboxylate was reacted with 4-chloropyridinium chloride in stage (i) (yield: 22%). Then, in stage (ii), the Boc protecting group was removed. When the reaction was complete and the methanol had been removed under vacuum, the residue was taken up in ethanol and cooled, and acetone was added. The resulting suspension was stirred for 30 min in an ice bath, and the precipitate was filtered out with suction, washed with acetone and dried under vacuum (yield: 92%).

Amine F-39: 3-(Pyridin-4-yl)-1-oxa-2,8-diazaspiro [4.5]dec-2-ene bis(2,2,2-trifluoroacetate)

Stage (i): tert-Butyl
4-methylenepiperidine-1-carboxylate

In a heated apparatus flushed with protecting gas, methyltriphenylphosphonium bromide (53.82 g, 150 mmol) was suspended in diethyl ether (300 ml) and cooled to 0° C. Potassium tert-butylate (15.78 g, 140 mmol) was added in portions, and the suspension was stirred for 30 min. Boc-4-piperidone (20 g, 100 mmol), dissolved in diethyl ether (200 ml), was slowly added dropwise, and then the mixture was heated to room temperature and stirred for 15 h. The reaction mixture was cooled, and ammonium chloride solution (300 ml, 10%) was added. After phase separation, the aqueous phase was extracted with ether (3×200 ml), and the combined organic phases were dried (MgSO$_4$) and concentrated under vacuum. The crude product was purified by column chromatography (silica gel) with ether/hexane (1:1). Yield: 18.57 g (93%)

Stage (ii): tert-Butyl 3-(pyridin-4-yl)-1-oxa-2,8-diazaspiro[4.5]dec-2-ene-8-carboxylate (a): (Z)—N-Hydroxyisonicotinimidoyl chloride: Pyridine-4-carbaldoxime (1 g, 8.19 mmol) was dissolved in DMF (10 ml); a solution of N-chlorosuccinimide (1.31 g, 9.83 mmol) in DMF (5 ml) was slowly added dropwise, and the reaction mixture was stirred at room temperature. When the reaction was complete (monitoring by thin-layer chromatography, here 6 h), diethyl ether (50 ml) and water (20 ml) were added, phase separation, extraction of the aqueous phase with diethyl ether (5×30 ml). The combined organic phases were washed with water (50 ml) and saturated sodium chloride solution (50 ml), dried (MgSO$_4$) and concentrated under vacuum. The crude substance was reacted without being purified and analysed further. Yield: 0.74 g (100%)

(b): tert-Butyl-4-methylenepiperidine-1-carboxylate (0.7 g, 3.55 mmol) was dissolved in dichloromethane (10 ml) and dissolved to 0° C. under protecting gas. (Z)—N-Hydroxyisonicotinimidoyl chloride (1.67 g, 10.64 mmol), dissolved in dichloromethane (15 ml), was added, followed by triethylamine (1.2 ml, 8.5 mmol) in dichloromethane (10 ml). The reaction mixture was heated slowly to room temperature and stirred for 15 h. It was diluted with dichloromethane (50 ml) and washed with water, 10% citric acid and saturated sodium chloride solution (in each case 30 ml), dried (MgSO$_4$) and concentrated under vacuum. The crude product was purified by column chromatography (silica gel) with ethyl acetate/hexane 10/1. Yield: 0.48 g (42%)

Stage (iii): 3-(Pyridin-4-yl)-1-oxa-2,8-diazaspiro [4.5]dec-2-ene bis(2,2,2-trifluoroacetate)

tert-Butyl 3-(pyridin-4-yl)-1-oxa-2,8-diazaspiro[4.5]dec-2-ene-8-carboxylate (0.48 g, 1.5 mmol) was dissolved in dichloromethane (10 ml) and cooled, and trifluoroacetic acid (1.2 ml, 15 mmol) was added slowly. After refluxing for 2 h, the solvent was removed under vacuum and the residue was co-evaporated with in each case 30 ml of toluene and methanol. Yield: 0.74 g (100%)

Amine F-40: 6-(Piperidin-1-ylmethyl)-2-(pyrrolidin-3-yl)-1,2,3,4-tetrahydroisoquinoline trihydrochloride Stage (i): 2,2,2-Trifluoro-1-(6-(piperidin-1-ylmethyl)-3,4-dihydroisoquinolin-2(1H)-yl)ethanone 2-(2,2,2-Trifluoroacetyl)-1,2,3,4-tetrahydroisoquinoline-6-carbaldehyde (2 g, 7.78 mmol) and piperidine (660 mg, 7.78 mmol) were dissolved in 1,2-dichloroethane (24 ml), and sodium triacetoxyborohydride (2.29 g, 10.89 mmol) was added. The reaction mixture was stirred for 15 h, then diluted with dichloromethane, and sat. sodium hydrogen carbonate solution (100 ml) was added. After phase separation, the aqueous phase was extracted with dichloromethane (3×100 ml). The combined organic phases were washed with sat.

sodium chloride solution (50 ml), dried over magnesium sulfate and concentrated under vacuum. The crude product was purified by column chromatography (silica gel, ethyl acetate/dichloromethane/methanol 10:1:1+ammonia solution (25% aq.)). Yield: 1.88 g (74%)

Stage (ii): 6-(Piperidin-1-ylmethyl)-1,2,3,4-tetrahydroisoquinoline dihydrochloride 2,2,2-Trifluoro-1-(6-(piperidin-1-ylmethyl)-3,4-dihydroisoquinolin-2(1H)-yl)ethanone (1.88 g, 5.76 mmol) was dissolved in methanol (23 ml); potassium carbonate (1.99 g, 14.4 mmol) was added and the reaction mixture was stirred for 15 h at RT. The solvent was then removed under vacuum, and the residue was taken up in dichloromethane and washed with water (15 ml). The aqueous phase was extracted with dichloromethane, and the combined organic phases were dried over sodium sulfate and concentrated under vacuum. The residue was taken up in an acetone/diethyl ether mixture, and the hydrochloride was precipitated with 2 M hydrogen chloride in diethyl ether (3 equiv.) and, after being filtered out with suction, was dried under vacuum. Yield: 1.62 g (93%)

Stage (i): tert-Butyl 3-(6-(piperidin-1-ylmethyl)-3,4-dihydroisoquinolin-2(1H)-yl)pyrrolidine-1-carboxylate 6-(Piperidin-1-ylmethyl)-1,2,3,4-tetrahydroisoquinoline dihydrochloride (0.5 g, 1.65 mmol), triethylamine (0.57 ml, 4.12 mmol) and tert-butyl 3-oxopyrrolidine-1-carboxylate (305 mg, 1.65 mmol) were dissolved in 1,2-dichloroethane (13 ml), and sodium triacetoxyborohydride (480 mg, 2.309 mmol) was added. The reaction mixture was stirred for 2 h, and then sat. sodium hydrogen carbonate solution was added. After phase separation, the aqueous phase was extracted with dichloromethane (2×). The combined organic phases were washed with sat. sodium chloride solution (1×), dried over magnesium sulfate and concentrated under vacuum. The crude product was purified by column chromatography (silica gel, ethyl acetate/methanol/ammonia (25% aq.) (200:20:1). Yield: 0.55 g (83%)

Stage (ii): 6-(Piperidin-1-ylmethyl)-2-(pyrrolidin-3-yl)-1,2,3,4-tetrahydroisoquinoline trihydrochloride 1.25 M hydrogen chloride in methanol (11 ml) was added to tert-butyl 3-(6-(piperidin-1-ylmethyl)-3,4-dihydroisoquinolin-2(1H)-yl)pyrrolidine-1-carboxylate (0.55 g, 1.38 mmol), and the mixture was refluxed for 3 h. The solvent was removed under vacuum and the residue was taken up in ethanol/acetone (5 ml). Diethyl ether (20 ml) was then added, and the resulting precipitate was filtered out and dried under vacuum. Yield: 0.41 g (73%)

Amine F-41:
2-(Pyridin-4-yl)-2,7-diazaspiro[4.4]nonane dihydrochloride

The synthesis was carried out analogously to the synthesis of amine F-14. To that end, tert-butyl 2,7-diazaspiro[4.4]nonane-2-carboxylate was reacted with 4-chloropyridinium chloride in stage (i) (yield: 50%). Then, in stage (ii), the Boc protecting group was removed. When the reaction was complete and the methanol had been removed under vacuum, the residue was taken up in ethanol and cooled, and acetone was added. The resulting suspension was stirred for 30 min in an ice bath, and the precipitate was filtered out with suction, washed with acetone and dried under vacuum. (Yield: 73%).

Amine F-42:
9-(Azetidin-1-yl)-3-azaspiro[5.5]undecane dihydrochloride

Stage (i): tert-Butyl 9-(azetidin-1-yl)-3-azaspiro[5.5]undecane-3-carboxylate tert-Butyl 9-oxo-3-azaspiro[5.5]undecane-3-carboxylate (stage (iv) Amine-F43) (1 g, 3.74 mmol) and azetidine (0.25 ml, 3.74 mmol) were placed in 1,2-dichloroethane (15 ml), and sodium triacetoxyborohydride (1.1 g, 5.23 mmol) was added. The reaction mixture was stirred for 3 d at room temperature, and then saturated sodium hydrogen carbonate solution was added. After phase separation, the aqueous phase was extracted with dichloromethane (2×). The combined organic phases were washed with saturated sodium chloride solution (1×), dried over magnesium sulfate and concentrated under vacuum. The crude product was purified by column chromatography (silica gel, ethyl acetate/methanol/ammonia (25% aq.), 100:10:1). Yield: 1 g (89%)

Stage (ii): 9-(Azetidin-1-yl)-3-azaspiro[5.5]undecane

Hydrogen chloride in methanol (1.25 mol/l, 15.5 ml) was added to tert-butyl 9-(azetidin-1-yl)-3-azaspiro[5.5]undecane-3-carboxylate (1 g, 3.24 mmol), and the mixture was refluxed for 45 min. The solvent was removed under vacuum and the residue was dissolved in a small amount of ethanol. A solid was then precipitated by addition of acetone, and finally diethyl ether was added and the resulting precipitate was filtered out with suction. Yield: 0.87 g (95%)

Amine F-43:
9-(Pyridin-4-yloxy)-3-azaspiro[5.5]undecane dihydrochloride

Stage (i): 1-(Benzyloxycarbonyl)piperidine-4-carboxylic acid

To piperidine-4-carboxylic acid (25 g) in THF (75 ml) there was added water (75 ml), followed by sodium bicarbonate (30.8 g). The mixture was cooled to 0° C., and Cbz chloride (38.9 ml) was added dropwise. The reaction mixture was then stirred for 5 h at room temperature (TLC monitoring). When the reaction was complete, the organic solvent was distilled off and the residue was taken up in water (200 ml) and washed with ethyl acetate (2×150 ml). The aqueous phase was acidified with dilute aqueous HCl solution and extracted with ethyl acetate. The organic phase was dried ($Na_2SO_4$) and concentrated under vacuum. Yield: 48.5 g (96%)

Stage (ii): 1-Benzyl 4-methylpiperidine-1,4-dicarboxylate 1-(Benzyloxycarbonyl)piperidine-4-carboxylic acid (48.5 g) in methanol (485 ml) was cooled to 0° C., and thionyl chloride (13.34 ml) was added dropwise. The mixture was then refluxed for 20 min (TLC monitoring). When the reaction was complete, the methanol was distilled off and the residue was taken up in water (15 ml) and with ethyl acetate (2×150 ml). The combined organic phases were extracted with water and sat. sodium chloride solution, dried (Na$_2$SO$_4$) and concentrated under vacuum. Yield: 38 g (67%)

Stage (iii): Benzyl 4-formylpiperidine-1-carboxylate

A solution of 1-benzyl 4-methylpiperidine-1,4-dicarboxylate (10 g) in toluene (100 ml), under nitrogen, was cooled to −78° C. Then DIBAL-H (60.9 ml) was added dropwise at −78° C., and the mixture was stirred for 1 h at that temperature (TLC monitoring). Because the reaction was incomplete, a further 0.2 eq. of DIBAL-H was added and stirring was carried out for a further 30 min (TLC monitoring: some starting material and the corresponding alcohol were detectable). Methanol (40 ml) followed by sat. sodium chloride solution (40 ml) were added slowly to the reaction mixture at −78° C. The mixture was filtered over celite, and the solvent was removed under vacuum. The residue was extracted with ethyl acetate (3×75 ml), dried (Na$_2$SO$_4$) and concentrated under vacuum. The crude product so obtained was purified by column chromatography (silica gel, 20% ethyl acetate/hexane). Yield: 4.3 g (49%)

Stage (iv): Benzyl 9-oxo-3-azaspiro[5.5]undec-7-ene-3-carboxylate

Methyl vinyl ketone (1.64 ml), ethanol (5 ml) and water (5 ml) were added to benzyl 4-formylpiperidine-1-carboxylate (5 g). The mixture was then added to a boiling solution of potassium hydroxide (0.22 g) in ethanol (10 ml), and the resulting reaction mixture was refluxed for 1 h (TLC monitoring). When the reaction was complete, the mixture was added to water (25 ml) and extracted with ethyl acetate (2×50 ml). The combined organic phases were dried (Na$_2$SO$_4$) and concentrated under vacuum. The crude product so obtained was purified by column chromatography (silical gel, 25% ethyl acetate/hexane). Yield: 2.8 g (46%)

Stage (v): tert-Butyl 9-oxo-3-azaspiro[5.5]undecane-3-carboxylate

Boc anhydride (9.4 ml) and potassium carbonate (7.56 g) were added to benzyl 9-oxo-3-azaspiro[5.5]undec-7-ene-3-carboxylate (8.2 g) in EtOH/water (9:1) (200 ml). Pd/C (1 g) was then added, and the mixture was subjected to hydrogenolysis for 4 h at 80 psi (TLC monitoring). When the reaction was complete, the mixture was filtered over celite and then rinsed with ethanol and ethyl acetate. The filtrate was dried (Na$_2$SO$_4$) and concentrated under vacuum. The residue was taken up in ethyl acetate and water, and the aqueous phase was extracted with ethyl acetate. The combined organic phases were dried (Na$_2$SO$_4$) and concentrated under vacuum. The crude product so obtained was purified by column chromatography (silica gel, 20% ethyl acetate/hexane). Yield: 2.92 g, 40%

Stage (vi): tert-Butyl 9-hydroxy-3-azaspiro[5.5]undecane-3-carboxylate tert-Butyl 9-oxo-3-azaspiro[5.5]undecane-3-carboxylate (1.5 g) was dissolved in THF (7.5 ml) and cooled to −5° C. NaBH$_4$ (0.212 g) was then added and the mixture was stirred for 1 h at room temperature (TLC monitoring). When the reaction was complete, acetic acid was added to the mixture, and the methanol was then distilled off. The residue was taken up in water (50 ml) and extracted with ethyl acetate (2×50 ml). The combined organic phases were dried (Na$_2$SO$_4$) and concentrated under vacuum. The crude product so obtained was purified by column chromatography (silica gel, 30% ethyl acetate/hexane). Yield: 1.2 g (80%)

Stage (vii): tert-Butyl 9-(pyridin-4-yloxy)-3-azaspiro [5.5]undecane-3-carboxylate 4-Chloropyridine hydrochloride (1.3 g) was added to sodium hydride (0.89 g) in DMSO (20 ml), and the mixture was stirred for 10 min. tert-Butyl 9-hydroxy-3-azaspiro[5.5] undecane-3-carboxylate (2.0 g) in DMSO (20 ml) was then added slowly, and the mixture was stirred overnight (TLC monitoring: conversion about 30-35%). A catalytic amount of sodium iodide was added, and the reaction mixture was stirred for 8 h at 80° C. (TLC monitoring). Methanol and NaHCO$_3$ solution were added to the reaction mixture, and stirring was carried out for 20 min. Extraction with ethyl acetate was then carried out, followed by washing with NaHCO$_3$ solution and cold water. The organic phase was dried (Na$_2$SO$_4$) and concentrated under vacuum. The resulting crude product was purified by column chromatography (silica gel, 70% ethyl acetate/hexane). Yield: 1.0 g (40%)

Stage (viii): 9-(Pyridin-4-yloxy)-3-azaspiro[5.5]undecane dihydrochloride tert-Butyl 9-(pyridin-4-yloxy)-3-azaspiro[5.5]undecane-3-carboxylate (1 g, 2.886 mmol) was dissolved in methanol (2 ml); hydrogen chloride in methanol (1.25 mol/l, 11.5 ml) was added, and the mixture was refluxed for 30 min. The solvent was removed under vacuum and the residue was dissolved in a small amount of ethanol. Acetone (about 25 ml) was then added, the mixture was stirred for 30 min at 0° C., and finally the resulting solid was filtered out with suction. Yield: 0.96 g (>99%)

Amine F-44: 9-(3,3-Difluoroazetidin-1-yl)-3-azaspiro[5.5]undecane dihydrochloride Stage (i): tert-Butyl 9-(3,3-difluoroazetidin-1-yl)-3-azaspiro[5.5]undecane-3-carboxylate tert-Butyl 9-oxo-3-azaspiro[5.5]undecane-3-carboxylate (stage (iv) Amine-F43) (1 g, 3.74 mmol) was added to 3,3-difluoroazetidine hydrochloride (0.484 g, 3.74 mmol) and triethylamine (0.52 ml, 3.74 mmol) in 1,2-dichloroethane (15 ml). The mixture was stirred for 5 min, and then sodium triacetoxyborohydride (1.1 g, 5.23 mmol) was added and stirring was carried out for 3 d at room temperature. Saturated sodium hydrogen carbonate solution was added and, after phase separation, the aqueous phase was extracted with dichloromethane (2×). The combined organic phases were washed with saturated sodium chloride solution (1×), dried over magnesium sulfate and concentrated under vacuum. Yield: 1.26 g (98%)

Stage (ii): 9-(3,3-Difluoroazetidin-1-yl)-3-azaspiro [5.5]undecane dihydrochloride tert-Butyl 9-(3,3-difluoroazetidin-1-yl)-3-azaspiro[5.5] undecane-3-carboxylate (1.26 g, 3.66 mmol) was dissolved in hydrogen chloride in methanol (1.25 mol/l, 29 ml) and refluxed for 45 min. The solvent was removed under vacuum and the residue was dissolved in a small amount of ethanol. A solid was then precipitated by addition of acetone. The mixture was stirred for 10 min at room temperature, then diethyl ether was added and stirring was carried out for a further 30 min at room temperature. The resulting precipitate was filtered out with suction, washed with diethyl ether and dried under vacuum. Yield: 1.1 g (95%)

Amine F-45: Dimethyl-[4-(2-methylamino-ethyl)-1-phenyl-cyclohexyl]-amine dihydrochloride (F-45)

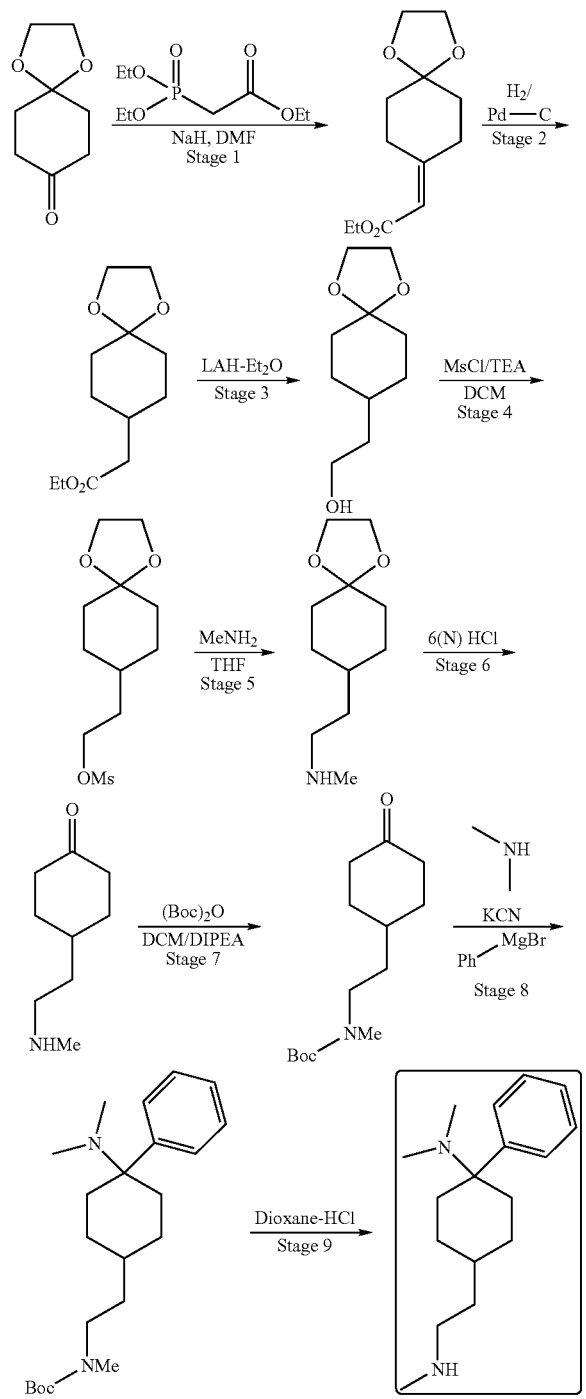

Stage 1:
A solution of triethyl phosphonoacetate (1.1 eq.) in THF (5 ml/mmol) was added slowly to a suspension, at 0° C., of 60% NaH (1 eq.) in dry THF (5 ml/mmol). The resulting reaction mixture was stirred for 30 min at RT. It was then cooled to 0° C., and 1,4-dioxa-spiro[4.5]decan-8-one (1 eq.) in dry THF (5 ml/mmol) was added slowly at a constant temperature. The reaction mixture was stirred for 16 h at 25° C. Quenching with ice and sat. sodium chloride solution was carried out, the aqueous phase was extracted with ethyl acetate, and the organic phase was washed successively with water and sodium chloride solution. The combined org. phases were dried over sodium sulfate and concentrated under reduced pressure. The crude product was purified by column chromatography (20% ethyl acetate in n-hexane).
Yield: 90

Stage 2:
A solution of the ester (1 eq.) obtained above in stage 1 in methanol (3 ml/mmol) was deoxygenated with argon for 15 minutes, and then 10% Pd/C (50% by weight) was added. The resulting reaction mixture was hydrogenated for 16 h under normal pressure and then filtered out over filtering earth (celite). The residue was washed with methanol, and the combined organic phases were concentrated completely. The crude product was used immediately in the next stage without being purified further. Yield: 90% (crude product)

Stage 3:
A solution of the ester obtained in stage 2 (1 eq.) in THF (5 ml/mmol) was added slowly in the course of 30 minutes to a suspension, at 0° C., of LAH (1 eq.) in dry THF (3 ml/mmol). When the addition was complete, the reaction mixture was stirred for 1 h at 25° C., cooled to 0° C. and quenched with sat. sodium sulfate solution and then filtered over celite. After concentrating the solvent completely, the resulting crude product was used in the next stage without being purified further.
Yield: 80% (crude product)

Stage 4:
Methanesulfonyl chloride (1.1 eq.) was added at 0° C., under a nitrogen atmosphere, to a solution of the alcohol obtained in stage 1 (1 eq.) in DCM (5 ml/mmol). When the addition was complete, the reaction mixture was stirred for 2 h at 25° C. and diluted with dichloromethane, and the organic phase was washed successively with water and sat. sodium chloride solution and then dried over sodium sulfate. The organic phase was concentrated under reduced pressure and the crude product was used immediately in the next stage.
Yield: 80% (crude product)

Stage 5:
2M methylamine solution in THF (10 ml) was added to a solution of the compound obtained in stage 4 (5 mmol) in THF. The resulting reaction mixture was heated for 16 h at 100° C. in a firmly closed vessel. The solvent was then removed completely under reduced pressure and the resulting crude product, which could not be purified, was used in the next stage.
Yield: 90% (crude product)

Stage 6:
Aqueous hydrochloric acid solution (6N, 2 ml/mmol) was added at 0° C. to the amine obtained in stage 5 (1 eq.). The resulting reaction mixture was stirred for 20 h at RT. Then the aqueous phase was washed with ethyl acetate and subsequently adjusted to pH 14 with 6 N aqueous sodium hydroxide solution. The aqueous phase was extracted with dichloromethane and the combined organic phases were washed successively with water and sat. sodium chloride solution. The combined org. phases were dried over sodium sulfate, the solvent was concentrated under reduced pressure, and the resulting crude product was used in the next stage without being purified further.
Yield: 80% (crude product)

Stage 7:

Diisopropylethylamine (2.5 eq.) and Boc$_2$(O) (1.2 eq.) were added at 0° C. to a solution of the amine obtained in stage 6 (1 eq.) in dichloromethane (3 ml/mmol). When the addition was complete, the mixture was stirred for 16 h at 25° C. The mixture was then diluted with dichloromethane, and the org. phase was washed successively with water and sat. sodium chloride solution and finally dried over sodium sulfate. The org. phase was concentrated under reduced pressure, and the crude product was purified by column chromatography (5% methanol in dichloromethane).

Yield: 60%

Stage 8:

40% aqueous dimethylamine solution (71 ml) and acetic acid (26.5 ml) and KCN (1.5 eq.) were added at 0° C. to a solution of the Boc amine obtained in stage 7 (84.3 mmol) in methanol (45 ml). The resulting reaction mixture was stirred for 16 h at RT. Then 35% ammonium hydroxide solution (300 ml) and ice (300 g) were added, the aqueous phase was extracted with ethyl acetate, and the combined org. phases were washed successively with water, sat. sodium chloride solution and aqueous iron sulfate solution. After drying over sodium sulfate, the org. phase was concentrated under reduced pressure. The crude product (25 g) was taken up in THF (50 ml), and phenylmagnesium bromide (337 ml, 1M in THF) was added at 0° C. When the addition was complete, the reaction mixture was stirred for 16 h at 25° C. For working up, the reaction mixture was quenched with sat. ammonium chloride solution and diluted with ethyl acetate, and the org. phase was washed with sat. sodium chloride solution. After drying over sodium sulfate, the org. phase was concentrated under reduced pressure and the resulting crude product was purified by column chromatography (5% methanol in dichloromethane).

Yield: 40%

Stage 9:

HCl in dioxane (2M, 6 ml/mmol) was added at 0° C. to a dioxane solution (2 ml/mmol) of the Boc amine obtained in stage 8. The resulting reaction mixture was stirred for 3 h at 25° C., and the solid was filtered out under protecting gas (very hygroscopic), washed with diethyl ether and finally dried under a high vacuum.

Yield: 80%

Amine F-46: 1-[4-(3-Fluorophenyl)-piperidin-4-yl]-4-methyl-piperazine dihydrochloride (F-46)

1-[4-(3-Fluorophenyl)piperidin-4-yl]-4-methyl-piperazine dihydrochloride (F-46) was prepared analogously to dimethyl-(4-phenyl-piperidin-4-yl)-amine dihydrochloride (F-07) using methylpiperazine and 3-fluorophenyl-magnesium bromide.

Amine F-47: 2-[4-(3-Fluorophenyl)-4-(4-methyl-piperazin-1-yl)-piperidin-1-yl]-ethyl-methyl-amine tetrahydrochloride (F-47)

2-[4-(3-Fluorophenyl)-4-(4-methyl-piperazin-1-yl)-piperidin-1-yl]-ethyl-methyl-amine tetrahydrochloride (F-47) was prepared analogously to dimethyl-[1-(3-methylamino-propyl)-4-phenyl-piperidin-4-yl]amine trihydrochloride (F-11) using methylpiperazine and 3-fluorophenylmagnesium bromide.

Amine F-48: Methyl-[3-(4-pyridin-4-yl-piperazin-1-yl)-propyl]-amine trihydrochloride (F-48)

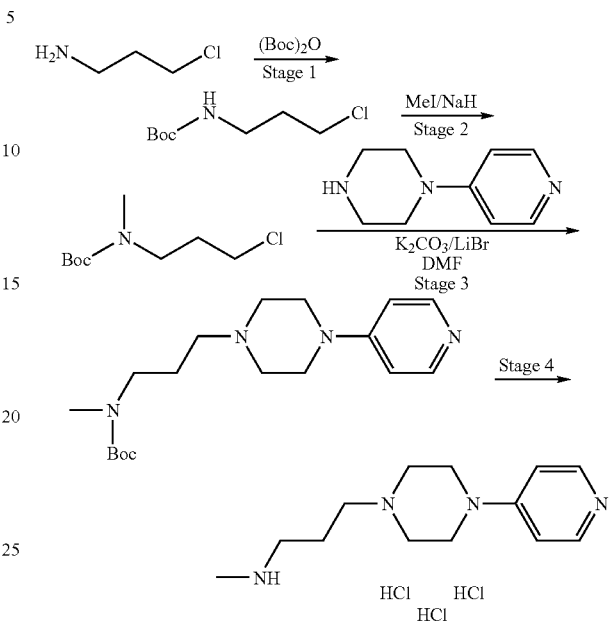

Stage 1:

An aqueous sodium dicarbonate solution (3.5 g in 57 ml of water) and solid sodium chloride (7.5 g) were added at 0° C. to a suspension of 3-chloropropylamine hydrochloride (38 mmol) in DCM (77 ml), and the mixture was stirred for 30 minutes. A solution of Boc anhydride (1.2 eq.) in dichloromethane (20 ml) was then slowly added dropwise. The reaction mixture was stirred overnight at RT. The reaction mixture was extracted with dichloromethane, and the org. phase was washed with water and sat. sodium chloride solution, dried over sodium sulfate (anhydrous) and concentrated. The desired product was used in the next stage without being purified further.

Yield: 83.7%

Stage 2:

Methyl iodide (3 eq.) was added at 0° C. to a solution of the Boc amine obtained in stage 1 (155 mmol) in DMF (600 ml). Sodium hydride (2 eq.) was then added in portions. The reaction mixture was stirred for 15 h at RT. For working up, the reaction mixture was quenched with water and extracted with n-hexane. The combined org. phases were washed with water and sat. sodium chloride solution, dried over sodium sulfate (anhydrous) and concentrated. The desired product was used in the next stage without being purified further.

Yield: quantitative

Stage 3:

DIPEA (2 eq.) and LiBr (1 eq.) were added to a solution of 4-(4-pyridyl)-piperazine (30.64 mmol) and the Boc amine obtained in stage 2 (1.5 eq.) in ethanol (150 ml). The reaction mixture was heated for 15 h at reflux and was then concentrated and diluted with dichloromethane and water. The org. phase was washed successively with water and sat. sodium chloride solution, dried over sodium sulfate (anhydrous) and concentrated under reduced pressure. The residue was purified by column chromatography over neutral alumina (eluant: DCM/MeOH) to yield the desired pure product.

Yield: 60%

Stage 4:

10 eq. of acetyl chloride were added at 0° C. to a solution of the Boc amine obtained in stage 3 in methanol. The progress of the reaction was monitored by means of thin-layer chromatography (10% MeOH/CHCl$_3$). When the reaction was complete, the solvent was removed under reduced pressure and the product was obtained in the form of a solid.

TABLE 3

Amine overview

| Amine | Structure | Name |
|---|---|---|
| F-01 | 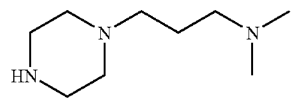 | Dimethyl-(3-piperazin-1-yl-propyl)amine (F-01) |
| F-02 | 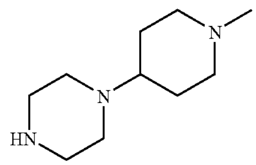 | 1-(1-Methyl-piperidin-4-yl) piperazine (F-02) |
| F-03 | 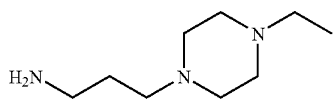 | 3-(4-Ethyl-piperazin-1-yl)-propylamine (F-03) |
| F-05 | 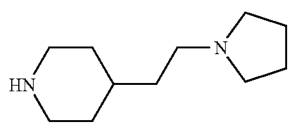 [SMILES: C1CCN(CCC2CCNCC2)C1] | 4-(2-Pyrrolidin-1-yl-ethyl) piperidine (F-05) |
| F-07 | 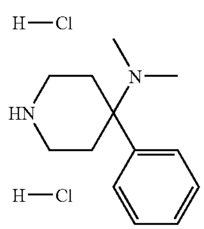 | Dimethyl-(4-phenyl-piperidin-4-yl)amine dihydrochloride (F-07) |
| F-08 | 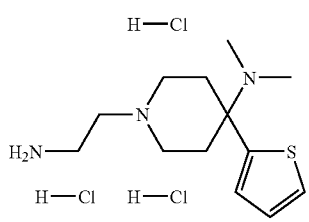 | [1-(2-Aminoethyl)-4-thiophen-2-yl-piperidin-4-yl]-dimethylamine trihydrochloride (F-08) |
| F-09 | 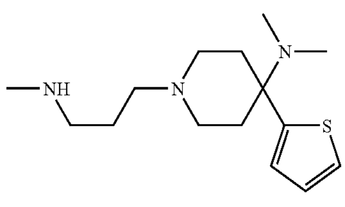 [SMILES: CNCCCN1CCC(c2cccs2)(N(C)C)CC1] | Dimethyl-[1-(3-methylaminopropyl)-4-thiophen-2-yl-piperidin-4-yl]amine (F-09) |
| F-10 | 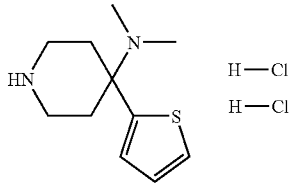 | Dimethyl-(4-thiophen-2-yl piperidin-4-yl)amine dihydrochloride (F-10) |

US 8,492,559 B2

TABLE 3-continued

Amine overview

| Amine | Structure | Name |
|---|---|---|
| F-11 | 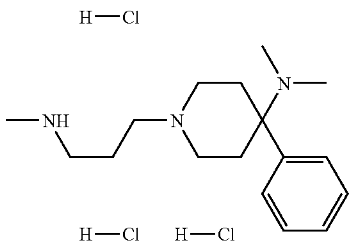 | Dimethyl-[1-(3-methylaminopropyl)-4-phenyl piperidin-4-yl]amine trihydrochloride (F-11) |
| F-12 | 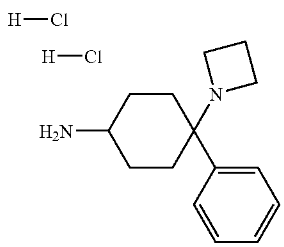 | [4-(Azetidin-1-yl)-4-phenyl-cyclohexyl]amine dihydrochloride (F-12) |
| F-13 | 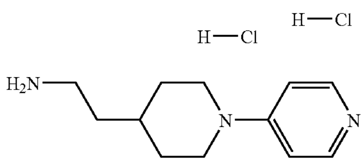 | 2-(1-Pyridin-4-yl-piperidin-4-yl)ethylamine dihydrochloride (F-13) |
| F-14 | 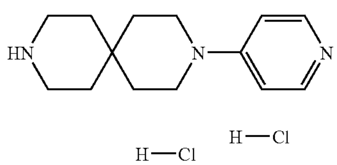 | 3-Pyridin-4-yl-3,9-diazaspiro[5.5]undecane dihydrochloride (F-14) |
| F-15 | 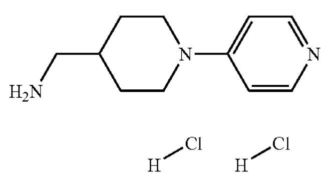 | (1-Pyridin-4-yl-piperidin-4-yl)methylamine dihydrochloride (F-15) |
| F-16 | 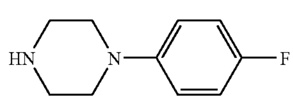 [SMILES: Fc1ccc(N2CCNCC2)cc1] | 1-(4-Fluorophenyl)piperazine (F-16) |
| F-17 | 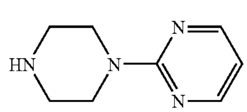 [SMILES: c1cnc(N2CCNCC2)nc1] | 2-Piperazin-1-yl pyrimidine (F-17) |
| F-18 | 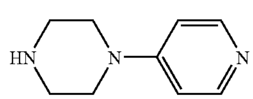 [SMILES: c1cc(N2CCNCC2)ccn1] | 1-Pyridin-4-yl piperazine (F-18) |
| F-19 | 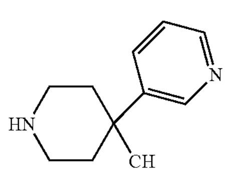 | 4-Pyridin-3-yl piperidin-4-ol (F-19) |

TABLE 3-continued

| Amine | Structure | Name |
|---|---|---|
| F-20 | 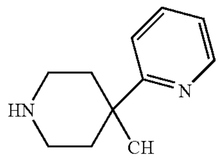 | 4-Pyridin-2-yl piperidin-4-ol (F-20) |
| F-21 | 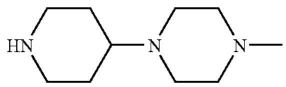 | 1-Methyl-4-piperidin-4-yl piperazine (F-21) |
| F-22 | 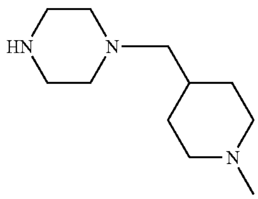 | 1-[(1-Methyl-piperidin-4-yl) methyl] piperazine (F-22) |
| F-23 | 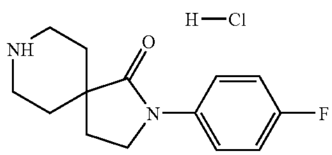 | 3-(4-Fluorophenyl)-3,8-diazaspiro[4.5]decan-4-one hydrochloride (F-23) |
| F-24 | 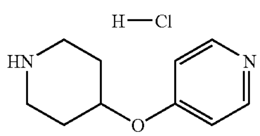 | 4-Piperidin-4-yloxypyridine hydrochloride (F-24) |
| F-25 | 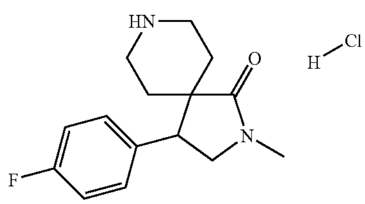 | 1-(4-Fluorophenyl)-3-methyl-3,8-diazaspiro[4.5]decan-4-one hydrochloride (F-25) |
| F-26 | 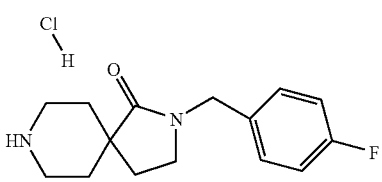 | 3-[(4-Fluorophenyl)-methyl]-3,8-diazaspiro[4.5]decan-4-one hydrochloride (F-26) |
| F-27 | 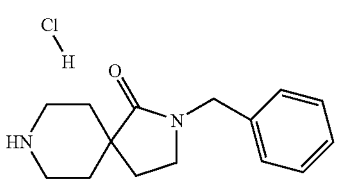 | 3-Benzyl-3,8-diazaspiro[4.5]decan-4-one hydrochloride (F-27) |
| F-28 | 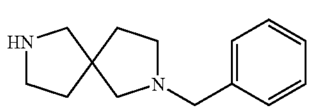 [SMILES: c1ccc(CN2CCC3(CCNC3)C2)cc1] | 3-Benzyl-3,7-diazaspiro[4.4]nonane (F-28) |

TABLE 3-continued

| Amine | Structure | Name |
|---|---|---|
| F-29 | 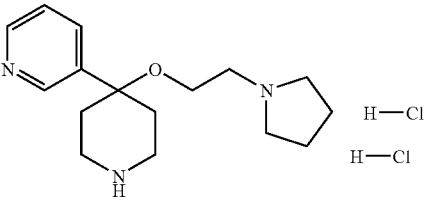 | 3-[4-(2-Pyrrolidin-1-yl-ethoxy-piperidin-4-yl]pyridine dihydrochloride (F-29) |
| F-30 | 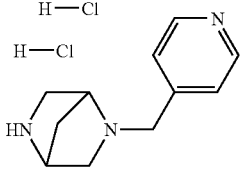 | 2-(Pyridin-4-yl-methyl)-2,5-diazabicyclo[2.2.1]heptane dihydrochloride (F-30) |
| F-31 | 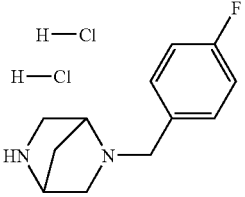 | 2-[(4-Fluorophenyl)methyl]-2,5-diazabicyclo[2.2.1]heptane dihydrochloride (F-31) |
| F-32 | 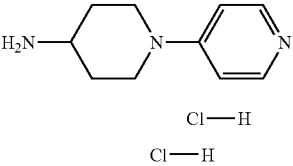 | (1-Pyridin-4-yl-piperidin-4-yl)amine dihydrochloride (F-32) |
| F-33 | 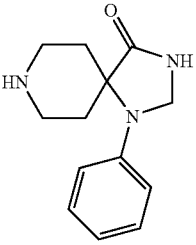 | 4-Phenyl-2,4,8-triazaspiro[4.5]decan-1-one (F-33) |
| F-34 | 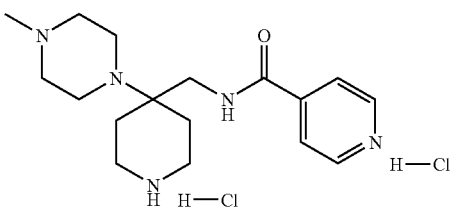 | N-[[4-(4-Methylpiperazin-1-yl)-piperidin-4-yl]methyl] pyridine-4-carboxylic acid amide dihydrochloride (F-34) |
| F-35 | 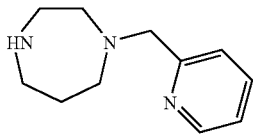 [SMILES: c1ccc(CN2CCCNCC2)nc1] | 1-(Pyridin-2-yl-methyl)-[1,4]diazepan (F-35) |
| F-36 | 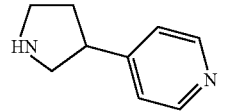 | 4-Pyrrolidin-3-yl-pyridine (F-36) |

TABLE 3-continued

Amine overview

| Amine | Structure | Name |
|---|---|---|
| F-37 | 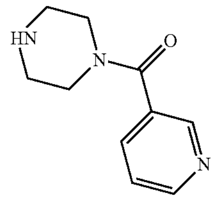 [SMILES: O=C(c1cccnc1)N1CCNCC1] | Piperazin-1-yl-pyridin-3-yl-methanone (F-37) |
| F-38 | 2HCl | 8-(Pyridin-4-yl)-2,8-diazaspiro[4.5]decane dihydrochloride (F-38) |
| F-39 | 2 F₃CCO₂H | 3-(Pyridin-4-yl)-1-oxa-2,8-diazaspiro[4.5]dec-2-ene bis(trifluoroacetate) (F-39) |
| F-40 | 3 HCl | 6-(Piperidin-1-ylmethyl)-2-(pyrrolidin-3-yl)-1,2,3,4-tetrahydroisoquinoline trihydrochloride (F-40) |
| F-41 | 2HCl | 2-(Pyridin-4-yl)-2,7-diazaspiro[4.4]nonane dihydrochloride (F-41) |
| F-42 | 2 HCl | 9-(Azetldln-1-yl)-3-azaspiro[5.5]undecane dihydrochloride (F-42) |
| F-43 | 2 HCl | 9-(Pyridin-4-yloxy)-3-azaspiro[5.5]undecane dihydrochloride (F-43) |

TABLE 3-continued

Amine overview

| Amine | Structure | Name |
|---|---|---|
| F-44 | 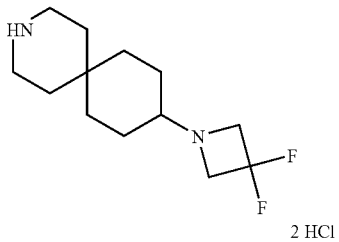 [SMILES: FC1(F)CN(C2CCC3(CCNCC3)CC2)C1 ; "2 HCl"] | 9-(3,3-Difluoroazetidin-1-yl)-3-azaspiro[5.5]undecane dihydrochloride (F-44) |
| F-45 | 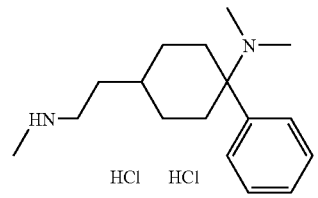 [SMILES: CNCCC1CCC(c2ccccc2)(N(C)C)CC1 ; Cl ; Cl] | Dimethyl-[4-(2-methylamino-ethyl)-1-phenyl-cyclohexyl]-amine dihydrochloride (F-45) |
| F-46 | 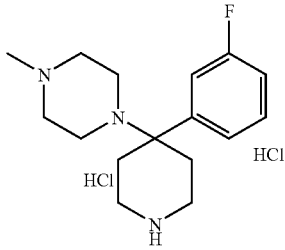 [SMILES: CN1CCN(C2(c3cccc(F)c3)CCNCC2)CC1 ; Cl ; Cl] | 1-[4-(3-Fluorophenyl)-piperidin-4-yl]-4-methyl-piperazine dihydrochloride (F-46) |
| F-47 | 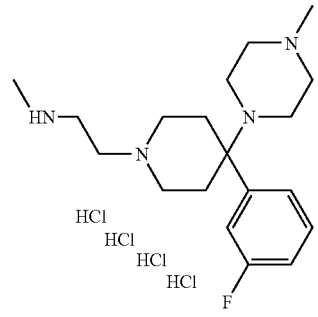 | 2-[4-(3-Fluorophenyl)-4-(4-methyl-piperazin-1-yl)-piperidin-1-yl]-ethyl-methyl-amine tetrahydrochloride (F-47) |
| F-48 | 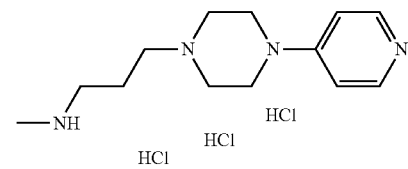 [SMILES: CNCCCN1CCN(c2ccncc2)CC1 ; Cl ; Cl ; Cl] | Methyl-[3-(4-pyridin-4-yl-piperazin-1-yl)-propyl]-amine trihydrochloride (F-48) |

Syntheses of Individual Substances

6) Synthesis of Indolamides G

General Method for the Synthesis of Indolamides G

FIG. 2: Synthesis of indolamides G

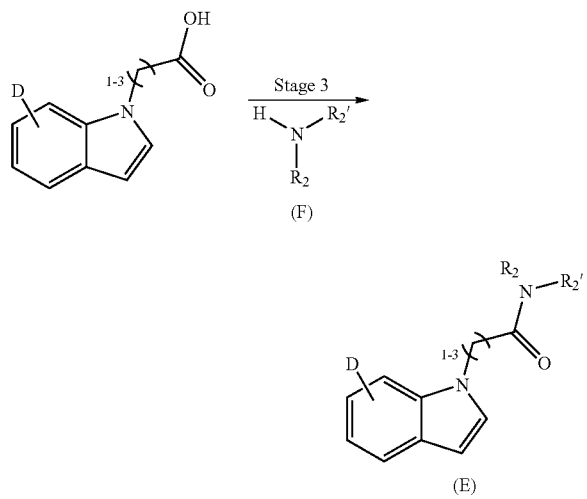

wherein $N(H)(R^2)(R^{2'})$ denotes $N(H)(R^8)\text{---}[CR^{9a}R^{9b}]_t\text{---}A(R^{10})(R^{11})$.

General procedure GP V—CU coupling: A solution of acid E (1 eq.) and carbonyldiimidazole (2 eq.) in dichloromethane/dimethyl formamide was stirred for 1 h at room temperature, then mixed with amine F (3 eq.) dissolved in dichloromethane and stirred for 12 h at room temperature. The reaction solution was washed 3 times with saturated sodium hydrogen carbonate solution, dried over magnesium sulfate and concentrated under reduced pressure. The desired product was obtained after purification by column chromatography (alox neutral, ethyl acetate/hexane or silica, DCM/MeOH optionally NEt₃).

General procedure GP VI—EDCl coupling: A cold solution (0° C.) of acid E (1.5 eq.), HOBt (0.3 eq.) and diisopropylethylamine (4 eq.) in dichloromethane was mixed with EDCI (1.5 eq.) and stirred for 15 min. Amine F (1 eq.) was then added and the mixture was stirred for 12 h at room temperature. The reaction solution was washed 3 times with 0.5N potassium hydroxide solution, dried over magnesium sulfate and concentrated under reduced pressure. The desired product was obtained after purification by column chromatography (alox neutral, ethyl acetate/hexane or silica, DCM/MeOH optionally NEt₃).

General procedure GP VII—CU coupling: 1,1'-Carbonyldiimidazole (1.05 eq.) and carboxylic acid E (1 eq.) were dissolved in dichloromethane or a dichloromethane/N,N-dimethyl formamide (3:2) mixture and stirred for 1 h at room temperature. Then amine F (optionally in the form of the corresponding hydrochloride (xHCl)) (1.5 eq.) dissolved in a mixture of dichloromethane/N,N-dimethyl formamide (3:2) and triethylamine (2-3 eq.) was added dropwise and the reaction mixture was stirred for 1 to 3 days at room temperature (DC control). The mixture was mixed with a little water and concentrated to small volume under vacuum. Then the residue was taken up in dichloromethane and washed with saturated sodium hydrogen carbonate solution and saturated sodium chloride solution. The aqueous phase was extracted with dichloromethane (twice) and the combined organic phases were washed again with saturated sodium chloride solution. Then the mixture was dried over sodium sulfate or magnesium sulfate and concentrated to small volume under vacuum. The crude product was purified by column chromatography (silica gel).

General procedure GP Va—TBTU coupling: The carboxylic acid E (1 equiv.), O-(1H-benzotriazol-1-yl)-N,N,N',N'-tetramethyluronium tetrafluoroborate (1 equiv.) and 1-hydroxybenzotriazole hydrate (1 equiv.) were placed in tetrahydrofuran, under protecting gas, and the mixture was stirred for 30 min at room temperature. A solution of the amine F (optionally in the form of the corresponding hydrochloride (xHCl) (1 equiv.) and diisopropylethylamine (DIPEA) (3-5 equiv.) in tetrahydrofuran was added, and the reaction mixture was stirred for 15 h to 3 d at room temperature. Tetrahydrofuran was then removed under vacuum, the residue was taken up in ethyl acetate or DCM and saturated sodium hydrogen carbonate solution, and the phases were separated. The aqueous phase was extracted with ethyl acetate (or DCM), and the combined organic phases were in turn washed with sat. sodium chloride solution, dried over sodium sulfate and concentrated under vacuum. The crude product was purified by column chromatography (silica gel) or by crystallization (from ethyl acetate).

General procedure GP Vb—HATU coupling: HATU (1.1 equiv.) was added to a solution of carboxylic acid E (1 equiv.) in THF, and the mixture was cooled to 0° C. DIPEA (2.5 equiv.) was added, and the reaction mixture was stirred for 10 min. A solution of the amine F in THF was then added dropwise, and the mixture was stirred for 16 h. Water was added and extraction with ethyl acetate was carried out (3×). The combined organic phases were extracted with water and sat. NaCl solution, dried over Na₂SO₄ and concentrated under vacuum. The crude product was purified by column chromatography (silica gel).

General procedure GP Vc—EDCI coupling: DIPEA (2.4-4 equiv.), EDCI (1.2-1.5 equiv.) and HOBt (1.0-1.2 equiv.) were added to a solution, at 0° C., of carboxylic acid E (1.0 equiv.) in DCM, and the resulting mixture was stirred for 15 min at 25° C. It was then cooled to 0° C. again, and the amine F (1 equiv.) in DCM (optionally plus DMF) was added. The reaction mixture was stirred for 16 h at 25° C. DCM was added, and the mixture was extracted with sodium bicarbonate solution, NH₄Cl solution, water and sat. NaCl solution, dried over Na₂SO₄ and concentrated under vacuum. The crude product was purified by column chromatography (silica gel).

| Example no. | Structure | Name |
|---|---|---|
| G-01 | 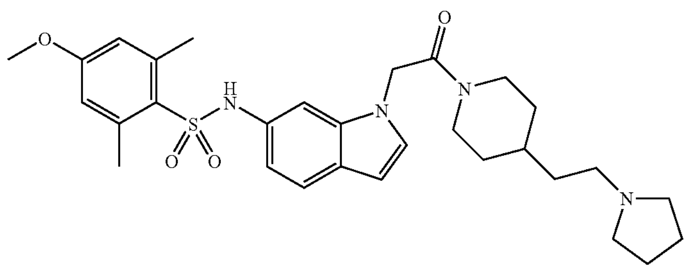 [SMILES: COc1cc(C)c(S(=O)(=O)Nc2ccc3ccn(CC(=O)N4CCC(CCN5CCCC5)CC4)c3c2)c(C)c1] | 4-Methoxy-2,6-dimethyl-N-[1-[2-oxo-2-[4-(2-pyrrolidin-1-yl-ethyl)-piperidin-1-yl]-ethyl]-1H-indol-6-yl]-benzenesulfonic acid amide (G-01) |
| G-02 | 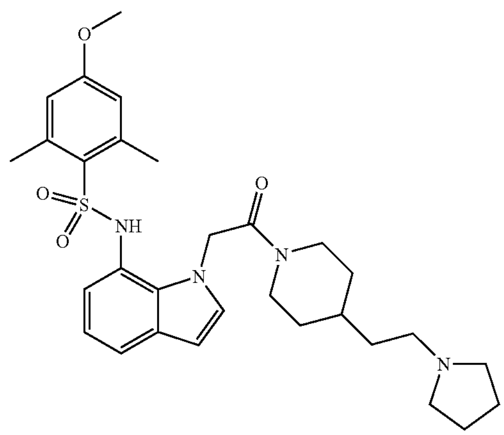 [SMILES: COc1cc(C)c(S(=O)(=O)Nc2cccc3ccn(CC(=O)N4CCC(CCN5CCCC5)CC4)c23)c(C)c1] | 4-Methoxy-2,6-dimethyl-N-[1-[2-oxo-2-[4-(2-pyrrolidin-1-yl-ethyl)-piperidin-1-yl]-ethyl -1H-indol-7-yl]-benzenesulfonic acid amide (G-02) |
| G-03 | 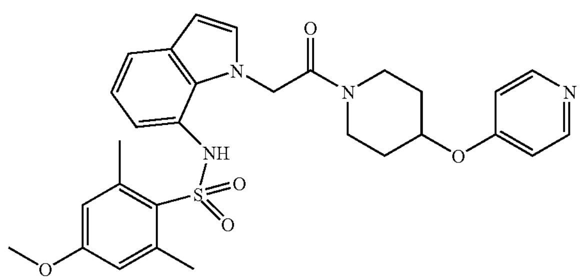 [SMILES: COc1cc(C)c(S(=O)(=O)Nc2cccc3ccn(CC(=O)N4CCC(Oc5ccncc5)CC4)c23)c(C)c1] | 4-Methoxy-2,6-dimethyl-N-[1-[2-oxo-2-(4-pyridin-4-yloxy-piperidin-1-yl)-ethyl]-1H-indol-7-yl]-benzenesulfonic acid amide (G-03) |
| G-04 | 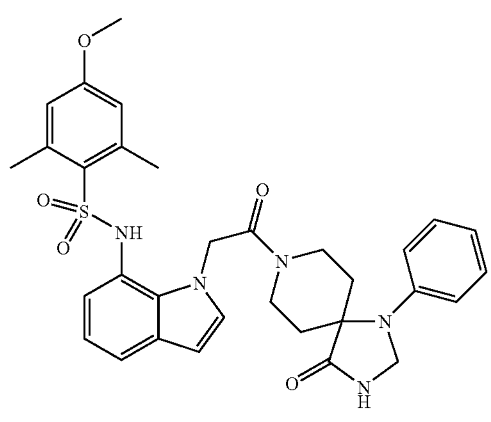 [SMILES: COc1cc(C)c(S(=O)(=O)Nc2cccc3ccn(CC(=O)N4CCC5(CC4)C(=O)NCN5c4ccccc4)c23)c(C)c1] | 4-Methoxy-2,6-dimethyl-N-[1-[2-oxo-2-(1-oxo-4-phenyl-2,4,8-triazaspiro[4.5]decan-8-yl)-ethyl]-1H-indol-7-yl]-benzenesulfonic acid amide (G-04) |

| | | |
|---|---|---|
| G-05 | 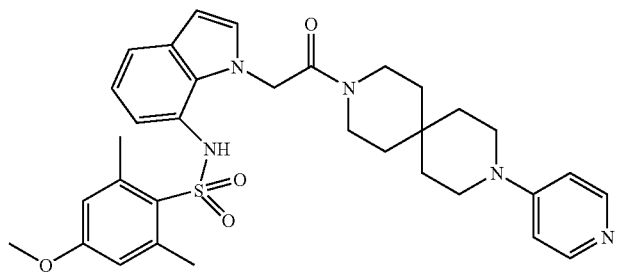 [SMILES: COc1cc(C)c(S(=O)(=O)Nc2cccc3ccn(CC(=O)N4CCC5(CC4)CCN(c4ccncc4)CC5)c23)c(C)c1] | 4-Methoxy-2,6-dimethyl-N-[1-[2-oxo-2-(9-pyridin-4-yl-3,9-diazaspiro[5.5]undecan-3-yl)-ethyl]-1H-indol-7-yl]-benzenesulfonic acid amide (G-05) |
| G-06 | 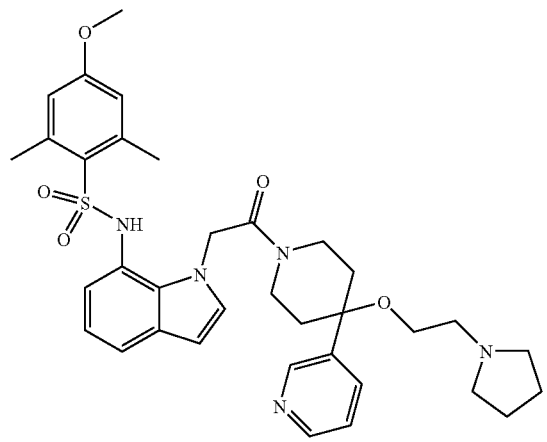 [SMILES: COc1cc(C)c(S(=O)(=O)Nc2cccc3ccn(CC(=O)N4CCC(OCCN5CCCC5)(c5cccnc5)CC4)c23)c(C)c1] | 4-Methoxy-2,6-dimethyl-N-[1-[2-oxo-2-[4-pyridin-3-yl-4-(2-pyrrolidin-1-yl-ethoxy)-piperidin-1-yl]-ethyl]-1H-indol-7-yl]-benzenesulfonic acid amide (G-06) |
| G-07 | 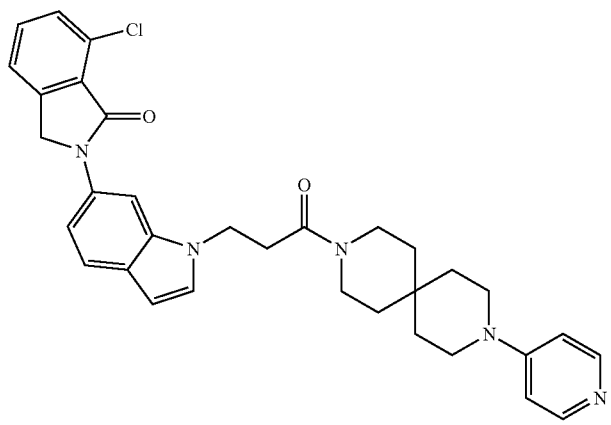 [SMILES: O=C(CCn1ccc2ccc(N3Cc4cccc(Cl)c4C3=O)cc21)N1CCC2(CC1)CCN(c1ccncc1)CC2] | 7-Chloro-2-[1-[3-oxo-3-(9-pyridin-4-yl-3,9-diazaspiro[5.5]undecan-3-yl)-propyl]-1H-indol-6-yl]-2,3-dihydro-isoindol-1-one (G-07) |
| G-08 | 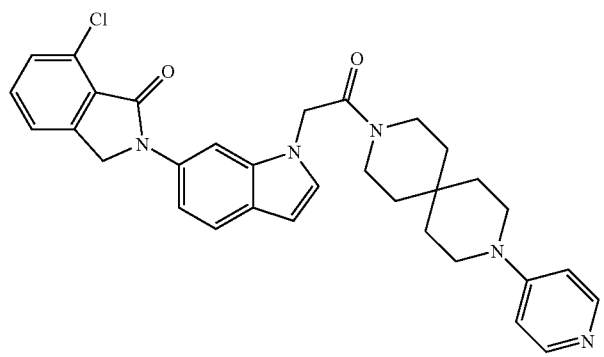 [SMILES: O=C(Cn1ccc2ccc(N3Cc4cccc(Cl)c4C3=O)cc21)N1CCC2(CC1)CCN(c1ccncc1)CC2] | 7-Chloro-2-[1-[2-oxo-2-(9-pyridin-4-yl-3,9-diazaspiro[5.5]undecan-3-yl)-ethyl]-1H-indol-6-yl]-2,3-dihydro-isoindol-1-one (G-08) |

| | | |
|---|---|---|
| G-10 | 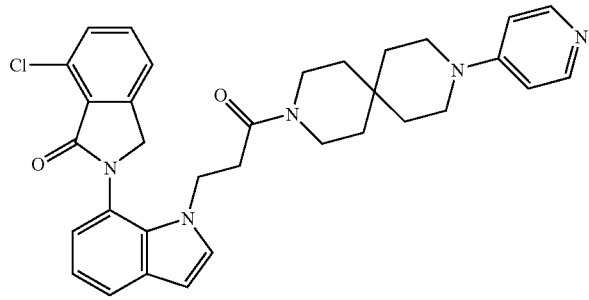 [SMILES: O=C(CCn1ccc2cccc(N3Cc4cccc(Cl)c4C3=O)c21)N1CCC2(CC1)CCN(c1ccncc1)CC2] | 7-Chloro-2-[1-[3-oxo-3-(9-pyridin-4-yl-3,9-diazaspiro[5.5]undecan-3-yl)-propyl]-1H-indol-7-yl]-2,3-dihydro-isoindol-1-one (G-10) |
| G-11 | 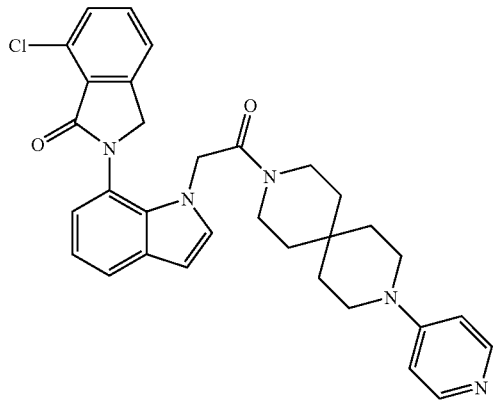 [SMILES: O=C(Cn1ccc2cccc(N3Cc4cccc(Cl)c4C3=O)c21)N1CCC2(CC1)CCN(c1ccncc1)CC2] | 7-Chloro-2-[1-[2-oxo-2-(9-pyridin-4-yl-3,9-diazaspiro[5.5]undecan-3-yl)-ethyl]-1H-indol-7-yl]-2,3-dihydro-isoindol-1-one (G-11) |
| G-12 | 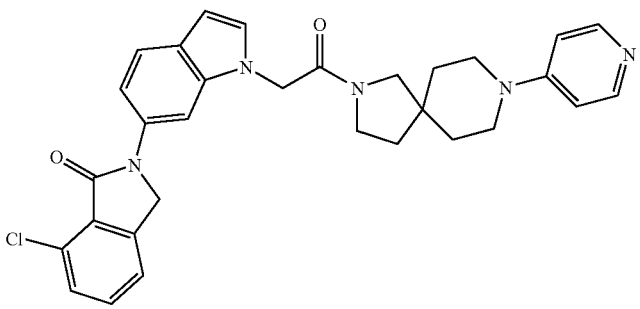 [SMILES: O=C(Cn1ccc2ccc(N3Cc4cccc(Cl)c4C3=O)cc21)N1CCC2(CCN(c3ccncc3)CC2)C1] | 7-Chloro-2-[1-[2-oxo-2-(8-pyridin-4-yl-3,8-diazaspiro[4.5]decan-3-yl)-ethyl]-1H-indol-6-yl]-2,3-dihydro-isoindol-1-one (G-12) |
| G-13 | 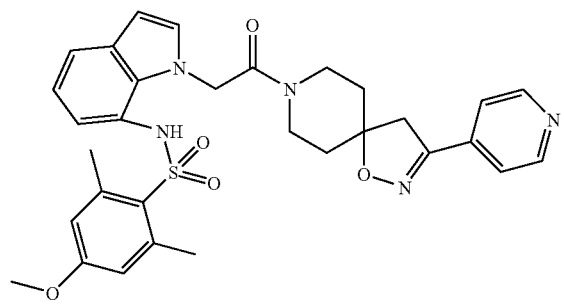 [SMILES: COc1cc(C)c(S(=O)(=O)Nc2cccc3ccn(CC(=O)N4CCC5(CC4)CC(c4ccncc4)=NO5)c23)c(C)c1] | 4-Methoxy-2,6-dimethyl-N-[1-[2-oxo-2-(3-pyridin-4-yl-1-oxa-2,8-diazaspiro[4.5]dec-2-en-8-yl)-ethyl]-1H-indol-7-yl]-benzenesulfonic acid amide (G-13) |
| G-14 | 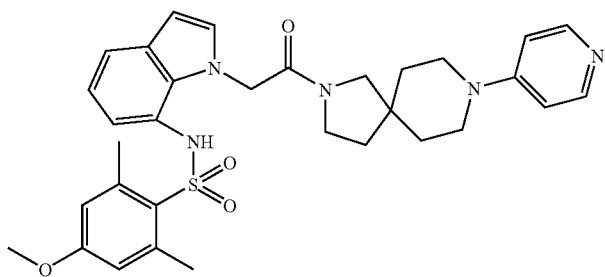 [SMILES: COc1cc(C)c(S(=O)(=O)Nc2cccc3ccn(CC(=O)N4CCC5(CCN(c6ccncc6)CC5)C4)c23)c(C)c1] | 4-Methoxy-2,6-dimethyl-N-[1-[2-oxo-2-(8-pyridin-4-yl-3,8-diazaspiro[4.5]decan-3-yl)-ethyl]-1H-indol-7-yl]-benzenesulfonic acid amide (G-14) |

G-15 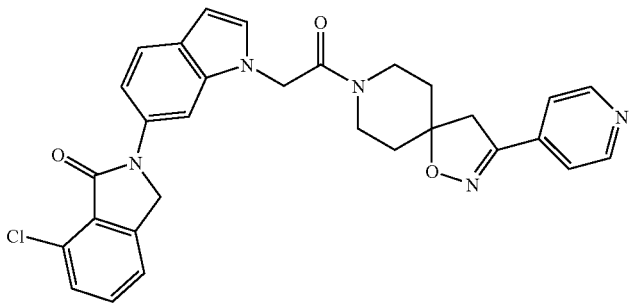 [SMILES: O=C(Cn1ccc2ccc(N3Cc4cccc(Cl)c4C3=O)cc21)N1CCC2(CC1)CC(c1ccncc1)=NO2]
7-Chloro-2-[1-[2-oxo-2-(3-pyridin-4-yl-1-oxa-2,8-diazaspiro[4.5]dec-2-en-8-yl)-ethyl]-1H-indol-6-yl]-2,3-dihydro-isoindol-1-one (G-15)

G-16 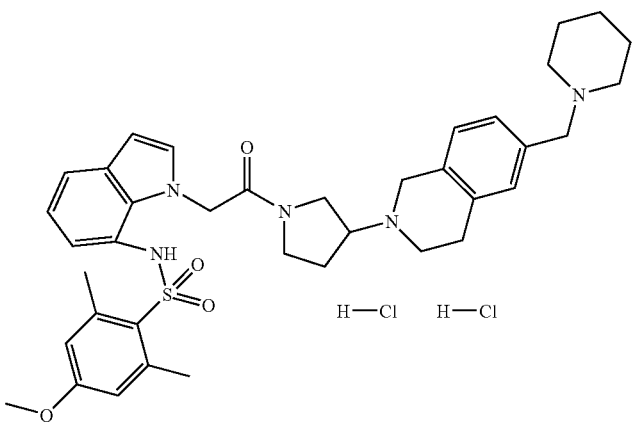
4-Methoxy-2,6-dimethyl-N-[1-[2-oxo-2-[3-[6-(piperidin-1-yl-methyl)-1,2,3,4-tetrahydro-isoquinolin-2-yl]-pyrrolidin-1-yl]-ethyl]-1H-indol-7-yl]-benzenesulfonic acid amide dihydrochloride (G-16)

G-17 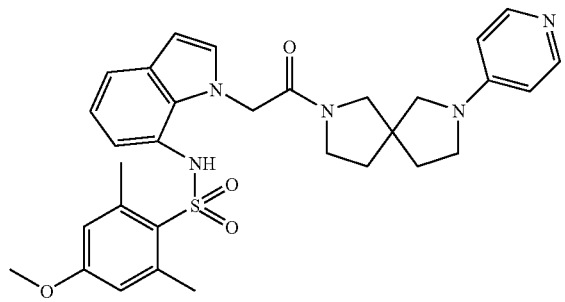 [SMILES: COc1cc(C)c(S(=O)(=O)Nc2cccc3ccn(CC(=O)N4CCC5(CCN(c6ccncc6)C5)C4)c23)c(C)c1]
4-Methoxy-2,6-dimethyl-N-[1-[2-oxo-2-(8-pyridin-4-yl-3,8-diazaspiro[4.4]nonan-3-yl)-ethyl]-1H-indol-7-yl]-benzenesulfonic acid amide (G-17)

G-18 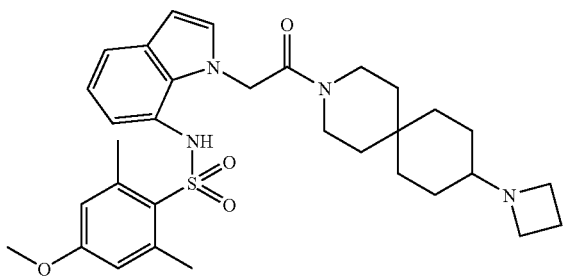 [SMILES: COc1cc(C)c(S(=O)(=O)Nc2cccc3ccn(CC(=O)N4CCC5(CCC(N6CCC6)CC5)CC4)c23)c(C)c1]
N-[1-[2-[9-(Azetidin-1-yl)-3-azaspiro[5.5]undecan-3-yl]-2-oxo-ethyl]-1H-indol-7-yl]-4-methoxy-2,6-dimethyl-benzenesulfonic acid amide (G-18)

G-19 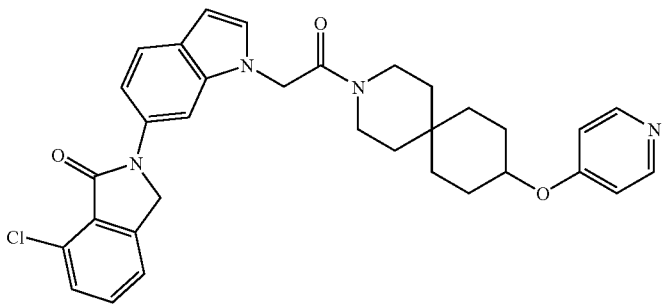 [SMILES: O=C(Cn1ccc2ccc(N3Cc4cccc(Cl)c4C3=O)cc21)N1CCC2(CCC(Oc3ccncc3)CC2)CC1]
7-Chloro-2-[1-[2-oxo-2-(9-pyridin-4-yloxy-3-azaspiro[5.5]undecan-3-yl)-ethyl]-1H-indol-6-yl]-2,3-dihydro-isoindol-1-one (G-19)

-continued

G-20 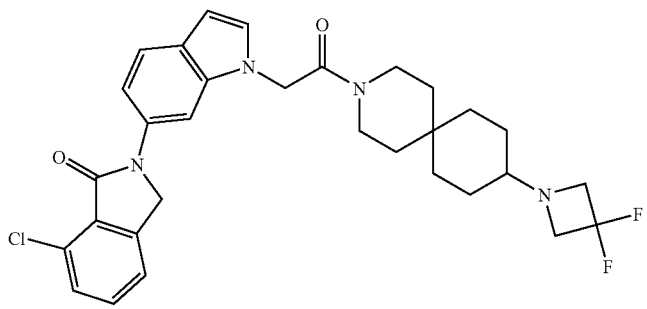 [SMILES: O=C(Cn1ccc2ccc(N3Cc4cccc(Cl)c4C3=O)cc21)N1CCC2(CCC(N3CC(F)(F)C3)CC2)CC1] 7-Chloro-2-[1-[2-[9-(3,3-difluoro-azetidin-1-yl)-3-azaspiro[5.5]undecan-3-yl]-2-oxo-ethyl]-1H-indol-6-yl]-2,3-dihydro-isoindol-1-one (G-20)

G-21 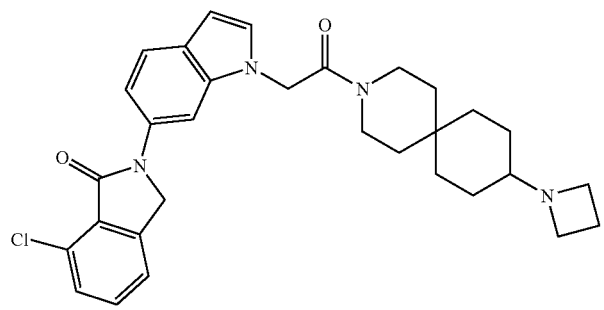 [SMILES: O=C(Cn1ccc2ccc(N3Cc4cccc(Cl)c4C3=O)cc21)N1CCC2(CCC(N3CCC3)CC2)CC1] 2-[1-[2-[9-(Azetidin-1-yl)-3-azaspiro[5.5]undecan-3-yl]-2-oxo-ethyl]1H-indol-6-yl]-7-chloro-2,3-dihydro-isoindol-1-one (G-21)

G-22 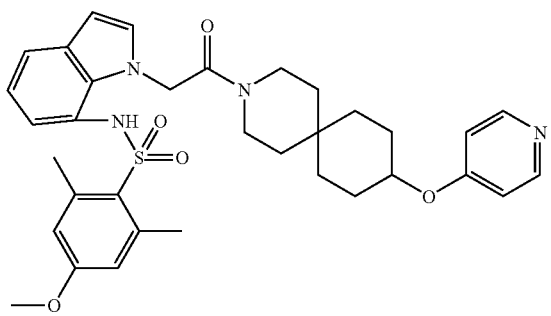 [SMILES: COc1cc(C)c(S(=O)(=O)Nc2cccc3ccn(CC(=O)N4CCC5(CCC(Oc6ccncc6)CC5)CC4)c23)c(C)c1] 4-Methoxy-2,6-dimethyl-N-[1-[2-oxo-2-(9-pyridin-4-yloxy-3-azaspiro[5.5]undecan-3-yl)-ethyl]-1H-indol-7-yl]-benzenesulfonic acid amide (G-22)

G-23 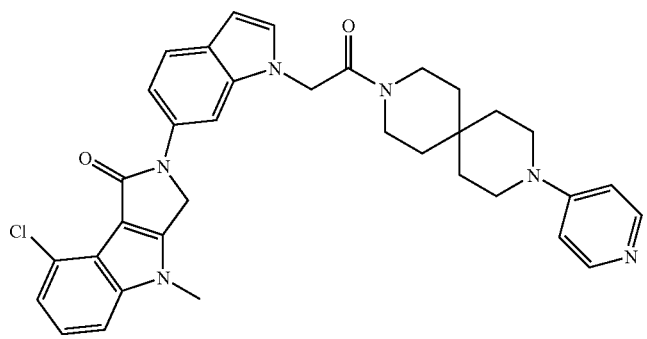 [SMILES: Cn1c2c(c3c(Cl)cccc31)C(=O)N(c1ccc3ccn(CC(=O)N4CCC5(CC4)CCN(c4ccncc4)CC5)c3c1)C2] 8-Chloro-4-methyl-2-[1-[2-oxo-2-(9-pyridin-4-yl-3,9-diazaspiro[5.5]undecan-3-yl)-ethyl]-1H-indol-6-yl]-3,4-dihydro-2H-pyrrolo[3,4-b]indol-1-one (G-23)

| | | |
|---|---|---|
| G-24 | 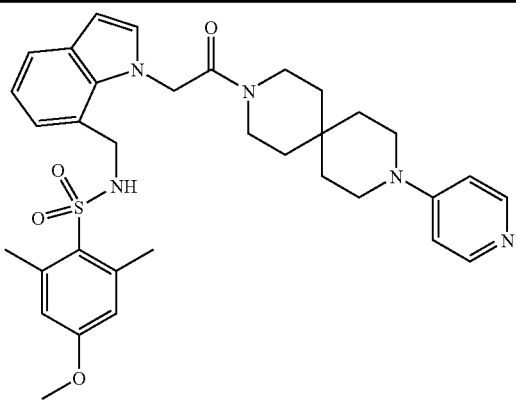 | 4-Methoxy-2,6-dimethyl-N-[[1-[2-oxo-2-(9-pyridin-4-yl-3,9-diazaspiro[5.5]undecan-3-yl)-ethyl]-1H-indol-7-yl]-methyl]-benzenesulfonic acid amide (G-24) |
| G-26 | 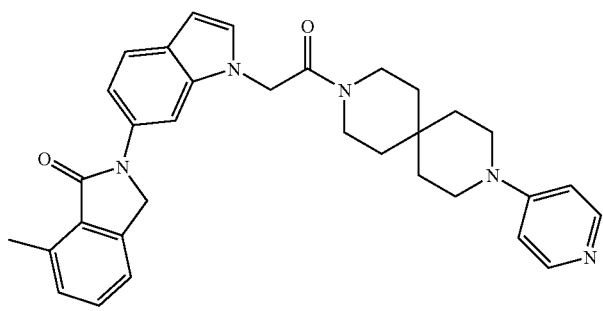 [SMILES: Cc1cccc2c1C(=O)N(c1ccc3ccn(CC(=O)N4CCC5(CC4)CCN(c4ccncc4)CC5)c3c1)C2] | 7-Methyl-2-[1-[2-oxo-2-(9-pyridin-4-yl-3,9-diazaspiro[5.5]undecan-3-yl)-ethyl]-1H-indol-6-yl]-2,3-dihydro-isoindol-1-one (G-26) |
| G-27 | 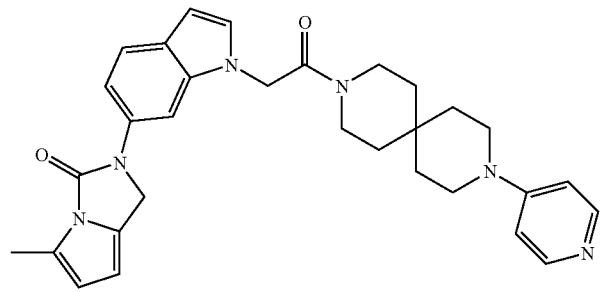 [SMILES: Cc1ccc2n1C(=O)N(c1ccc3ccn(CC(=O)N4CCC5(CC4)CCN(c4ccncc4)CC5)c3c1)C2] | 5-Methyl-2-[1-[2-oxo-2-(9-pyridin-4-yl-3,9-diazaspiro[5.5]undecan-3-yl)-ethyl]-1H-indol-6-yl]-1,2-dihydro-pyrrolo[2,1-e]imidazol-3-one (G-27) |
| G-31 | 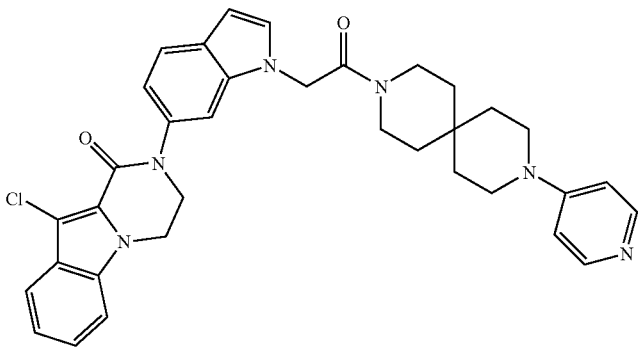 [SMILES: O=C(Cn1ccc2ccc(N3CCn4c(c(Cl)c5ccccc54)C3=O)cc21)N1CCC2(CC1)CCN(c1ccncc1)CC2] | 10-Chloro-2-[1-[2-oxo-2-(9-pyridin-4-yl-3,9-diazaspiro[5.5]undecan-3-yl)-ethyl]-1H-indol-6-yl]-3,4-dihydro-2H-pyrazino[1,2-a]indol-1-one (G-31) |
| G-33 | 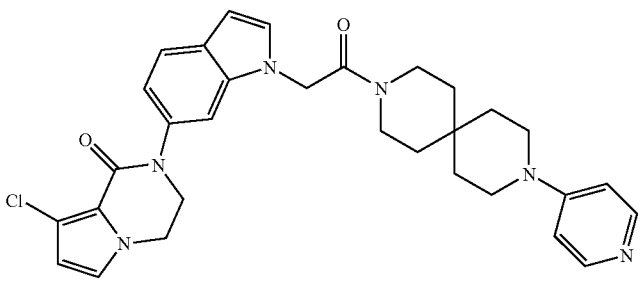 [SMILES: O=C(Cn1ccc2ccc(N3CCn4ccc(Cl)c4C3=O)cc21)N1CCC2(CC1)CCN(c1ccncc1)CC2] | 8-Chloro-2-[1-[2-oxo-2-(9-pyridin-4-yl-3,9-diazaspiro[5.5]undecan-3-yl)-ethyl]-1H-indol-6-yl]-3,4-dihydro-2H-pyrrolo[1,2-a]pyrazin-1-one (G-33) |

-continued

| Example no. | Indole acid (E) | Amine (F) | Yield | Analysis (LC/MS)[1] | Synthesised by/ Comment |
|---|---|---|---|---|---|
| G-01 | 2-[6-[[(4-Methoxy-2,6-dimethyl-phenyl)sulfonyl]amino]-1H-indol-1-yl]acetic acid (E-03) | 4-(2-Pyrrolidin-1-yl-ethyl) piperidine (F-05) | 43% (0.17 mmol) | $R_t$ = 3.0 min; m/z = 553.2 [MH]$^+$ | GP V |
| G-02 | 2-[7-[[(4-Methoxy-2,6-dimethyl-phenyl)sulfonyl]amino]-1H-indol-1-yl]acetic acid (E-02) | 4-(2-Pyrrolidin-1-yl-ethyl) piperidine (F-05) | 30% (0.11 mmol) | $R_t$ = 3.3 min; m/z = 553.2 [MH]$^+$ | GP V |
| G-03 | 2-[7-[[(4-Methoxy-2,6-dimethyl-phenyl)sulfonyl]amino]-1H-indol-1-yl]acetic acid (E-02) | 4-Piperidin-4-yloxypyridine hydrochloride (F-24) | 6% (10 mg) | | GP VII |
| G-04 | 2-[7-[[(4-Methoxy-2,6-dimethyl-phenyl)sulfonyl]amino]-1H-indol-1-yl]acetic acid (E-02) | 4-Phenyl-2,4,8-triazaspiro[4.5]decan-1-one (F-33) | 38% (2.0 mmol) | $R_t$ = 5.2 min; m/z = 602.1 [MH]$^+$ | GP V |
| G-05 | 2-[7-[[(4-Methoxy-2,6-dimethyl-phenyl)sulfonyl]amino]-1H-indol-1-yl]acetic acid (E-02) | 3-Pyridin-4-yl-3,9-diazaspiro[5.5] undecane dihydrochloride (F-14) | 14% (160 mgl) | $R_t$ = 3.6 min; m/z = 602.1 [MH]$^+$ | GP VII |
| G-06 | 2-[7-[[(4-Methoxy-2,6-dimethyl-phenyl)sulfonyl]amino]-1H-indol-1-yl]acetic acid (E-02) | 3-[4-(2-Pyrrolidin-1 ethoxy)piperidin-4-yl] pyridine dihydrochloride (F-29) | 16% (0.08 mmol) | $R_t$ = 2.8 min; m/z = 646.1 [MH]$^+$ | GP VI |
| G-07 | 3-[6-(4-Chloro-3-oxo-1,2-dihydro-isoindol-2-yl)-1H-indol-1-yl]propionic acid (E-15) | 3-Pyridin-4-yl-3,9-diazaspiro[5.5] undecane dihydrochloride (F-14) | 44% (0.16 mmol) | $R_t$ = 3.2 min; m/z = 568.3 [MH]$^+$ | GP VI |
| G-08 | 2-[6-(4-Chloro-3-oxo-1,2-dihydro-isoindol-2-yl)-1H-indol-1-yl]acetic acid (E-16) | 3-Pyridin-4-yl-3,9-diazaspiro[5.5] undecane dihydrochloride (F-14) | 54% (0.21 mmol) | $R_t$ = 3.2 min; m/z = 554.3 [MH]$^+$ | GP VI |
| G-10 | 3-[7-(4-Chloro-3-oxo-1,2-dihydro-isoindol-2-yl)-1H-indol-1-yl]-propionic acid (E-17) | 3-Pyridin-4-yl-3,9-diazaspiro[5.5]-undecane dihydrochloride (F-14) | 57% (0.24 mmol) | $R_t$ = 3.2 min; m/z = 568.4 [MH]$^+$ | GP VI |
| G-11 | 2-[7-(4-Chloro-3-oxo-1,2-dihydro-isoindol-2-yl)-1H-indol-1-yl]-acetic acid (E-19) | 3-Pyridin-4-yl-3,9-diazaspiro[5.5]-undecane dihydrochloride (F-14) | 63 % (0.27 mmol) | $R_t$ = 2.9 min; m/z = 554.4 [MH]$^+$ | GP VI |
| G-12 | 2-[6-(4-Chloro-3-oxo-1,2-dihydro-isoindol-2-yl)-1H-indol-1-yl]-acetic acid (E-16) | 8-(Pyridin-4-yl)-2,8-diazaspiro[4.5]decane dihydrochloride (F-38) | 34% (0.08 g) | $R_t$ = 3.1 min; m/z = 540.2 [MH]$^+$ | GP Va |
| G-13 | 2-[7-[[(4-Methoxy-2,6-dimethyl-phenyl)sulfonyl]amino]1H indol-1-yl]-acetic acid (E-02) | 3-(Pyridin-4-yl)-1-oxa-2,8-diazaspiro[4.5]-dec-2-ene bis(trifluoroacetate) (F-39) | 44% (0.1 g) | $R_t$ = 34.2 min; m/z = 588.3 [MH]$^+$ | GP Va |
| G-14 | 2-[7-[[(4-Methoxy-2, 6-dimethyl-phenyl)sulfonyl]amino]-1H-indol-1-yl]-acetic acid (E-02) | 8-(Pyridin-4-yl)-2,8-diazaspiro[4.5]decane dihydrochloride (F-38) | 53% (0.12 g) | $R_t$ = 3.5 min; m/z = 588.3 [MH]$^+$ | GP Va |
| G-15 | 2-[6-(4-Chloro-3-oxo-1,2-dihydro-isoindol-2-yl)-1H-indol-1-yl]-acetic acid (E-16) | 3-(Pyridin-4-yl)-1-oxa-2,8-diazaspiro[4.5]-dec-2-ene bis(trifluoroacetate) (F-39) | 39% (0.08 g) | $R_t$ = 3.7 min; m/z = 540.2 [MH]$^+$ | GP Va |
| G-16 | 2-[7-[[(4-Methoxy-2, 6-dimethyl-phenyl)sulfonyl]amino]-1H-indol-1-yl]-acetic acid (E-02) | 6-(Piperidin-1-ylmethyl)-2-(pyrrolidin-3-yl)-1,2,3,4-tetrahydroisoquinoline dihydrochloride (F-40) | 74% (0.14 g) | $R_t$ = 2.7 min; m/z = 670.4 [MH]$^+$ | GP Va |
| G-17 | 2-[7-[[(4-Methoxy-2,6-dimethyl-phenyl)sulfonyl]amino]-1H-indol-1-yl]-acetic acid (E-02) | 2-(Pyridin-4-yl)-2,7-diazaspiro[4.4]nonane dihydrochloride (F-41) | 34% (0.1 g) | $R_t$ = 3.5 min; m/z = 574.3 [MH]$^+$ | GP Va |
| G-18 | 2-[7-[[(4-Methoxy-2,6-dimethyl-phenyl)sulfonyl]amino]-1H-indol-1-yl]-acetic acid (E-02) | 9-(Azetidin-1-yl)-3-azaspiro[5.5]-undecane dihydrochloride (F-42) | 29% (0.08 g) | $R_t$ = 3.6 min; m/z = 579.4 [MH]$^+$ | GP Va |

-continued

| | | | | | |
|---|---|---|---|---|---|
| G-19 | 2-[6-(4-Chloro-3-oxo-1,2-dihydro-isoindol-2-yl)-1H-indol-1-yl]-acetic acid (E-16) | 9-(Pyridin-4-yloxy)-3-azaspiro[5.5]undecane dihydrochloride (F-43) | 72% (0.3 g) | $R_t$ = 3.5 min; m/z = 569.3 $[MH]^+$ | GP Va |
| G-20 | 2-[6-(4-Chloro-3-oxo-1,2-dihydro-isoindol-2-yl)-1H-indol-1-yl]-acetic acid (E-16) | 9-(3,3-Difluoroazetidin-1-yl)-3-azaspiro[5.5]undecane dihydrochloride (F-44) | 39% (0.13 g) | $R_t$ = 3.3 min; m/z = 567.3 $[MH]^+$ | GP Va |
| G-21 | 2-[6-(4-Chloro-3-oxo-1,2-dihydro-isoindol-2-yl)-1H-indol-1-yl]-acetic acid (E-16) | 9-(Azetidin-1-yl)-3-azaspiro[5.5]undecane dihydrochloride (F-42) | 51% (0.15 g) | $R_t$ = 3.2 min; m/z = 531.3 $[MH]^+$ | GP Va |
| G-22 | 2-[7-[[(4-Methoxy-2,6-dimethyl-phenyl)sulfonyl]amino]-1H-indol-1-yl]-acetic acid (E-02) | 9-(Pyridin-4-yloxy)-3-azaspiro[5.5]undecane dihydrochloride (F-43) | 81% (0.32 g) | $R_t$ = 3.8 min; m/z = 617.3 $[MH]^+$ | GP Va |
| G-23 | 2-(6-(8-Chloro-4-methyl-1-oxopyrrolo[3,4-b]indol-2(1H,3H,4H)-yl)-1H-indol-1-yl)acetic acid (E-20) | 3-Pyridin-4-yl-3,9-diazaspiro[5.5]undecane trifluoroacetate (F-14) | 40% | $R_t$ = 3.6 min; m/z = 607.3 $[MH]^+$ | GP Vb |
| G-24 | | | | $R_t$ = 3.7 min; m/z = 616.5 $[MH]^+$ | for synthesis see below |
| G-26 | 2-(6-(7-Methyl-1-oxoisoindolin-2-yl)-1H-indol-1-yl)acetic acid (E-21) | 3-Pyridin-4-yl-3,9-diazaspiro[5.5]undecane (F-14) | 24% | $R_t$ = 3.6 min; m/z = 534.4 $[MH]^+$ | GP Vc |
| G-27 | 2-(6-(5-Methyl-3-oxo-1H-pyrrolo[1,2-c]imidazol-2(3H)-yl)-1H-indol-1-yl)acetic acid (E-22) | 3-Pyridin-4-yl-3,9-diazaspiro[5.5]undecane (F-14) | 30% | $R_t$ = 3.7 min; m/z = 523.4 $[MH]^+$ | GP Vc |
| G-31 | 2-(6-(10-Chloro-1-oxo-3,4-dihydropyrazino[1,2-a]indol-2(1H)-yl)-1H-indol-1-yl)acetic acid (E-23) | 3-Pyridin-4-yl-3,9-diazaspiro[5.5]undecane (F-14) | 12% | $R_t$ = 3.7 min; m/z = 607.3 $[MH]^+$ | GP Vc |
| G-33 | 2-(6-(8-Chloro-1-oxo-3,4-dihydropyrrolo[1,2-a]pyrazin-2(1H)-yl)-1H-indol-1-yl)acetic acid (E-24) | 3-Pyridin-4-yl-3,9-diazaspiro[5.5]undecane (F-14) | 25% | $R_t$ = 3.0 min; m/z = 557.3 $[MH]^+$ | GP Vc |

[1]Equipment and methods for HPLC-MS analysis: HPLC: Waters Alliance 2795 with PDA Waters 2998; MS: Micromass Quattro Micro ™ API; column: Waters Atlantis ® T3, 3 μm, 100 Å, 2.1 × 30 mm; column temp: 40° C., Eluent A: purified water +0.1% formic acid; Eluent B: acetonitrile (gradient grade) +0.1% formic acid; Gradient: 0% B to 100% B in 8.8 min, 100% B for 0.4 min, 100% B to 0% B in 0.01 min, 0% B for 0.8 min; Flow: 1.0 ml/min; Ionisation: ES+, 25 V; make up: 100 μl/min 70% methanol + 0.2% formic acid; UV: 200 – 400 nm.

Exemplary compound G-24: 4-Methoxy-2,6-dimethyl-N-[[1-[2-oxo-2-(9-pyridin-4-yl-3,9-diazaspiro[5.5]undecan-3-yl)-ethyl]-1H-indol-7-yl]-methyl]-benzenesulfonic acid amide

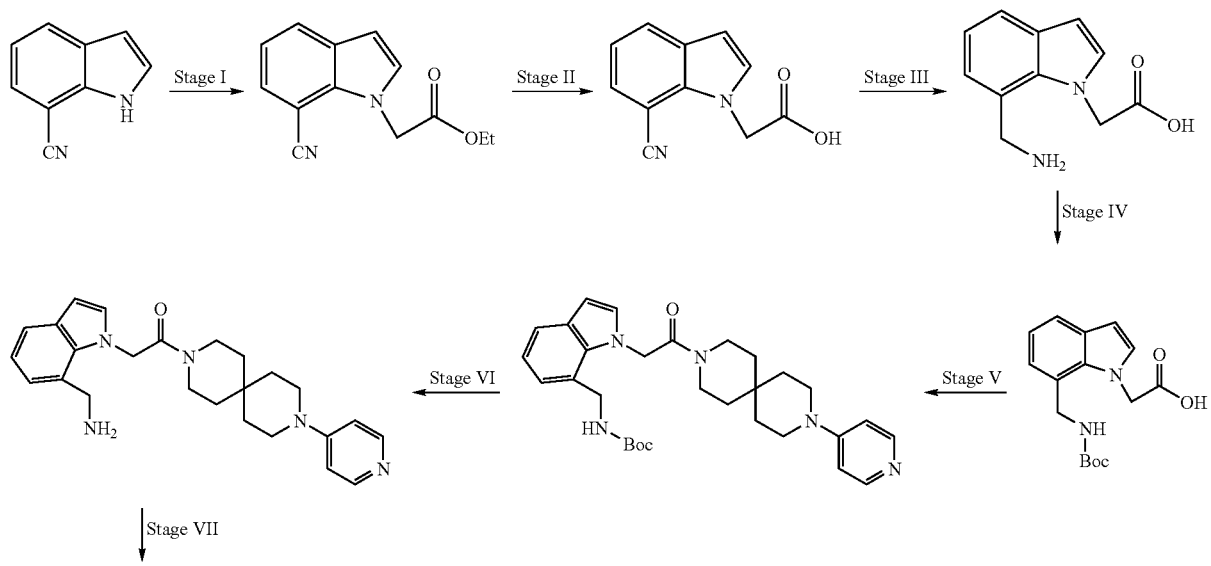

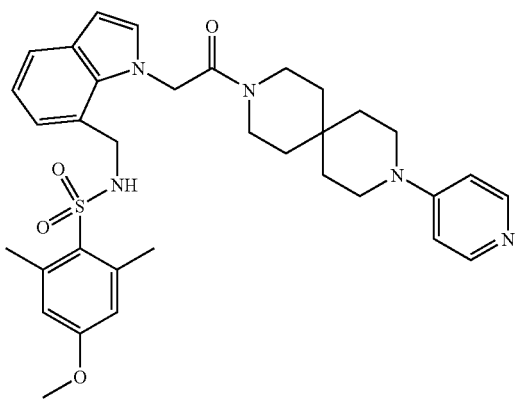

Stage I: Ethyl 2-(7-cyano-1H-indol-1-yl)acetate

A solution of 1H-indole-7-carbonitrile (2.0 g, 14.08 mmol, 1.0 equiv.) in dry DMF (10 ml) was added at 0° C. to a suspension of NaH (0.845 g, 21.12 mmol, 1.5 equiv. 60% in mineral oil) in DMF (10 ml), and the mixture was stirred for 30 min. Ethyl bromoacetate (1.9 ml, 16.9 mmol, 1.2 equiv.) was added at 0° C., and stirring was carried out for 1 h at RT. When the reaction was complete (TLC monitoring), the mixture was cooled and diluted with water (60 ml). Extraction with ethyl acetate (3×80 ml) was carried out, and the combined organic phases were washed with sat. NaCl solution (2×100 ml), dried over $Na_2SO_4$ and concentrated under vacuum. The crude product was purified by column chromatography (silica gel, 8-10% ethyl acetate/hexane) and the desired product was isolated in the form of a yellow solid. Yield: 80% (2.6 g, 11.37 mmol)

Stage II: 2-(7-Cyano-1H-indol-1-yl)acetic acid

A solution of $LiOH.H_2O$ (1.4 g, 34.06 mmol, 3.0 equiv.) in water (10 ml) was added at 0° C. to a solution of ethyl 2-(7-cyano-1H-indol-1-yl)acetate (2.6 g, 11.37 mmol, 1.0 equiv.) in THF, and the mixture was stirred for 2 h at RT. When the reaction was complete (TLC monitoring), the mixture was concentrated under vacuum and the residue was taken up in water (50 ml). Extraction with ethyl acetate (50 ml) was carried out, and then the aqueous phase was adjusted to pH≈3-4 with 10% HCl solution. Extraction with DCM (2×50 ml) was then carried out, and the combined organic phases were washed with sat. NaCl solution, dried over $Na_2SO_4$ and concentrated under vacuum. The desired product was isolated in the form of a light-yellow solid.
Yield: 92% (2.1 g, 10.5 mmol)

Stage III: 2-(7-(Aminomethyl)-1H-indol-1-yl)acetic acid

Raney Ni (7.0 g) was added to a solution of 2-(7-cyano-1H-indol-1-yl)acetic acid (700 mg, 3.5 mmol) in MeOH (15 ml), and the mixture was hydrogenated for 6 h at RT and 60 psi hydrogen in a Parr apparatus. The reaction mixture was filtered over celite and the filtrate was concentrated under vacuum. The crude product so obtained was used directly in the following stage without being purified further. Yield: 96% (692 mg, 3.36 mmol)

Stage IV: 2-(7-((tert-Butoxycarbonylamino)methyl)-1H-indol-1-yl)acetic acid

1 N NaOH (6 ml) was added at 0° C. to a solution of 2-(7-(aminomethyl)-1H-indol-1-yl)acetic acid (692 mg, 3.36 mmol, 1.0 equiv.) in dioxane, followed by $(Boc)_2O$ (1.1 ml, 5.08 mmol, 1.5 equiv.). The resulting reaction mixture was stirred for 16 h at RT and then the solvent was removed under vacuum. The residue was taken up in water (25 ml) and extracted with ethyl acetate (2×20 ml). The aqueous phase was then adjusted to an acidic pH value with $KHSO_4$ solution at 0° C. Extraction with DCM (3×30 ml) was then carried out, and the combined organic phases were washed with sat. NaCl solution (40 ml), dried over $Na_2SO_4$ and concentrated under vacuum. The crude product so obtained was used directly in the following stage without being purified further.
Yield: 36% (372 mg, 1.22 mmol)

Stage V: tert-Butyl (1-(2-oxo-2-(9-(pyridin-4-yl)-3,9-diazaspiro[5.5]undecan-3-yl)ethyl)-1H-indol-7-yl)methylcarbamate HATU (464 mg, 1.22 mmol, 1.0 equiv.) and DIPEA (0.8 ml, 4.88 mmol, 4.0 equiv.) were added at 0° C. to a suspension of 2-(7-((tert-butoxycarbonylamino)methyl)-1H-indol-1-yl)acetic acid (372 mg, 1.22 mmol, 1.0 equiv.) in THF (8 ml), and the mixture was stirred for 15 min. A solution of 3-pyridin-4-yl-3,9-diazaspiro[5.5]undecane (F-14) (283 mg, 1.22 mmol, 1.0 equiv.), dissolved in a mixture of THF (4 ml) and DMF (0.5 ml), was added, and stirring was carried out for 14 h at RT. The reaction mixture was diluted with ethyl acetate (30 ml) and extracted with sodium bicarbonate solution (2×20 ml), $NH_4Cl$ solution (2×20 ml), water (20 ml) and sat. NaCl solution (20 ml) and dried over $Na_2SO_4$. The solvent was removed under vacuum and the crude product was purified by column chromatography (Alox neutral; 0.5% MeOH/DCM), and the desired product was thus obtained in the form of a white solid.
Yield: 95% (600 mg, 1.16 mmol)

Stage VI: 2-(7-(Aminomethyl)-1H-indol-1-yl)-1-(9-(pyridin-4-yl)-3,9-diazaspiro-[5.5]undecan-3-yl)ethanone Dioxane-HCl (6 ml) was added to a solution of tert-butyl (1-(2-oxo-2-(9-(pyridin-4-yl)-3,9-diazaspiro[5.5]undecan-3-yl)ethyl)-1H-indol-7-yl)methylcarbamate (600 mg, 1.16 mmol, 1.0 equiv.) in dioxane (6 ml), and the mixture was stirred for 1 h at RT. When the reaction was complete (TLC monitoring), the solvent was removed under vacuum and the residue was adjusted to a basic pH value with TEA and was concentrated again. The crude product was purified by column chromatography (Alox neutral; 5-10% MeOH/DCM), and the desired product was thus obtained in the form of a white solid.

Yield: 45% (220 mg, 0.53 mmol)

Stage VII: 4-Methoxy-2,6-dimethyl-N-((1-(2-oxo-2-(9-(pyridin-4-yl)-3,9-diazaspiro-[5.5]undecan-3-yl)ethyl)-1H-indol-7-yl)methyl)benzenesulfonamide A mixture of 2-(7-(aminomethyl)-1H-indol-1-yl)-1-(9-(pyridin-4-yl)-3,9-diazaspiro-[5.5]undecan-3-yl)ethanone (220 mg, 0.53 mmol, 1.0 equiv.) and NaHCO$_3$ (134 mg, 1.59 mmol, 3.0 equiv.) in THF-water(1:1, 20 ml) was added at 0° C. to a solution of 2,6-dimethyl-4-methoxyphenylsulfonyl chloride (136 mg, 0.58 mmol, 1.1 equiv.) in THF (5 ml), and the mixture was stirred for 16 h at RT. The reaction mixture was diluted with water (15 ml) and extracted with ethyl acetate (3×30 ml). The combined organic phases were washed with sat. NaCl solution (40 ml) and dried over Na$_2$SO$_4$. The solvent was removed under vacuum and the crude product was purified by column chromatography (silica gel; 6-8% MeOH/DCM), and the desired product was thus obtained in the form of a white solid.

Yield: 38% (64 mg, 0.104 mmol)

Library Syntheses

Parallel Method for the Synthesis of Indolamides G_Cc

FIG. 5: Parallel synthesis of indolamides G_CC

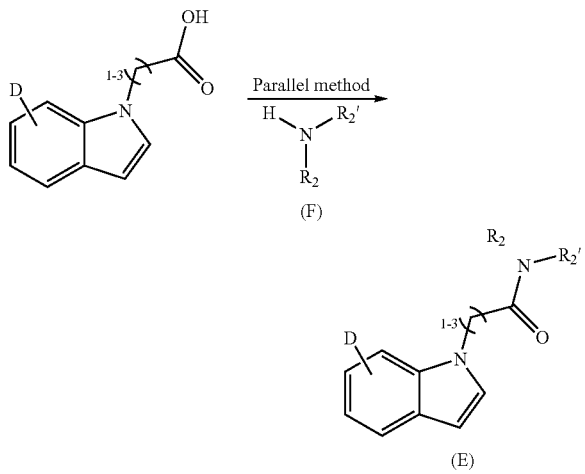

The acid structural units E were reacted in a parallel synthesis with the amines F to form the amides G_CC, as illustrated in the figure above. The correlation between product and reagent, structural unit and method is shown in the synthesis matrix.

The crude products from the parallel synthesis were analysed by HPLC-MS[2] and then purified by Reverse Phase HPLC-MS[2]. The products were able to be identified by means of analytical HPLC-MS measurements[3].

[2] Equipment and methods for HPLC-MS analysis: Parallel synthesis method: HPLC: Waters Alliance 2795 with PDA Waters 2996; MS: ZQ 2000 MassLynx Single Quadrupol MS Detector; Column: Atlantis dC18 30×2.1 mm, 3 µm; Column temperature: 40° C., Eluent A: purified water+0.1% formic acid; Eluent B: acetonitrile (gradient grade)+0.1% formic acid; Gradient: 0% B to 100% B in 2.3 min, 100% B for 0.4 min, 100% B to 0% B in 0.01 min, 0% B for 0.8 min; Flow: 1.0 ml/min; Ionisation: ES+, 25V; make up: 100 µl/min 70% methanol+0.2% formic acid; UV: 200-400 nm.

[3] Equipment and methods for HPLC-MS purification: Prep Pump: Waters 2525; Make Up Pump: Waters 515; Auxilliary Detector: Waters DAD 2487; MS Detector: Waters Micromass ZQ; Injector/Fraction Collector: Waters Sample Manager 2767; Gradient: Initial: 60% Water 40% Methanol->12-14.5 min: 0% Water 100% Methanol->14.5-15 min: 60% Water 40% Methanol; Flow: 35 ml/min Column: Macherey-Nagel, C18 Gravity, 100×21 mm, 5µ.

Parallel Synthesis: Synthesis Instructions for the Preparation of Indolamides G_CC A solution of 1,1'-carbonyldiimidazole (200 µM) in 0.5 ml dichloromethane was added to a solution of acid E (100 µM) in a mixture of 1.8 ml dichloromethane and 0.2 ml DMF and the mixture is shaken for 1 hour at room temperature. Then a solution[4] of amine F (200 µM) was added. The reaction mixture was shaken for 18 hours at room temperature.

[4] The amines in the form of hydrochloride were mixed with a 0.5 M excess (relative to the hydrochloride) of Hünig's base and with 500 µl N,N-dimethyl formamide, then topped up to a total volume of 2 ml with dichloromethane, causing them to be dissolved or suspended. The amines in the form of the free base were dissolved or suspended in dichloromethane and/or N,N-dimethyl formamide.

3 ml of semi-saturated sodium hydrogen carbonate solution were added to the reaction mixture and it was mixed intensively. The organic phase was removed and transferred to a tared vessel. Then the aqueous phase was extracted once again with 3 ml dichloromethane. The combined organic phases were concentrated under reduced pressure in vacuum centrifuges (GeneVac). The final purification was performed by HPLC-MS[3]. The final analysis was performed by LC-MS[2].

| Example no. | Example name | Indole acid no. | Indole acid name | Amine no. | Amine name |
|---|---|---|---|---|---|
| G_CC-1 | 4-Methoxy-2,6-dimethyl-N-[1-[2-[4-(1-methyl-piperidin-4-yl)-piperazin-1-yl]-2-oxo-ethyl]-1H-indol-6-yl]-benzenesulfonic acid amide (G_CC-1) | E-03 | 2-[6-[[(4-Methoxy-2,6-dimethyl-phenyl)sulfonyl]amino]-1H-indol-1-yl] acetic acid (E-03) | F-02 | 1-(1-Methyl-piperidin-4-yl) piperazine (F-02) |
| G_CC-2 | 4-Methoxy-2,6-dimethyl-N-[1-[2-[4-(4-methyl-piperazin-1-yl)-piperidin-1-yl]-2-oxo-ethyl]-1H-indol-6-yl]-benzenesulfonic acid amide (G_CC-2) | E-03 | 2-[6-[[(4-Methoxy-2,6-dimethyl-phenyl)sulfonyl]amino]-1H-indol-1-yl] acetic acid (E-03) | F-21 | 1-Methyl-4-piperidin-4-yl piperazine (F-21) |
| G_CC-3 | 4-Methoxy-2,6-dimethyl-N-[1-[2-oxo-2-(4-pyrimidin-2-yl-piperazin-1-yl)-ethyl]-1H-indol-6-yl]-benzenesulfonic acid amide (G_CC-3) | E-03 | 2-[6-[[(4-Methoxy-2,6-dimethyl-phenyl)sulfonyl]amino]-1H-indol-1-yl] acetic acid (E-03) | F-17 | 2-Piperazin-1-yl pyrimidine (F-17) |
| G_CC-4 | 4-Methoxy-2,6-dimethyl-N-[1-[2-[4-[(1-methyl-piperidin-4-yl)-methyl]-piperazin-1-yl]-2-oxo-ethyl]-1H-indol-6-yl]-benzenesulfonic acid amide (G_CC-4) | E-03 | 2-[6-[[(4-Methoxy-2,6-dimethyl-phenyl)sulfonyl]amino]-1H-indol-1-yl] acetic acid (E-03) | F-22 | 1-[(1-Methyl-piperidin-4-yl) methyl] piperazine (F-22) |

-continued

| Example no. | Example name | Indole acid no. | Indole acid name | Amine no. | Amine name |
|---|---|---|---|---|---|
| G_CC-5 | N-[1-[2-[4-(4-fluorophenyl)-piperazin-1-yl]-2-oxo-ethyl]-1H-indol-7-yl]-4-methoxy-2,6-dimethyl-benzenesulfonic acid amide (G_CC-5) | E-02 | 2-[7-[[(4-Methoxy-2,6-dimethyl-phenyl)sulfonyl]amino]-1H-indol-1-yl] acetic acid (E-02) | F-16 | 1-(4-Fluoro-phenyl)piperazine (F-16) |
| G_CC-6 | 4-Methoxy-2,6-dimethyl-N-[1-[2-oxo-2-(4-pyrimidin-2-yl-piperazin-1-yl)-ethyl]-1H-indol-7-yl]-benzenesulfonic acid amide (G_CC-6) | E-02 | 2-[7-[[(4-Methoxy-2,6-dimethyl-phenyl)sulfonyl]amino]-1H-indol-1-yl] acetic acid (E-02) | F-17 | 2-Piperazin-1-yl pyrimidine (F-17) |
| G_CC-7 | 4-Methoxy-2,6-dimethyl-N-[1-[2-[4-[(1-methyl-piperidin-4-yl)-methyl]-piperazin-1-yl]-2-oxo-ethyl]-1H-indol-7-yl]-benzenesulfonic acid amide (G_CC-7) | E-02 | 2-[7-[[(4-Methoxy-2,6-dimethyl-phenyl)sulfonyl]amino]-1H-indol-1-yl] acetic acid (E-02) | F-22 | 1-[(1-Methyl-piperidin-4-yl)methyl] piperazine (F-22) |
| G_CC-8 | 4-Chloro-2,5-dimethyl-N-[1-[2-[4-[(1-methyl-piperidin-4-yl)-methyl]-piperazin-1-yl]-2-oxo-ethyl]-1H-indol-6-yl]-benzenesulfonic acid amide (G_CC-8) | E-04 | 2-[6-[[(4-Chloro-2,5-dimethyl-phenyl)sulfonyl]amino]-1H-indol-1-yl] acetic acid (E-04) | F-22 | 1-[(1-Methyl-piperidin-4-yl)methyl] piperazine (F-22) |
| G_CC-9 | 2-[6-[[(4-Methoxy-2,6-dimethyl-phenyl)sulfonyl]amino]-1H-indol-1-yl]-N-[(1-pyridin-4-yl-piperidin-4-yl)-methyl]-acetamide (G_CC-9) | E-03 | 2-[6-[[(4-Methoxy-2,6-dimethyl-phenyl)sulfonyl]amino]-1H-indol-1-yl] acetic acid (E-03) | F-15 | (1-Pyridin-4-yl-piperidin-4-yl)methylamine dihydrochloride (F-15) |
| G_CC-10 | N-[1-[2-(3-Benzyl-3,7-diazaspiro[4.4]nonan-7-yl)-2-oxo-ethyl]-1H-indol-6-yl]-4-methoxy-2,6-dimethyl-benzenesulfonic acid amide (G_CC-10) | E-03 | 2-[6-[[(4-Methoxy-2,6-dimethyl-phenyl)sulfonyl]amino]-1H-indol-1-yl] acetic acid (E-03) | F-28 | 3-Benzyl-3,7-diazaspiro[4.4]nonane (F-28) |
| G_CC-11 | N-[3-(4-Dimethylamino-4-phenyl-piperidin-1-yl)-propyl]-2-[6-[[(4-methoxy-2,6-dimethyl-phenyl)sulfonyl]amino]-1H-indol-1-yl]-N-methyl-acetamide (G_CC-11) | E-03 | 2-[6-[[(4-Methoxy-2,6-dimethyl-phenyl)sulfonyl]amino]-1H-indol-1-yl] acetic acid (E-03) | F-11 | Dimethyl-[1-(3-methylaminopropyl)-4-phenyl piperidin-4-yl]amine trihydrochloride (F-11) |
| G_CC-12 | N-[1-[2-[3-(4-Fluorophenyl)-4-oxo-3,8-diazaspiro[4.5]decan-8-yl]-2-oxo-ethyl]-1H-indol-7-yl]-4-methoxy-2,6-dimethyl-benzenesulfonic acid amide (G_CC-12) | E-02 | 2-[7-[[(4-Methoxy-2,6-dimethyl-phenyl)sulfonyl]amino]-1H-indol-1-yl] acetic acid (E-02) | F-23 | 3-(4-Fluorophenyl)-3,8-diazaspiro[4.5]decan-4-one hydrochloride (F-23) |
| G_CC-13 | N-[1-[2-(3-Benzyl-3,7-diazaspiro[4.4]nonan-7-yl)-2-oxo-ethyl]-1H-indol-7-yl]-4-methoxy-2,6-dimethyl-benzenesulfonic acid amide (G_CC-13) | E-02 | 2-[7-[[(4-Methoxy-2,6-dimethyl-phenyl)sulfonyl]amino]-1H-indol-1-yl] acetic acid (E-02) | F-28 | 3-Benzyl-3,7-diazaspiro[4.4]nonane (F-28) |
| G_CC-14 | N-[3-(4-Dimethylamino-4-phenyl-piperidin-1-yl)-propyl]-2-[7-[[(4-methoxy-2,6-dimethyl-phenyl)sulfonyl]amino]-1H-indol-1-yl]-N-methyl-acetamide (G_CC-14) | E-02 | 2-[7-[[(4-Methoxy-2,6-dimethyl-phenyl)sulfonyl]amino]-1H-indol-1-yl] acetic acid (E-02) | F-11 | Dimethyl-[1-(3-methylaminopropyl)-4-phenyl piperidin-4-yl]amine trihydrochloride (F-11) |
| G_CC-15 | 2-[6-[[(4-Chloro-2,5-dimethyl-phenyl)sulfonyl]amino]-1H-indol-1-yl]-N-[3-(4-dimethylamino-4-phenyl-piperidin-1-yl)-propyl]-N-methyl-acetamide (G_CC-15) | E-04 | 2-[6-[[(4-Chloro-2,5-dimethyl-phenyl)sulfonyl]amino]-1H-indol-1-yl] acetic acid (E-04) | F-11 | Dimethyl-[1-(3-methylaminopropyl)-4-phenyl piperidin-4-yl]amine trihydrochloride (F-11) |
| G_CC-16 | N-[3-(4-Dimethylamino-4-phenyl-piperidin-1-yl)-propyl]-N-methyl-2-[7-[(naphthalen-1-ylsulfonyl)amino]-1H-indol-1-yl]-acetamide (G_CC-16) | E-07 | 2-[7-[(Naphthalen-1-ylsulfonyl)amino]-1H-indol-1-yl] acetic acid (E-07) | F-11 | Dimethyl-[1-(3-methylaminopropyl)-4-phenyl piperidin-4-yl]amine trihydrochloride (F-11) |
| G_CC-17 | N-[4-(Azetidin-1-yl)-4-phenyl-cyclohexyl]-2-[7-[[(4-methoxy-2,6-dimethyl-phenyl)sulfonyl]amino]-1H-indol-1-yl]-acetamide (G_CC-17) | E-02 | 2-[7-[[(4-Methoxy-2,6-dimethyl-phenyl)sulfonyl]amino]-1H-indol-1-yl] acetic acid (E-02) | F-12 | [4-(Azetidin-1-yl)-4-phenyl-cyclohexyl]amine dihydrochloride (F-12) |
| G_CC-18 | N-[3-(4-Dimethylamino-4-thiophen-2-yl-piperidin-1-yl)-propyl]-2-[7-[[(4-methoxy-2,6-dimethyl-phenyl)sulfonyl]amino]-1H-indol-1-yl]-N-methyl-acetamide (G_CC-18) | E-02 | 2-[7-[[(4-Methoxy-2,6-dimethyl-phenyl)sulfonyl]amino]-1H-indol-1-yl] acetic acid (E-02) | F-09 | Dimethyl-[1-(3-methylaminopropyl)-4-thiophen-2-yl-piperidin-4-yl]amine (F-09) |

| Example no. | Example name | Indole acid no. | Indole acid name | Amine no. | Amine name |
|---|---|---|---|---|---|
| G_CC-19 | N-[2-(4-Dimethylamino-4-thiophen-2-yl-piperidin-1-yl)-ethyl]-2-[7-[[(4-methoxy-2,6-dimethyl-phenyl)sulfonyl]amino]-1H-indol-1-yl]-acetamide (G_CC-19) | E-02 | 2-[7-[[(4-Methoxy-2,6-dimethyl-phenyl)sulfonyl]amino]-1H-indol-1-yl] acetic acid (E-02) | F-08 | [1-(2-Aminoethyl)-4-thiophen-2-yl-piperidin-4-yl]-dimethylamine trihydrochloride (F-08) |
| G_CC-20 | N-[1-[2-(4-Dimethylamino-4-thiophen-2-yl-piperidin-1-yl)-2-oxo-ethyl]-1H-indol-7-yl]-4-methoxy-2,6-dimethyl-benzenesulfonic acid amide (G_CC-20) | E-02 | 2-[7-[[(4-Methoxy-2,6-dimethyl-phenyl)sulfonyl]amino]-1H-indol-1-yl] acetic acid (E-02) | F-10 | Dimethyl-(4-thiophen-2-yl piperidin-4-yl)amine dihydrochloride (F-10) |
| G_CC-21 | 2-[7-[[(4-Methoxy-2,6-dimethyl-phenyl)sulfonyl]amino]-1H-indol-1-yl]-N-[2-(1-pyridin-4-yl-piperidin-4-yl)-ethyl]-acetamide (G_CC-21) | E-02 | 2-[7-[[(4-Methoxy-2,6-dimethyl-phenyl)sulfonyl]amino]-1H-indol-1-yl] acetic acid (E-02) | F-13 | 2-(1-Pyridin-4-yl-piperidin-4-yl)ethylamine dihydrochloride (F-13) |
| G_CC-22 | N-[2-(4-Dimethylamino-4-thiophen-2-yl-piperidin-1-yl)-ethyl]-3-[6-[[(4-methoxy-2,6-dimethyl-phenyl)sulfonyl]amino]-1H-indol-1-yl]-propionamide (G_CC-22) | E-05 | 3-[6-[[(4-Methoxy-2,6-dimethyl-phenyl)sulfonyl]amino]-1H-indol-1-yl] propionic acid (E-05) | F-08 | [1-(2-Aminoethyl)-4-thiophen-2-yl-piperidin-4-yl]-dimethylamine trihydrochloride (F-08) |
| G_CC-23 | 3-[6-[[(4-Methoxy-2,6-dimethyl-phenyl)sulfonyl]amino]-1H-indol-1-yl]-N-[2-(1-pyridin-4-yl-piperidin-4-yl)-ethyl]-propionamide (G_CC-23) | E-05 | 3-[6-[[(4-Methoxy-2,6-dimethyl-phenyl)sulfonyl]amino]-1H-indol-1-yl] propionic acid (E-05) | F-13 | 2-(1-Pyridin-4-yl-piperidin-4-yl)ethylamine dihydrochloride (F-13) |
| G_CC-24 | 2-[6-[[(4-Chloro-2,5-dimethyl-phenyl)sulfonyl]amino]-1H-indol-1-yl]-N-[2-(1-pyridin-4-yl-piperidin-4-yl)-ethyl]-acetamide (G_CC-24) | E-04 | 2-[6-[[(4-Chloro-2,5-dimethyl-phenyl)sulfonyl]amino]-1H-indol-1-yl] acetic acid (E-04) | F-13 | 2-(1-Pyridin-4-yl-piperidin-4-yl)ethylamine dihydrochloride (F-13) |
| G_CC-25 | N-[3-(4-Dimethylamino-4-thiophen-2-yl-piperidin-1-yl)-propyl]-N-methyl-2-[7-[(naphthalen-1-ylsulfonyl)amino]-1H-indol-1-yl]-acetamide (G_CC-25) | E-07 | 2-[7-[(Naphthalen-1-ylsulfonyl)amino]-1H-indol-1-yl] acetic acid (E-07) | F-09 | Dimethyl-[1-(3-methylaminopropyl)-4-thiophen-2-yl-piperidin-4-yl]amine (F-09) |
| G_CC-26 | 2-[7-[[(4-Chloro-2,5-dimethyl-phenyl)sulfonyl]amino]-1H-indol-1-yl]-N-[3-(4-dimethylamino-4-thiophen-2-yl-piperidin-1-yl)-propyl]-N-methyl-acetamide (G_CC-26) | E-08 | 2-[7-[[(4-Chloro-2,5-dimethyl-phenyl)sulfonyl]amino]-1H-indol-1-yl] acetic acid (E-08) | F-09 | Dimethyl-[1-(3-methylaminopropyl)-4-thiophen-2-yl-piperidin-4-yl]amine (F-09) |
| G_CC-27 | 2-[7-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-acetamide (G_CC-27) | E-08 | 2-[7-[[(4-Chloro-2,5-dimethyl-phenyl)sulfonyl]amino]-1H-indol-1-yl] acetic acid (E-08) | F-08 | [1-(2-Aminoethyl)-4-thiophen-2-yl-piperidin-4-yl]-dimethylamine trihydrochloride (F-08) |
| G_CC-28 | 2-[7-[[(4-Chloro-2,5-dimethyl-phenyl)sulfonyl]amino]-1H-indol-1-yl]-N-[2-(1-pyridin-4-yl-piperidin-4-yl)-ethyl]-acetamide (G_CC-28) | E-08 | 2-[7-[[(4-Chloro-2,5-dimethyl-phenyl)sulfonyl]amino]-1H-indol-1-yl] acetic acid (E-08) | F-13 | 2-(1-Pyridin-4-yl-piperidin-4-yl)ethylamine dihydrochloride (F-13) |
| G_CC-29 | N-[3-(4-Dimethylamino-4-thiophen-2-yl-piperidin-1-yl)-propyl]-2-[6-[[(4-methoxy-2,6-dimethyl-phenyl)sulfonyl]amino]-1H-indol-1-yl]-N-methyl-acetamide (G_CC-29) | E-03 | 2-[6-[[(4-Methoxy-2,6-dimethyl-phenyl)sulfonyl]amino]-1H-indol-1-yl] acetic acid (E-03) | F-09 | Dimethyl-[1-(3-methylaminopropyl)-4-thiophen-2-yl-piperidin-4-yl]amine (F-09) |
| G_CC-30 | N-[2-(4-Dimethylamino-4-thiophen-2-yl-piperidin-1-yl)-ethyl]-2-[6-[[(4-methoxy-2,6-dimethyl-phenyl)sulfonyl]amino]-1H-indol-1-yl]-acetamide (G_CC-30) | E-03 | 2-[6-[[(4-Methoxy-2,6-dimethyl-phenyl)sulfonyl]amino]-1H-indol-1-yl] acetic acid (E-03) | F-08 | [1-(2-Aminoethyl)-4-thiophen-2-yl-piperidin-4-yl]-dimethylamine trihydrochloride (F-08) |
| G_CC-31 | N-[1-[2-[1-(4-Fluorophenyl)-3-methyl-4-oxo-3,8-diazaspiro[4.5]decan-8-yl]-2-oxo-ethyl]-1H-indol-7-yl]-4-methoxy-2,6-dimethyl-benzenesulfonic acid amide (G_CC-31) | E-02 | 2-[7-[[(4-Methoxy-2,6-dimethyl-phenyl)sulfonyl]amino]-1H-indol-1-yl] acetic acid (E-02) | F-25 | 1-(4-Fluorophenyl)-3-methyl-3,8-diazaspiro[4.5]decan-4-one hydrochloride (F-25) |
| G_CC-32 | N-[1-[2-(3-Benzyl-4-oxo-3,8-diazaspiro[4.5]decan-8-yl)-2-oxo-ethyl]-1H-indol-7-yl]-4-methoxy-2,6-dimethyl-benzenesulfonic acid amide (G_CC-32) | E-02 | 2-[7-[[(4-Methoxy-2,6-dimethyl-phenyl)sulfonyl]amino]-1H-indol-1-yl] acetic acid (E-02) | F-27 | 3-Benzyl-3,8-diazaspiro[4.5]decan-4-one hydrochloride (F-27) |

| Example no. | Example name | Indole acid no. | Indole acid name | Amine no. | Amine name |
|---|---|---|---|---|---|
| G_CC-33 | N-[1-[2-[2-[(4-Fluorophenyl)-methyl]-2,5-diazabicyclo[2.2.1]heptan-5-yl]-2-oxo-ethyl]-1H-indol-6-yl]-4-methoxy-2,6-dimethyl-benzenesulfonic acid amide (G_CC-33) | E-03 | 2-[6-[[(4-Methoxy-2,6-dimethyl-phenyl)sulfonyl]amino]-1H-indol-1-yl] acetic acid (E-03) | F-31 | 2-[(4-Fluoro-phenyl)methyl]-2,5-diazabicyclo[2.2.1]heptane dihydrochloride (F-31) |
| G_CC-34 | 4-Methoxy-2,6-dimethyl-N-[1-[2-oxo-2-[2-(pyridin-4-yl-methyl)-2,5-diazabicyclo[2.2.1]heptan-5-yl]-ethyl]-1H-indol-7-yl]-benzenesulfonic acid amide (G_CC-34) | E-02 | 2-[7-[[(4-Methoxy-2,6-dimethyl-phenyl)sulfonyl]amino]-1H-indol-1-yl] acetic acid (E-02) | F-30 | 2-(Pyridin-4-yl-methyl)-2,5-diazabicyclo[2.2.1]heptane dihydrochloride (F-30) |
| G_CC-35 | 4-Methoxy-2,6-dimethyl-N-[1-[3-oxo-3-(3-pyridin-4-yl-3,9-diazaspiro[5.5]undecan-9-yl)-propyl]-1H-indol-6-yl]-benzenesulfonic acid amide (G_CC-35) | E-05 | 3-[6-[[(4-Methoxy-2,6-dimethyl-phenyl)sulfonyl]amino]-1H-indol-1-yl] propionic acid (E-05) | F-14 | 3-Pyridin-4-yl-3,9-diazaspiro[5.5]undecane dihydrochloride (F-14) |
| G_CC-36 | 4-Chloro-2,5-dimethyl-N-[1-[2-oxo-2-(3-pyridin-4-yl-3,9-diazaspiro[5.5]undecan-9-yl)-ethyl]-1H-indol-6-yl]-benzenesulfonic acid amide (G_CC-36) | E-04 | 2-[6-[[(4-Chloro-2,5-dimethyl-phenyl)sulfonyl]amino]-1H-indol-1-yl] acetic acid (E-04) | F-14 | 3-Pyridin-4-yl-3,9-diazaspiro[5.5]undecane dihydrochloride (F-14) |
| G_CC-37 | N-[1-[2-Oxo-2-(3-pyridin-4-yl-3,9-diazaspiro[5.5]undecan-9-yl)-ethyl]-1H-indol-6-yl]-2-(trifluoromethyl)-benzenesulfonic acid amide (G_CC-37) | E-06 | 2-[6-[[[2-(Trifluoromethyl)-phenyl]sulfonyl]amino]-1H-indol-1-yl] acetic acid (E-06) | F-14 | 3-Pyridin-4-yl-3,9-diazaspiro[5.5]undecane dihydrochloride (F-14) |
| G_CC-38 | N-[1-[2-Oxo-2-(3-pyridin-4-yl-3,9-diazaspiro[5.5]undecan-9-yl)-ethyl]-1H-indol-7-yl]-naphthalene-1-sulfonic acid amide (G_CC-38) | E-07 | 2-[7-[(Naphthalen-1-ylsulfonyl)amino]-1H-indol-1-yl] acetic acid (E-07) | F-14 | 3-Pyridin-4-yl-3,9-diazaspiro[5.5]undecane dihydrochloride (F-14) |
| G_CC-39 | 4-Chloro-2,5-dimethyl-N-[1-[2-oxo-2-(3-pyridin-4-yl-3,9-diazaspiro[5.5]undecan-9-yl)-ethyl]-1H-indol-7-yl]-benzenesulfonic acid amide (G_CC-39) | E-08 | 2-[7-[[(4-Chloro-2,5-dimethyl-phenyl)sulfonyl]amino]-1H-indol-1-yl] acetic acid (E-08) | F-14 | 3-Pyridin-4-yl-3,9-diazaspiro[5.5]undecane dihydrochloride (F-14) |
| G_CC-40 | 4-Methoxy-2,6-dimethyl-N-[1-[3-[4-(1-methyl-piperidin-4-yl)-piperazin-1-yl]-3-oxo-propyl]-1H-indol-7-yl]-benzenesulfonic acid amide (G_CC-40) | E-14 | 3-[7-[[(4-Methoxy-2,6-dimethyl-phenyl)sulfonyl]amino]-1H-indol-1-yl] propionic acid (E-14) | F-02 | 1-(1-Methyl-piperidin-4-yl) piperazine (F-02) |
| G_CC-41 | 4-Methoxy-2,6-dimethyl-N-[1-[3-oxo-3-[4-(2-pyrrolidin-1-yl-ethyl)-piperidin-1-yl]-propyl]-1H-indol-7-yl]-benzenesulfonic acid amide (G_CC-41) | E-14 | 3-[7-[[(4-Methoxy-2,6-dimethyl-phenyl)sulfonyl]amino]-1H-indol-1-yl] propionic acid (E-14) | F-05 | 4-(2-Pyrrolidin-1-yl-ethyl) piperidine (F-05) |
| G_CC-42 | 4-Methoxy-2,6-dimethyl-N-[1-[3-[4-(4-methyl-piperazin-1-yl)-piperidin-1-yl]-3-oxo-propyl]-1H-indol-7-yl]-benzenesulfonic acid amide (G_CC-42) | E-14 | 3-[7-[[(4-Methoxy-2,6-dimethyl-phenyl)sulfonyl]amino]-1H-indol-1-yl] propionic acid (E-14) | F-21 | 1-Methyl-4-piperidin-4-yl piperazine (F-21) |
| G_CC-43 | 4-Methoxy-2,6-dimethyl-N-[1-[3-[4-[(1-methyl-piperidin-4-yl)-methyl]-piperazin-1-yl]-3-oxo-propyl]-1H-indol-7-yl]-benzenesulfonic acid amide (G_CC-43) | E-14 | 3-[7-[[(4-Methoxy-2,6-dimethyl-phenyl)sulfonyl]amino]-1H-indol-1-yl] propionic acid (E-14) | F-22 | 1-[(1-Methyl-piperidin-4-yl) methyl] piperazine (F-22) |
| G_CC-44 | N-[1-[3-[4-(3-Dimethylamino-propyl)-piperazin-1-yl]-3-oxo-propyl]-1H-indol-7-yl]-4-methoxy-2,6-dimethyl-benzenesulfonic acid amide (G_CC-44) | E-14 | 3-[7-[[(4-Methoxy-2,6-dimethyl-phenyl)sulfonyl]amino]-1H-indol-1-yl] propionic acid (E-14) | F-01 | Dimethyl-(3-piperazin-1-yl-propyl)amine (F-01) |
| G_CC-45 | N-[1-[3-(4-Hydroxy-4-pyridin-2-yl-piperidin-1-yl)-3-oxo-propyl]-1H-indol-7-yl]-4-methoxy-2,6-dimethyl-benzenesulfonic acid amide (G_CC-45) | E-14 | 3-[7-[[(4-Methoxy-2,6-dimethyl-phenyl)sulfonyl]amino]-1H-indol-1-yl] propionic acid (E-14) | F-20 | 4-Pyridin-2-yl piperidin-4-ol (F-20) |
| G_CC-46 | N-[3-(4-Dimethylamino-4-thiophen-2-yl-piperidin-1-yl)-propyl]-3-[7-[[(4-methoxy-2,6-dimethyl-phenyl)sulfonyl]amino]-1H-indol-1-yl]-N-methyl-propionamide (G_CC-46) | E-14 | 3-[7-[[(4-Methoxy-2,6-dimethyl-phenyl)sulfonyl]amino]-1H-indol-1-yl] propionic acid (E-14) | F-09 | Dimethyl-[1-(3-methylaminopropyl)-4-thiophen-2-yl-piperidin-4-yl]amine (F-09) |

-continued

| Example no. | Example name | Indole acid no. | Indole acid name | Amine no. | Amine name |
|---|---|---|---|---|---|
| G_CC-47 | 3-[7-[[(4-Methoxy-2,6-dimethyl-phenyl)sulfonyl]amino]-1H-indol-1-yl]-N-[2-(1-pyridin-4-yl-piperidin-4-yl)-ethyl]-propionamide (G_CC-47) | E-14 | 3-[7-[[(4-Methoxy-2,6-dimethyl-phenyl)sulfonyl]amino]-1H-indol-1-yl] propionic acid (E-14) | F-13 | 2-(1-Pyridin-4-yl-piperidin-4-yl)ethylamine dihydrochloride (F-13) |
| G_CC-48 | N-[1-[3-(4-Dimethylamino-4-phenyl-piperidin-1-yl)-3-oxo-propyl]-1H-indol-7-yl]-4-methoxy-2,6-dimethyl-benzenesulfonic acid amide (G_CC-48) | E-14 | 3-[7-[[(4-Methoxy-2,6-dimethyl-phenyl)sulfonyl]amino]-1H-indol-1-yl] propionic acid (E-14) | F-07 | Dimethyl-(4-phenyl-piperidin-4-yl)amine dihydrochloride (F-07) |
| G_CC-49 | N-[3-(4-Dimethylamino-4-phenyl-piperidin-1-yl)-propyl]-3-[7-[[(4-methoxy-2,6-dimethyl-phenyl)sulfonyl]amino]-1H-indol-1-yl]-N-methyl-propionamide (G_CC-49) | E-14 | 3-[7-[[(4-Methoxy-2,6-dimethyl-phenyl)sulfonyl]amino]-1H-indol-1-yl] propionic acid (E-14) | F-11 | Dimethyl-[1-(3-methylaminopropyl)-4-phenyl piperidin-4-yl]amine trihydrochloride (F-11) |
| G_CC-50 | N-[4-(Azetidin-1-yl)-4-phenyl-cyclohexyl]-3-[7-[[(4-methoxy-2,6-dimethyl-phenyl)sulfonyl]amino]-1H-indol-1-yl]-propionamide (G_CC-50) | E-14 | 3-[7-[[(4-Methoxy-2,6-dimethyl-phenyl)sulfonyl]amino]-1H-indol-1-yl] propionic acid (E-14) | F-12 | [4-(Azetidin-1-yl)-4-phenyl-cyclohexyl]amine dihydrochloride (F-12) |
| G_CC-51 | N-[2-(4-Dimethylamino-4-thiophen-2-yl-piperidin-1-yl)-ethyl]-3-[7-[[(4-methoxy-2,6-dimethyl-phenyl)sulfonyl]amino]-1H-indol-1-yl]-propionamide (G_CC-51) | E-14 | 3-[7-[[(4-Methoxy-2,6-dimethyl-phenyl)sulfonyl]amino]-1H-indol-1-yl] propionic acid (E-14) | F-08 | [1-(2-Aminoethyl)-4-thiophen-2-yl-piperidin-4-yl]-dimethylamine trihydrochloride (F-08) |
| G_CC-52 | N-[1-[3-Oxo-3-(3-pyridin-4-yl-3,9-diazaspiro[5.5]undecan-9-yl)-propyl]-1H-indol-7-yl]-2-(trifluoromethyl)-benzenesulfonic acid amide (G_CC-52) | E-09 | 3-[7-[[[2-(Trifluoromethyl)-phenyl]sulfonyl]amino]-1H-indol-1-yl] propionic acid (E-09) | F-14 | 3-Pyridin-4-yl-3,9-diazaspiro[5.5]undecane dihydrochloride (F-14) |
| G_CC-53 | N-[1-[2-Oxo-2-(3-pyridin-4-yl-3,9-diazaspiro[5.5]undecan-9-yl)-ethyl]-1H-indol-7-yl]-2-(trifluoromethyl)-benzenesulfonic acid amide (G_CC-53) | E-13 | 2-[7-[[[2-(Trifluoromethyl)-phenyl]sulfonyl]amino]-1H-indol-1-yl] acetic acid (E-13) | F-14 | 3-Pyridin-4-yl-3,9-diazaspiro[5.5]undecane dihydrochloride (F-14) |
| G_CC-54 | 4-Methoxy-2,6-dimethyl-N-[1-[3-oxo-3-(3-pyridin-4-yl-3,9-diazaspiro[5.5]undecan-9-yl)-propyl]-1H-indol-7-yl]-benzenesulfonic acid amide (G_CC-54) | E-14 | 3-[7-[[(4-Methoxy-2,6-dimethyl-phenyl)sulfonyl]amino]-1H-indol-1-yl] propionic acid (E-14) | F-14 | 3-Pyridin-4-yl-3,9-diazaspiro[5.5]undecane dihydrochloride (F-14) |
| G_CC-56 | N-[3-(4-Ethyl-piperazin-1-yl)-propyl]-3-[7-[[(4-methoxy-2,6-dimethyl-phenyl)sulfonyl]amino]-1H-indol-1-yl]-propionamide (G_CC-56) | E-14 | 3-[7-[[(4-Methoxy-2,6-dimethyl-phenyl)sulfonyl]amino]-1H-indol-1-yl] propionic acid (E-14) | F-03 | 3-(4-Ethyl-piperazin-1-yl)-propylamine (F-03) |
| G_CC-57 | 4-Methoxy-2,6-dimethyl-N-[1-[2-oxo-2-[4-pyridin-3-yl-4-(2-pyrrolidin-1-yl-ethoxy)-piperidin-1-yl]-ethyl]-1H-indol-6-yl]-benzenesulfonic acid amide (G-CC-57) | E-03 | 2-[6-[[(4-Methoxy-2,6-dimethyl-phenyl)sulfonyl]amino]-1H-indol-1-yl] acetic acid (E-03) | F-29 | 3-[4-(2-Pyrrolidin-1-yl-ethoxy)piperidin-4-yl] pyridine dihydrochloride (F-29) |
| G_CC-59 | 4-Chloro-2,5-dimethyl-N-[1-[3-[4-(1-methyl-piperidin-4-yl)-piperazin-1-yl]-3-oxo-propyl]-1H-indol-7-yl]-benzenesulfonic acid amide (G_CC-59) | E-10 | 3-[7-[[(4-Chloro-2,5-dimethyl-phenyl)sulfonyl]amino]-1H-indol-1-yl] propionic acid (E-10) | F-02 | 1-(1-Methyl-piperidin-4-yl) piperazine (F-02) |
| G_CC-60 | 4-Chloro-2,5-dimethyl-N-[1-[3-oxo-3-[4-(2-pyrrolidin-1-yl-ethyl)-piperidin-1-yl]-propyl]-1H-indol-7-yl]-benzenesulfonic acid amide (G_CC-60) | E-10 | 3-[7-[[(4-Chloro-2,5-dimethyl-phenyl)sulfonyl]amino]-1H-indol-1-yl] propionic acid (E-10) | F-05 | 4-(2-Pyrrolidin-1-yl-ethyl) piperidine (F-05) |
| G_CC-61 | 4-Chloro-2,5-dimethyl-N-[1-[3-[4-(4-methyl-piperazin-1-yl)-piperidin-1-yl]-3-oxo-propyl]-1H-indol-7-yl]-benzenesulfonic acid amide (G_CC-61) | E-10 | 3-[7-[[(4-Chloro-2,5-dimethyl-phenyl)sulfonyl]amino]-1H-indol-1-yl] propionic acid (E-10) | F-21 | 1-Methyl-4-piperidin-4-yl piperazine (F-21) |
| G_CC-62 | 4-Chloro-2,5-dimethyl-N-[1-[3-[4-[(1-methyl-piperidin-4-yl)-methyl]-piperazin-1-yl]-3-oxo-propyl]-1H-indol-7-yl]-benzenesulfonic acid amide (G_CC-62) | E-10 | 3-[7-[[(4-Chloro-2,5-dimethyl-phenyl)sulfonyl]amino]-1H-indol-1-yl] propionic acid (E-10) | F-22 | 1-[(1-Methyl-piperidin-4-yl) methyl] piperazine (F-22) |
| G_CC-63 | 7-Chloro-2-[1-[3-oxo-3-(4-pyridin-4-yl-piperazin-1-yl)-propyl]-1H-indol-6-yl]-2,3-dihydro-isoindol-1-one (G_CC-63) | E-15 | 3-[6-(4-Chloro-3-oxo-1,2-dihydro-isoindol-2-yl)-1H-indol-1-yl] propionic acid (E-15) | F-18 | 1-Pyridin-4-yl piperazine (F-18) |

| Example no. | Example name | Indole acid no. | Indole acid name | Amine no. | Amine name |
|---|---|---|---|---|---|
| G_CC-64 | 7-Chloro-2-[1-[3-[4-[(1-methyl-piperidin-4-yl)-methyl]-piperazin-1-yl]-3-oxo-propyl]-1H-indol-6-yl]-2,3-dihydro-isoindol-1-one (G_CC-64) | E-15 | 3-[6-(4-Chloro-3-oxo-1,2-dihydro-isoindol-2-yl)-1H-indol-1-yl] propionic acid (E-15) | F-22 | 1-[(1-Methyl-piperidin-4-yl) methyl] piperazine (F-22) |
| G_CC-65 | 4-Chloro-2,5-dimethyl-N-[1-[3-oxo-3-(3-pyridin-4-yl-3,9-diazaspiro[5.5]undecan-9-yl)-propyl]-1H-indol-6-yl]-benzenesulfonic acid amide (G_CC-65) | E-12 | 3-[6-[[(4-Chloro-2,5-dimethyl-phenyl)sulfonyl]amino]-1H-indol-1-yl] propionic acid (E-12) | F-14 | 3-Pyridin-4-yl-3,9-diazaspiro[5.5]undecane dihydrochloride (F-14) |
| G_CC-66 | 8-[3-[6-(4-Chloro-3-oxo-1,2-dihydro-isoindol-2-yl)-1H-indol-1-yl]-propanoyl]-3-[(4-fluorophenyl)-methyl]-3,8-diazaspiro[4.5]decan-4-one (G_CC-66) | E-15 | 3-[6-(4-Chloro-3-oxo-1,2-dihydro-isoindol-2-yl)-1H-indol-1-yl] propionic acid (E-15) | F-26 | 3-[(4-Fluorophenyl)-methyl]-3,8-diazaspiro[4.5]decan-4-one hydrochloride (F-26) |
| G_CC-67 | 7-Chloro-2-[1-[3-oxo-3-(3-pyridin-4-yl-3,9-diazaspiro[5.5]undecan-9-yl)-propyl]-1H-indol-6-yl]-2,3-dihydro-isoindol-1-one (G_CC-67) | E-15 | 3-[6-(4-Chloro-3-oxo-1,2-dihydro-isoindol-2-yl)-1H-indol-1-yl] propionic acid (E-15) | F-14 | 3-Pyridin-4-yl-3,9-diazaspiro[5.5]undecane dihydrochloride (F-14) |
| G_CC-68 | 7-Chloro-2-[1-[3-oxo-3-(4-pyridin-4-yloxy-piperidin-1-yl)-propyl]-1H-indol-6-yl]-2,3-dihydro-isoindol-1-one (G_CC-68) | E-15 | 3-[6-(4-Chloro-3-oxo-1,2-dihydro-isoindol-2-yl)-1H-indol-1-yl] propionic acid (E-15) | F-24 | 4-Piperidin-4-yloxypyridine hydrochloride (F-24) |
| G_CC-69 | 7-Chloro-2-[1-[3-(4-hydroxy-4-pyridin-3-yl-piperidin-1-yl)-3-oxo-propyl]-1H-indol-6-yl]-2,3-dihydro-isoindol-1-one (G_CC-69) | E-15 | 3-[6-(4-Chloro-3-oxo-1,2-dihydro-isoindol-2-yl)-1H-indol-1-yl] propionic acid (E-15) | F-19 | 4-Pyridin-3-yl piperidin-4-ol (F-19) |
| G_CC-70 | 3-[7-[[(4-Chloro-2,5-dimethyl-phenyl)sulfonyl]amino]-1H-indol-1-yl]-N-[2-(1-pyridin-4-yl-piperidin-4-yl)-ethyl]-propionamide (G_CC-70) | E-10 | 3-[7-[[(4-Chloro-2,5-dimethyl-phenyl)sulfonyl]amino]-1H-indol-1-yl] propionic acid (E-10) | F-13 | 2-(1-Pyridin-4-yl-piperidin-4-yl)ethylamine dihydrochloride (F-13) |
| G_CC-71 | 3-[6-[[(4-Chloro-2,5-dimethyl-phenyl)sulfonyl]amino]-1H-indol-1-yl]-N-[2-(1-pyridin-4-yl-piperidin-4-yl)-ethyl]-propionamide (G_CC-71) | E-12 | 3-[6-[[(4-Chloro-2,5-dimethyl-phenyl)sulfonyl]amino]-1H-indol-1-yl] propionic acid (E-12) | F-13 | 2-(1-Pyridin-4-yl-piperidin-4-yl)ethylamine dihydrochloride (F-13) |
| G_CC-72 | 3-[6-(4-Chloro-3-oxo-1,2-dihydro-isoindol-2-yl)-1H-indol-1-yl]-N-[2-(1-pyridin-4-yl-piperidin-4-yl)-ethyl]-propionamide (G_CC-72) | E-15 | 3-[6-(4-Chloro-3-oxo-1,2-dihydro-isoindol-2-yl)-1H-indol-1-yl] propionic acid (E-15) | F-13 | 2-(1-Pyridin-4-yl-piperidin-4-yl)ethylamine dihydrochloride (F-13) |
| G_CC-73 | 3-[7-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-propionamide (G_CC-73) | E-10 | 3-[7-[[(4-Chloro-2,5-dimethyl-phenyl)sulfonyl]amino]-1H-indol-1-yl] propionic acid (E-10) | F-08 | [1-(2-Aminoethyl)-4-thiophen-2-yl-piperidin-4-yl]-dimethylamine trihydrochloride (F-08) |
| G_CC-74 | 3-[6-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-propionamide (G_CC-74) | E-12 | 3-[6-[[(4-Chloro-2,5-dimethyl-phenyl)sulfonyl]amino]-1H-indol-1-yl] propionic acid (E-12) | F-08 | [1-(2-Aminoethyl)-4-thiophen-2-yl-piperidin-4-yl]-dimethylamine trihydrochloride (F-08) |
| G_CC-76 | 2-[6-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-acetamide (G_CC-76) | E-03 | 2-[6-[[(4-Methoxy-2,6-dimethyl-phenyl)sulfonyl]amino]-1H-indol-1-yl]-acetic acid (E-03) | F-48 | Methyl-[3-(4-pyridin-4-yl-piperazin-1-yl)-propyl]-amine trihydrochloride (F-48) |
| G_CC-77 | N-[2-(4-Dimethylamino-4-phenyl-cyclohexyl)-ethyl]-2-[7-[[(4-methoxy-2,6-dimethyl-phenyl)sulfonyl]amino]-1H-indol-1-yl]-N-methyl-acetamide (G_CC-77) | E-02 | 2-[7-[[(4-Methoxy-2,6-dimethyl-phenyl)sulfonyl]amino]-1H-indol-1-yl]-acetic acid (E-02) | F-45 | Dimethyl-[4-(2-methylamino-ethyl)-1-phenyl-cyclohexyl]-amine dihydrochloride (F-45) |
| G_CC-81 | N-[2-[4-(3-Fluorophenyl)-4-(4-methyl-piperazin-1-yl)-piperidin-1-yl]-ethyl]-3-[6-[[(4-methoxy-2,6-dimethyl-phenyl)sulfonyl]amino]-1H-indol-1-yl]-N-methyl-propanamide | E-05 | 3-[6-[[(4-Methoxy-2,6-dimethyl-phenyl)sulfonyl]amino]-1H-indol-1-yl]-propionic acid (E-05) | F-47 | 2-[4-(3-Fluorophenyl)-4-(4-methyl-piperazin-1-yl)-piperidin-1-yl]-ethyl-methyl-amine tetrahydrochloride (F-47) |

-continued

| Example no. | Example name | Indole acid no. | Indole acid name | Amine no. | Amine name |
|---|---|---|---|---|---|
| G_CC-84 | N-[1-[2-[4-(3-Fluorophenyl)-4-(4-methyl-piperazin-1-yl)-piperidin-1-yl]-2-oxo-ethyl]-1H-indol-7-yl]-4-methoxy-2,6-dimethyl-benzenesulfonic acid amide (G_CC-84) | E-02 | 2-[7-[[(4-Methoxy-2,6-dimethyl-phenyl)sulfonyl]amino]-1H-indol-1-yl]-acetic acid (E-02) | F-46 | 1-[4-(3-Fluorophenyl)-piperidin-4-yl]-4-methyl-piperazine dihydrochloride (F-46) |
| G_CC-88 | 2-[7-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-acetamide (G_CC-88) | E-02 | 2-[7-[[(4-Methoxy-2,6-dimethyl-phenyl)sulfonyl]amino]-1H-indol-1-yl]-acetic acid (E-02) | F-48 | Methyl-[3-(4-pyridin-4-yl-piperazin-1-yl)-propyl]-amine trihydrochloride (F-48) |
| G_CC-91 | 4-Methoxy-2,6-dimethyl-N-[1-[2-oxo-2-(3-pyridin-4-yl-3,9-diazaspiro[5.5]undecan-9-yl)-ethyl]-1H-indol-7-yl]-benzenesulfonic acid amide (G_CC-91) | E-02 | 2-[7-[[(4-Methoxy-2,6-dimethyl-phenyl)sulfonyl]amino]-1H-indol-1-yl]-acetic acid (E-02) | F-14 | 3-Pyridin-4-yl-3,9-diazaspiro[5.5]-undecane dihydrochloride (F-14) |
| G_CC-92 | 4-Methoxy-2,6-dimethyl-N-[1-[2-oxo-2-(4-pyridin-4-yloxy-piperidin-1-yl)-ethyl]-1H-indol-7-yl]-benzenesulfonic acid amide (G_CC-92) | E-02 | 2-[7-[[(4-Methoxy-2,6-dimethyl-phenyl)sulfonyl]amino]-1H-indol-1-yl]-acetic acid (E-02) | F-24 | 4-Piperidin-4-yloxy-pyridine hydrochloride (F-24) |
| G_CC-95 | N-[2-(4-Dimethylamino-4-phenyl-cyclohexyl)-ethyl]-2-[6-[[(4-methoxy-2,6-dimethyl-phenyl)sulfonyl]amino]-1H-indol-1-yl]-N-methyl-acetamide (G_CC-95) | E-03 | 2-[6-[[(4-Methoxy-2,6-dimethyl-phenyl)sulfonyl]amino]-1H-indol-1-yl]-acetic acid (E-03) | F-45 | Dimethyl-[4-(2-methylamino-ethyl)-1-phenyl-cyclohexyl]-amine dihydrochloride (F-45) |
| G_CC-99 | N-[2-[4-(3-Fluorophenyl)-4-(4-methyl-piperazin-1-yl)-piperidin-1-yl]-ethyl]-2-[6-[[(4-methoxy-2,6-dimethyl-phenyl)sulfonyl]amino]-1H-indol-1-yl]-N-methyl-acetamide (G_CC-99) | E-03 | 2-[6-[[(4-Methoxy-2,6-dimethyl-phenyl)sulfonyl]amino]-1H-indol-1-yl]-acetic acid (E-03) | F-47 | 2-[4-(3-Fluorophenyl)-4-(4-methyl-piperazin-1-yl)-piperidin-1-yl]-ethyl-methyl-amine tetrahydrochloride (F-47) |
| G_CC-102 | N-[2-[4-(3-Fluorophenyl)-4-(4-methyl-piperazin-1-yl)-piperidin-1-yl]-ethyl]-2-[7-[[(4-methoxy-2,6-dimethyl-phenyl)sulfonyl]amino]-1H-indol-1-yl]-N-methyl-acetamide (G_CC-102) | E-02 | 2-[7-[[(4-Methoxy-2,6-dimethyl-phenyl)sulfonyl]amino]-1H-indol-1-yl]-acetic acid (E-02) | F-47 | 2-[4-(3-Fluorophenyl)-4-(4-methyl-piperazin-1-yl)-piperidin-1-yl]-ethyl-methyl-amine tetrahydrochloride (F-47) |
| G_CC-103 | 2-[6-(4-Chloro-3-oxo-1,2-dihydro-isoindol-2-yl)-1H-indol-1-yl]-N-[2-(1-pyridin-4-yl-piperidin-4-yl)-ethyl]-acetamide (G_CC-103) | E-16 | 2-[6-(4-Chloro-3-oxo-1,2-dihydro-isoindol-2-yl)-1H-indol-1-yl]-acetic acid (E-16) | F-13 | 2-(1-Pyridin-4-yl-piperidin-4-yl)-ethyl-amine dihydrochloride (F-13) |
| G_CC-106 | 7-Chloro-2-[1-[3-oxo-3-(3-pyridin-4-yl-3,9-diazaspiro[5.5]undecan-9-yl)-propyl]-1H-indol-7-yl]-2,3-dihydro-isoindol-1-one (G_CC-106) | E-17 | 3-[7-(4-Chloro-3-oxo-1,2-dihydro-isoindol-2-yl)-1H-indol-1-yl]-propionic acid (E-17) | F-14 | 3-Pyridin-4-yl-3,9-diazaspiro[5.5]-undecane dihydrochloride (F-14) |
| G_CC-108 | N-[[1-[2-[6-[[(4-Methoxy-2,6-dimethyl-phenyl)sulfonyl]amino]-1H-indol-1-yl]-acetyl]-4-(4-methyl-piperazin-1-yl)-piperidin-4-yl]-methyl]-pyridine-4-carboxylic acid amide (G_CC-108) | E-03 | 2-[6-[[(4-Methoxy-2,6-dimethyl-phenyl)sulfonyl]amino]-1H-indol-1-yl]-acetic acid (E-03) | F-34 | N-[[4-(4-Methyl-piperazin-1-yl)-piperidin-4-yl]-methyl]-pyridine-4-carboxylic acid amide dihydrochloride (F-34) |
| G_CC-111 | 2-[6-(4-Chloro-3-oxo-1,2-dihydro-isoindol-2-yl)-1H-indol-1-yl]-N-[(1-pyridin-4-yl-piperidin-4-yl)-methyl]-acetamide (G_CC-111) | E-16 | 2-[6-(4-Chloro-3-oxo-1,2-dihydro-isoindol-2-yl)-1H-indol-1-yl]-acetic acid (E-16) | F-15 | (1-Pyridin-4-yl-piperidin-4-yl)-methyl-amine dihydrochloride (F-15) |
| G_CC-113 | 2-[6-(4-Chloro-3-oxo-1,2-dihydro-isoindol-2-yl)-1H-indol-1-yl]-N-[2-[4-(3-fluorophenyl)-4-(4-methyl-piperazin-1-yl)-piperidin-1-yl]-ethyl]-N-methyl-acetamide (G_CC-113) | E-16 | 2-[6-(4-Chloro-3-oxo-1,2-dihydro-isoindol-2-yl)-1H-indol-1-yl]-acetic acid (E-16) | F-47 | 2-[4-(3-Fluorophenyl)-4-(4-methyl-piperazin-1-yl)-piperidin-1-yl]-ethyl-methyl-amine tetrahydrochloride (F-47) |
| G_CC-116 | 3-[6-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-propionamide (G_CC-116) | E-05 | 3-[6-[[(4-Methoxy-2,6-dimethyl-phenyl)sulfonyl]amino]-1H-indol-1-yl]-propionic acid (E-05) | F-48 | Methyl-[3-(4-pyridin-4-yl-piperazin-1-yl)-propyl]-amine trihydrochloride (F-48) |

| Example no. | Example name | Indole acid no. | Indole acid name | Amine no. | Amine name |
|---|---|---|---|---|---|
| G_CC-117 | N-[2-(4-Dimethylamino-4-phenyl-cyclohexyl)-ethyl]-3-[6-[[(4-methoxy-2,6-dimethyl-phenyl)sulfonyl]amino]-1H-indol-1-yl]-N-methyl-propionamide (G_CC-117) | E-05 | 3-[6-[[(4-Methoxy-2,6-dimethyl-phenyl)sulfonyl]amino]-1H-indol-1-yl]-propionic acid (E-05) | F-45 | Dimethyl-[4-(2-methylamino-ethyl)-1-phenyl-cyclohexyl]-amine dihydrochloride (F-45) |
| G_CC-119 | 3-[6-(4-Chloro-3-oxo-1,2-dihydro-isoindol-2-yl)-1H-indol-1-yl]-N-methyl-N-[3-(4-pyridin-4-yl-piperazin-1-yl)-propyl]-propionamide (G_CC-119) | E-15 | 3-[6-(4-Chloro-3-oxo-1,2-dihydro-isoindol-2-yl)-1H-indol-1-yl]-propionic acid (E-15) | F-48 | Methyl-[3-(4-pyridin-4-yl-piperazin-1-yl)-propyl]-amine trihydrochloride (F-48) |
| G_CC-120 | 4-Methoxy-2,6-dimethyl-N-[1-[2-oxo-2-[4-(2-pyrrolidin-1-yl-ethyl)-piperidin-1-yl]-ethyl]-1H-indol-6-yl]-benzenesulfonic acid amide (G_CC-120) | E-03 | 2-[6-[[(4-Methoxy-2,6-dimethyl-phenyl)sulfonyl]amino]-1H-indol-1-yl]-acetic acid (E-03) | F-05 | 4-(2-Pyrrolidin-1-yl-ethyl)-piperidine (F-05) |
| G_CC-123 | 3-[7-(4-Chloro-3-oxo-1,2-dihydro-isoindol-2-yl)-1H-indol-1-yl]-N-[(1-pyridin-4-yl-piperidin-4-yl)-methyl]-propionamide (G_CC-123) | E-17 | 3-[7-(4-Chloro-3-oxo-1,2-dihydro-isoindol-2-yl)-1H-indol-1-yl]-propionic acid (E-17) | F-15 | (1-Pyridin-4-yl-piperidin-4-yl)-methyl-amine dihydrochloride (F-15) |
| G_CC-127 | 3-[6-(4-Chloro-3-oxo-1,2-dihydro-isoindol-2-yl)-1H-indol-1-yl]-N-[2-(4-dimethylamino-4-phenyl-cyclohexyl)-ethyl]-N-methyl-propionamide (G_CC-127) | E-15 | 3-[6-(4-Chloro-3-oxo-1,2-dihydro-isoindol-2-yl)-1H-indol-1-yl]-propionic acid (E-15) | F-45 | Dimethyl-[4-(2-methylamino-ethyl)-1-phenyl-cyclohexyl]-amine dihydrochloride (F-45) |
| G_CC-128 | 7-Chloro-2-[1-[2-[4-(3-fluoro-phenyl)-4-(4-methyl-piperazin-1-yl)-piperidin-1-yl]-2-oxo-ethyl]-1H-indol-6-yl]-2,3-dihydro-isoindol-1-one (G_CC-128) | E-16 | 2-[6-(4-Chloro-3-oxo-1,2-dihydro-isoindol-2-yl)-1H-indol-1-yl]-acetic acid (E-16) | F-46 | 1-[4-(3-Fluoro-phenyl)-piperidin-4-yl]-4-methyl-piperazine dihydrochloride (F-46) |
| G_CC-138 | 2-[6-(4-Chloro-3-oxo-1,2-dihydro-isoindol-2-yl)-1H-indol-1-yl]-N-methyl-N-[3-(4-pyridin-4-yl-piperazin-1-yl)-propyl]-acetamide (G_CC-138) | E-16 | 2-[6-(4-Chloro-3-oxo-1,2-dihydro-isoindol-2-yl)-1H-indol-1-yl]-acetic acid (E-16) | F-48 | Methyl-[3-(4-pyridin-4-yl-piperazin-1-yl)-propyl]-amine trihydrochloride (F-48) |
| G_CC-139 | 4-Methoxy-2,6-dimethyl-N-[1-[2-oxo-2-[4-(pyridine-3-carbonyl)-piperazin-1-yl]-ethyl]-1H-indol-7-yl]-benzenesulfonic acid amide (G_CC-139) | E-02 | 2-[7-[[(4-Methoxy-2,6-dimethyl-phenyl)sulfonyl]amino]-1H-indol-1-yl]-acetic acid (E-02) | F-37 | Piperazin-1-yl-pyridin-3-yl-methanone (F-37) |

Pharmacological Data

The pharmacological data was determined as described above. The following data is provided in the table below by way of example:

| Compound | B1R antagonism, rat [10 μM] % inhibition | B1R antagonism, human [10 μM] % inhibition |
|---|---|---|
| G-01 | 78 | 98 |
| G-02 | 100 | 95 |
| G-03 | 90 | |
| G-04 | 62 | 68 |
| G-05 | 96 | 100 |
| G-06 | 70 | 83 |
| G-07 | 100 | 96 |
| G-08 | 97 | 98 |
| G-10 | 76 | 100 |
| G-11 | −21 | 46 |
| G-12 | 92 | 98 |
| G-13 | 96 | 73 |
| G-14 | 96 | 99 |
| G-15 | 54 | 81 |
| G-16 | 96 | 100 |
| G-17 | 95 | 100 |
| G-18 | 99 | 99 |
| G-19 | 94 | 97 |
| G-20 | 13 | 43 |
| G-21 | 43 | 99 |
| G-22 | 99 | 100 |
| G-23 | 106 | 100 |
| G-24 | 103 | 98 |
| G-26 | 102 | 98 |
| G-27 | 99 | 96 |
| G-31 | 54 | 80 |
| G-33 | 46 | 93 |
| G_CC-1 | 62 | |
| G_CC-2 | 70 | 46 |
| G_CC-3 | 82 | |
| G_CC-4 | 99 | |
| G_CC-5 | 59 | |
| G_CC-6 | 73 | |
| G_CC-7 | 100 | |
| G_CC-8 | 100 | 26 |
| G_CC-9 | 65 | |
| G_CC-10 | 69 | |
| G_CC-11 | 87 | |
| G_CC-12 | 58 | |
| G_CC-13 | 58 | |
| G_CC-14 | 86 | |
| G_CC-15 | 65 | |

-continued

| Compound | B1R antagonism, rat [10 μM] % inhibition | B1R antagonism, human [10 μM] % inhibition |
|---|---|---|
| G_CC-16 | 67 | |
| G_CC-17 | 52 | |
| G_CC-18 | 87 | |
| G_CC-19 | 68 | |
| G_CC-20 | 86 | |
| G_CC-21 | 97 | |
| G_CC-22 | 59 | |
| G_CC-23 | 63 | |
| G_CC-24 | 89 | |
| G_CC-25 | 58 | |
| G_CC-26 | 81 | |
| G_CC-27 | 56 | |
| G_CC-28 | 82 | |
| G_CC-29 | 92 | |
| G_CC-30 | 53 | |
| G_CC-31 | 91 | |
| G_CC-32 | 101 | 73 |
| G_CC-33 | 71 | |
| G_CC-34 | 58 | |
| G_CC-35 | 72 | |
| G_CC-36 | 63 | |
| G_CC-37 | 91 | |
| G_CC-38 | 96 | |
| G_CC-39 | 95 | |
| G_CC-40 | 86 | |
| G_CC-41 | 76 | |
| G_CC-42 | 66 | |
| G_CC-43 | 103 | 100 |
| G_CC-44 | 73 | |
| G_CC-45 | 59 | |
| G_CC-46 | 94 | |
| G_CC-47 | 102 | 100 |
| G_CC-48 | 59 | |
| G_CC-49 | 92 | |
| G_CC-50 | 62 | |
| G_CC-51 | 93 | |
| G_CC-52 | 100 | |
| G_CC-53 | 101 | |
| G_CC-54 | 96 | 99 |
| G_CC-56 | 54 | |
| G_CC-57 | 100 | |
| G_CC-59 | 87 | |
| G_CC-60 | 87 | |
| G_CC-61 | 79 | |
| G_CC-62 | 99 | 94 |
| G_CC-63 | 100 | |
| G_CC-64 | 89 | |
| G_CC-65 | 53 | |
| G_CC-66 | 52 | |
| G_CC-67 | 95 | 99 |
| G_CC-68 | 69 | |
| G_CC-69 | 65 | |
| G_CC-70 | 100 | |
| G_CC-71 | 54 | |
| G_CC-72 | 71 | |
| G_CC-73 | 55 | |
| G_CC-74 | 51 | |
| G_CC-76 | 104 | 92 |
| G_CC-77 | 104 | |
| G_CC-81 | 103 | |
| G_CC-84 | 102 | |
| G_CC-88 | 101 | 100 |
| G_CC-91 | 100 | 100 |
| G_CC-92 | 98 | |
| G_CC-95 | 96 | |
| G_CC-99 | 93 | |
| G_CC-102 | 89 | |
| G_CC-103 | 88 | |
| G_CC-106 | 86 | |
| G_CC-108 | 84 | |
| G_CC-111 | 81 | |
| G_CC-113 | 78 | |
| G_CC-116 | 74 | |
| G_CC-117 | 74 | |
| G_CC-119 | 72 | |
| G_CC-120 | 72 | |
| G_CC-123 | 67 | |
| G_CC-127 | 63 | |
| G_CC-128 | 61 | |
| G_CC-138 | 52 | |
| G_CC-139 | 50 | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A substituted indole compound corresponding to the formula (I):

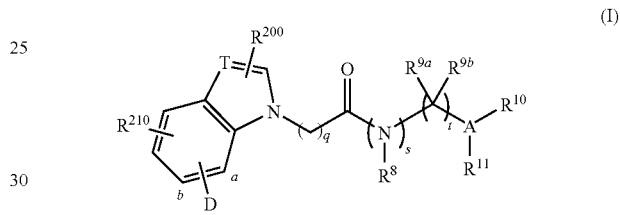

(I)

wherein

T denotes CH;

q=1, 2 or 3;

s=0 or 1;

t=0, 1, 2 or 3;

D in position a or b is bound to the indole skeleton and denotes the group D2:

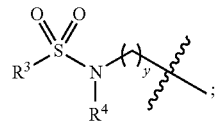

D2 wherein y denotes 0 or 1;

$R^3$ denotes aryl, heteroaryl or an aryl or heteroaryl bound via a $C_{1-3}$ alkylene group, wherein aryl and heteroaryl can each be anellated with a 4-, 5-, 6- or 7-membered, saturated or mono- or polyunsaturated but not aromatic cyclic structure which optionally may be substituted at one or more of its carbon ring members with one or more substituents each independently selected from the group consisting of F, Cl, Br, I, —$CF_3$, —O—$CF_3$, $C_{1-6}$ alkyl and O—$C_{1-6}$ alkyl and which optionally may contain one or more heteroatoms or heteroatom groups independently selected from the group consisting of N, $NR^{50a}$, O, S, S=O and $S(=O)_2$, wherein $R^{50a}$ denotes H, $C_{1-6}$ alkyl, —C(=O)—$R^{51a}$, $C_{3-8}$ cycloalkyl, aryl, heteroaryl or a $C_{3-8}$ cycloalkyl, aryl or heteroaryl bound via a $C_{1-3}$ alkylene group and $R^{51a}$ denotes $C_{1-6}$ alkyl, $C_{3-8}$ cycloalkyl, aryl, heteroaryl or a $C_{3-8}$ cycloalkyl, aryl or heteroaryl bound via a $C_{1-3}$ alkylene group;

$R^4$ denotes H, $C_{1-6}$ alkyl, $C_{3-8}$ cycloalkyl, aryl or heteroaryl or a $C_{3-8}$ cycloalkyl, aryl or heteroaryl bound via a $C_{1-6}$ alkylene group;

$R^{200}$ denotes 0 to 2 substituents each independently selected from the group consisting of F, Cl, Br, I, $CF_3$, $OCF_3$, OH, O—$C_{1-6}$ alkyl, $C_{1-6}$ alkyl, aryl and heteroaryl and/or two adjacent substituents $R^{200}$ form an anellated aryl or heteroaryl ring;

$R^{210}$ denotes 0 to 3 substituents each independently selected from the group consisting of F, Cl, Br, I, $CF_3$, $OCF_3$, OH, O—$C_{1-6}$ alkyl, $C_{1-6}$ alkyl, aryl and heteroaryl;

$R^8$ denotes H, $C_{1-6}$ alkyl, $C_{3-8}$ cycloalkyl, aryl or heteroaryl or a $C_{3-8}$ cycloalkyl, aryl or heteroaryl bound via a $C_{1-6}$ alkylene group;

$R^{9a}$ and $R^{9b}$ each independently denote H, F, Cl, OH, $C_{1-6}$ alkyl, O—$C_{1-6}$ alkyl, $C_{3-8}$ cycloalkyl, aryl or heteroaryl or a $C_{3-8}$ cycloalkyl, aryl or heteroaryl bound via a $C_{1-6}$ alkylene group;

A denotes N or CH;

with the proviso that if s denotes 1 and t denotes 0, then A denotes CH; and with the proviso that if s and t each denote 0 then A denotes N;

$R^{10}$ and $R^{11}$ together with A represent a spirocyclic or cyclic group corresponding to formula (II) or formula (III):

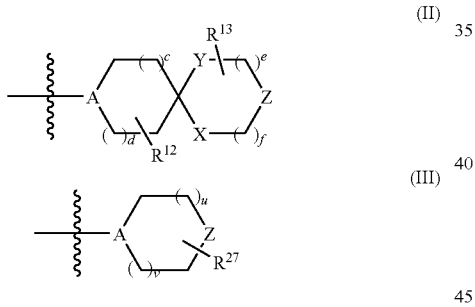

wherein c, d, e, f, u and v each independently denote 0, 1 or 2;

$R^{12}$, $R^{13}$ and $R^{27}$ each independently denote 0 to 4 substituents each independently selected from the group consisting of F, Cl, OH, =O, $C_{1-6}$ alkyl, O—$C_{1-6}$ alkyl, $C_{3-8}$ cycloalkyl, aryl, heteroaryl, and $C_{3-8}$ cycloalkyl, aryl or heteroaryl bound via a $C_{1-6}$ alkylene group, and/or two of the 0 to 4 substituents $R^{27}$ together represent a $C_{1-3}$ alkylene bridge such that the cyclic structure of formula (III) assumes a bicyclically bridged form, and/or two adjacent substituents out of the 0 to 4 substituents $R^{13}$ form an anellated aryl or heteroaryl ring, and/or two adjacent substituents out of the 0 to 4 substituents $R^{27}$ form an anellated aryl or heteroaryl ring;

X denotes $CR^{14a}R^{14b}$, $NR^{15}$ or O;

Y denotes $CR^{16a}R^{16b}$, $NR^{17}$ or O;

with the proviso that if Y denotes $NR^{17}$, then X does not denote $NR^{15}$; and with the proviso that X and Y do not simultaneously denote O;

wherein $R^{14a}$, $R^{14b}$, $R^{16a}$ and $R^{16b}$ each independently denote H, F, Cl, OH, $C_{1-6}$ alkyl, O—$C_{1-6}$ alkyl, $C_{3-8}$ cycloalkyl, aryl or heteroaryl or denote a $C_{3-8}$ cycloalkyl, aryl or heteroaryl bound via a $C_{1-6}$ alkylene group, and/or $R^{14a}$ and $R^{14b}$ can together denote =O, and/or $R^{16a}$ and $R^{16b}$ can together denote =O;

$R^{15}$ and $R^{17}$ each independently denote H, $C_{1-6}$ alkyl, $C_{3-8}$ cycloalkyl, aryl or heteroaryl or denote a $C_{3-8}$ cycloalkyl, aryl or heteroaryl bound via a $C_{1-6}$ alkylene group;

Z in formula (II) denotes $CR^{18a}R^{18b}$, $NR^{19}$ or O; or if X denotes O and f denotes 0, then Z in formula (II) denotes —$(C(R^{124})$=$C(R^{125}))$—, wherein $R^{124}$ and $R^{125}$ together with the carbon atoms linking them form a fused aryl or heteroaryl ring; or if X denotes O and f denotes 0, then Z in formula (II) denotes =$(N(CR^{126}))$—, wherein the N atom is singly bound to the O atom, and $R^{126}$ denotes H, $C_{1-6}$ alkyl, $C_{3-8}$ cycloalkyl, aryl or heteroaryl or denotes a $C_{3-8}$ cycloalkyl, aryl or heteroaryl bound via a $C_{1-6}$ alkylene group;

Z in formula (III) denotes $CR^{18a}R^{18b}$, $NR^{19}$, O, S, S(=O) or S(=O)$_2$; wherein $R^{18a}$ denotes H, $C_{1-6}$ alkyl, $C_{3-8}$ cycloalkyl, aryl or heteroaryl or denotes a $C_{3-8}$ cycloalkyl, aryl or heteroaryl bound via a $C_{1-6}$ alkylene group, or $R^{18a}$ denotes a group corresponding to formula (IV):

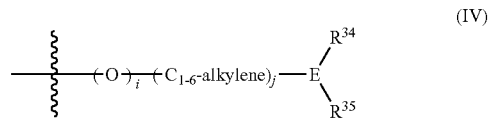

wherein i and j each independently denote 0 or 1;

E denotes N or CH, with the proviso that if i denotes 1 and j denotes 0, then E denotes CH;

$R^{34}$ and $R^{35}$ each independently denote H, $C_{1-6}$ alkyl, $C_{3-8}$ cycloalkyl, aryl or heteroaryl or an aryl, heteroaryl or $C_{3-8}$ cycloalkyl bound via a $C_{1-3}$ alkylene group; or $R^{34}$ and $R^{35}$ together with E form a 5- or 6-membered aryl or heteroaryl ring; or $R^{34}$ and $R^{35}$ together with E form a saturated heterocyclic structure corresponding to formula (V):

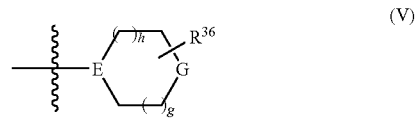

wherein h and g each independently denote 0, 1 or 2;

G denotes $CR^{37a}R^{37b}$, $NR^{38}$, O, S, S=O or S(=O)$_2$, with the proviso that if E denotes CH, then G does not denote $CR^{37a}R^{37b}$;

$R^{36}$ denotes 0 to 4 substituents which are each independently selected from the group consisting of F, Cl, Br, I, OH, SH, =O, O—$C_{1-6}$ alkyl, $C_{1-6}$ alkyl, $C_{3-8}$ cycloalkyl, aryl, heteroaryl and $C_{3-8}$ cycloalkyl, aryl or heteroaryl bound via a $C_{1-6}$ alkylene group, and/or two adjacent substituents $R^{36}$ together represent an anellated aryl or heteroaryl ring;

$R^{37a}$ and $R^{37b}$ each independently denote H, F, Cl, Br, I, OH, SH, =O, O—$C_{1-6}$ alkyl, $C_{1-6}$ alkyl, $C_{3-8}$ cycloalkyl, aryl or heteroaryl or denote a $C_{3-8}$ cycloalkyl, aryl or heteroaryl bound via a $C_{1-6}$ alkylene group;

$R^{38}$ denotes H, $C_{1-6}$ alkyl, $C_{3-8}$ cycloalkyl, aryl or heteroaryl or denotes an aryl, heteroaryl or $C_{3-8}$ cycloalkyl bound via a $C_{1-3}$ alkylene group;

$R^{18b}$ denotes H, OH, $C_{1-6}$ alkyl, $C_{3-8}$ cycloalkyl, O—$C_{1-6}$ alkyl, O—($C_{3-8}$ cycloalkyl), ($C_{1-6}$ alkylene)-O—$C_{1-6}$ alkyl, ($C_{1-6}$ alkylene)-O—($C_{3-8}$ cycloalkyl), aryl, heteroaryl, O-aryl or O-heteroaryl or denotes an aryl, O-aryl, heteroaryl or O-heteroaryl bound via a $C_{1-6}$ alkylene group; or $R^{18b}$ denotes a group corresponding to formula (VI):

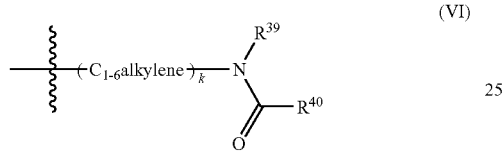

(VI)

wherein
k denotes 0 or 1;
$R^{39}$ denotes H, $C_{1-6}$ alkyl, $C_{3-8}$ cycloalkyl, aryl or heteroaryl or denotes a $C_{3-8}$ cycloalkyl, aryl or heteroaryl bound via a $C_{1-3}$ alkylene group;
$R^{40}$ denotes $C_{1-6}$ alkyl, $C_{3-8}$ cycloalkyl, aryl or heteroaryl or denotes a $C_{3-8}$ cycloalkyl, aryl or heteroaryl bound via a $C_{1-6}$ alkylene group; or
$R^{39}$ and $R^{40}$ together with the N—C(=O) group linking them form a ring corresponding to formula (VII):

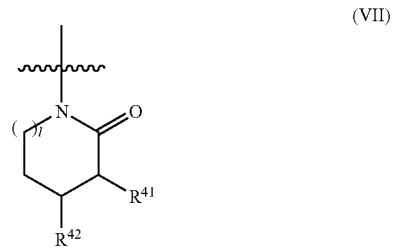

(VII)

wherein
I denotes 0, 1 or 2; and
$R^{41}$ and $R^{42}$ together with the carbon atoms linking them form an anellated aryl or heteroaryl ring;
$R^{19}$ denotes H; or $(P)_z$—$R^{22}$, wherein
z denotes 0 or 1;
P denotes (C=O), S(=O)$_2$ or C(=O)—N($R^{24}$), wherein the N atom in the C(=O)—N($R^{24}$) group is linked to $R^{22}$, wherein
$R^{24}$ denotes H, $C_{1-6}$ alkyl, $C_{3-8}$ cycloalkyl or an aryl, heteroaryl or $C_{3-8}$ cycloalkyl bound via a $C_{1-3}$ alkylene group;
$R^{22}$ denotes $C_{1-6}$ alkyl, $C_{3-8}$ cycloalkyl, aryl or heteroaryl or an aryl or heteroaryl bound via a $C_{1-6}$ alkylene group; or $R^{22}$ denotes a group corresponding to formula (VIII):

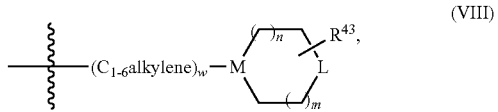

(VIII)

wherein
n denotes 0, 1 or 2;
m denotes 0, 1 or 2;
w denotes 0 or 1,
M denotes CH or N;
with the proviso that if P denotes C(=O)—$NR^{24}$ and w denotes 0, then M denotes CH; and
with the proviso that if z and w simultaneously each denote 0, then M denotes CH;
$R^{43}$ denotes 0 to 4 substituents each independently selected from the group consisting of F, Cl, OH, =O, $O_{1-6}$ alkyl, O—$C_{1-6}$ alkyl, $C_{3-8}$ cycloalkyl, aryl, heteroaryl, and $C_{3-8}$ cycloalkyl, aryl or heteroaryl bound via a $C_{1-6}$ alkylene group, and/or two adjacent substituents out of the 0 to 4 substituents $R^{43}$ together represent an anellated aryl or heteroaryl ring; and
L denotes $CR^{44a}R^{44b}$, $NR^{45}$, O, S, S=O or S(=O)$_2$; wherein
$R^{44a}$ and $R^{44b}$ each independently denote H, F, Cl, Br, I, OH, $C_{1-6}$ alkyl, O—$C_{1-6}$ alkyl, $C_{3-8}$ cycloalkyl, aryl or heteroaryl, or a $C_{3-8}$ cycloalkyl, aryl or heteroaryl bound via a $C_{1-6}$ alkylene group; or
$R^{44a}$ and $R^{44b}$ together denote =O; and
$R^{45}$ denotes H, $C_{1-6}$ alkyl, $C_{3-8}$ cycloalkyl, aryl or heteroaryl or denotes an aryl, heteroaryl or $C_{3-8}$ cycloalkyl bound via a $C_{1-3}$ alkylene group;

wherein the aforementioned $C_{1-6}$ alkyl, $C_{1-3}$ alkylene and $C_{1-6}$ alkylene groups may each be branched or unbranched, and the aforementioned $C_{1-6}$ alkyl, $C_{1-3}$ alkylene, $C_{1-6}$ alkylene, $C_{3-8}$ cycloalkyl, aryl and heteroaryl groups may each be unsubstituted or mono- or polysubstituted with identical or different substituents;
or a physiologically compatible salt thereof.

2. A compound according to claim 1, wherein said compound is in the form of a mixture of stereoisomers in any mixing ratio.

3. A compound according to claim 2, wherein said mixture is a racemic mixture.

4. A compound according to claim 1, wherein said compound is in the form of an isolated stereoisomer.

5. A compound according to claim 1, wherein
$R^3$ denotes an unsubstituted or mono- or identically or differently polysubstituted aryl or heteroaryl group selected from the group consisting of phenyl, naphthyl, chromanyl, indolyl, benzofuranyl, benzothiophenyl; benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl, or a phenyl or naphthyl bound via an unsubstituted or mono- or identically or differently polysubstituted $C_{1-3}$ alkylene group;
wherein substituents of said aryl or heteroaryl groups are each independently selected from the group consisting of —O—$C_{1-3}$ alkyl, $C_{1-6}$ alkyl, F, Cl, Br, I, $CF_3$, $OCF_3$, OH, SH, phenyl, phenoxy, naphthyl, furyl, thienyl and pyridinyl, and substituents of said alkylene groups are each independently selected from the group consisting of —O—$C_{1-3}$ alkyl, F, Cl, Br, I, $CF_3$, $OCF_3$, OH, SH, phenyl, phenoxy, naphthyl, furyl, thienyl and pyridinyl, and $R^4$ is selected from the group consisting of H, methyl, ethyl, n-propyl, isopropyl, n-butyl, isobutyl, sec-butyl, tert-butyl and cyclopropyl.

6. A compound according to claim 5, wherein $R^3$ is an unsubstituted or mono- or polysubstituted phenyl, naphthyl, chromanyl, benzothiophenyl, benzooxadiazolyl, thienyl, pyridinyl, imidazothiazolyl, dibenzofuranyl group or an unsubstituted or mono- or polysubstituted phenyl group bound via a $C_{1-3}$ alkylene group.

7. A compound according to claim 1, wherein $R^8$ denotes H, branched or unbranched $C_{1-6}$ alkyl, cyclopropyl, cyclobutyl, cyclopentyl, cyclohexyl, —$CH_2CF_3$, phenyl, benzyl, phenylethyl, phenylpropyl; or cyclopropyl, cyclobutyl, cyclopentyl, cyclohexyl bound via a $C_{1-3}$ alkylene group, each unsubstituted or mono- or polysubstituted with identical or different substituents.

8. A compound according to claim 1, wherein $R^{9a}$ and $R^{9b}$ each each independently denote H, F, methyl, ethyl, isopropyl, $CF_3$, methoxy, cyclopropyl, phenyl, benzyl, phenylethyl, $C_{1-3}$ alkylene-cyclopropyl, $C_{1-3}$ alkylene-cyclobutyl, $C_{1-3}$ alkylene-cyclopentyl, $C_{1-3}$ alkylene-cyclohexyl or $C_{1-3}$ alkylene-$CF_3$, each unsubstituted or mono- or polysubstituted with identical or different substituents.

9. A compound according to claim 8, wherein $R^{9a}$ and $R^{9b}$ both denote H.

10. A compound according to claim 1, wherein
(a1) the formula (II) assumes the following substructure (IIa):

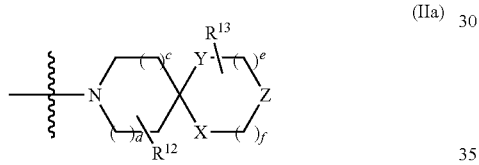

(IIa)

or
(a2) the formula (III) assumes one of the following substructures (IIIa) or (III b):

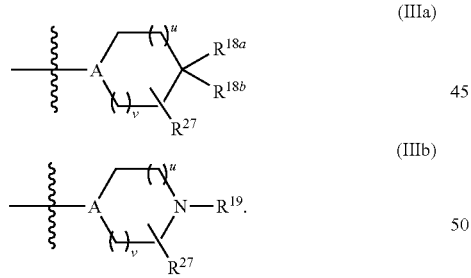

(IIIa)

(IIIb)

11. A compound according to claim 10, wherein
(a1) the substructure having formula (IIa) assumes the following substructure (IIb):

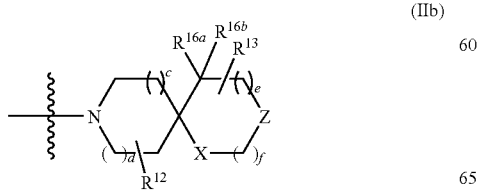

(IIb)

or
(a2) the substructures having formulas (IIIa) and (IIIb) assume one of the following substructures (IIIc), (IIId), (IIIe) or (IIIf):

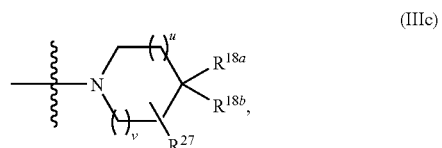

(IIIc)

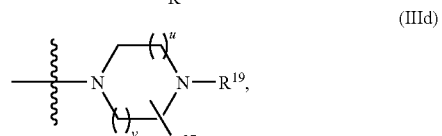

(IIId)

(IIIe)

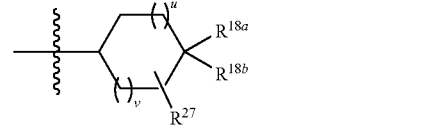

(IIIf)

12. A compound according to claim 11, wherein
(a1) the substructure having formula (IIa) assumes the substructure (IIb), and s and t each denote 0; or
(a2) the substructures having formulas (IIIa) and (IIIb) assume one of the substructures (IIIc) or (IIId), and s and t each denote 0; or
(a3) the substructures having formulas (IIIa) and (IIIb) assume one of the substructures (IIIc) or (IIId), and two of the substituents $R^{27}$ together form a $C_{1-3}$ alkylene bridge such that the cyclic compound represented in substructure (IIIc) or (IIId) assumes a bicyclically bridged form, and s and t each denote 0; or
(a4) the substructures having formulas (IIIa) and (IIIb) assume one of the substructures (IIIc), (IIId), (IIIe) or (IIIf);
s denotes 1;
t denotes 0, 1, 2 or 3;
$R^8$ denotes H, $C_{1-6}$ alkyl or $C_{3-6}$ cycloalkyl, in each case unsubstituted or mono- or polysubstituted with identical or different substituents, and
$R^{9a}$ and $R^{9b}$ each independently denote H, $C_{1-6}$ alkyl or $C_{3-6}$ cycloalkyl.

13. A compound according to claim 1, wherein
(a1) s and t each denote 0, and formula (II) assumes the following substructure (IIc)

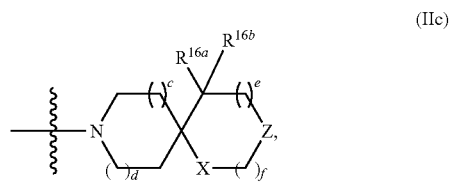

(IIc)

wherein
c, d, e and f each each independently denote 0, 1 or 2;
X denotes $CR^{14a}R^{14b}$, $NR^{15}$ or O, Z denotes $CR^{18a}R^{18b}$ or $NR^{19}$, or if X denotes O and f denotes 0, then Z may denote =(N($CR^{126}$))—, wherein the N atom is singly bound to the O atom; wherein $R^{126}$ denotes H, $C_{1-4}$ alkyl or an unsubstituted or mono- or polysubstituted phenyl, pyridyl, imidazolyl, triazolyl, pyrimidyl, thiazolyl or thienyl optionally bound via a $C_{1-3}$ alkylene group, wherein the substituents are independently selected from the group consisting of F, Cl, $CF_3$, $C_{1-4}$ alkyl, $OCF_3$, OH and O—$C_{1-4}$ alkyl, $R^{14a}$, $R^{14b}$, $R^{16a}$ and $R^{16b}$ each independently denote H or an unsubstituted or mono- or polysubstituted phenyl, pyridyl, imidazolyl, triazolyl, pyrimidyl, thiazolyl or thienyl optionally bound via a $C_{1-3}$ alkylene group, wherein the substituents are each independently selected from the group consisting of F, Cl, $CF_3$, $C_{1-4}$ alkyl, $OCF_3$, OH and O—$C_{1-4}$ alkyl, and/or $R^{16a}$ and $R^{16b}$ together denote =O;

$R^{15}$ denotes H, $C_{1-4}$ alkyl or an unsubstituted or mono- or polysubstituted phenyl, pyridyl, imidazolyl, triazolyl, pyrimidyl, thiazolyl or thienyl optionally bound via a $C_{1-3}$ alkylene group, wherein the substituents are selected from the group consisting of F, Cl, $CF_3$, $C_{1-4}$ alkyl, $OCF_3$, OH and O—$C_{1-4}$ alkyl, $R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or unsubstituted or mono- or polysubstituted phenyl, pyridyl, imidazolyl, triazolyl, pyrimidyl, thiazolyl or thienyl bound by an —(O)$_{0-1}$—$C_{1-6}$ alkylene group; wherein the substituents are each each independently selected from the group consisting of F, Cl, $CF_3$, $C_{1-4}$ alkyl, $OCF_3$, OH and O—$C_{1-4}$ alkyl; or $R^{18a}$ denotes a structure corresponding to formula (IVa)

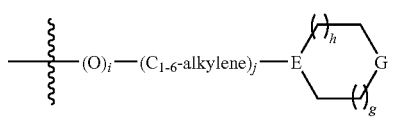

(IVa)

wherein
denotes 0 or 1;
j denotes 0 or 1;
h and g each independently denote 0 or 1,
E denotes N or CH; with the proviso that if i denotes 1 and j denotes 0, then E denotes CH;
G denotes $CR^{37a}R^{37b}$ or $NR^{38}$; wherein
$R^{37a}$ and $R^{37b}$ each independently denote H; F or $C_{1-4}$ alkyl, each unsubstituted or mono- or polysubstituted with identical or different substituents; and
$R^{38}$ denotes H; $C_{1-6}$ alkyl, $C_{3-6}$ cycloalkyl or pyridyl;

$R^{18b}$ denotes H, OH, $C_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a $C_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by $C_{1-6}$ alkylene-NH(C=O), each unsubstituted or mono- or polysubstituted with identical or different substituents, wherein the substituents are each independently selected from the group consisting of F, Cl, $CF_3$, $C_{1-4}$ alkyl, $OCF_3$, OH and O—$C_{1-4}$ alkyl;

$R^{19}$ denotes H, $C_{1-6}$ alkyl, $C_{3-8}$ cycloalkyl, —(C=O)—$C_{1-6}$ alkyl; $C_{1-6}$ alkylene-NH($C_{1-6}$ alkyl), $C_{1-6}$ alkylene-N($C_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a $C_{1-6}$ alkylene group; each unsubstituted or mono- or polysubstituted with identical or different substituents, wherein the substituents are independently selected from the group consisting of F, Cl, $CF_3$, $C_{1-4}$ alkyl, $OCF_3$, OH and O—$C_{1-4}$ alkyl, or a structure corresponding to formula (VIIIa):

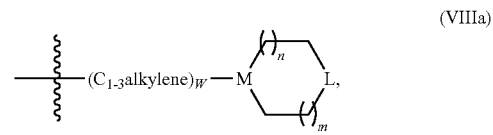

(VIIIa)

wherein w denotes 0 or 1;

n denotes 0 or 1;

m denotes 0 or 1;

M denotes CH or N, with the proviso that if w denotes 0 then M denotes CH;

L denotes $CR^{44a}R^{44b}$ or $NR^{45}$; wherein $R^{44a}$ and $R^{44b}$ each independently denote H; F or $C_{1-6}$ alkyl, each unsubstituted or mono- or polysubstituted with identical or different substituents; and $R^{45}$ denotes H, $C_{1-6}$ alkyl, $C_{3-6}$ cycloalkyl or pyridyl; or (a2) s and t each denote 0 and the formula (III) assumes one of the substructures (IIIc') or (IIId')

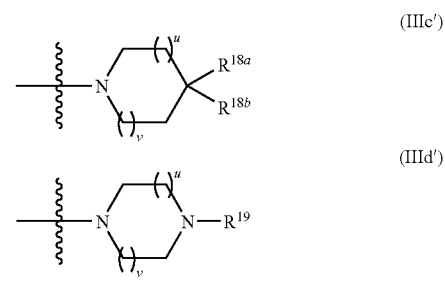

(IIIc')

(IIId')

wherein u and v each independently denote 0, 1 or 2, $R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or unsubstituted or mono- or polysubstituted phenyl, pyridyl, imidazolyl, triazolyl, pyrimidyl, thiazolyl or thienyl bound by an —(O)$_{0-1}$—$C_{1-6}$ alkylene group; wherein the substituents are independently selected from the group consisting of F, Cl, $CF_3$, $C_{1-4}$ alkyl, $OCF_3$, OH and O—$C_{1-4}$ alkyl; or $R^{18a}$ denotes a structure corresponding to formula (IVa):

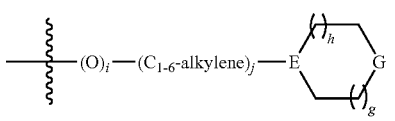
(IVa)

wherein i denotes 0 or 1;
j denotes 0 or 1;
h and g, each independently, denote 0 or 1,
E denotes N or CH; with the proviso that if i denotes 1 and j denotes 0, then E denotes CH,
G denotes $CR^{37a}R^{37b}$ or $NR^{38}$; wherein
$R^{37a}$ and $R^{37b}$ each independently denote H, F, or unsubstituted, monosubstituted or identically or differently polysubstituted $C_{1-4}$ alkyl; and
$R^{38}$ denotes H; $C_{1-6}$ alkyl, $C_{3-6}$ cycloalkyl or pyridyl;
or
$R^{18a}$ denotes the following structure:

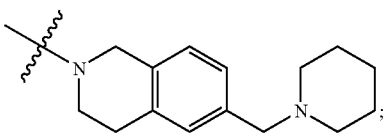 [SMILES: *N1CCc2cc(CN3CCCCC3)ccc2C1 ; ";"]

$R^{18b}$ denotes H, OH, $C_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a $C_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by $C_{1-6}$ alkylene-NH (C=O), each unsubstituted or mono- or polysubstituted with identical or different substituents, wherein the substituents are independently selected from the group consisting of F, Cl, $CF_3$, $C_{1-4}$ alkyl, $OCF_3$, OH and O—$C_{1-4}$ alkyl;
$R^{19}$ denotes H, $C_{1-6}$ alkyl, $C_{3-8}$ cycloalkyl, —(C=O)—$C_{1-6}$ alkyl; $C_{1-6}$ alkylene-NH($C_{1-6}$ alkyl), $C_{1-6}$ alkylene-N($C_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a $C_{1-6}$ alkylene group; each unsubstituted or mono- or polysubstituted with identical or different substituents, wherein the substituents are independently selected from the group consisting of F, Cl, $CF_3$, $C_{1-4}$ alkyl, $OCF_3$, OH and O—$C_{1-4}$ alkyl; or a structure corresponding to formula (VIIIa):

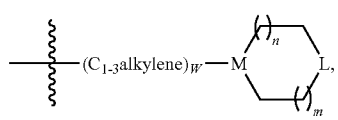
(VIIIa)

wherein
w denotes 0 or 1;
n denotes 0 or 1;
m denotes 0 or 1;
M denotes CH or N, with the proviso that if w denotes 0 then M denotes CH;
L denotes $CR^{44a}R^{44b}$ or $NR^{45}$; wherein
$R^{44a}$ and $R^{44b}$ each independently denote H, F, or unsubstituted, monosubstituted or identically or differently polysubstituted $C_{1-6}$ alkyl; and
$R^{45}$ denotes H, $C_{1-6}$ alkyl, $C_{3-6}$ cycloalkyl or pyridyl;
or
(a3) s and t each denote 0, and the formula (III) assumes one of the following substructures (A) to (H):

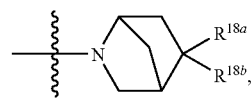
(A)

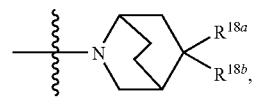
(B)

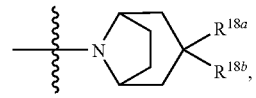
(C)

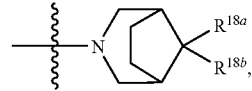
(D)

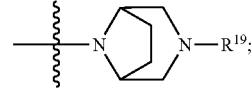
(E)

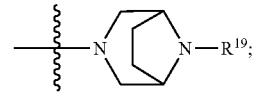
(F)

(G)

or

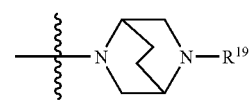
(H)

and wherein
$R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or unsubstituted or mono- or polysubstituted phenyl, pyridyl, imidazolyl, triazolyl, pyrimidyl, thiazolyl or thienyl bound by an —(O)$_{0-1}$—$C_{1-6}$ alkylene group; wherein the substituents are independently selected from the group consisting of F, Cl, $CF_3$, $C_{1-4}$ alkyl, $OCF_3$, OH and O—$C_{1-4}$ alkyl, or
$R^{18a}$ denotes a structure corresponding to formula (IVa)

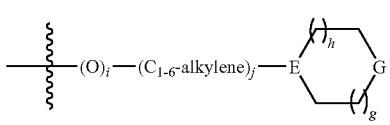
(IVa)

wherein
i denotes 0 or 1;
j denotes 0 or 1;
h and g, each independently, denote 0 or 1,
E denotes N or CH; with the proviso that if i denotes 1 and j denotes 0, then E denotes CH,
G denotes $CR^{37a}R^{37b}$ or $NR^{38}$; wherein
  $R^{37a}$ and $R^{37b}$ each independently denote H; F or $C_{1-4}$ alkyl, each unsubstituted or mono- or polysubstituted with identical or different substituents; and
  $R^{38}$ denotes H; $C_{1-6}$ alkyl, $C_{3-6}$ cycloalkyl or pyridyl;
$R^{18b}$ denotes H, OH, $C_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a $C_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by $C_{1-6}$ alkylene-NH(C=O), each unsubstituted or mono- or polysubstituted with identical or different substituents, wherein the substituents are independently selected from the group consisting of F, Cl, $CF_3$, $C_{1-4}$ alkyl, $OCF_3$, OH and O—$C_{1-4}$ alkyl;
$R^{19}$ denotes H, $C_{1-6}$ alkyl, $C_{3-8}$ cycloalkyl, —(C=O)—$C_{1-6}$ alkyl; $C_{1-6}$ alkylene-NH($C_{1-6}$ alkyl), $C_{1-6}$ alkylene-N($C_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a $C_{1-6}$ alkylene group; each unsubstituted or mono- or polysubstituted with identical or different substituents, wherein the substituents are independently selected from the group consisting of F, Cl, $CF_3$, $C_{1-4}$ alkyl, $OCF_3$, OH and O—$C_{1-4}$ alkyl; or a structure corresponding to formula (VIIIa)

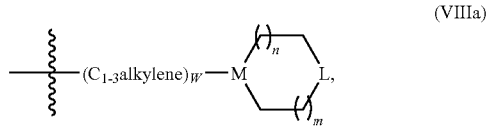

(VIIIa)

wherein
w denotes 0 or 1;
n denotes 0 or 1;
m denotes 0 or 1;
M denotes CH or N, with the proviso that if w denotes 0, then M denotes CH;
L denotes $CR^{44a}R^{44b}$ or $NR^{45}$; wherein
  $R^{44a}$ and $R^{44b}$ each independently denote H, F, or unsubstituted, monosubstituted or identically or differently polysubstituted $C_{1-6}$ alkyl; and
  $R^{45}$ denotes H, $C_{1-6}$ alkyl, $C_{3-6}$ cycloalkyl or pyridyl;
or
(a4)
s denotes 1,
t denotes 0, 1, 2 or 3,
$R^8$ denotes H, $C_{1-4}$ alkyl or $C_{3-6}$ cycloalkyl
$R^{9a}$ and $R^{9b}$ each independently denote H, $C_{1-4}$ alkyl or $C_{3-6}$ cycloalkyl;

the formula (III) assumes one of the following substructures (IIIc'), (IIId'), (IIIe') or (IIIf'):

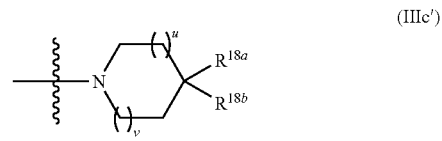

(IIIc')

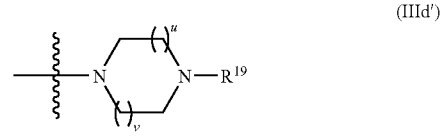

(IIId')

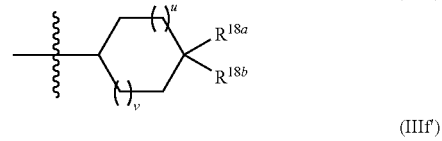

(IIIe')

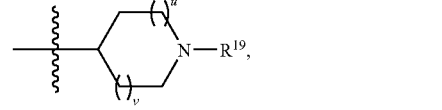

(IIIf')

wherein
u and v each independently denote 0, 1 or 2,
$R^{18a}$ denotes H, $C_{1-4}$ alkyl, $C_{3-6}$ cycloalkyl, —NH($C_{1-6}$ alkyl), —N($C_{1-6}$ alkyl)$_2$, unsubstituted or mono- or polysubstituted phenyl, pyridyl, imidazolyl, triazolyl, pyrimidyl, thiazolyl or thienyl, or unsubstituted or mono- or polysubstituted phenyl, pyridyl, imidazolyl, triazolyl, pyrimidyl, thiazolyl or thienyl bound by an —(O)$_{0-1}$—$C_{1-6}$ alkylene group; wherein the substituents are independently selected from the group consisting of F, Cl, $CF_3$, $C_{1-4}$ alkyl, $OCF_3$, OH and O—$C_{1-4}$ alkyl; or
$R^{18a}$ denotes a structure corresponding to formula (IVa):

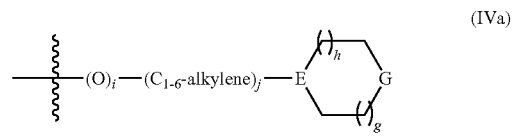

(IVa)

wherein
i denotes 0 or 1;
j denotes 0 or 1;
h and g each independently denote 0 or 1;
E denotes N or CH; with the proviso that if i denotes 1 and j denotes 0, then E denotes CH,
G denotes $CR^{37a}R^{37b}$ or $NR^{38}$; wherein
  $R^{37a}$ and $R^{37b}$ each independently denote H, F, or unsubstituted, monosubstituted or identically or differently polysubstituted $C_{1-4}$ alkyl; and
  $R^{38}$ denotes H; $C_{1-6}$ alkyl, $C_{3-6}$ cycloalkyl or pyridyl;
$R^{18b}$ denotes H, OH, $C_{1-6}$ alkyl, phenyl, pyridyl, imidazolyl, triazolyl, pyrimidyl, thiazolyl or thienyl, each unsubstituted or mono- or polysubstituted with identical or different substituents; phenyl, pyridyl, imidazolyl, triazolyl, pyrimidyl, thiazolyl or thienyl bound via a $C_{1-6}$ alkylene group, each unsubstituted or mono- or polysubstituted with identical or different substituents; O-phenyl or O-pyridyl, each unsubstituted or mono- or polysubstituted with identical or different substituents, phenyl, pyridyl or thienyl bridged by $C_{1-6}$ alkylene-NH (C=O), each unsubstituted or mono- or polysubstituted with identical or different substituents independently selected from the group consisting of F, Cl, $CF_3$, $C_{1-4}$ alkyl, $OCF_3$, OH and O—$C_{1-4}$ alkyl;

$R^{19}$ denotes H, $C_{1-6}$ alkyl, $C_{3-8}$ cycloalkyl, —(C=O)—$C_{1-6}$ alkyl; $C_{1-6}$ alkylene-NH($C_{1-6}$ alkyl), $C_{1-6}$ alkylene-N($C_{1-6}$ alkyl)$_2$ or phenyl, pyridyl, thienyl, thiazolyl, triazolyl, pyrimidinyl or imidazolyl; each unsubstituted or mono- or polysubstituted with identical or different substituents; or phenyl, pyridyl, thienyl, thiazolyl, pyrimidinyl, triazolyl or imidazolyl bound via a $C_{1-6}$ alkylene group; each unsubstituted or mono- or polysubstituted with identical or different substituents, wherein the substituents are independently selected from the group consisting of F, Cl, $CF_3$, $C_{1-4}$ alkyl, $OCF_3$, OH and O—$C_{1-4}$ alkyl; or a structure corresponding to formula (VIIIa):

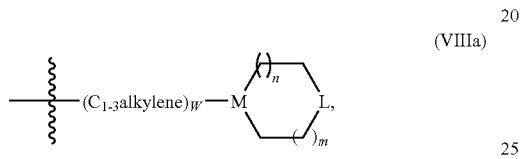

(VIIIa)

wherein w denotes 0 or 1;

n denotes 0 or 1;

m denotes 0 or 1;

M denotes CH or N, with the proviso that if w denotes 0, then M denotes CH; and

L denotes $CR^{44a}R^{44b}$ or $NR^{45}$; wherein $R^{44a}$ and $R^{44b}$ each independently denote H, F, or unsubstituted, monosubstituted or identically or differently polysubstituted $C_{1-6}$ alkyl; and $R^{45}$ denotes H, $C_{1-6}$ alkyl, $C_{3-6}$ cycloalkyl or pyridyl.

14. A compound according to claim 1, wherein the substructure (II) assumes one of the following substructures:

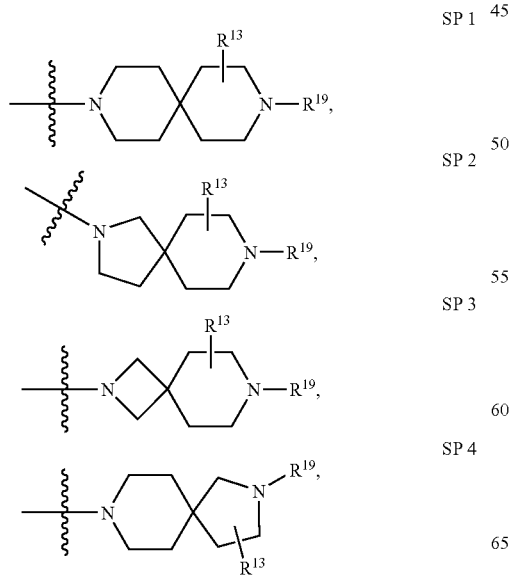

SP 1

SP 2

SP 3

SP 4

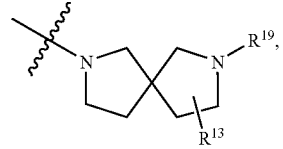

SP 5

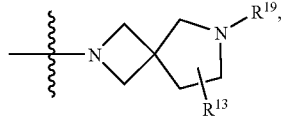

SP 6

SP 7

SP 8

SP 9

SP 10

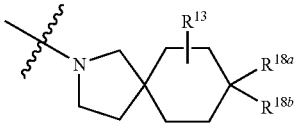

SP 11

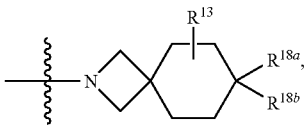

SP 12

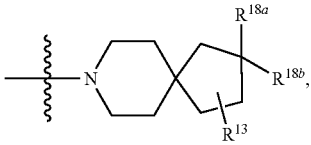

SP 13

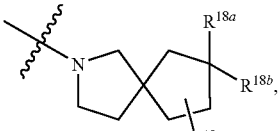

SP 14

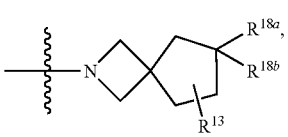

SP 16

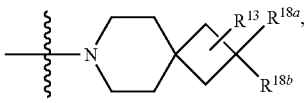

SP 17

-continued

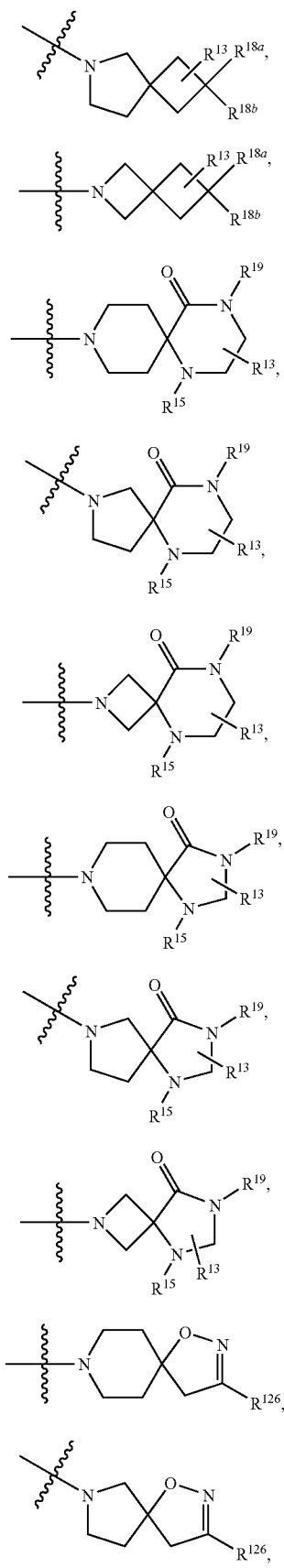

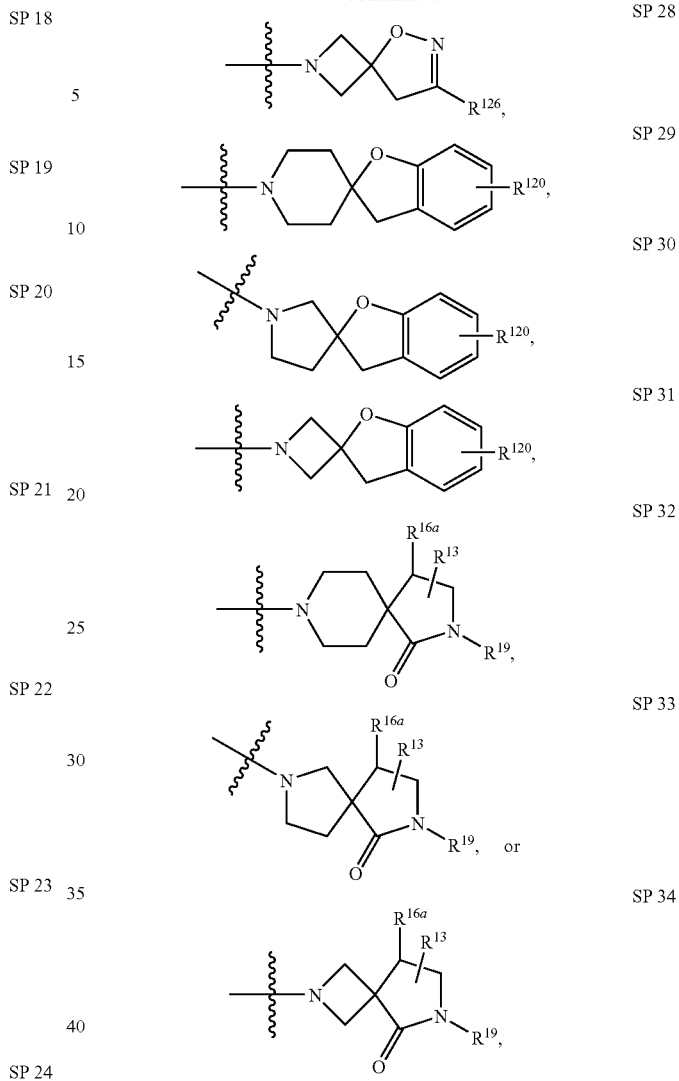

wherein

R[13] denotes 1 or 2 substituents selected from H and unsubstituted, monosubstituted or identically or differently polysubstituted phenyl with substituents independently selected from the group consisting of F, Cl, $CF_3$, $C_{1-4}$ alkyl, $OCF_3$, OH and O—$C_{1-4}$ alkyl; and/or two substituents R[13] together form =O; and/or two adjacent substituents R[13] together form an anellated aryl or heteroaryl ring unsubstituted or mono- or polysubstituted with identical or different substituents independently selected from the group consisting of F, Cl, $CF_3$, $C_{1-4}$ alkyl, $OCF_3$, OH and O—$C_{1-4}$ alkyl;

R[15] denotes H; $C_{1-6}$ alkyl; $C_{3-8}$ cycloalkyl; unsubstituted, monosubstituted or identically or differently polysubstituted phenyl or pyridyl; or unsubstituted, monosubstituted or identically or differently polysubstituted phenyl or pyridyl bound via a $C_{1-6}$ alkylene group, wherein the substituents are independently selected from the group consisting of F, Cl, $CF_3$, $C_{1-4}$ alkyl, $OCF_3$, OH and O—$C_{1-4}$ alkyl;

R[16a] denotes H; $C_{1-6}$ alkyl; or unsubstituted, monosubstituted or identically or differently polysubstituted phenyl or pyridyl, wherein the substituents are independently selected from the group consisting of F, Cl, CF$_3$, C$_{1-4}$ alkyl, OCF$_3$, OH and O—C$_{1-4}$ alkyl;

R$^{18a}$ denotes H; C$_{1-6}$ alkyl; C$_{3-8}$ cycloalkyl, N(C$_{1-6}$ alkyl)$_2$; NH(C$_{1-6}$ alkyl), azetidinyl; pyrrolidinyl, piperidinyl, 4-(C$_{1-6}$ alkyl)-piperazinyl; phenyl or pyridyl, each unsubstituted or mono- or polysubstituted with identical or different substituents; or N(C$_{1-6}$ alkyl)$_2$; NH(C$_{1-6}$ alkyl), azetidinyl; pyrrolidinyl, piperidinyl, 4-(C$_{1-6}$ alkyl)-piperazinyl; phenyl, imidazolyl, triazolyl or pyridyl bound by an —(O)$_{0/1}$—C$_{1-6}$ alkylene group, each unsubstituted or mono- or polysubstituted with identical or different substituents, wherein the substituents of C$_{1-6}$ alkyl; C$_{3-8}$ cycloalkyl, azetidinyl; pyrrolidinyl, piperidinyl and 4-(C$_{1-6}$ alkyl)-piperazinyl are independently selected from the group consisting of F, Cl, CF$_3$, =O, C$_{1-4}$ alkyl, OCF$_3$, OH and O—C$_{1-4}$ alkyl; and wherein the substituents of phenyl, imidazolyl, triazolyl or pyridyl are independently selected from the group consisting of F, Cl, CF$_3$, C$_{1-4}$ alkyl, OCF$_3$, OH and O—C$_{1-4}$ alkyl;

R$^{18b}$ denotes H; OH; C$_{1-6}$ alkyl; phenyl or pyridyl, each unsubstituted or mono- or polysubstituted with identical or different substituents, or phenyl or pyridyl bound via a C$_{1-6}$ alkylene group, each unsubstituted or mono- or polysubstituted with identical or different substituents; wherein the substituents of phenyl and pyridyl are independently selected from the group consisting of F, Cl, CF$_3$, C$_{1-4}$ alkyl, OCF$_3$, OH and O—C$_{1-4}$ alkyl;

R$^{19}$ denotes H; C$_{1-6}$ alkyl; C$_{3-8}$ cycloalkyl, phenyl, pyridyl, thienyl, imidazolyl, thiazolyl or triazolyl, each unsubstituted or mono- or polysubstituted with identical or different substituents, or phenyl or pyridyl bound via a C$_{1-6}$ alkylene group or (C=O) group, each unsubstituted or mono- or polysubstituted with identical or different substituents, wherein the substituents of phenyl, pyridyl, thienyl, imidazolyl, thiazolyl and triazolyl are independently selected from the group consisting of F, Cl, CF$_3$, C$_{1-4}$ alkyl, OCF$_3$, OH and O—C$_{1-4}$ alkyl;

R$^{120}$ denotes H; F; Cl; OH; OCH$_3$, O—CF$_3$, C$_{1-6}$ alkyl; CF$_3$; or phenyl which is unsubstituted or mono- or polysubstituted with substituents independently selected from the group consisting of F, Cl, CF$_3$, C$_{1-4}$ alkyl, OCF$_3$, OH and O—C$_{1-4}$ alkyl; and R$^{126}$ denotes H; C$_{1-6}$ alkyl; C$_{3-6}$ cycloalkyl; phenyl or pyridyl; or C$_{3-6}$ cycloalkyl, phenyl or pyridyl bound via a C$_{1-3}$ alkylene group, each unsubstituted or mono- or polysubstituted with identical or different substituents, wherein the substituents of phenyl and pyridyl are independently selected from the group consisting of F, Cl, CF$_3$, C$_{1-4}$ alkyl, OCF$_3$, OH and O—C$_{1-4}$ alkyl.

15. A compound according to claim 1, wherein in formula (I) the following substructure (B)

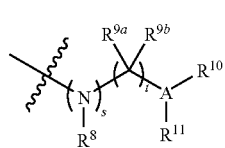

(B)

is selected from the group consisting of:

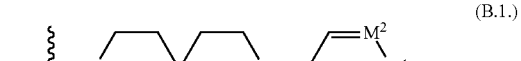

(B.1.)

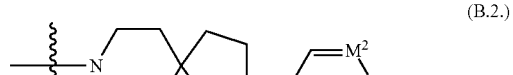

(B.2.)

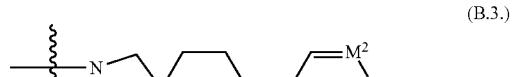

(B.3.)

(B.4.)

(B.5.)

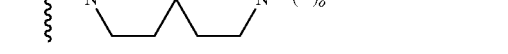

(B.6.)

(B.7.)

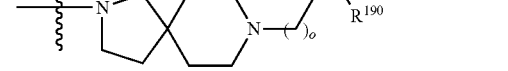

(B.8.)

(B.9.)

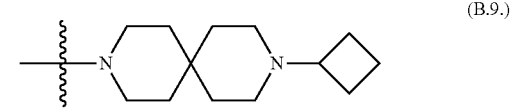

(B.10.)

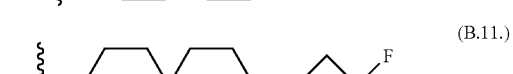

(B.11.)

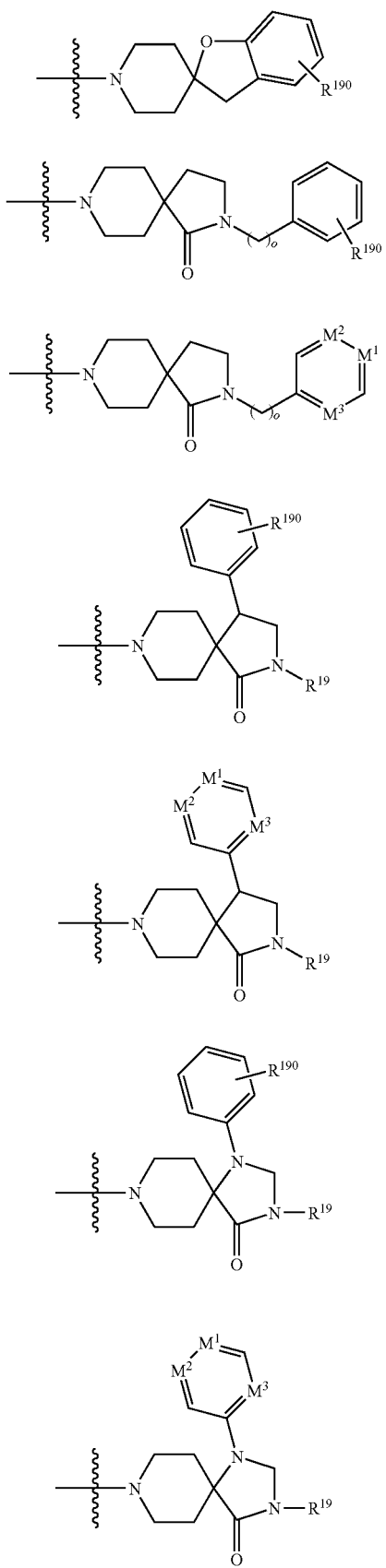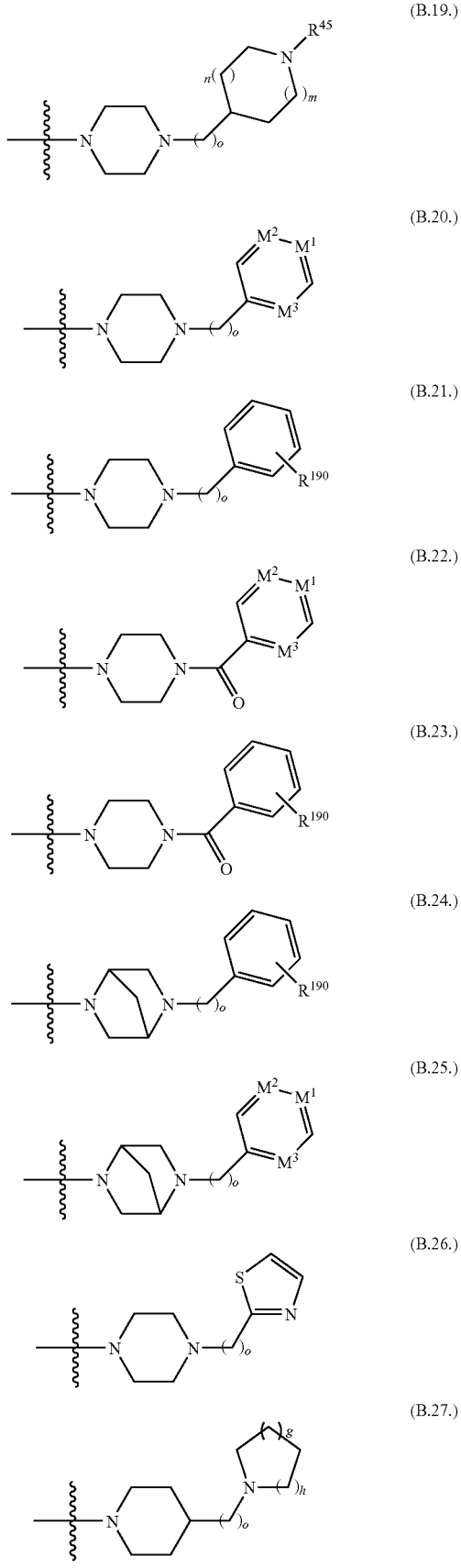

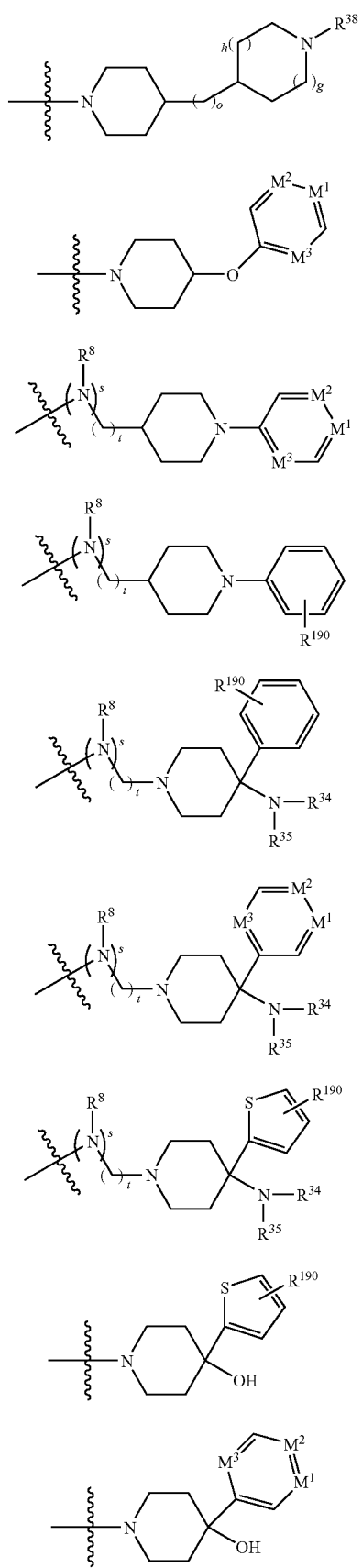
(B.28.)
(B.29.)
(B.30.)
(B.31.)
(B.32.)
(B.33.)
(B.34.)
(B.35.)
(B.36.)
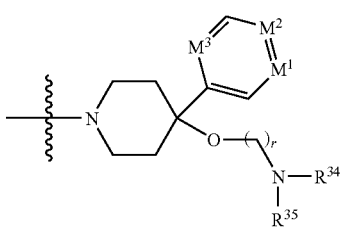
(B.37.)
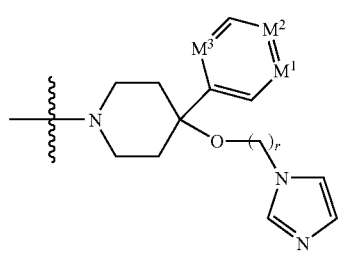
(B.38.)
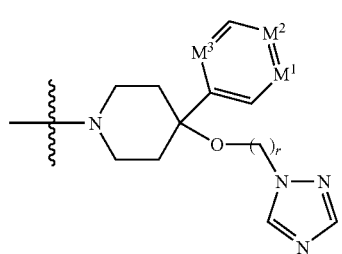
(B.39.)
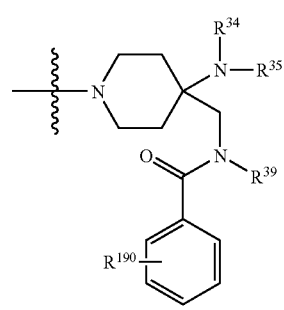
(B.40.)
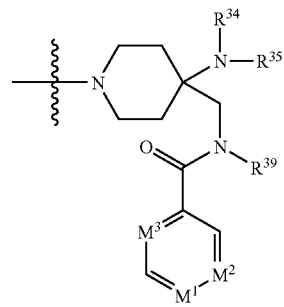
(B.40.)
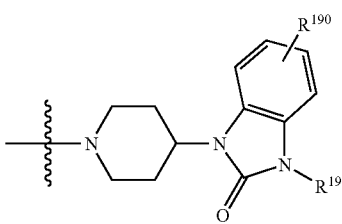
(B.41.)

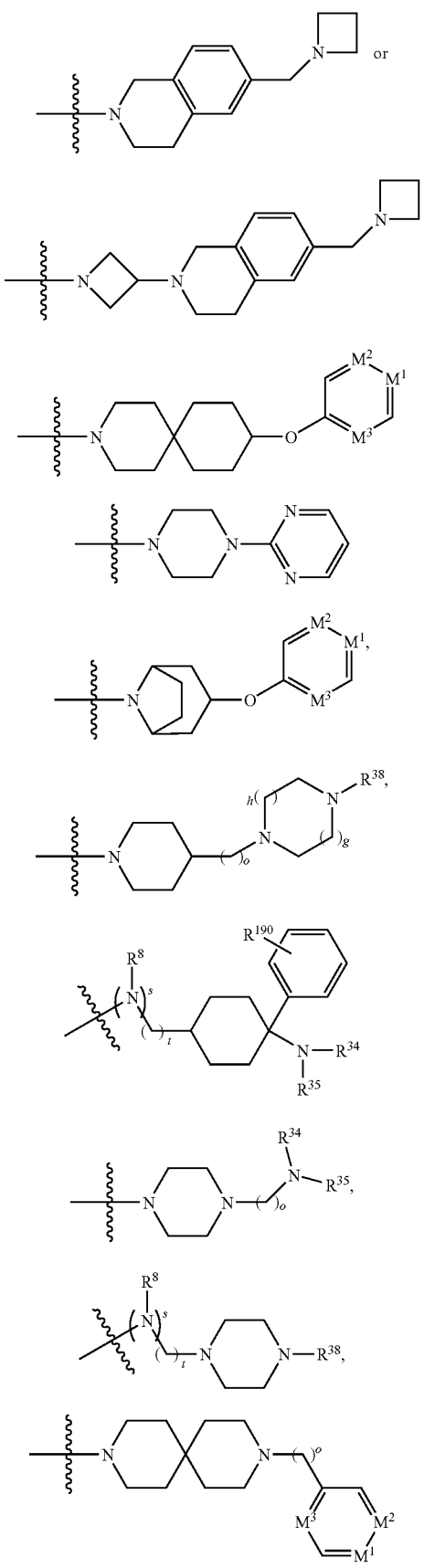
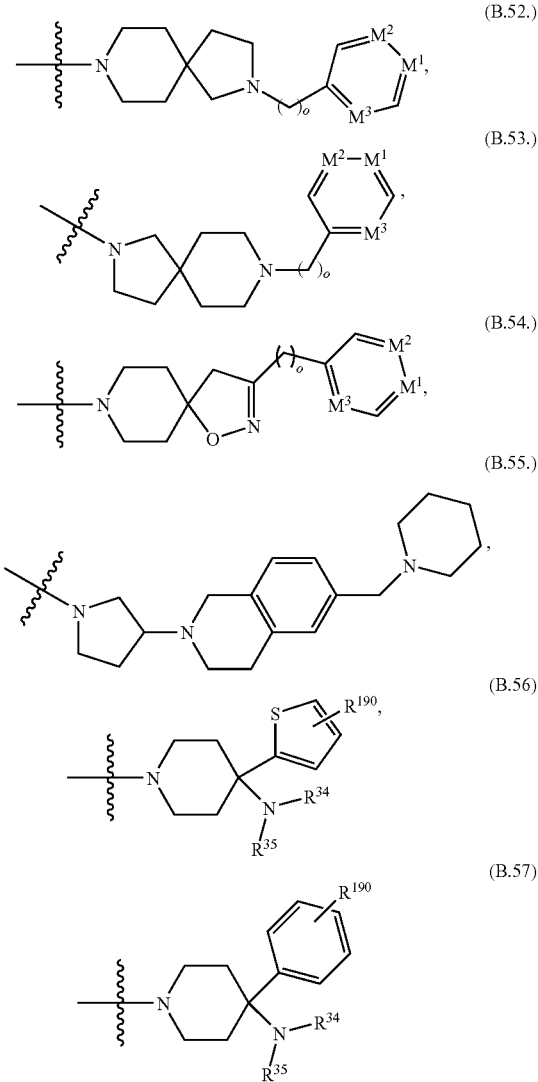

wherein
h = 0 or 1;
g = 0 or 1;
m = 0 or 1;
n = 0 or 1;
o = 0, 1, 2 or 3;
r = 1, 2 or 3,
s = 0 or 1;
t = 0, 1, 2 or 3, with the proviso that if s denotes 0, then t likewise denotes 0;

$M^1$, $M^2$ and $M^3$ each denote N or CH, wherein one of $M^1$, $M^2$ and $M^3$ denotes N, and the other two each denote CH;

$R^8$ denotes H; branched or unbranched $C_{1-6}$ alkyl or $C_{3-6}$ cycloalkyl, each unsubstituted or mono- or polysubstituted with identical or different substituents;

$R^{19}$ denotes H; $C_{1-6}$ alkyl or $C_{3-6}$ cycloalkyl, each unsubstituted or mono- or polysubstituted with identical or different substituents;

$R^{34}$ and $R^{35}$ each independently denote methyl or ethyl or together with the N-atom linking them form an azetidinyl; pyrrolidinyl, piperidinyl, 4-($C_{1-6}$ alkyl)-piperazinyl group, each unsubstituted or mono- or polysubstituted with identical or different substituents;

$R^{38}$ denotes H, $C_{1-6}$ alkyl, $C_{3-6}$ cycloalkyl or pyridyl;

$R^{39}$ denotes H; $C_{1-6}$ alkyl or $C_{3-6}$ cycloalkyl, each unsubstituted or mono- or polysubstituted with identical or different substituents; and $R^{45}$ denotes H, $C_{1-6}$ alkyl, $C_{3-6}$ cycloalkyl or pyridyl; and $R^{190}$ represents 0 to 4 substituents each independently selected from the group consisting of F, Cl, O—$CF_3$, $CF_3$ and CN.

16. A compound according to claim 1, selected from the group consisting of:

| No. | Compound |
| --- | --- |
| G-01 | 4-Methoxy-2,6-dimethyl-N-[1-[2-oxo-2-[4-(2-pyrrolidin-1-yl-ethyl)-piperidin-1-yl]-ethyl]-1H-indol-6-yl]-benzenesulfonic acid amide |
| G-02 | 4-Methoxy-2,6-dimethyl-N-[1-[2-oxo-2-[4-(2-pyrrolidin-1-yl-ethyl)-piperidin-1-yl]-ethyl]-1H-indol-7-yl]-benzenesulfonic acid amide |
| G-03 | 4-Methoxy-2,6-dimethyl-N-[1-[2-oxo-2-(4-pyridin-4-yloxy-piperidin-1-yl)-ethyl]-1H-indol-7-yl]-benzenesulfonic acid amide |
| G-04 | 4-Methoxy-2,6-dimethyl-N-[1-[2-oxo-2-(1-oxo-4-phenyl-2,4,8-triazaspiro[4.5]decan-8-yl)-ethyl]-1H-indol-7-yl]-benzenesulfonic acid amide |
| G-05 | 4-Methoxy-2,6-dimethyl-N-[1-[2-oxo-2-(9-pyridin-4-yl-3,9-diazaspiro[5.5]undecan-3-yl)-ethyl]-1H-indol-7-yl]-benzenesulfonic acid amide |
| G-06 | 4-Methoxy-2,6-dimethyl-N-[1-[2-oxo-2-[4-pyridin-3-yl-4-(2-pyrrolidin-1-yl-ethoxy)-piperidin-1-yl]-ethyl]-1H-indol-7-yl]-benzenesulfonic acid amide |
| G-13 | 4-Methoxy-2,6-dimethyl-N-(1-(2-oxo-2-(3-(pyridin-4-yl)-1-oxa-2,8-diazaspiro[4.5]dec-2-en-8-yl)ethyl)-1H-indol-7-yl)benzenesulfonic acid amide |
| G-14 | 4-Methoxy-2,6-dimethyl-N-(1-(2-oxo-2-(8-(pyridin-4-yl)-2,8-diazaspiro[4.5]decan-2-yl)ethyl)-1H-indol-7-yl)benzenesulfonic acid amide |
| G-16 | 4-Methoxy-2,6-dimethyl-N-(1-(2-oxo-2-(3-(6-(piperidin-1-ylmethyl)-3,4-dihydroisoquinolin-2(1H)-yl)pyrrolidin-1-yl)ethyl)-1H-indol-7-yl)benzenesulfonic acid amide |
| G-17 | 4-Methoxy-2,6-dimethyl-N-(1-(2-oxo-2-(7-(pyridin-4-yl)-2,7-diazaspiro[4.4]nonan-2-yl)ethyl)-1H-indol-7-yl)benzenesulfonic acid amide |
| G-18 | N-(1-(2-(9-(azetidin-1-yl)-3-azaspiro[5.5]undecan-3-yl)-2-oxoethyl)-1H-indol-7-yl)-4-methoxy-2,6-dimethylbenzenesulfonic acid amide |
| G-22 | 4-Methoxy-2,6-dimethyl-N-(1-(2-oxo-2-(9-(pyridin-4-yloxy)-3-azaspiro[5.5]undecan-3-yl)ethyl)-1H-indol-7-yl)benzenesulfonic acid amide |
| G-24 | 4-Methoxy-2,6-dimethyl-N-[[1-[2-oxo-2-(9-pyridin-4-yl-3,9-diazaspiro[5.5]undecan-3-yl)-ethyl]-1H-indol-7-yl]-methyl]-benzenesulfonic acid amide |
| G_CC-1 | 4-Methoxy-2,6-dimethyl-N-[1-[2-[4-(1-methyl-piperidin-4-yl)-piperazin-1-yl]-2-oxo-ethyl]-1H-indol-6-yl]-benzenesulfonic acid amide |
| G_CC-2 | 4-Methoxy-2,6-dimethyl-N-[1-[2-[4-(4-methyl-piperazin-1-yl)-piperidin-1-yl]-2-oxo-ethyl]-1H-indol-6-yl]-benzenesulfonic acid amide |
| G_CC-3 | 4-Methoxy-2,6-dimethyl-N-[1-[2-oxo-2-(4-pyrimidin-2-yl-piperazin-1-yl)-ethyl]-1H-indol-6-yl]-benzenesulfonic acid amide |
| G_CC-4 | 4-Methoxy-2,6-dimethyl-N-[1-[2-[4-[(1-methyl-piperidin-4-yl)-methyl]-piperazin-1-yl]-2-oxo-ethyl]-1H-indol-6-yl]-benzenesulfonic acid amide |
| G_CC-5 | N-[1-[2-[4-(4-fluorophenyl)-piperazin-1-yl]-2-oxo-ethyl]-1H-indol-7-yl]-4-methoxy-2,6-dimethyl-benzenesulfonic acid amide |
| G_CC-6 | 4-Methoxy-2,6-dimethyl-N-[1-[2-oxo-2-(4-pyrimidin-2-yl-piperazin-1-yl)-ethyl]-1H-indol-7-yl]-benzenesulfonic acid amide |
| G_CC-7 | 4-Methoxy-2,6-dimethyl-N-[1-[2-[4-[(1-methyl-piperidin-4-yl)-methyl]-piperazin-1-yl]-2-oxo-ethyl]-1H-indol-7-yl]-benzenesulfonic acid amide |
| G_CC-8 | 4-Chloro-2,5-dimethyl-N-[1-[2-[4-[(1-methyl-piperidin-4-yl)-methyl]-piperazin-1-yl]-2-oxo-ethyl]-1H-indol-6-yl]-benzenesulfonic acid amide |
| G_CC-9 | 2-[6-[[(4-Methoxy-2,6-dimethyl-phenyl)sulfonyl]amino]-1H-indol-1-yl]-N-[(1-pyridin-4-yl-piperidin-4-yl)-methyl]-acetamide |
| G_CC-10 | N-[1-[2-(3-Benzyl-3,7-diazaspiro[4.4]nonan-7-yl)-2-oxo-ethyl]-1H-indol-6-yl]-4-methoxy-2,6-dimethyl-benzenesulfonic acid amide |
| G_CC-11 | N-[3-(4-Dimethylamino-4-phenyl-piperidin-1-yl)-propyl]-2-[6-[[(4-methoxy-2,6-dimethyl-phenyl)sulfonyl]amino]-1H-indol-1-yl]-N-methyl-acetamide |
| G_CC-12 | N-[1-[2-[3-(4-Fluorophenyl)-4-oxo-3,8-diazaspiro[4.5]decan-8-yl]-2-oxo-ethyl]-1H-indol-7-yl]-4-methoxy-2,6-dimethyl-benzenesulfonic acid amide |
| G_CC-13 | N-[1-[2-(3-Benzyl-3,7-diazaspiro[4.4]nonan-7-yl)-2-oxo-ethyl]-1H-indol-7-yl]-4-methoxy-2,6-dimethyl-benzenesulfonic acid amide |
| G_CC-14 | N-[3-(4-Dimethylamino-4-phenyl-piperidin-1-yl)-propyl]-2-[7-[[(4-methoxy-2,6-dimethyl-phenyl)sulfonyl]amino]-1H-indol-1-yl]-N-methyl-acetamide |
| G_CC-15 | 2-[6-[[(4-Chloro-2,5-dimethyl-phenyl)sulfonyl]amino]-1H-indol-1-yl]-N-[3-(4-dimethylamino-4-phenyl-piperidin-1-yl)-propyl]-N-methyl-acetamide |
| G_CC-16 | N-[3-(4-Dimethylamino-4-phenyl-piperidin-1-yl)-propyl]-N-methyl-2-[7-[(naphthalen-1-ylsulfonyl)amino]-1H-indol-1-yl]-acetamide |
| G_CC-17 | N-[4-(Azetidin-1-yl)-4-phenyl-cyclohexyl]-2-[7-[[(4-methoxy-2,6-dimethyl-phenyl)sulfonyl]amino]-1H-indol-1-yl]-acetamide |
| G_CC-18 | N-[3-(4-Dimethylamino-4-thiophen-2-yl-piperidin-1-yl)-propyl]-2-[7-[[(4-methoxy-2,6-dimethyl-phenyl)sulfonyl]amino]-1H-indol-1-yl]-N-methyl-acetamide |
| G_CC-19 | N-[2-(4-Dimethylamino-4-thiophen-2-yl-piperidin-1-yl)-ethyl]-2-[7-[[(4-methoxy-2,6-dimethyl-phenyl)sulfonyl]amino]-1H-indol-1-yl]-acetamide |
| G_CC-20 | N-[1-[2-(4-Dimethylamino-4-thiophen-2-yl-piperidin-1-yl)-2-oxo-ethyl]-1H-indol-7-yl]-4-methoxy-2,6-dimethyl-benzenesulfonic acid amide |
| G_CC-21 | 2-[7-[[(4-Methoxy-2,6-dimethyl-phenyl)sulfonyl]amino]-1H-indol-1-yl]-N-[2-(1-pyridin-4-yl-piperidin-4-yl)-ethyl]-acetamide |

-continued

| No. | Compound |
|---|---|
| G_CC-22 | N-[2-(4-Dimethylamino-4-thiophen-2-yl-piperidin-1-yl)-ethyl]-3-[6-[[(4-methoxy-2,6-dimethyl-phenyl)sulfonyl]amino]-1H-indol-1-yl]-propionamide |
| G_CC-23 | 3-[6-[[(4-Methoxy-2,6-dimethyl-phenyl)sulfonyl]amino]-1H-indol-1-yl]-N-[2-(1-pyridin-4-yl-piperidin-4-yl)-ethyl]-propionamide |
| G_CC-24 | 2-[6-[[(4-Chloro-2,5-dimethyl-phenyl)sulfonyl]amino]-1H-indol-1-yl]-N-[2-(1-pyridin-4-yl-piperidin-4-yl)-ethyl]-acetamide |
| G_CC-25 | N-[3-(4-Dimethylamino-4-thiophen-2-yl-piperidin-1-yl)-propyl]-N-methyl-2-[7-[(naphthalen-1-ylsulfonyl)amino]-1H-indol-1-yl]-acetamide |
| G_CC-26 | 2-[7-[[(4-Chloro-2,5-dimethyl-phenyl)sulfonyl]amino]-1H-indol-1-yl]-N-[3-(4-dimethylamino-4-thiophen-2-yl-piperidin-1-yl)-propyl]-N-methyl-acetamide |
| G_CC-27 | 2-[7-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-acetamide |
| G_CC-28 | 2-[7-[[(4-Chloro-2,5-dimethyl-phenyl)sulfonyl]amino]-1H-indol-1-yl]-N-[2-(1-pyridin-4-yl-piperidin-4-yl)-ethyl]-acetamide |
| G_CC-29 | N-[3-(4-Dimethylamino-4-thiophen-2-yl-piperidin-1-yl)-propyl]-2-[6-[[(4-methoxy-2,6-dimethyl-phenyl)sulfonyl]amino]-1H-indol-1-yl]-N-methyl-acetamide |
| G_CC-30 | N-[2-(4-Dimethylamino-4-thiophen-2-yl-piperidin-1-yl)-ethyl]-2-[6-[[(4-methoxy-2,6-dimethyl-phenyl)sulfonyl]amino]-1H-indol-1-yl]-acetamide |
| G_CC-31 | N-[1-[2-[1-(4-Fluorophenyl)-3-methyl-4-oxo-3,8-diazaspiro[4.5]decan-8-yl]-2-oxo-ethyl]-1H-indol-7-yl]-4-methoxy-2,6-dimethyl-benzenesulfonic acid amide |
| G_CC-32 | N-[1-[2-(3-Benzyl-4-oxo-3,8-diazaspiro[4.5]decan-8-yl)-2-oxo-ethyl]-1H-indol-7-yl]-4-methoxy-2,6-dimethyl-benzenesulfonic acid amide |
| G_CC-33 | N-[1-[2-[2-[(4-Fluorophenyl)-methyl]-2,5-diazabicyclo[2.2.1]heptan-5-yl]-2-oxo-ethyl]-1H-indol-6-yl]-4-methoxy-2,6-dimethyl-benzenesulfonic acid amide |
| G_CC-34 | 4-Methoxy-2,6-dimethyl-N-[1-[2-oxo-2-[2-(pyridin-4-yl-methyl)-2,5-diazabicyclo[2.2.1]heptan-5-yl]-ethyl]-1H-indol-7-yl]-benzenesulfonic acid amide |
| G_CC-35 | 4-Methoxy-2,6-dimethyl-N-[1-[3-oxo-3-(3-pyridin-4-yl-3,9-diazaspiro[5.5]undecan-9-yl)-propyl]-1H-indol-6-yl]-benzenesulfonic acid amide |
| G_CC-36 | 4-Chloro-2,5-dimethyl-N-[1-[2-oxo-2-(3-pyridin-4-yl-3,9-diazaspiro[5.5]undecan-9-yl)-ethyl]-1H-indol-6-yl]-benzenesulfonic acid amide |
| G_CC-37 | N-[1-[2-Oxo-2-(3-pyridin-4-yl-3,9-diazaspiro[5.5]undecan-9-yl)-ethyl]-1H-indol-6-yl]-2-(trifluoromethyl)-benzenesulfonic acid amide |
| G_CC-38 | N-[1-[2-Oxo-2-(3-pyridin-4-yl-3,9-diazaspiro[5.5]undecan-9-yl)-ethyl]-1H-indol-7-yl]-naphthalene-1-sulfonic acid amide |
| G_CC-39 | 4-Chloro-2,5-dimethyl-N-[1-[2-oxo-2-(3-pyridin-4-yl-3,9-diazaspiro[5.5]undecan-9-yl)-ethyl]-1H-indol-7-yl]-benzenesulfonic acid amide |
| G_CC-40 | 4-Methoxy-2,6-dimethyl-N-[1-[3-[4-(1-methyl-piperidin-4-yl)-piperazin-1-yl]-3-oxo-propyl]-1H-indol-7-yl]-benzenesulfonic acid amide |
| G_CC-41 | 4-Methoxy-2,6-dimethyl-N-[1-[3-oxo-3-[4-(2-pyrrolidin-1-yl-ethyl)-piperidin-1-yl]-propyl]-1H-indol-7-yl]-benzenesulfonic acid amide |
| G_CC-42 | 4-Methoxy-2,6-dimethyl-N-[1-[3-[4-(4-methyl-piperazin-1-yl)-piperidin-1-yl]-3-oxo-propyl]-1H-indol-7-yl]-benzenesulfonic acid amide |
| G_CC-43 | 4-Methoxy-2,6-dimethyl-N-[1-[3-[4-[(1-methyl-piperidin-4-yl)-methyl]-piperazin-1-yl]-3-oxo-propyl]-1H-indol-7-yl]-benzenesulfonic acid amide |
| G_CC-44 | N-[1-[3-[4-(3-Dimethylamino-propyl)-piperazin-1-yl]-3-oxo-propyl]-1H-indol-7-yl]-4-methoxy-2,6-dimethyl-benzenesulfonic acid amide |
| G_CC-45 | N-[1-[3-(4-Hydroxy-4-pyridin-2-yl-piperidin-1-yl)-3-oxo-propyl]-1H-indol-7-yl]-4-methoxy-2,6-dimethyl-benzenesulfonic acid amide |
| G_CC-46 | N-[3-(4-Dimethylamino-4-thiophen-2-yl-piperidin-1-yl)-propyl]-3-[7-[[(4-methoxy-2,6-dimethyl-phenyl)sulfonyl]amino]-1H-indol-1-yl]-N-methyl-propionamide |
| G_CC-47 | 3-[7-[[(4-Methoxy-2,6-dimethyl-phenyl)sulfonyl]amino]-1H-indol-1-yl]-N-[2-(1-pyridin-4-yl-piperidin-4-yl)-ethyl]-propionamide |
| G_CC-48 | N-[1-[3-(4-Dimethylamino-4-phenyl-piperidin-1-yl)-3-oxo-propyl]-1H-indol-7-yl]-4-methoxy-2,6-dimethyl-benzenesulfonic acid amide |
| G_CC-49 | N-[3-(4-Dimethylamino-4-phenyl-piperidin-1-yl)-propyl]-3-[7-[[(4-methoxy-2,6-dimethyl-phenyl)sulfonyl]amino]-1H-indol-1-yl]-N-methyl-propionamide |
| G_CC-50 | N-[4-(Azetidin-1-yl)-4-phenyl-cyclohexyl]-3-[7-[[(4-methoxy-2,6-dimethyl-phenyl)sulfonyl]amino]-1H-indol-1-yl]-propionamide |
| G_CC-51 | N-[2-(4-Dimethylamino-4-thiophen-2-yl-piperidin-1-yl)-ethyl]-3-[7-[[(4-methoxy-2,6-dimethyl-phenyl)sulfonyl]amino]-1H-indol-1-yl]-propionamide |
| G_CC-52 | N-[1-[3-Oxo-3-(3-pyridin-4-yl-3,9-diazaspiro[5.5]undecan-9-yl)-propyl]-1H-indol-7-yl]-2-(trifluoromethyl)-benzenesulfonic acid amide |
| G_CC-53 | N-[1-[2-Oxo-2-(3-pyridin-4-yl-3,9-diazaspiro[5.5]undecan-9-yl)-ethyl]-1H-indol-7-yl]-2-(trifluoromethyl)-benzenesulfonic acid amide |
| G_CC-54 | 4-Methoxy-2,6-dimethyl-N-[1-[3-oxo-3-(3-pyridin-4-yl-3,9-diazaspiro[5.5]undecan-9-yl)-propyl]-1H-indol-7-yl]-benzenesulfonic acid amide |
| G_CC-56 | N-[3-(4-Ethyl-piperazin-1-yl)-propyl]-3-[7-[[(4-methoxy-2,6-dimethyl-phenyl)sulfonyl]amino]-1H-indol-1-yl]-propionamide |
| G_CC-57 | 4-Methoxy-2,6-dimethyl-N-[1-[2-oxo-2-[4-pyridin-3-yl-4-(2-pyrrolidin-1-yl-ethoxy)-piperidin-1-yl]-ethyl]-1H-indol-6-yl]-benzenesulfonic acid amide |
| G_CC-59 | 4-Chloro-2,5-dimethyl-N-[1-[3-[4-(1-methyl-piperidin-4-yl)-piperazin-1-yl]-3-oxo-propyl]-1H-indol-7-yl]-benzenesulfonic acid amide |
| G_CC-60 | 4-Chloro-2,5-dimethyl-N-[1-[3-oxo-3-[4-(2-pyrrolidin-1-yl-ethyl)-piperidin-1-yl]-propyl]-1H-indol-7-yl]-benzenesulfonic acid amide |
| G_CC-61 | 4-Chloro-2,5-dimethyl-N-[1-[3-[4-(4-methyl-piperazin-1-yl)-piperidin-1-yl]-3-oxo-propyl]-1H-indol-7-yl]-benzenesulfonic acid amide |
| G_CC-62 | 4-Chloro-2,5-dimethyl-N-[1-[3-[4-[(1-methyl-piperidin-4-yl)-methyl]-piperazin-1-yl]-3-oxo-propyl]-1H-indol-7-yl]-benzenesulfonic acid amide |

-continued

| No. | Compound |
|---|---|
| G_CC-65 | 4-Chloro-2,5-dimethyl-N-[1-[3-oxo-3-(3-pyridin-4-yl-3,9-diazaspiro[5.5]undecan-9-yl)-propyl]-1H-indol-6-yl]-benzenesulfonic acid amide |
| G_CC-70 | 3-[7-[[(4-Chloro-2,5-dimethyl-phenyl)sulfonyl]amino]-1H-indol-1-yl]-N-[2-(1-pyridin-4-yl-piperidin-4-yl)-ethyl]-propionamide |
| G_CC-71 | 3-[6-[[(4-Chloro-2,5-dimethyl-phenyl)sulfonyl]amino]-1H-indol-1-yl]-N-[2-(1-pyridin-4-yl-piperidin-4-yl)-ethyl]-propionamide |
| G_CC-73 | 3-[7-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-propionamide |
| G_CC-74 | 3-[6-[[(4-Chloro-2,5-dimethyl-phenyl)sulfonyl]amino]-1H-indol-1-yl]-N-[2-(4-dimethylamino-4-thiophen-2-yl-piperidin-1-yl)-ethyl]-propionamide |
| G_CC-76 | 2-[6-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-acetamide (G_CC-76) |
| G_CC-77 | N-[2-(4-Dimethylamino-4-phenyl-cyclohexyl)-ethyl]-2-[7-[[(4-methoxy-2,6-dimethyl-phenyl)sulfonyl]amino]-1H-indol-1-yl]-N-methyl-acetamide (G_CC-77) |
| G_CC-81 | N-[2-[4-(3-Fluorophenyl)-4-(4-methyl-piperazin-1-yl)-piperidin-1-yl]-ethyl]-3-[6-[[(4-methoxy-2,6-dimethyl-phenyl)sulfonyl]amino]-1H-indol-1-yl]-N-methyl-propionamide (G_CC-81) |
| G_CC-84 | N-[1-[2-[4-(3-Fluorophenyl)-4-(4-methyl-piperazin-1-yl)-piperidin-1-yl]-2-oxo-ethyl]-1H-indol-7-yl]-4-methoxy-2,6-dimethyl-benzenesulfonic acid amide (G_CC-84) |
| G_CC-88 | 2-[7-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-acetamide (G_CC-88) |
| G_CC-91 | 4-Methoxy-2,6-dimethyl-N-[1-[2-oxo-2-(3-pyridin-4-yl-3,9-diazaspiro[5.5]undecan-9-yl)-ethyl]-1H-indol-7-yl]-benzenesulfonic acid amide (G_CC-91) |
| G_CC-92 | 4-Methoxy-2,6-dimethyl-N-[1-[2-oxo-2-(4-pyridin-4-yloxy-piperidin-1-yl)-ethyl]-1H-indol-7-yl]-benzenesulfonic acid amide (G_CC-92) |
| G_CC-95 | N-[2-(4-Dimethylamino-4-phenyl-cyclohexyl)-ethyl]-2-[6-[[(4-methoxy-2,6-dimethyl-phenyl)sulfonyl]amino]-1H-indol-1-yl]-N-methyl-acetamide (G_CC-95) |
| G_CC-99 | N-[2-[4-(3-Fluorophenyl)-4-(4-methyl-piperazin-1-yl)-piperidin-1-yl]-ethyl]-2-[6-[[(4-methoxy-2,6-dimethyl-phenyl)sulfonyl]amino]-1H-indol-1-yl]-N-methyl-acetamide (G_CC-99) |
| G_CC-102 | N-[2-[4-(3-Fluorophenyl)-4-(4-methyl-piperazin-1-yl)-piperidin-1-yl]-ethyl]-2-[7-[[(4-methoxy-2,6-dimethyl-phenyl)sulfonyl]amino]-1H-indol-1-yl]-N-methyl-acetamide (G_CC-102) |
| G_CC-108 | N-[[1-[2-[6-[[(4-Methoxy-2,6-dimethyl-phenyl)sulfonyl]amino]-1H-indol-1-yl]-acetyl]-4-(4-methyl-piperazin-1-yl)-piperidin-4-yl]-methyl]-pyridine-4-carboxylic acid amide (G_CC-108) |
| G_CC-116 | 3-[6-[[(4-Methoxy-2,6-dimethyl-phenyl)sulfonyl]amino]-1H-indol-1-yl]-N-methyl-N-[3-(4-pyridin-4-yl-piperazin-1-yl)-propyl]-propionamide (G_CC-116) |
| G_CC-117 | N-[2-(4-Dimethylamino-4-phenyl-cyclohexyl)-ethyl]-3-[6-[[(4-methoxy-2,6-dimethyl-phenyl)sulfonyl]amino]-1H-indol-1-yl]-N-methyl-propionamide (G_CC-117) |
| G_CC-120 | 4-Methoxy-2,6-dimethyl-N-[1-[2-oxo-2-[4-(2-pyrrolidin-1-yl-ethyl)-piperidin-1-yl]-ethyl]-1H-indol-6-yl]-benzenesulfonic acid amide (G_CC-120) |
| G_CC-139 | 4-Methoxy-2,6-dimethyl-N-[1-[2-oxo-2-[4-(pyridin-3-carbonyl)-piperazin-1-yl]-ethyl]-1H-indol-7-yl]-benzenesulfonic acid amide (G_CC-139) | or a physiologically compatible salt thereof.

17. A pharmaceutical composition comprising a compound according to claim 1 and at least one pharmaceutically acceptable carrier or auxiliary substance.

18. A method of treating or inhibiting a condition selected from the group consisting of pain, inflammation, and obesity, in a subject in need thereof, said method comprising administering to said subject a pharmacologically effective amount of a compound according to claim 1.

19. A method according to claim 18, wherein said condition is pain selected from the group consisting of acute pain, visceral pain, neuropathic pain, chronic pain and inflammatory pain.

* * * * *